US012545675B2

(12) United States Patent
Ward et al.

(10) Patent No.: US 12,545,675 B2
(45) Date of Patent: *Feb. 10, 2026

(54) ANTI-WOLBACHIA PYRIDO[2,3-D]PYRIMIDINE COMPOUNDS

(71) Applicants: Liverpool School of Tropical Medicine, Liverpool (GB); The University of Liverpool, Liverpool (GB); Eisai R&D Management Co., Ltd., Bunkyo-Ku (JP)

(72) Inventors: Stephen A. Ward, Liverpool (GB); Mark J. Taylor, Liverpool (GB); Paul M. O'Neill, Liverpool (GB); Weiqian David Hong, Liverpool (GB); Farid Benayoud, North Andover, MA (US)

(73) Assignees: Liverpool School of Tropical Medicine, Liverpool (GB); The University of Liverpool, Liverpool (GB); Eisai R&D Management Co., Ltd., Bunkyo-Ku (JP)

( * ) Notice: Subject to any disclaimer, the term of this patent is extended or adjusted under 35 U.S.C. 154(b) by 192 days.

This patent is subject to a terminal disclaimer.

(21) Appl. No.: 17/956,435

(22) Filed: Sep. 29, 2022

(65) Prior Publication Data

US 2023/0348460 A1 Nov. 2, 2023

Related U.S. Application Data

(63) Continuation of application No. 16/478,281, filed as application No. PCT/IB2018/000216 on Jan. 17, 2018, now Pat. No. 11,518,760.

(30) Foreign Application Priority Data

Jan. 17, 2017 (GB) ..................................... 1700814

(51) Int. Cl.
*C07D 471/04* (2006.01)
*C07D 239/86* (2006.01)
*C07D 495/04* (2006.01)

(52) U.S. Cl.
CPC ......... *C07D 471/04* (2013.01); *C07D 239/86* (2013.01); *C07D 495/04* (2013.01)

(58) Field of Classification Search
CPC ... C07D 471/04; C07D 239/86; C07D 495/04
See application file for complete search history.

(56) References Cited

U.S. PATENT DOCUMENTS

| | | | | |
|---|---|---|---|---|
| 6,262,059 | B1 | 7/2001 | Pamukcu et al. | |
| 11,518,760 | B2 * | 12/2022 | Ward | A61P 31/04 |
| 2009/0182140 | A1 | 7/2009 | Furukubo et al. | |
| 2010/0160314 | A1 | 6/2010 | Lipford et al. | |
| 2010/0317607 | A1 * | 12/2010 | Wynne | C07D 409/12 514/230.2 |
| 2013/0345249 | A1 | 12/2013 | Debec et al. | |
| 2015/0126500 | A1 | 5/2015 | Li et al. | |
| 2016/0289229 | A1 | 10/2016 | Aktoudianakis et al. | |
| 2019/0345175 | A1 | 11/2019 | Fritz-Langhals | |
| 2024/0108629 | A1 | 4/2024 | Turner et al. | |

FOREIGN PATENT DOCUMENTS

| | | | |
|---|---|---|---|
| CN | 103087077 | A | 5/2013 |
| CN | 106083742 | A | 11/2016 |
| CN | 110128419 | A | 8/2019 |
| EP | 2532661 | A1 | 12/2012 |
| GB | 1057612 | A | 2/1967 |
| JP | 2007/513996 | A | 5/2007 |
| WO | WO-99/43681 | A1 | 9/1999 |
| WO | WO-2001/032632 | A2 | 5/2001 |
| WO | WO-03/055890 | A1 | 7/2003 |
| WO | WO-2009/001060 | A2 | 12/2008 |
| WO | WO-2010/042489 | A2 | 4/2010 |

(Continued)

OTHER PUBLICATIONS

Gilson, et al, Optimization of 2-Anilino 4-Amino Substituted Quinazolines into Potent Antimalarial Agents with Oral in Vivo Activity, J. of Med. Chem., 60(3), 1171-1188 (2017). (Year: 2017).*
Abbiati et al., "Palladium-Assisted Multicomponent Synthesis of 2-Aryl-4-aminoquinolines and 2-Aryl-4-amino[1,8]naphthyridines," Journal of Organic Chemistry, 70:6454-6460 (2005).
Abuzar et al., "Synthesis of some new 7-chloro-4-substituted quinolines as potential antiparasitic agents. (1)," European Journal of Medicinal Chemistry, 21(1):5-8 (1986).
Bakowski et al., "Advances in Antiwolbachial Drug Discovery for Treatment of Parasitic Filarial Worm Infections," Tropical Medicine and Infectious Disease, 4(108): pp. 1-26 (2019).

(Continued)

*Primary Examiner* — Erich A Leeser
(74) *Attorney, Agent, or Firm* — Foley Hoag LLP; David P. Halstead; Benjamin A. Vaughan

(57) ABSTRACT

The present invention relates to compounds of Formulae I and II as defined herein, and salts and solvates thereof.

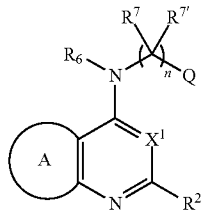

The present invention also relates to pharmaceutical compositions comprising compounds of Formulae I and II, and to the use of compounds of Formulae I and II in the treatment or prevention of filarial worm infection, as well as other diseases or conditions in which filarial worm infection is implicated.

16 Claims, No Drawings

(56) References Cited

FOREIGN PATENT DOCUMENTS

| | | | |
|---|---|---|---|
| WO | WO-2011/011522 | A2 | 1/2011 |
| WO | WO-2011/135259 | A1 | 11/2011 |
| WO | WO-2016/112317 | A1 | 7/2016 |
| WO | WO-2018/134685 | A2 | 7/2018 |
| WO | WO-2022/240213 | A1 | 11/2022 |
| WO | WO-2023/134708 | A1 | 7/2023 |
| WO | WO-2023/134739 | A1 | 7/2023 |

OTHER PUBLICATIONS

Cabrera et al., "2,4-Diaminothienopyrimidines as Orally Active Antimalarial Agents," Journal of Medicinal Chemistry, 57(3):1014-1022 (2014).
Cabrera et al., "Structure-Activity Relationship Studies of Orally Active Antimalarial 2,4-Diamino-thienopyrimidines," Journal of Medicinal Chemistry, 58(18):7572-7579 (2015).
CAS Registry No. 1452967-51-9, ChemBridge Corporation (2013).
CAS Registry No. 1453002-20-4, ChemBridge Corporation (2013).
Chakraborti et al., "3D-QSAR Studies on thieno [3,2-d]pyrimidines as Phosphodiesterase IV Inhibitors," Bioorganic & Medicinal Chemistry Letters, 13(8):1403-1408 (2003).
ChemBridge Product Guide., "High Quality, Small Molecule Screening Libraries," <http://v.AVV./.chembridge.com/screening libraries/ on Aug. 9, 2015.>: 1-2 (2015).
Crespo et al., "Design, Synthesis, and Biological Activities of New Thieno [3,2-d]pyrimidines as Selective Type 4 Phosphodiesterase Inhibitors," Journal of Medicinal Chemistry, 41:4021-4035 (1998).
Font et al., "New insights into the structural requirements for pro-apoptotic agents based on 2,4-diaminoquinazoline, 2,4-diaminopyrido [2,3-]pyrimidine and 2,4-diaminopyrimidine derivatives," European Journal of Medicinal Chemistry, 46(9):3887-3899 (2011).
International Search Report and Written Opinion for International Application No. PCT/IB2018/000216 mailed Sep. 24, 2018 (Our reference HGX-05425).
Liu et al., "Design, synthesis and biological evaluation of novel thieno[3,2-d]pyrimidine derivatives possessing diaryl semicarbazone scaffolds as potent antitumor agents," European Journal of Medicinal Chemistry, 87:782-793 (2014).
Machine translation for CN 106083742 (2016).
Moreno et al., "Sulfur and selenium derivatives of quinazoline and pyrido [2,3-]pyrimidine: Synthesis and study of their potential cytotoxic activity," European Journal of Medicinal Chemistry, 47:283-298 (2011).
Ngan., "Filariasis: What is filariasis?" DermNet NZ: 4 pages (2021).
Nishikawa et al., "Cytokinin Activity of 4-Aminopyridopyrimidines toward the Growth of Tobacco Callus," Biosci Biotech Biochem, 58(9):1709-1710 (1994).
Odingo et al., "Synthesis and evaluation of the 2,4-diaminoquinazoline series as anti- tubercular agents," Bioorganic & Medicinal Chemistry, 22(24):6965-6979 (2014).
Sangshetti et al., "Two decades of antifilarial drug discovery: a review," RSC Advances, 7:20628-20666 (2017).
Singh et al., "Chemotherapy of filariasis-on the search of new agents effective on the reproductive system of female adult worms," Zeitschrift Fur Naturforschung C: A Journal of Biosciences, 45(11-12):1210-1214 (1990).
Tewari et al., "Synthesis and Antifilarial Profile of 7-Chloro-4-(substituted Amino) Quinolines: a New Class of Antifilarial Agents," Bioorganic & Medicinal Letters, 10:1409-1412 (2000).
Tikad et al., "Efficient one-pot synthesis of 2,4-di(het)aryl and 2,4-diamino pyrido[3,2-d]pyrimidines involving regioselective SNAr and palladium-catalyzed reactions," Organic & Biomolecular Chemistry, 7(24):5113-5118 (2009).
United Kingdom Search Report for Application No. GB1700814.5 mailed Nov. 9, 2017.
Vandewaa et al., "Anti-filarial effects of nine quinoline-containing drugs on adult filariae in vitro," Journal of Parasitology, 75(3):367-372 (1989).
Zhao et al. Chemical Abstract, 165:607135 for CN 106083742 (2016).
Zhou et al., "A highly selective Cd2+ sensor of naphthyridine: fluorescent enhancement and red-shift by the synergistic action of forming binuclear complex," Tetrahedron Letters, 49(21):3380-3384 (2008).
"Development of AWZ1066S, a Small Molecule Anti-Wolbachia Candidate Macrofilaricide Drug" dated Oct. 20, 2021; URL: https// clinicaltrials.gov/ct2/show/NCT05084560 retrieved on Jul. 13, 2023.
"Heartworm by the Numbers", American Heartworm Society, chrome-extension://efaidnbmnnnibpcajpcglclefindmkaj/https://d3ft8sckhnqim2.cloudfront.net/images/pdf/2019HeartwormByTheNumbers.pdf?1548859511 (2016).
Anonymous, "Current Canine Guidelines for the Prevention, Diagnosis, and Management of Heartworm (Dirofilaria immitis) Infection in Dogs", American Heartworm Society, URL: chrome-extension://efaidnbmnnnibpcajpcglclefindmkaj/https://d3ft8sckhnqim2.cloudfront.net/images/pdf/2018_AHS_Canine_Guidelines_rev_7-25-19.pdf?1564157216 (2018).
Anonymous, "Summary of the Current Feline Guidelines for the Prevention, Diagnosis, and Management of Heartworm (Dirofilaria immitis) Infection in Cats", American Heartworm Society, URL: chrome- extension://efaidnbmnnnibpcajpcglclefindmkaj/https:// d3ft8sckhnqim2.cloudfront.net/images/pdf/Feline-Guidelines-Summary.pdf?1393457997 (2014).
Bosshardt et al., "Prophylactic activity of tetracycline against Brugia pahangi infection in jirds (Meriones unguiculatus)", The Journal of parasitology 79.5: 775-777 (1993).
Bourguinat et al., "Macrocyclic lactone resistance in Dirofilaria immitis", Veterinary parasitology 181.2-4: 388-392 (2011).
Bourguinat et al., "Macrocyclic lactone resistance in Dirofilaria immitis: failure of heartworm preventives and investigation of genetic markers for resistance", Veterinary parasitology 210.3-4: 167-178 (2015).
Bowman et al., "Prevalence and geographic distribution of Dirofilaria immitis, Borrelia burgdorferi, Ehrlichia canis, and Anaplasma phagocytophilum in dogs in the United States: results of a national clinic-based serologic survey", Veterinary parasitology 160.1-2: 138-148 (2009).
Clark et al., "Efficacy of ivermectin and pyrantel pamoate combined in a chewable formulation against heartworm, hookworm, and ascarid infections in dogs", American journal of veterinary research 53.4: 517-520 (1992).
Di Cesare et al. "Field clinical study evaluating the efficacy and safety of an oral formulation containing milbemycin oxime/ praziquantel (Milbemax®, Novartis Animal Health) in the chemoprevention of the zoonotic canine infection by Dirofilaria repens", Parasites & vectors 7: 1-8 (2014).
Genchi et al., "Subcutaneous dirofilariosis (Dirofilaria repens): an infection spreading throughout the old world", Parasites & vectors 10: 1-6 (2017).
Hawryluk. "Marcrofilaricides: An unmet medical need for filarial diseases" ACS Infectious Diseases. 6(4): 662-671 (2020).
Hong et al., "AWZ1066S, a highly specific anti-Wolbachia drug candidate for a short-course treatment of filariasis" PNAS, 116(4):1414-1419 (2019).
International Search Report and Written Opinion for International Application No. PCT/EP22/50922 dated May 2, 2022.
Jaffe et al., "Comparative properties of schistosomal and filarial dihydrofolate reductases" Biochemical Pharmacology, 21(5): 719-731 (1972).
Khowawisetsut et al., "Therapeutic trial of doxycyclines ivermectin for the treatment of Brugia malayi naturally infected cats", Veterinary parasitology 245: 42-47 (2017).
Kramer et al., "Evaluation of lung pathology in Dirofilaria immitis-experimentally infected dogs treated with doxycycline or a combination of doxycycline and ivermectin before administration of melarsomine dihydrochloride", Veterinary parasitology 176.4: 357-360 (2011).

(56) References Cited

OTHER PUBLICATIONS

Kryda et al., "Laboratory and field studies to investigate the efficacy of a novel, orally administered combination product containing moxidectin, sarolaner and pyrantel for the prevention of heartworm disease (Dirofilaria immitis) in dogs", Parasites & vectors 12: 1-12 (2019).
Lee et al., "Public health issues concerning the widespread distribution of canine heartworm disease", Trends in parasitology 26.4: 168-173 (2010).
Mallawarachchi et al., "A preliminary survey of filarial parasites in dogs and cats in Sri Lanka", PLoS One 13.11: e0206633 (2018).
Mallawarachchi et al., "Human infection with sub-periodic *Brugia* spp. in Gampaha District, Sri Lanka: a threat to filariasis elimination status?", Parasites & vectors 11: 1-6 (2018).
Mao et al., "Synthesis and biological evaluation of novel N-pyridylpyrazolecarboxamides containing benzothiazole", Phosphorus, Sulfur, and Silicon and the Related Elements 192.1: 42-46 (2017).
McCall et al., "Evaluation of ivermectin and milbemycin oxime efficacy against Dirofilaria immitis infections of three and four months' duration in dogs", American journal of veterinary research 57.8: 1189-1192 (1996).
McCall et al., "Heartworm disease in animals and humans", Advances in parasitology 66: 193-285 (2008).
McTier et al., "ProHeart® 12, a moxidectin extended-release injectable formulation for prevention of heartworm (Dirofilaria immitis) disease in dogs in the USA for 12 months", Parasites & vectors 12: 1-14 (2019).
Morchón et al., "Heartworm disease (Dirofilaria immitis) and their vectors in Europe-new distribution trends", Frontiers in physiology 3: 23265 (2012).
Namani et al., "Design, Synthesis and Biological Evaluation of Benzimidazolyl and Benzothiazolyl Picolinamide Derivatives as Antimicrobial Agents", Asian Journal of Chemistry 27.12: 4575 (2015).
Paul et al., "Efficacy of ivermectin against Dirofilaria immitis larvae in dogs 30 and 45 days after induced infection," American Journal of Veterinary Research 47.4 (1986): 883-884.
Pollono et al., "The prevention of Dirofilaria repens infection with ivermectin/pyrantel chewables", Parassitologia 40.4: 457-459 (1998).
Prichard et al., "Perspectives on the utility of moxidectin for the control of parasitic nematodes in the face of developing anthelmintic resistance", International Journal for Parasitology: Drugs and Drug Resistance 10: 69-83 (2019).
Pulaski et al., "Establishment of macrocyclic lactone resistant Dirofilaria immitis isolates in experimentally infected laboratory dogs", Parasites & vectors 7: 1-9 (2014).
Snyder et al., "Assessment of the effectiveness of a combination product of spinosad and milbemycin oxime on the prophylaxis of canine heartworm infection", Veterinary Parasitology 180.3-4: 262-266 (2011).
Taylor et al., "Lymphatic filariasis and onchocerciasis", The Lancet 376.9747: 1175-1185 (2010).
Turner et al., "Novel anti-Wolbachia drugs, a new approach in the treatment and prevention of veterinary filariasis?", Veterinary parasitology 279: 109057 (2020).
United Kingdom Search Report for Application No. GB2100635.8 dated Jun. 11, 2021.
United Kingdom Search Report for Application No. GB2303582.7 dated Jan. 31, 2024.
Wolstenholme et al., "The emergence of macrocyclic lactone resistance in the canine heartworm, Dirofilaria immitis", Parasitology 142.10: 1249-1259 (2015).

* cited by examiner

ANTI-WOLBACHIA PYRIDO[2,3-D]PYRIMIDINE COMPOUNDS

RELATED APPLICATIONS

The present application is a continuation of U.S. application Ser. No. 16/478,281, filed Jul. 16, 2022; which is the U.S. National Phase of International Patent Application No. PCT/IB18/00216, filed Jan. 17, 2018, which claims the benefit of priority to Great Britain Application No. 1700814.5, filed Jan. 17, 2017.

INTRODUCTION

This application relates to compounds of Formulae I and II as defined herein and salts or solvates thereof.

The compounds of Formula I and Formula II and their salts generally have anti-*Wolbachia* activity, and may be used to treat diseases or conditions mediated, at least in part, by a filarial worm infection.

The present application further provides pharmaceutical compositions comprising a compound of Formulae I or II and/or a pharmaceutically acceptable salt or solvate thereof and a pharmaceutically acceptable excipient.

The present application also provides methods of treating a disease or condition mediated, at least in part, by a filarial worm infection comprising administering to a subject in need a compound of Formula I or Formula II and/or a pharmaceutically acceptable salt or solvate thereof.

BACKGROUND OF THE INVENTION

Filarial nematodes are an important group of human pathogens infecting around 150 million people throughout the tropics with more than 1.5 billion at risk of infection. Filariasis accounts for some of the most debilitating global diseases that affect the 'poorest of the poor' resulting in a profound socio-economic impact on the most vulnerable in society.

Lymphatic filariasis is transmitted by infected mosquitoes. When an infected mosquito bites and takes a blood feed, worm larvae transfer from the mosquito onto the bite site where they enter into the body and move towards the lymphatic system—the system in the body which regulates the balance of fluids and fights infection. Here it will take the larvae 6 months to 1 year to develop into adult worms; the males will grow to approximately 2 to 4 cm long and the females to 4 to 10 cm long.

After mating, the female worms release thousands of larvae into the lymphatic system. These larvae migrate into the blood stream and transfer back into a mosquito when it bites. Once inside the mosquito, the larvae move to the mosquito stomach where they shed their sheaths before entering the mosquito body cavity and eventually into the flight muscles. After 10 to 14 days the juvenile worms are ready to migrate into the mouth-parts of the mosquito and the cycle is completed when the mosquito bites again.

*Wuchereria bancrofti, Brugia malayi*, and *Brugia timori* are causative agents of lymphatic filariasis, or elephantiasis, in humans. People suffering with lymphatic filariasis can develop hydrocele and lymphedema leading to elephantiasis. It is estimated that up to 120 million people in 83 countries worldwide are affected by lymphatic filariasis.

Onchocerciasis is transmitted by black flies which live and breed in rivers. *Onchocerca volvulus* is a causative agent of onchocerciasis, or river blindness, in humans. Manifestations of onchocerciasis result primarily from the intense inflammatory reaction to *Wolbachia* bacteria released into the skin and eyes upon the death of microfilaria. Onchocerciasis affects up to 37 million people worldwide and is most abundant in Africa.

Two of the major constraints of treatment of filarial diseases are (i) the absence of a macrofilaricidal drug (or for onchocerciasis, one which permanently sterilizes the worm) and (ii) the risk of worms developing drug-resistance. For example, currently available treatments for onchocerciasis include ivermectin, which kills worm larvae, but has little or no activity against adult *Onchocerca volvulus* parasites. Thus, infected patients must be retreated with ivermectin for several years until the adult worms die naturally. The most commonly used dose interval is 12 months; however, retreatment with ivermectin may be considered at intervals as short as 3 months. In addition, there are also potential signs of resistance to ivermectin within the parasite in a few areas (Osei-Atweneboana M Y, et al. (2011) Phenotypic Evidence of Emerging Ivermectin Resistance in *Onchocerca volvulus*. PLoS Negl Trop Dis 5(3): e998).

In addition, there is a danger in treating patients co-infected with both (i) *Wuchereria bancrofti, Brugia malayi, Brugia timori*, and/or *Onchocerca volvulus*; and (ii) *Loa loa* with ivermectin. In such co-infected patients, ivermectin treatment can cause severe reactions, including encephalopathy, leading to coma or even death.

Thus, alternative, and more effective, treatments for filarial worm diseases and, in particular, onchocerciasis and lymphatic filariasis are needed.

*Wolbachia* is a genus of bacteria that infects arthropods, including insects and crusteans, and filarial worms such as *Onchocerca volvulus, Wuchereria bancrofti, Brugia malayi*, and *Brugia timori*. The bacteria reside in cytoplasmic vacuoles and are essential for development, reproduction and long-term survival of filarial worms. Accordingly, eliminating the bacteria with antibiotic drugs kills the worms and delivers a new and practical solution for eradicating the debilitating diseases mediated by these worms.

Antibiotics, such as doxycycline, minocycline, and rifampicin, have been demonstrated to be effective against *Wolbachia*. Taylor et al., (2005) Lancet 365(9477):2116-2121 and Townson S, et al., (2006) Filaria J. 5:4. However, it has been reported that other classes of antibiotics, such as penicillins, aminoglycosides, and macrolides are ineffective at depleting *Wolbachia* from filariae (Hoerauf A, et al. (1999) Journal of Clinical Investigation 103(1):11-18 and Hoerauf A, et al. (2000) Trop Med Int Health 5(4):275-279).

Existing anti-*Wolbachia* drugs are non-optimal; they require a relatively long course of treatment (~4 weeks) and often exclude certain subjects, including pregnant women and children under the age of 9 (e.g., treatment with tetracyclines).

Thus, there exists a need for alternative and/or improved anti-*Wolbachia* treatments, such as those providing a shorter treatment regimen (e.g., 7 days or less) and/or usable in currently restricted populations (Taylor et al. Parasitology, 141(1):119-27).

SUMMARY OF THE INVENTION

In one aspect, the present invention provides a compound of Formula I or II as defined herein, and/or a salt or solvate thereof.

In another aspect, the present invention provides a pharmaceutical composition which comprises a compound of Formula I or II as defined herein, or a pharmaceutically acceptable salt or solvate thereof, and one or more pharmaceutically acceptable excipients.

In another aspect, the present invention provides a compound of Formula I or II as defined herein, or a pharmaceutically acceptable salt or solvate thereof, or a pharmaceutical composition as defined herein, for use in therapy.

In another aspect, the present invention provides a compound of Formula I or II as defined herein, or a pharmaceutically acceptable salt or solvate thereof, or a pharmaceutical composition as defined herein, for use in the treatment or prevention of a filarial worm infection.

In another aspect, the present invention provides a compound of Formula I or II as defined herein, or a pharmaceutically acceptable salt or solvate thereof, or a pharmaceutical composition as defined herein, for use in the treatment or prevention of a disease or condition mediated by a filarial worm infection.

In another aspect, the present invention provides a compound of Formula I or II as defined herein, or a pharmaceutically acceptable salt or solvate thereof, or a pharmaceutical composition as defined herein, for use in the treatment of a microbial infection.

In another aspect, the present invention provides the use of a compound of Formula I or II as defined herein, or a pharmaceutically acceptable salt or solvate thereof, in the manufacture of a medicament for the treatment or prevention of a filarial worm infection.

In another aspect, the present invention provides the use of a compound of Formula I or II as defined herein, or a pharmaceutically acceptable salt or solvate thereof, in the manufacture of a medicament for the treatment or prevention of a disease or condition mediated by a filarial worm infection.

In another aspect, the present invention provides the use of a compound of Formula I or II as defined herein, or a pharmaceutically acceptable salt or solvate thereof, in the manufacture of a medicament for the treatment of a microbial infection.

In another aspect, the present invention provides a method of treating or preventing a filarial worm infection, said method comprising administering to a subject in need thereof an effective amount of a compound of Formula I or II as defined herein, or a pharmaceutically acceptable salt or solvate thereof.

In another aspect, the present invention provides a method of treating or preventing a disease mediated by a filarial worm infection, said method comprising administering to a subject in need thereof an effective amount of a compound of Formula I or II as defined herein, or a pharmaceutically acceptable salt or solvate thereof.

In another aspect, the present invention provides a method of treating a microbial infection, said method comprising administering to a subject in need thereof a therapeutically effective amount of a compound of Formula I or II as defined herein, or a pharmaceutically acceptable salt or solvate thereof, or a pharmaceutical composition as defined herein.

In another aspect, the present invention provides a combination comprising a compound of Formula I or II, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of Formula Ia", "compounds of Formula II" and "compounds of Formula IIa", and the more general term "compounds" refer to and include any and all compounds described by and/or with reference to Formula I, Ia, II and IIa respectively. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, Ia, II and IIa, either by themselves or in combination with additional agents.

The various hydrocarbon-containing moieties provided herein may be described using a prefix designating the minimum and maximum number of carbon atoms in the moiety, e.g. "($C_{a-b}$)" or "$C_a$-$C_b$" or "(a-b)C". For example, ($C_{a-b}$)alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene ($-CH_2-$), the ethylene isomers ($-CH(CH_3)-$ and $-CH_2CH_2-$), the propylene isomers ($-CH(CH_3)CH_2-$, $-CH(CH_2CH{=})-$, $-C(CH_3){=}-$, and $-CH_2CH_2CH_2-$), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene ($—C_6H_4—$) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2—$). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydro-naphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2—$). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, $—CF_3$, $—CHF_2$, $—CH_2F$, $—CF_2CF_3$, $—CHFCF_3$, $—CH_2CF_3$, $—CF_2CH_3$, $—CHFCH_3$, $—CF_2CF_2CF_3$, $—CF_2CH_2CH_3$, $—CF{=}CF_2$, $—CCl{=}CH_2$, $—CBr{=}CH_2$, $—CI{=}CH_2$, $—C{\equiv}C—CF_3$, $—CHFCH_2CH_3$ and $—CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, $—OCF_3$, $—OCHF_2$, $—OCH_2F$, $—OCF_2CF_3$, $—OCHFCF_3$, $—OCH_2CF_3$, $—OCF_2CH_3$, $—OCHFCH_3$, $—OCF_2CF_2CF_3$, $—OCF_2CH_2CH_3$, $—OCF{=}CF_2$, $—OCCl{=}CH_2$, $—OCBr{=}CH_2$, $—OCHFCH_2CH_3$ and $—OCHFCH_2CF_3$. Haloalkoxy groups can be substituted or unsubstituted. Suitably, a haloalkyoxy group is selected from $—OCHF_2$ and $—OCF_3$, suitably $—OCF_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.$0^{2,7}$]dodeca-2(7),3,5-trienyl, 12-oxa-10-aza-tricyclo[6.3.1.$0^{2,7}$]dodeca-2(7),3,5-trienyl, 12-aza-tricyclo[7.2.1.$0^{2,7}$]dodeca-2(7),3,5-trienyl, 10-aza-tricyclo[6.3.2.$0^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers are provided, e.g. ($C_{n-m}$)alkylheteroaryl, the range refers to the whole group. Suitably, the constitutent alkyl group has 1-6 carbons, suitable 1-3 carbons.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroycloalkyl groups can be substituted or unsubstituted. Where carbon numbers are provided, e.g. ($C_{n-m}$)alkylheterocycloalkyl, the range refers to the whole group. Suitably, the constitutent alkyl group has 1-6 carbons, suitable 1-3 carbons.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —$CF_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by themselves or in conjunction with another term or terms, "subject(s)" and "patient(s)", suitably refer to mammals, in particular humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

Compounds

In one aspect, the present invention relates to compounds of Formula I:

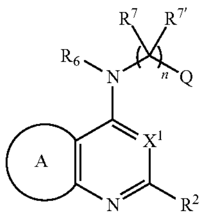

(I)

or a salt or solvate thereof, wherein,

A represents a fused aromatic ring selected from,

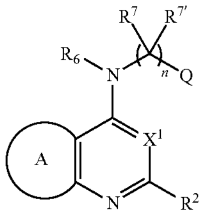

(I)

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 1, 2 and 3;

$R^2$ is selected from —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

with the provisos that:

(i) when $X^1$ is N, $X^2$ and $X^3$ cannot both be CH;

(ii) when Q is phenyl, $R^b$ is not such that Q is a 3,4-di-O—$C_{1-6}$ alkyl phenyl, a 3,5-di-O—$C_{1-6}$ alkyl phenyl or a 3,4,5-tri-O—$C_{1-6}$ alkyl phenyl; and (iii) the compound of Formula (I) is not N-(4-fluorobenzyl)-2-(piperidinyl-1-yl)pyrido[2,3-d]pyrimidin-4-amine, N-(4-fluorobenzyl)-2-(piperidinyl-1-yl)pyrido[3,2-d]pyrimidin-4-amine, N-(4-fluorobenzyl)-2-(piperidinyl-1-yl)thieno[3,2-d]pyrimidin-4-amine.

The invention will now be further described by way of the following numbered paragraphs:

1. A compound of Formula I, or a salt or solvate thereof, wherein,

A represents a fused aromatic ring selected from,

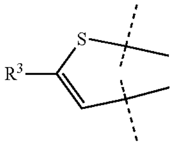

and

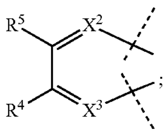

;

$X^1$, $X^2$ and $X^3$ are independently selected from N and CH;

Q is a group selected from an $C_{3-11}$cycloalkyl optionally substituted by 1-21 $R^b$, 3-15 membered heterocycloalkyl optionally substituted by 1-28 $R^b$, $C_{6-11}$ aryl group optionally substituted with by 1-11 $R^b$, 5-15 membered heteroaryl optionally substituted by 1-15 $R^b$;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 1, 2 and 3;

$R^2$ is selected from —CN, —C(═O)$R^d$, —C(═O)O$R^d$, —C(═O)N$R^cR^d$, —C(O)C(═O)$R^d$, —N$R^cR^d$, —N$R^c$ ($C_{1-6}$alkyl)$NR^cR^d$, —$NR^cC$(═O)$R^d$, —$NR^cC$(═O)$OR^d$, —$NR^cC$(═O)$NR^cR^d$, —$NR^cS$(═$O)_2R^d$, —$NR^cS$(═$O)_2NR^cR^d$, —$OR^d$, —$SR^d$, —OC(═O)$R^d$, —OC(═O)$NR^cR^d$, —OC(═O)$OR^d$, —S(═O)$R^d$, —S(═$O)_2R^d$, —OS(═O)$R^d$, —OS(═$O)_2R^d$, —OS(═$O)_2OR^d$, —S(═O)$NR^cR^d$, —OS(═$O)_2NR^cR^d$, —S(═$O)_2NR^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, ($C_{7-16}$)alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered heteroarylalkyl optionally substituted by 1-27 $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)$OR^d$, —C(═O)$NR^cR^d$, —C(O)C(═O)$R^d$, —$NR^cR^d$, —$NR^cC$(═O)$R^d$, —$NR^cC$(═O)$OR^d$, —$NR^cC$(═O)$NR^cR^d$, —$NR^cS$(═$O)_2R^d$, —$NR^cS$(═$O)_2NR^cR^d$, —$OR^d$, —$SR^d$, —OC(═O)$R^d$, —OC(═O)$NR^cR^d$, —OC(═O)$OR^d$, —S(═$O)_2R^d$, —S(═O)$R^d$, —OS(═O)$R^d$, —OS(═$O)_2R^d$, —OS(═$O)_2OR^d$, —S(═O)$NR^cR^d$, —OS(═$O)_2NR^cR^d$, and —S(═$O)_2NR^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

with the provisos that:

(i) when $X^1$ is N, $X^2$ and $X^3$ cannot both be CH;

(ii) when Q is phenyl, $R^b$ is not such that Q is a 3,4-di-O—$C_{1-6}$ alkyl phenyl, a 3,5-di-O—$C_{1-6}$ alkyl phenyl or a 3,4,5-tri-O—$C_{1-6}$ alkyl phenyl; and (iii) the compound of Formula (I) is not N-(4-fluorobenzyl)-2-(piperidinyl-1-yl)pyrido[2,3-d]pyrimidin-4-amine, N-(4-fluorobenzyl)-2-(piperidinyl-1-yl)pyrido[3,2-d]pyrimidin-4-amine, N-(4-fluorobenzyl)-2-(piperidinyl-1-yl)thieno[3,2-d]pyrimidin-4-amine.

2. A compound according to any one of the preceding paragraphs, or a salt or solvate thereof, wherein A is

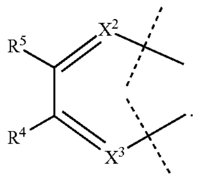

3. A compound according to any one of the preceding paragraphs, or a salt or solvate thereof, wherein $X^1$ is N.

4. A compound according to any one of the preceding paragraphs, or a salt or solvate thereof, wherein one of $X^2$ and $X^3$ is N and the other is CH.

5. A compound according to any one of the preceding paragraphs, or a salt or solvate thereof, wherein $X^2$ is CH and $X^3$ is N.

6. A compound according to any one of paragraphs 1 to 3, or a salt or solvate thereof, wherein $X^1$ is N and A is selected from

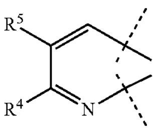

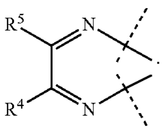

7. A compound according to any one of paragraphs 1 to 3, or a salt or solvate thereof, wherein A is

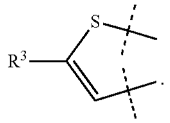

8. A compound according to any one of the preceding paragraphs, or a salt or solvate thereof, wherein Q is a group selected from a 3-15 membered heterocycloalkyl optionally substituted by one or more $R^b$, $C_{6-11}$ aryl group optionally substituted with by one or more $R^b$, and a 5-15 membered heteroaryl optionally substituted by one or more $R^b$.

9. A compound according to any one of the preceding paragraphs, or a salt or solvate thereof, wherein Q is a group selected from a 3-15 membered heterocycloalkyl optionally substituted by 1-28 $R^b$, $C_{6-11}$ aryl group optionally substituted with by 1-11 $R^b$, and a 5-15 membered heteroaryl optionally substituted by 1-15 $R^b$.

10. A compound according to any one of the preceding paragraphs, or a salt or solvate thereof, wherein Q is a group selected from a $C_{6-11}$ aryl group optionally substituted with by 1-11 $R^b$ and a 5-15 membered heteroaryl optionally substituted by 1-15 $R^b$.

11. A compound according to any one of the preceding paragraphs, or a salt or solvate thereof, wherein Q is a group selected from a $C_6$ aryl group optionally substituted with by one or more $R^b$ and a 5-6 membered heteroaryl optionally substituted by one or more $R^b$.

12. A compound according to any one of the preceding paragraphs, or a salt or solvate thereof, wherein Q is selected from a phenyl or pyridyl group optionally substituted with 1-5 $R^b$.

13. A compound according to any one of the preceding paragraphs, or a salt or solvate thereof, wherein Q is a group of Formula III (wherein the dotted line indicates the point of attachment):

(III)

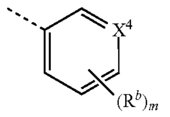

wherein $X^4$ is selected from CH and N;

m is selected from 0, 1 and 2; and $R^b$ is as previously defined.

14. A compound according to any one of the preceding paragraphs, or a salt or solvate thereof, wherein Q is a group of Formula IIIa:

(IIIa)

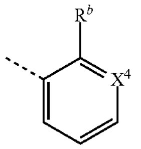

wherein $X^4$ is selected from CH and N, suitably N; and $R^b$ is as previously defined.

15. A compound according to any one of the preceding paragraphs, or a salt or solvate thereof, wherein each $R^b$ is independently selected from hydroxyl, =O, halogen, CN, $C_{1-6}$ haloalkyl, $C_{1-6}$ haloalkoxy, $C_{3-6}$ cycloalkyl, $C_{1-6}$ alkyl, O—$C_{1-6}$ alkyl, $C_{3-6}$ cycloalkyl, 3-7 membered heterocycloalkyl, —$NR^cR^d$, —$NR^cC(=O)R^d$, —$OR^d$, —$SR^d$, —$S(=O)_2R^d$, —$S(=O)R^d$, —$S(=O)NR^cR^d$, and —$S(=O)_2NR^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

16. A compound according to any one of the preceding paragraphs, or a salt or solvate thereof, wherein each $R^b$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —$NR^cR^d$, and —$S(=O)_2R^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

17. A compound according to any one of the preceding paragraphs, or a salt or solvate thereof, wherein each $R^b$ is independently selected from hydroxyl, halogen, CN, $C_{1-6}$ haloalkyl, $C_{1-6}$ haloalkoxy, $C_{1-6}$ alkyl and O—$C_{1-6}$ alkyl.

18. A compound according to any one of the preceding paragraphs, or a salt or solvate thereof, wherein each $R^b$ is independently selected from fluoro, chloro, and $CF_3$.

19. A compound according to any one of the preceding paragraphs, or a salt or solvate thereof, wherein Q is selected from:

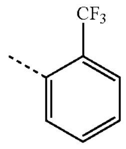

and

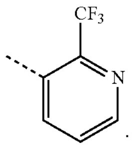

.

20. A compound according to any one of the preceding paragraphs, or a salt or solvate thereof, wherein $R^6$ is selected from hydrogen, methyl and ethyl.

21. A compound according to any one of the preceding paragraphs, or a salt or solvate thereof, wherein $R^6$ is selected from hydrogen and methyl.

22. A compound according to any one of the preceding paragraphs, or a salt or solvate thereof, wherein $R^7$ and $R^{7'}$ are independently selected from hydrogen, methyl and cyclopropyl.

23. A compound according to any one of the preceding paragraphs, or a salt or solvate thereof, wherein $R^7$ and $R^{7'}$ are independently selected from hydrogen and methyl.

24. A compound according to any one of the preceding paragraphs, or a salt or solvate thereof, wherein $R^{7'}$ is hydrogen.

25. A compound according to any one of paragraphs 1 to 21, or a salt or solvate thereof, wherein $R^7$ and $R^{7'}$, together with the atom to which they are attached form a $C_{3-6}$ cycloalkyl ring, optionally substituted by one or more $R^a$.

26. A compound according to any one of paragraphs 1 to 21, or a salt or solvate thereof, wherein $R^7$ and $R^{7'}$, together with the atom to which they are attached form a cyclopropyl ring, optionally substituted by one or more $R^a$.

27. A compound according to any one of paragraphs 1 to 24 wherein $R^6$ and $R^{7'}$ are both hydrogen.

28. A compound according to any one of paragraphs 1 to 24 wherein $R^6$, $R^7$ and $R^{7'}$ are each hydrogen.

29. A compound according to any one of paragraphs 1 to 19, or a salt or solvate thereof, wherein $R^6$ and $R^7$ together with the atoms to which they are attached form an azetidinyl, pyrrolidinyl, piperidinyl or morpholinyl ring.

30. A compound according to any one of the preceding paragraphs, or a salt or solvate thereof, wherein n is 1 or 2.

31. A compound according to any one of the preceding paragraphs, or a salt or solvate thereof, wherein n is 1.

32. A compound according to any one of the preceding paragraphs, or a salt or solvate thereof, wherein $R^2$ is selected from —CN, —$C(=O)R^d$, —$C(=O)OR^d$, —$C(=O)NR^cR^d$, —$C(O)C(=O)R^d$, —$NR^cR^d$, —$NR^c(C_{1-6}alkyl)NR^cR^d$, —$NR^cC(=O)R^d$, —$NR^cC(=O)OR^d$, —$NR^cC(=O)NR^cR^d$, —$NR^cS(=O)_2R^d$, —$NR^cS(=O)_2NR^cR^d$, —$OR^d$, —$SR^d$—$OC(=O)R^d$, —$OC(=O)NR^cR^d$, —$OC(=O)OR^d$, —$S(=O)R^d$, —$S(=O)_2R^d$, —$OS(=O)R^d$, —$OS(=O)_2R^d$, —$OS(=O)_2OR^d$, —$S(=O)NR^cR^d$, —$OS(=O)_2NR^cR^d$, —$S(=O)_2NR^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{1-11}$aryl optionally substituted by 1-11 $R^e$, $(C_{7-16})$alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

33. A compound according to any one of the preceding paragraphs, or a salt or solvate thereof, wherein $R^2$ is selected from —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, ($C_{7-16}$)alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

34. A compound according to any one of the preceding paragraphs, or a salt or solvate thereof, wherein $R^2$ is selected from —CN, —C(═O)$R^d$, —C(═O)O$R^d$, —C(═O)N$R^cR^d$, —N$R^cR^d$, —N$R^c$($C_{1-6}$alkyl)N$R^cR^d$, —N$R^c$C(═O)$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

35. A compound according to any one of the preceding paragraphs, or a salt or solvate thereof, wherein $R^2$ is selected from —CN, —C(═O)$R^d$, C(═O)N$R^cR^d$, —N$R^cR^d$, —N$R^c$($C_{1-6}$alkyl)N$R^cR^d$, —N$R^c$C(═O)N$R^cR^d$, —O$R^d$, —S$R^d$, —S(═O)$_2R^d$, $C_{1-10}$ haloalkyl, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

36. A compound according to any one of the preceding paragraphs, or a salt or solvate thereof, wherein $R^2$ is selected from N$R^cR^d$, —N$R^c$($C_{1-6}$alkyl)N$R^cR^d$, —N$R^c$C(═O)N$R^cR^d$, —O$R^d$, —S$R^d$, $C_{1-10}$ haloalkyl, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

37. A compound according to any one of the preceding paragraphs, or a salt or solvate thereof, wherein $R^2$ is selected from N$R^cR^d$, —N$R^c$($C_{1-6}$alkyl)N$R^cR^d$, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

38. A compound according to any one of the preceding paragraphs, or a salt or solvate thereof, wherein $R^2$ is selected from N$R^cR^d$, —N$R^c$($C_{1-6}$alkyl)N$R^cR^d$, $C_{1-10}$alkyl optionally substituted by 1-13 $R^e$, and 3-15 membered heterocycloalkyl optionally substituted by 1-28 $R^e$. Suitably, $R^o$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

39. A compound according to any one of the preceding paragraphs, or a salt or solvate thereof, wherein $R^2$ is selected from N$R^cR^d$ and a 3-15 membered heterocycloalkyl optionally substituted by 1-28 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

40. A compound according to any one of the preceding paragraphs, or a salt or solvate thereof, wherein $R^2$ is selected from N$R^cR^d$ and a 5-10 membered heterocycloalkyl optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

41. A compound according to any one of the preceding paragraphs, or a salt or solvate thereof, wherein $R^2$ is selected from N$R^cR^d$ and a 5-7 membered heterocycloalkyl optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

42. A compound according to any one of the preceding paragraphs, or a salt or solvate thereof, wherein $R^2$ is selected from N$R^cR^d$, azetidinyl, pyrrolidinyl, piperidinyl, piperazinyl and morpholinyl, wherein said azetidinyl, pyrrolidinyl, piperidinyl, piperazinyl and morpholinyl are optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

43. A compound according to any one of the preceding paragraphs, or a salt or solvate thereof, wherein $R^2$ is selected from N$R^cR^d$; and

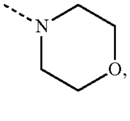, 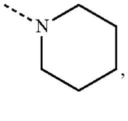, 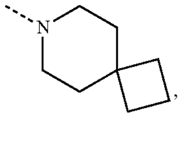,

-continued

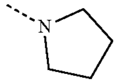, and 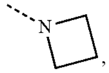, each of which may optionally be substituted with one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

44. A compound according to any one of the preceding paragraphs, or a salt or solvate thereof, wherein $R^2$ is selected from

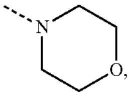, 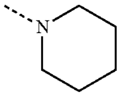, 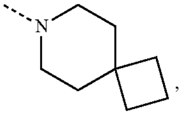, 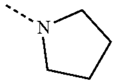, 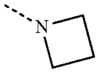, each of which may optionally be substituted with one or more $R^e$.

45. A compound according to any one of paragraphs 1 to 43, or a salt or solvate thereof, wherein $R^2$ is selected from

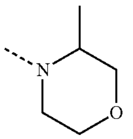 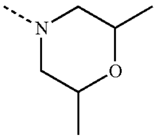, 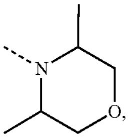, 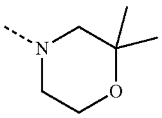 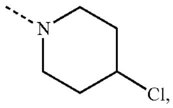, 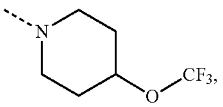, 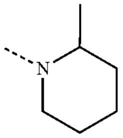, 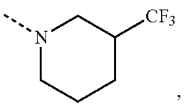, 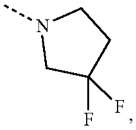, 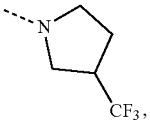, and 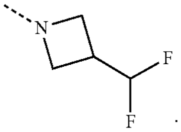.

46. A compound according to any one of the preceding paragraphs, or a salt or solvate thereof, wherein $R^o$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —$NR^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

47. A compound according to any one of the preceding paragraphs, or a salt or solvate thereof, wherein $R^e$ is independently selected from hydroxyl, ═O, halogen, CN, $C_{1-6}$ haloalkyl, $C_{1-6}$ haloalkoxy, $C_{1-6}$ alkyl and O—$C_{1-6}$ alkyl.

48. A compound according to any one of the preceding paragraphs, or a salt or solvate thereof, wherein $R^e$ is independently selected from halogen, CN, $C_{1-6}$ haloalkyl, $C_{1-6}$ haloalkoxy, $C_{1-6}$ alkyl and O—$C_{1-6}$ alkyl.

49. A compound according to any one of the preceding paragraphs, or a salt or solvate thereof, wherein $R^e$ is independently selected from halogen, CN, $C_{1-3}$ haloalkyl, $C_{1-3}$ haloalkoxy, $C_{1-3}$ alkyl and O—$C_{1-3}$ alkyl.

50. A compound according to any one of the preceding paragraphs, or a salt or solvate thereof, wherein $R^e$ is independently selected from fluoro, chloro, CN, $CF_3$, $OCF_3$ and $C_{1-3}$ alkyl.

51. A compound according to any one of the preceding paragraphs, or a salt or solvate thereof, wherein each $R^e$ is independently selected from fluoro, chloro, CN, $CF_3$, $OCF_3$, and methyl.

52. A compound according to any one of the preceding paragraphs, or a salt or solvate thereof, wherein each $R^o$ is independently selected from hydrogen, hydroxyl, $C_{1-6}$ haloalkyl, $C_{3-6}$ cycloalkyl, $C_{1-6}$ alkyl and O—$C_{1-6}$ alkyl;

53. A compound according to any one of the preceding paragraphs, or a salt or solvate thereof, wherein each $R^o$ is independently selected from hydrogen and $C_{1-6}$ alkyl, suitably $C_{1-6}$ alkyl.

54. A compound according to any one of the preceding paragraphs, or a salt or solvate thereof, wherein each $R^o$ is independently selected from hydrogen and $C_{1-3}$ alkyl, suitably $C_{1-3}$ alkyl.

55. A compound according to any one of the preceding paragraphs, or a salt or solvate thereof, wherein each $R^d$ is independently selected from hydrogen, 3-7 membered heterocycloalkyl, $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

56. A compound according to any one of the preceding paragraphs, or a salt or solvate thereof, wherein each $R^d$ is independently selected from 3-7 membered heterocycloalkyl, $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

57. A compound according to any one of the preceding paragraphs, or a salt or solvate thereof, wherein each $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

58. A compound according to any one of the preceding paragraphs, or a salt or solvate thereof, wherein $R^c$ and $R^d$ are independently selected from $C_{1-6}$ alkyl.

59. A compound according to any one of the preceding paragraphs wherein $R^3$, $R^4$ and $R^5$ are independently selected from hydrogen, halogen and $C_{1-6}$ alkyl.

60. A compound according to any one of the preceding paragraphs wherein $R^3$ is H.

61. A compound according to any one of the preceding paragraphs wherein $R^4$ is H.

62. A compound according to any one of the preceding paragraphs wherein $R^5$ is H.

63. A compound according to any one of the preceding paragraphs wherein $R^4$ and $R^5$ are H.

64. A compound according to any one of the preceding paragraphs wherein $R^3$, $R^4$ and $R^5$ are H.

65. A compound according to paragraph 1, or a salt or solvate thereof, which is a sub-Formula Ia:

(Ia)

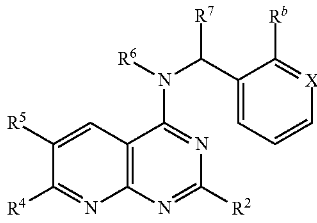

wherein, $R^6$ is selected from hydrogen and $C_{1-6}$ alkyl;

$R^7$ is selected from hydrogen, =O, $C_{3-6}$ cycloalkyl, $C_{1-6}$ alkyl, where said $C_{3-6}$ cycloalkyl, $C_{1-6}$ alkyl are optionally substituted by one or more $R^a$; or $R^6$ and $R^7$, together with the atoms to which they are attached form a 3-7 membered heterocyclic ring, optionally substituted with one or more $R^a$;

$R^2$ is selected from —CN, —C(=O)$R^d$, —C(=O)O$R^d$, —C(=O)N$R^c$$R^d$, —C(O)C(=O)$R^d$, —N$R^c$$R^d$, —N$R^c$($C_{1-6}$alkyl)N$R^c$$R^d$, —N$R^c$C(=O)$R^d$, —N$R^c$C(=O)O$R^d$, —N$R^c$C(=O)N$R^c$$R^d$, —N$R^c$S(=O)$_2$$R^d$, —N$R^c$S(=O)$_2$N$R^c$$R^d$, —O$R^d$, —S$R^d$—OC(=O)$R^d$, —OC(=O)N$R^c$$R^d$, —OC(=O)O$R^d$, —S(=O)$R^d$, —S(=O)$_2$$R^d$, —OS(=O)$R^d$, —OS(=O)$_2$$R^d$, —OS(=O)$_2$O$R^d$, —S(=O)N$R^c$$R^d$, —OS(=O)$_2$N$R^c$$R^d$, —S(=O)$_2$N$R^c$$R^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{1-11}$aryl optionally substituted by 1-11 $R^e$, ($C_{7-16}$)alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl, 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, =O, halogen, CN, $C_{1-6}$ haloalkyl, $C_{1-6}$ haloalkoxy, $C_{3-6}$ cycloalkyl, $C_{1-6}$ alkyl, O—$C_{1-6}$ alkyl, $C_{3-6}$ cycloalkyl, 3-7 membered heterocycloalkyl, —C(=O)$R^d$, —C(=O)O$R^d$, —C(=O)N$R^c$$R^d$, —C(O)C(=O)$R^d$, —N$R^c$$R^d$, —N$R^c$C(=O)$R^d$, —N$R^c$C(=O)O$R^d$, —N$R^c$C(=O)N$R^c$$R^d$, —N$R^c$S(=O)$_2$$R^d$, —N$R^c$S(=O)$_2$N$R^c$$R^d$, —O$R^d$, —S$R^d$, —OC(=O)$R^d$, —OC(=O)N$R^c$$R^d$, —OC(=O)O$R^d$, —S(=O)$_2$$R^d$, —S(=O)$R^d$, —OS(=O)$R^d$, —OS(=O)$_2$$R^d$, —OS(=O)$_2$O$R^d$, —S(=O)N$R^c$$R^d$, —OS(=O)$_2$N$R^c$$R^d$, and —S(=O)$_2$N$R^c$$R^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl and O—$C_{1-6}$ alkyl, $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, =O, halogen, CN, $C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-7 membered ring, optionally substituted with one or more $R^a$; and $R^4$ and $R^5$ are independently selected from hydrogen, hydroxyl, halogen, CN, $C_{1-6}$ haloalkyl, $C_{1-6}$ haloalkoxy, and $C_{1-6}$ alkyl; optionally substituted by one or more $R^a$.

66. A compound according to paragraph 65, or a salt or solvate thereof, wherein $R^4$ and $R^5$ are hydrogen.

67. A compound according to any one of paragraphs 65 and 66, or a salt or solvate thereof, wherein each $R^b$ is independently selected from fluoro, chloro, and $CF_3$.

68. A compound according to any one of paragraphs 65 to 67 wherein $R^6$ and $R^7$ are both hydrogen.

69. A compound according to any one of paragraphs 65 to 68, or a salt or solvate thereof, wherein $R^2$ is selected from —CN, —C(=O)$R^d$, C(=O)N$R^c$$R^d$, —N$R^c$$R^d$, —N$R^c$($C_{1-6}$alkyl)N$R^c$$R^d$, —N$R^c$C(=O)N$R^c$$R^d$, —O$R^d$, —S$R^d$, —S(=O)$_2$$R^d$, $C_{1-10}$ haloalkyl, $C_{1-10}$ alkyl optionally substituted by 1-13 $R^e$, $C_{6-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$. Suitably, $R^o$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

70. A compound according to any one of paragraphs 65 to 69, or a salt or solvate thereof, wherein $R^2$ is selected from N$R^c$$R^d$, —N$R^o$($C_{1-6}$alkyl)N$R^c$$R^d$, $C_{1-10}$ alkyl optionally substituted by 1-13 $R^e$, and 3-15 membered heterocycloalkyl optionally substituted by 1-28 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

71. A compound according to any one of paragraphs 65 to 70, or a salt or solvate thereof, wherein $R^2$ is selected from $NR^cR^d$; and

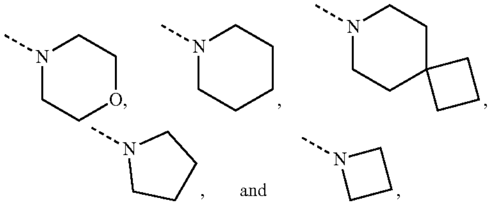

each of which may optionally be substituted with one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

72. A compound according to any one of paragraphs 65 to 71, or a salt or solvate thereof, wherein $R^2$ is selected from

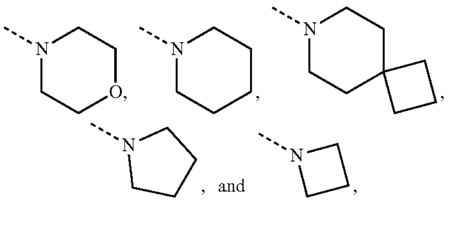

each of which may optionally be substituted with one or more $R^e$.

73. A compound according to any one of paragraphs 65 to 72, or a salt or solvate thereof, wherein $R^2$ is selected from

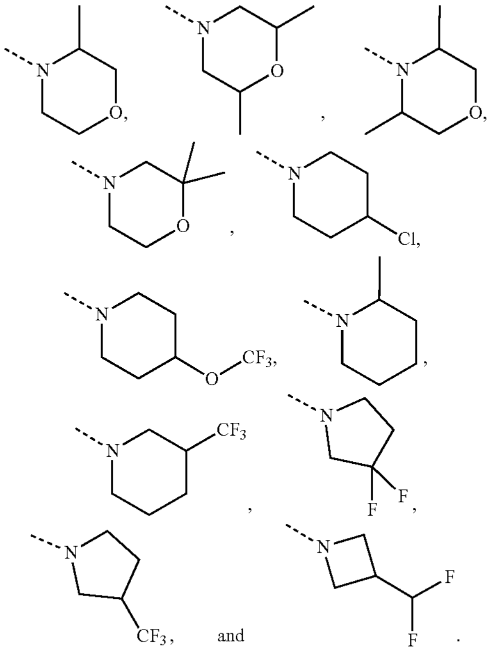

74. A compound according to any one of paragraphs 65 to 72, or a salt or solvate thereof, wherein each $R^o$ is independently selected from fluoro, chloro, CN, $CF_3$, $OCF_3$, and methyl.

75. A compound according to any one of paragraphs 65 to 74, or a salt or solvate thereof, wherein $R^c$ and $R^d$ are independently selected from $C_{1-6}$ alkyl.

76. A compound, or a salt or solvate thereof, selected from:

2-chloro-N-(2-(trifluoromethyl)benzyl)pyrido[2,3-d]pyrimidin-4-amine $N^2$-isopropyl-$N^4$-(2-(trifluoromethyl)benzyl)pyrido[2,3-d]pyrimidine-2,4-diamine $N^2$-isopropyl-$N^4$-(2-(trifluoromethyl)benzyl)pyrido[2,3-d]pyrimidine-2,4-diamine methanesulfonate 2-chloro-N-(2-fluorobenzyl)thieno[3,2-d]pyrimidin-4-amine $N^4$-(2-fluorobenzyl)-$N^2$-isopropylthieno[3,2-d]pyrimidine-2,4-diamine $N^4$-benzyl-$N^2$-isopropylthieno[3,2-d]pyrimidine-2,4-diamine $N^2$-isopropyl-$N^4$-(4-methoxybenzyl)thieno[3,2-d]pyrimidine-2,4-diamine $N^4$-(3-fluorobenzyl)-$N^2$-isopropylthieno[3,2-d]pyrimidine-2,4-diamine $N^4$-(4-fluorobenzyl)-$N^2$-isopropylthieno[3,2-d]pyrimidine-2,4-diamine $N^2$-isopropyl-$N^4$-(3-methoxybenzyl)thieno[3,2-d]pyrimidine-2,4-diamine $N^4$-(2-chlorobenzyl)-$N^2$-isopropylthieno[3,2-d]pyrimidine-2,4-diamine $N^4$-(3-chlorobenzyl)-$N^2$-isopropylthieno[3,2-d]pyrimidine-2,4-diamine $N^4$-(4-chlorobenzyl)-$N^2$-isopropylthieno[3,2-d]pyrimidine-2,4-diamine $N^2$-isopropyl-$N^4$-(2-methoxybenzyl)thieno[3,2-d]pyrimidine-2,4-diamine 2-chloro-N-(2-chlorobenzyl)thieno[3,2-d]pyrimidin-4-amine N-(2-fluorobenzyl)thieno[3,2-d]pyrimidin-4-amine N-(2-(trifluoromethyl)benzyl)thieno[3,2-d]pyrimidin-4-amine N-(2-(trifluoromethoxy)benzyl)thieno[3,2-d]pyrimidin-4-amine $N^4$-((2,2-difluorobenzo[d][1,3]dioxol-5-yl)methyl)-$N^2$-isopropylthieno[3,2-d]pyrimidine-2,4-diamine $N^4$-(2-fluoro-3-methoxybenzyl)-$N^2$-isopropylthieno[3,2-d]pyrimidine-2,4-diamine $N^4$-(2,6-dichlorobenzyl)-$N^2$-isopropylthieno[3,2-d]pyrimidine-2,4-diamine $N^2$-isopropyl-$N^4$-(2-(trifluoromethyl)benzyl)thieno[3,2-d]pyrimidine-2,4-diamine $N^2$-isopropyl-$N^4$-(2-(trifluoromethoxy)benzyl)thieno[3,2-d]pyrimidine-2,4-diamine $N^4$-(2-chloro-6-fluorobenzyl)-$N^2$-isopropylthieno[3,2-d]pyrimidine-2,4-diamine N-(2,4-dimethylphenyl)thieno[3,2-d]pyrimidin-4-amine $N^4$-(2,4-dimethylphenyl)-$N^2$-isopropylthieno[3,2-d]pyrimidine-2,4-diamine $N^4$-(2-chlorobenzyl)-$N^2$-isopropyl-$N^2$-methylthieno[3,2-d]pyrimidine-2,4-diamine 1-(3-(thieno[3,2-d]pyrimidin-4-ylamino)propyl)pyrrolidin-2-one 1-(3-((2-((2-methoxybenzyl)amino)thieno[3,2-d]pyrimidin-4-yl)amino)propyl)pyrrolidin-2-one 1-(3-((2-(benzyl(methyl)amino)thieno[3,2-d]pyrimidin-4-yl)amino)propyl)pyrrolidin-2-one N-(thieno[3,2-d]pyrimidin-4-yl)-2-(trifluoromethyl)benzamide N-(1-(2-chlorophenyl)ethyl)thieno[3,2-d]pyrimidin-4-amine 2-chloro-N-(thieno[3,2-d]pyrimidin-4-yl)benzamide $N^2$-(tert-butyl)-$N^4$-(2-(trifluoromethyl)benzyl)thieno[3,2-d]pyrimidine-2,4-diamine $N^2$-(2,2,2-trifluoroethyl)-$N^4$-(2-(trifluoromethyl)benzyl)thieno[3,2-d]pyrimidine-2,4-diamine $N^2$-cyclopropyl-$N^4$-(2-(trifluoromethyl)benzyl)thieno[3,2-d]pyrimidine-2,4-diamine N-methyl-N-(2-(trifluoromethyl)benzyl)thieno[3,2-d]pyrimidin-4-amine $N^2$-isopropyl-$N^4$-(2-(trifluoromethyl)phenethyl)thieno[3,2-d]pyrimidine-2,4-diamine 2-chloro-N-(2-(trifluoromethyl)benzyl)thieno[3,2-d]pyrimidin-4-amine 2-chloro-N-(1-(2-chlorophenyl)cyclopropyl)thieno[3,2-d]pyrimidin-4-amine $N^4$-(1-(2-chlorophenyl)cyclopropyl)-$N^2$-isopropylthieno[3,2-d]pyrimidine-2,4-diamine 2-chloro-N-methyl-N-(2-(trifluoromethyl)benzyl)thieno[3,2-d]pyrimidin-4-amine $N^2$-isopropyl-$N^4$-methyl-$N^4$-(2-(trifluoromethyl)benzyl)thieno[3,2-d]pyrimidine-2,4-diamine N-(3-methoxy-2-(trifluoromethyl)benzyl)thieno[3,2-d]pyrimidin-4-amine 2-chloro-N-(1-(2-(trifluoromethyl)phenyl)ethyl)thieno[3,2-d]pyrimidin-4-amine $N^2$-isopropyl-$N^4$-(1-(2-(trifluoromethyl)phenyl)ethyl)thieno[3,2-d]pyrimidine-2,4-diamine N-ethyl-N-(2-(trifluoromethyl)benzyl)thieno[3,2-d]pyrimidin-4-amine 2-methyl-N-(2-(trifluoromethyl)benzyl)thieno[3,2-d]pyrimidin-4-amine 2-(trifluoromethyl)-N-(2-(trifluoromethyl)benzyl)thieno[3,2-d]pyrimidin-4-amine 2-chloro-N-(2-(trifluoromethyl)benzyl)quinazolin-4-amine $N^2$-isopropyl-$N^4$-(2-(trifluoromethyl)benzyl)quinazoline-2,4-diamine $N^2$-isopropyl-$N^4$-(2-(trifluoromethyl)phenyl)thieno[3,2-d]pyrimidine-2,4-diamine N-(4-fluoro-2-(trifluoromethyl)benzyl)thieno[3,2-d]pyrimidin-4-amine N-((3-(trifluoromethyl)pyridin-2-yl)methyl)thieno[3,2-d]pyrimidin-4-amine N-methyl-2-(trifluoromethyl)-N-(2-(trifluoromethyl)benzyl)thieno[3,2-d]pyrimidin-4-amine N,2-dimethyl-N-(2-(trifluoromethyl)benzyl)thieno[3,2-d]pyrimidin-4-amine N,6-dimethyl-2-(trifluoromethyl)-N-(2-(trifluoromethyl)benzyl)thieno[3,2-d]pyrimidin-4-amine 2-methyl-N-(1-(2-(trifluoromethyl)phenyl)ethyl)thieno[3,2-d]pyrimidin-4-amine N,2-dimethyl-N-(1-(2-(trifluoromethyl)phenyl)ethyl)thieno[3,2-d]pyrimidin-4-amine 2-chloro-N-methyl-N-(1-(2-(trifluoromethyl)phenyl)ethyl)thieno[3,2-d]pyrimidin-4-amine 2-methoxy-N-methyl-N-(1-(2-(trifluoromethyl)phenyl)ethyl)thieno[3,2-d]pyrimidin-4-amine N,2,6-trimethyl-N-(1-(2-(trifluoromethyl)phenyl)ethyl)thieno[3,2-d]pyrimidin-4-amine 2-(2-methyl-4-(methyl(1-(2-(trifluoromethyl)phenyl)ethyl)amino)thieno[3,2-d]pyrimidin-6-yl)propan-2-ol N-(4-fluoro-2-(trifluoromethyl)benzyl)quinazolin-4-amine N-(4-fluoro-2-(trifluoromethyl)benzyl)-2-methylquinazolin-4-amine 4-(methyl(1-(2-(trifluoromethyl)phenyl)ethyl)amino)thieno[3,2-d]pyrimidine-2-carbonitrile N-(4-fluoro-2-(trifluoromethyl)benzyl)-N-methylquinazolin-4-amine 1-(3-((4-((2-(trifluoromethyl)benzyl)amino)thieno[3,2-d]pyrimidin-2-yl)amino)propyl)pyrrolidin-2-one $N^2$-(2-(dimethylamino)ethyl)-$N^4$-(2-(trifluoromethyl)benzyl)thieno[3,2-d]pyrimidine-2,4-diamine $N^2$-(2-morpholinoethyl)-$N^4$-(2-(trifluoromethyl)benzyl)thieno[3,2-d]pyrimidine-2,4-diamine $N^2$-(2-(pyrrolidin-1-yl)ethyl)-$N^4$-(2-(trifluoromethyl)benzyl)thieno[3,2-d]pyrimidine-2,4-diamine $N^2$-(2-(4-methylpiperazin-1-yl)ethyl)-$N^4$-(2-(trifluoromethyl)benzyl)thieno[3,2-d]pyrimidine-2,4-diamine 2-(pyrrolidin-1-yl)-N-(2-(trifluoromethyl)benzyl)thieno[3,2-d]pyrimidin-4-amine 2-morpholino-N-(2-(trifluoromethyl)benzyl)thieno[3,2-d]pyrimidin-4-amine 2-(4-methylpiperazin-1-yl)-N-(2-(trifluoromethyl)benzyl)thieno[3,2-d]pyrimidin-4-amine 6-iodo-N-(1-(2-(trifluoromethyl)phenyl)ethyl)thieno[3,2-d]pyrimidin-4-amine N-(2-(methylsulfonyl)benzyl)thieno[3,2-d]pyrimidin-4-amine 6-phenyl-N-(1-(2-(trifluoromethyl)phenyl)ethyl)thieno[3,2-d]pyrimidin-4-amine 6-cyclopropyl-N-(1-(2-(trifluoromethyl)phenyl)ethyl)thieno[3,2-d]pyrimidin-4-amine 6-(1-methyl-1H-pyrazol-4-yl)-N-(1-(2-(trifluoromethyl)phenyl)ethyl)thieno[3,2-d]pyrimidin-4-amine 4-((1-(2-(trifluoromethyl)phenyl)ethyl)amino)thieno[3,2-d]pyrimidine-6-carbonitrile N-((2-(trifluoromethyl)pyridin-3-yl)methyl)thieno[3,2-d]pyrimidin-4-amine 2-(((2-chlorothieno[3,2-d]pyrimidin-4-yl)amino)methyl)benzonitrile 7-methyl-N-(1-(2-(trifluoromethyl)phenyl)ethyl)thieno[3,2-d]pyrimidin-4-amine 7-bromo-N-(1-(2-(trifluoromethyl)phenyl)ethyl)thieno[3,2-d]pyrimidin-4-amine N-(2-(trifluoromethyl)benzyl)thieno[2,3-d]pyrimidin-4-amine 4-((1-(2-(trifluoromethyl)phenyl)ethyl)amino)thieno[3,2-d]pyrimidine-7-carbonitrile $N^2$-isopropyl-$N^4$-(4-(trifluoromethyl)benzyl)thieno[3,2-d]pyrimidine-2,4-diamine $N^2$-isopropyl-$N^4$-(4-(methylsulfonyl)benzyl)quinazoline-2,4-diamine $N^2$-isopropyl-$N^4$-(4-(trifluoromethyl)benzyl)quinazoline-2,4-diamine $N^2$-isopropyl-$N^4$-(2-(methylsulfonyl)benzyl)quinazoline-2,4-diamine $N^2$-isopropyl-$N^4$-((6-(trifluoromethyl)pyridin-3-yl)methyl)quinazoline-2,4-diamine $N^4$-(4-cyanobenzyl)-$N^2$-isopropylthieno[3,2-d]pyrimidine-2,4-diamine $N^2$-isopropyl-$N^4$-(2-(methylsulfonyl)benzyl)thieno[3,2-d]pyrimidine-2,4-diamine $N^2$-isopropyl-$N^4$-(4-(methylsulfonyl)benzyl)thieno[3,2-d]pyrimidine-2,4-diamine $N^2$-isopropyl-$N^4$-((6-(trifluoromethyl)pyridin-3-yl)methyl)thieno[3,2-d]pyrimidine-2,4-diamine $N^4$-(4-cyanobenzyl)-$N^2$-isopropylquinazoline-2,4-diamine $N^4$-(4-cyanobenzyl)-$N^2$-isopropylpyrido[3,2-d]pyrimidine-2,4-diamine $N^2$-isopropyl-$N^4$-(2-(methylsulfonyl)benzyl)pyrido[3,2-d]pyrimidine-2,4-diamine $N^2$-isopropyl-$N^4$-(4-(methylsulfonyl)benzyl)pyrido[3,2-d]pyrimidine-2,4-diamine
$N^2$-isopropyl-$N^4$-(4-(trifluoromethyl)benzyl)pyrido[3,2-d]pyrimidine-2,4-diamine
$N^2$-isopropyl-$N^4$-((6-(trifluoromethyl)pyridin-3-yl)methyl)pyrido[3,2-d]pyrimidine-2,4-diamine
$N^4$-(4-cyanobenzyl)-$N^2$-isopropylpyrido[2,3-d]pyrimidine-2,4-diamine
$N^2$-isopropyl-$N^4$-(2-(methylsulfonyl)benzyl)pyrido[2,3-d]pyrimidine-2,4-diamine
$N^2$-isopropyl-$N^4$-(4-(methylsulfonyl)benzyl)pyrido[2,3-d]pyrimidine-2,4-diamine
$N^2$-isopropyl-$N^4$-(4-(trifluoromethyl)benzyl)pyrido[2,3-d]pyrimidine-2,4-diamine
$N^2$-isopropyl-$N^4$-((6-(trifluoromethyl)pyridin-3-yl)methyl)pyrido[2,3-d]pyrimidine-2,4-diamine
$N^2$-isopropyl-$N^4$-(4-methoxybenzyl)thieno[3,2-d]pyrimidine-2,4-diamine
$N^2$-isopropyl-$N^4$-(2-methoxybenzyl)thieno[3,2-d]pyrimidine-2,4-diamine
$N^4$-(3,4-dimethoxybenzyl)-$N^2$-isopropylthieno[3,2-d]pyrimidine-2,4-diamine
$N^4$-(4-fluorobenzyl)-$N^2$-isopropylquinazoline-2,4-diamine
$N^4$-(2-fluorobenzyl)-$N^2$-isopropylquinazoline-2,4-diamine
$N^4$-(4-chlorobenzyl)-$N^2$-isopropylquinazoline-2,4-diamine
$N^4$-(2-chlorobenzyl)-$N^2$-isopropylquinazoline-2,4-diamine
$N^2$-isopropyl-$N^4$-(4-methoxybenzyl)quinazoline-2,4-diamine
$N^2$-isopropyl-$N^4$-(2-methoxybenzyl)quinazoline-2,4-diamine
$N^4$-(3,4-dimethoxybenzyl)-$N^2$-isopropylquinazoline-2,4-diamine
$N^2$-(azetidin-3-yl)-$N^4$-(2-(trifluoromethyl)benzyl)pyrido[2,3-d]pyrimidine-2,4-diamine
$N^2$-(1-methylazetidin-3-yl)-$N^4$-(2-(trifluoromethyl)benzyl)pyrido[2,3-d]pyrimidine-2,4-diamine
$N^2$-methyl-$N^4$-(2-(trifluoromethyl)benzyl)pyrido[2,3-d]pyrimidine-2,4-diamine
$N^2$-(oxetan-3-yl)-$N^4$-(2-(trifluoromethyl)benzyl)pyrido[2,3-d]pyrimidine-2,4-diamine
2-((methylamino)methyl)-N-(2-(trifluoromethyl)benzyl)pyrido[2,3-d]pyrimidin-4-amine
4-((2-(trifluoromethyl)benzyl)amino)pyrido[2,3-d]pyrimidine-2-carboxamide
$N^2$-(azetidin-3-yl)-$N^4$-((2-(trifluoromethyl)pyridin-3-yl)methyl)pyrido[2,3-d]pyrimidine-2,4-diamine
$N^2$-(1-methylazetidin-3-yl)-$N^4$-((2-(trifluoromethyl)pyridin-3-yl)methyl)pyrido[2,3-d]pyrimidine-2,4-diamine
$N^2$-methyl-$N^4$-((2-(trifluoromethyl)pyridin-3-yl)methyl)pyrido[2,3-d]pyrimidine-2,4-diamine
$N^2$-isopropyl-$N^4$-((2-(trifluoromethyl)pyridin-3-yl)methyl)pyrido[2,3-d]pyrimidine-2,4-diamine
$N^2$-isopropyl-$N^4$-((2-(trifluoromethyl)pyridin-3-yl)methyl)pyrido[2,3-d]pyrimidine-2,4-diamine methanesulfonate
$N^2$-isopropyl-$N^4$-((2-(trifluoromethyl)pyridin-3-yl)methyl)quinazoline-2,4-diamine
$N^2$-isopropyl-$N^4$-((2-(trifluoromethyl)pyridin-3-yl)methyl)pyrido[3,2-d]pyrimidine-2,4-diamine
$N^2$-isopropyl-$N^4$-((2-(trifluoromethyl)pyridin-3-yl)methyl)thieno[3,2-d]pyrimidine-2,4-diamine
2-((methylamino)methyl)-N-(2-(trifluoromethyl)benzyl)thieno[3,2-d]pyrimidin-4-amine
4-((2-(trifluoromethyl)benzyl)amino)thieno[3,2-d]pyrimidine-2-carboxamide
$N^2$-cyclopropyl-$N^4$-(2-(trifluoromethyl)benzyl)pyrido[2,3-d]pyrimidine-2,4-diamine
$N^2$-cyclopropyl-$N^4$-(2-(trifluoromethyl)benzyl)pyrido[2,3-d]pyrimidine-2,4-diamine methanesulfonate
4-((2-(trifluoromethyl)benzyl)amino)pyrido[2,3-d]pyrimidin-2-ol
$N^2$-(oxetan-3-yl)-$N^4$-((2-(trifluoromethyl)pyridin-3-yl)methyl)pyrido[2,3-d]pyrimidine-2,4-diamine
$N^2$-cyclopropyl-$N^4$-((2-(trifluoromethyl)pyridin-3-yl)methyl)pyrido[2,3-d]pyrimidine-2,4-diamine
$N^2$-cyclopropyl-$N^4$-((2-(trifluoromethyl)pyridin-3-yl)methyl)pyrido[2,3-d]pyrimidine-2,4-diamine methanesulfonate
$N^2$-isopropyl-$N^4$-methyl-N4-((2-(trifluoromethyl)pyridin-3-yl)methyl)pyrido[2,3-d]pyrimidine-2,4-diamine
$N^2$-isopropyl-$N^2$,$N^4$-dimethyl-$N^4$-((2-(trifluoromethyl)pyridin-3-yl)methyl)pyrido[2,3-d]pyrimidine-2,4-diamine
$N^2$-isopropyl-$N^2$-methyl-$N^4$-((2-(trifluoromethyl)pyridin-3-yl)methyl)pyrido[2,3-d]pyrimidine-2,4-diamine
$N^2$-isopropyl-$N^2$-methyl-$N^4$-((2-(trifluoromethyl)pyridin-3-yl)methyl)pyrido[2,3-d]pyrimidine-2,4-diamine methanesulfonate
2-(azetidin-1-yl)-N-((2-(trifluoromethyl)pyridin-3-yl)methyl)pyrido[2,3-d]pyrimidin-4-amine
2-(isopropylthio)-N-((2-(trifluoromethyl)pyridin-3-yl)methyl)pyrido[2,3-d]pyrimidin-4-amine
$N^2$-isopropyl-$N^4$-((2-(trifluoromethyl)pyridin-3-yl)methyl)-1,8-naphthyridine-2,4-diamine
$N^4$-(2-fluoro-6-(trifluoromethyl)benzyl)-$N^2$-isopropylpyrido[2,3-d]pyrimidine-2,4-diamine
4-(6-chloro-5-methyl-7-((pyridin-2-ylmethyl)amino)pyrazolo[1,5-a]pyrimidin-3-yl)morpholin-3-one
$N^2$-(tert-butyl)-$N^4$-((2-(trifluoromethyl)pyridin-3-yl)methyl)pyrido[2,3-d]pyrimidine-2,4-diamine
$N^4$-(2-fluoro-6-(trifluoromethyl)benzyl)-$N^2$,$N^2$-dimethylpyrido[2,3-d]pyrimidine-2,4-diamine
N-((2-(trifluoromethyl)pyridin-3-yl)methyl)pyrido[2,3-d]pyrimidin-4-amine
3-methyl-1-(4-(((2-(trifluoromethyl)pyridin-3-yl)methyl)amino)pyrido[2,3-d]pyrimidin-2-yl)azetidin-3-ol
2-(2-methylazetidin-1-yl)-N-((2-(trifluoromethyl)pyridin-3-yl)methyl)pyrido[2,3-d]pyrimidin-4-amine
2-(2,2-dimethylazetidin-1-yl)-N-((2-(trifluoromethyl)pyridin-3-yl)methyl)pyrido[2,3-d]pyrimidin-4-amine
2-(pyrrolidin-1-yl)-N-((2-(trifluoromethyl)pyridin-3-yl)methyl)pyrido[2,3-d]pyrimidin-4-amine
$N^2$-cyclopropyl-$N^2$-methyl-$N^4$-((2-(trifluoromethyl)pyridin-3-yl)methyl)pyrido[2,3-d]pyrimidine-2,4-diamine
$N^2$-isopropyl-$N^2$-methyl-$N^4$-((2-(trifluoromethyl)pyridin-3-yl)methyl)quinazoline-2,4-diamine
2-methyl-N-((2-(trifluoromethyl)pyridin-3-yl)methyl)pyrido[2,3-d]pyrimidin-4-amine
2-(isopropylsulfinyl)-N-((2-(trifluoromethyl)pyridin-3-yl)methyl)pyrido[2,3-d]pyrimidin-4-amine
2-(isopropylsulfonyl)-N-((2-(trifluoromethyl)pyridin-3-yl)methyl)pyrido[2,3-d]pyrimidin-4-amine
4-(((2-(trifluoromethyl)pyridin-3-yl)methyl)amino)pyrido[2,3-d]pyrimidin-2-ol
N-isopropyl-4-(2-(2-(trifluoromethyl)phenyl)azetidin-1-yl)pyrido[2,3-d]pyrimidin-2-amine
N-isopropyl-N-methyl-4-(2-(2-(trifluoromethyl)phenyl)azetidin-1-yl)pyrido[2,3-d]pyrimidin-2-amine
N-isopropyl-4-(2-(2-(trifluoromethyl)phenyl)piperidin-1-yl)pyrido[2,3-d]pyrimidin-2-amine
N-isopropyl-N-methyl-4-(2-(2-(trifluoromethyl)phenyl)piperidin-1-yl)pyrido[2,3-d]pyrimidin-2-amine
N-isopropyl-4-(3-(2-(trifluoromethyl)phenyl)morpholino)pyrido[2,3-d]pyrimidin-2-amine N-isopropyl-N-methyl-4-(3-(2-(trifluoromethyl)phenyl)morpholino)pyrido[2,3-d]pyrimidin-2-amine
N-isopropyl-4-(2-(2-(trifluoromethyl)phenyl)pyrazolidin-1-yl)pyrido[2,3-d]pyrimidin-2-amine
N-isopropyl-N-methyl-4-(2-(2-(trifluoromethyl)phenyl)pyrazolidin-1-yl)pyrido[2,3-d]pyrimidin-2-amine
2-((difluoromethyl)thio)-N-((2-(trifluoromethyl)pyridin-3-yl)methyl)pyrido[2,3-d]pyrimidin-4-amine
2-morpholino-N-((2-(trifluoromethyl)pyridin-3-yl)methyl)pyrido[2,3-d]pyrimidin-4-amine
2-(3-methylmorpholino)-N-((2-(trifluoromethyl)pyridin-3-yl)methyl)pyrido[2,3-d]pyrimidin-4-amine
2-(3-methylmorpholino)-N-((2-(trifluoromethyl)pyridin-3-yl)methyl)pyrido[2,3-d]pyrimidin-4-amine methanesulfonate
2-(3,3-difluoropyrrolidin-1-yl)-N-((2-(trifluoromethyl)pyridin-3-yl)methyl)pyrido[2,3-d]pyrimidin-4-amine
2-(3,3-difluoropyrrolidin-1-yl)-N-((2-(trifluoromethyl)pyridin-3-yl)methyl)pyrido[2,3-d]pyrimidin-4-amine methanesulfonate
2-(4-fluoropiperidin-1-yl)-N-((2-(trifluoromethyl)pyridin-3-yl)methyl)pyrido[2,3-d]pyrimidin-4-amine
2-(4,4-difluoropiperidin-1-yl)-N-(2-(trifluoromethyl)benzyl)pyrido[2,3-d]pyrimidin-4-amine
2-(4,4-difluoropiperidin-1-yl)-N-((2-(trifluoromethyl)pyridin-3-yl)methyl)pyrido[2,3-d]pyrimidin-4-amine
$N^2$-isopropyl-$N^4$-((2-(trifluoromethyl)pyridin-3-yl)methyl)pyrido[2,3-d]pyrimidine-2,4-diamine methanesulfonate
2-(4-chloropiperidin-1-yl)-N-(2-(trifluoromethyl)benzyl)pyrido[2,3-d]pyrimidin-4-amine
2-(4-chloropiperidin-1-yl)-N-((2-(trifluoromethyl)pyridin-3-yl)methyl)pyrido[2,3-d]pyrimidin-4-amine
2-(3-fluoroazetidin-1-yl)-N-((2-(trifluoromethyl)pyridin-3-yl)methyl)pyrido[2,3-d]pyrimidin-4-amine
2-(3,3-difluoroazetidin-1-yl)-N-((2-(trifluoromethyl)pyridin-3-yl)methyl)pyrido[2,3-d]pyrimidin-4-amine
2-(3-(trifluoromethyl)azetidin-1-yl)-N-((2-(trifluoromethyl)pyridin-3-yl)methyl)pyrido[2,3-d]pyrimidin-4-amine
2-(4-(trifluoromethyl)-1H-pyrazol-1-yl)-N-((2-(trifluoromethyl)pyridin-3-yl)methyl)pyrido[2,3-d]pyrimidin-4-amine
1-(4-fluorophenyl)-3-(4-(((2-(trifluoromethyl)pyridin-3-yl)methyl)amino)pyrido[2,3-d]pyrimidin-2-yl)urea
1-(3-fluorophenyl)-3-(4-(((2-(trifluoromethyl)pyridin-3-yl)methyl)amino)pyrido[2,3-d]pyrimidin-2-yl)urea
1-(2-fluorophenyl)-3-(4-(((2-(trifluoromethyl)pyridin-3-yl)methyl)amino)pyrido[2,3-d]pyrimidin-2-yl)urea
1-ethyl-3-(4-(((2-(trifluoromethyl)pyridin-3-yl)methyl)amino)pyrido[2,3-d]pyrimidin-2-yl)urea
(S)-2-(3-methylmorpholino)-N-(2-(trifluoromethyl)benzyl)pyrido[2,3-d]pyrimidin-4-amine
(S)-2-(3-methylmorpholino)-N-(2-(trifluoromethyl)benzyl)pyrido[2,3-d]pyrimidin-4-amine methanesulfonate
(R)-2-(3-methylmorpholino)-N-(2-(trifluoromethyl)benzyl)pyrido[2,3-d]pyrimidin-4-amine
(S)-2-(3-methylmorpholino)-N-((2-(trifluoromethyl)pyridin-3-yl)methyl)pyrido[2,3-d]pyrimidin-4-amine
(R)-2-(3-methylmorpholino)-N-((2-(trifluoromethyl)pyridin-3-yl)methyl)pyrido[2,3-d]pyrimidin-4-amine
2-(4-chloropiperidin-1-yl)-4-(2-(2-(trifluoromethyl)phenyl)azetidin-1-yl)pyrido[2,3-d]pyrimidine
2-(4,4-difluoropiperidin-1-yl)-4-(2-(2-(trifluoromethyl)phenyl)azetidin-1-yl)pyrido[2,3-d]pyrimidine
3-methyl-4-(4-(2-(2-(trifluoromethyl)phenyl)azetidin-1-yl)pyrido[2,3-d]pyrimidin-2-yl)morpholine
2-(3,3-difluoropyrrolidin-1-yl)-4-(2-(2-(trifluoromethyl)phenyl)azetidin-1-yl)pyrido[2,3-d]pyrimidine
2-(3-(trifluoromethyl)azetidin-1-yl)-4-(2-(2-(trifluoromethyl)phenyl)azetidin-1-yl)pyrido[2,3-d]pyrimidine
2-(4-chloropiperidin-1-yl)-4-(2-(2-(trifluoromethyl)pyridin-3-yl)azetidin-1-yl)pyrido[2,3-d]pyrimidine
2-(4,4-difluoropiperidin-1-yl)-4-(2-(2-(trifluoromethyl)pyridin-3-yl)azetidin-1-yl)pyrido[2,3-d]pyrimidine
3-methyl-4-(4-(2-(2-(trifluoromethyl)pyridin-3-yl)azetidin-1-yl)pyrido[2,3-d]pyrimidin-2-yl)morpholine
2-(3,3-difluoropyrrolidin-1-yl)-4-(2-(2-(trifluoromethyl)pyridin-3-yl)azetidin-1-yl)pyrido[2,3-d]pyrimidine
2-(3-(trifluoromethyl)azetidin-1-yl)-4-(2-(2-(trifluoromethyl)pyridin-3-yl)azetidin-1-yl)pyrido[2,3-d]pyrimidine
2-((4-chloropiperidin-1-yl)methyl)-N-((2-(trifluoromethyl)pyridin-3-yl)methyl)pyrido[2,3-d]pyrimidin-4-amine
2-((4,4-difluoropiperidin-1-yl)methyl)-N-((2-(trifluoromethyl)pyridin-3-yl)methyl)pyrido[2,3-d]pyrimidin-4-amine
2-((3-methylmorpholino)methyl)-N-((2-(trifluoromethyl)pyridin-3-yl)methyl)pyrido[2,3-d]pyrimidin-4-amine
2-((3,3-difluoropyrrolidin-1-yl)methyl)-N-((2-(trifluoromethyl)pyridin-3-yl)methyl)pyrido[2,3-d]pyrimidin-4-amine
2-((3-(trifluoromethyl)azetidin-1-yl)methyl)-N-((2-(trifluoromethyl)pyridin-3-yl)methyl)pyrido[2,3-d]pyrimidin-4-amine
2-((4-chloropiperidin-1-yl)methyl)-N-((2-(trifluoromethyl)pyridin-3-yl)methyl)pyrido[2,3-d]pyrimidin-4-amine
2-((4,4-difluoropiperidin-1-yl)methyl)-N-((2-(trifluoromethyl)pyridin-3-yl)methyl)pyrido[2,3-d]pyrimidin-4-amine
2-((3-methylmorpholino)methyl)-N-((2-(trifluoromethyl)pyridin-3-yl)methyl)pyrido[2,3-d]pyrimidin-4-amine
2-((3,3-difluoropyrrolidin-1-yl)methyl)-N-((2-(trifluoromethyl)pyridin-3-yl)methyl)pyrido[2,3-d]pyrimidin-4-amine
2-((3-(trifluoromethyl)azetidin-1-yl)methyl)-N-((2-(trifluoromethyl)pyridin-3-yl)methyl)pyrido[2,3-d]pyrimidin-4-amine
2-(4-(methylsulfonyl)piperidin-1-yl)-N-((2-(trifluoromethyl)pyridin-3-yl)methyl)pyrido[2,3-d]pyrimidin-4-amine
2-(4,4-dimethylpiperidin-1-yl)-N-((2-(trifluoromethyl)pyridin-3-yl)methyl)pyrido[2,3-d]pyrimidin-4-amine
1-(4-(((2-(trifluoromethyl)pyridin-3-yl)methyl)amino)pyrido[2,3-d]pyrimidin-2-yl)piperidine-4-carbonitrile
2-(4-(trifluoromethyl)piperidin-1-yl)-N-((2-(trifluoromethyl)pyridin-3-yl)methyl)pyrido[2,3-d]pyr-imidin-4-amine
N-((2-(trifluoromethyl)pyridin-3-yl)methyl)-2-(3-(trifluoromethyl)pyrrolidin-1-yl)pyrido[2,3-d]pyrimidin-4-amine
1-(4-(((2-(trifluoromethyl)pyridin-3-yl)methyl)amino)pyrido[2,3-d]pyrimidin-2-yl)azetidine-3-carbonitrile
1-(4-(((2-(trifluoromethyl)pyridin-3-yl)methyl)amino)pyrido[2,3-d]pyrimidin-2-yl)pyrrolidine-2-carbonitrile
2-(2,2-dimethylmorpholino)-N-((2-(trifluoromethyl)pyridin-3-yl)methyl)pyrido[2,3-d]pyrimidin-4-amine
2-(3,3-dimethylmorpholino)-N-((2-(trifluoromethyl)pyridin-3-yl)methyl)pyrido[2,3-d]pyrimidin-4-amine
2-(2-methylmorpholino)-N-((2-(trifluoromethyl)pyridin-3-yl)methyl)pyrido[2,3-d]pyrimidin-4-amine
2-(3-fluoropyrrolidin-1-yl)-N-((2-(trifluoromethyl)pyridin-3-yl)methyl)pyrido[2,3-d]pyrimidin-4-amine
2-(4-(methylsulfonyl)piperidin-1-yl)-N-(2-(trifluoromethyl)benzyl)pyrido[2,3-d]pyrimidin-4-amine
2-(4,4-dimethylpiperidin-1-yl)-N-(2-(trifluoromethyl)benzyl)pyrido[2,3-d]pyrimidin-4-amine 1-(4-((2-(trifluoromethyl)benzyl)amino)pyrido[2,3-d]pyrimidin-2-yl)azetidine-3-carbonitrile 2-(3,3-dimethylmorpholino)-N-(2-(trifluoromethyl)benzyl)pyrido[2,3-d]pyrimidin-4-amine 2-(2,2-dimethylmorpholino)-N-(2-(trifluoromethyl)benzyl)pyrido[2,3-d]pyrimidin-4-amine 2-(2-methylmorpholino)-N-(2-(trifluoromethyl)benzyl)pyrido[2,3-d]pyrimidin-4-amine 2-(3-(trifluoromethyl)piperidin-1-yl)-N-((2-(trifluoromethyl)pyridin-3-yl)methyl)pyrido[2,3-d]pyrimidin-4-amine 4-methyl-1-(4-(((2-(trifluoromethyl)pyridin-3-yl)methyl)amino)pyrido[2,3-d]pyrimidin-2-yl)piperidine-4-carbonitrile 1-(4-(((2-(trifluoromethyl)pyridin-3-yl)methyl)amino)pyrido[2,3-d]pyrimidin-2-yl)piperidine-3-carbonitrile 2-(2,2-difluoro-7-azaspiro[3.5]nonan-7-yl)-N-((2-(trifluoromethyl)pyridin-3-yl)methyl)pyrido[2,3-d]pyrimidin-4-amine 2-(2,2-difluoro-7-azaspiro[3.5]nonan-7-yl)-N-((2-(trifluoromethyl)pyridin-3-yl)methyl)pyrido[2,3-d]pyrimidin-4-amine methanesulfonate 2-(3-cyclopropylmorpholino)-N-((2-(trifluoromethyl)pyridin-3-yl)methyl)pyrido[2,3-d]pyrimidin-4-amine 2-((6S)-2,6-dimethylmorpholino)-N-((2-(trifluoromethyl)pyridin-3-yl)methyl)pyrido[2,3-d]pyrimidin-4-amine 2-(2-oxa-5-azabicyclo[2.2.1]heptan-5-yl)-N-((2-(trifluoromethyl)pyridin-3-yl)methyl)pyrido[2,3-d]pyrimidin-4-amine 2-(4-oxa-7-azaspiro[2.5]octan-7-yl)-N-((2-(trifluoromethyl)pyridin-3-yl)methyl)pyrido[2,3-d]pyrimidin-4-amine 4-(4-(((2-(trifluoromethyl)pyridin-3-yl)methyl)amino)pyrido[2,3-d]pyrimidin-2-yl)morpholine-2-carbonitrile 2-(3-(fluoromethyl)piperidin-1-yl)-N-((2-(trifluoromethyl)pyridin-3-yl)methyl)pyrido[2,3-d]pyri-midin-4-amine 2-(2-(trifluoromethyl)piperidin-1-yl)-N-((2-(trifluoromethyl)pyridin-3-yl)methyl)pyrido[2,3-d]pyrimidin-4-amine 2-(2,2-difluoro-7-azaspiro[3.5]nonan-7-yl)-N-(2-(trifluoromethyl)benzyl)pyrido[2,3-d]pyrimidin-4-amine (2-(trifluoromethyl)pyridin-3-yl)metha 4-methyl-1-(4-((2-(trifluoromethyl)benzyl)amino)pyrido[2,3-d]pyrimidin-2-yl)piperidine-4-carbonitrile 1-(4-((2-(trifluoromethyl)benzyl)amino)pyrido[2,3-d]pyrimidin-2-yl)piperidine-3-carbonitrile 2-(3-(methylsulfonyl)pyrrolidin-1-yl)-N-((2-(trifluoromethyl)pyridin-3-yl)methyl)pyrido[2,3-d]pyrimidin-4-amine N-((2-(trifluoromethyl)pyridin-3-yl)methyl)-2-(2-(trifluoromethyl)pyrrolidin-1-yl)pyrido[2,3-d]pyrimidin-4-amine 2-(3-chloropyrrolidin-1-yl)-N-((2-(trifluoromethyl)pyridin-3-yl)methyl)pyrido[2,3-d]pyrimidin-4-amine N-(2-(trifluoromethyl)benzyl)-2-(3-(trifluoromethyl)pyrrolidin-1-yl)pyrido[2,3-d]pyrimidin-4-amine 2-(2-oxa-5-azabicyclo[2.2.1]heptan-5-yl)-N-(2-(trifluoromethyl)benzyl)pyrido[2,3-d]pyrimidin-4-amine 2-((6S)-2,6-dimethylmorpholino)-N-(2-(trifluoromethyl)benzyl)pyrido[2,3-d]pyrimidin-4-amine 2-(3-isopropylmorpholino)-N-((2-(trifluoromethyl)pyridin-3-yl)methyl)pyrido[2,3-d]pyrimidin-4-amine 2-((2R,3R)-2,3-dimethylmorpholino)-N-((2-(trifluoromethyl)pyridin-3-yl)methyl)pyrido[2,3-d]pyrimidin-4-amine 2-((2S,5R)-2,5-dimethylmorpholino)-N-((2-(trifluoromethyl)pyridin-3-yl)methyl)pyrido[2,3-d]pyrimidin-4-amine 2-(6-oxa-9-azaspiro[4.5]decan-9-yl)-N-((2-(trifluoromethyl)pyridin-3-yl)methyl)pyrido[2,3-d]pyrimidin-4-amine 2-(4-(trifluoromethoxy)piperidin-1-yl)-N-((2-(trifluoromethyl)pyridin-3-yl)methyl)pyrido[2,3-d]pyrimidin-4-amine 2-(4-(trifluoromethoxy)piperidin-1-yl)-N-((2-(trifluoromethyl)pyridin-3-yl)methyl)pyrido[2,3-d]pyrimidin-4-amine methanesulfonate 2-(3-(difluoromethyl)azetidin-1-yl)-N-((2-(trifluoromethyl)pyridin-3-yl)methyl)pyrido[2,3-d]pyrimidin-4-amine 2-((3R)-3,5-dimethylmorpholino)-N-((2-(trifluoromethyl)pyridin-3-yl)methyl)pyrido[2,3-d]pyrimidin-4-amine 2-(3-(difluoromethyl)azetidin-1-yl)-N-(2-(trifluoromethyl)benzyl)pyrido[2,3-d]pyrimidin-4-amine 2-((3R)-3,5-dimethylmorpholino)-N-(2-(trifluoromethyl)benzyl)pyrido[2,3-d]pyrimidin-4-amine 2-(2-cyclopropylmorpholino)-N-((2-(trifluoromethyl)pyridin-3-yl)methyl)pyrido[2,3-d]pyrimidin-4-amine 2-((2S,5S)-2,5-dimethylmorpholino)-N-((2-(trifluoromethyl)pyridin-3-yl)methyl)pyrido[2,3-d]pyrimidin-4-amine (R)-2-(3-(difluoromethoxy)pyrrolidin-1-yl)-N-((2-(trifluoromethyl)pyridin-3-yl)methyl)pyrido[2,3-d]pyrimidin-4-amine (S)-2-(3-(difluoromethoxy)pyrrolidin-1-yl)-N-((2-(trifluoromethyl)pyridin-3-yl)methyl)pyrido[2,3-d]pyrimidin-4-amine 2-(2-(difluoromethyl)morpholino)-N-((2-(trifluoromethyl)pyridin-3-yl)methyl)pyrido[2,3-d]pyrimidin-4-amine 4-(4-((2-(trifluoromethyl)benzyl)amino)pyrido[2,3-d]pyrimidin-2-yl)morpholine-2-carbonitrile 2-(2-(difluoromethyl)morpholino)-N-(2-(trifluoromethyl)benzyl)pyrido[2,3-d]pyrimidin-4-amine 2-(8-oxa-5-azaspiro[3.5]nonan-5-yl)-N-(2-(trifluoromethyl)benzyl)pyrido[2,3-d]pyrimidin-4-amine 2-(9-oxa-6-azaspiro[4.5]decan-6-yl)-N-(2-(trifluoromethyl)benzyl)pyrido[2,3-d]pyrimidin-4-amine 2-((2R,3S)-2,3-dimethylmorpholino)-N-((2-(trifluoromethyl)pyridin-3-yl)methyl)pyrido[2,3-d]pyrimidin-4-amine (3R)-3-methyl-4-(4-(2-(2-(trifluoromethyl)pyridin-3-yl)azetidin-1-yl)pyrido[2,3-d]pyrimidin-2-yl)morpholine (3S)-3-methyl-4-(4-(2-(2-(trifluoromethyl)pyridin-3-yl)azetidin-1-yl)pyrido[2,3-d]pyrimidin-2-yl)morpholine (3R)-3-methyl-4-(4-(2-(2-(trifluoromethyl)phenyl)azetidin-1-yl)pyrido[2,3-d]pyrimidin-2-yl)morpholine (3S)-3-methyl-4-(4-(2-(2-(trifluoromethyl)phenyl)azetidin-1-yl)pyrido[2,3-d]pyrimidin-2-yl)morpholine 2-(3-(difluoromethoxy)piperidin-1-yl)-N-((2-(trifluoromethyl)pyridin-3-yl)methyl)pyrido[2,3-d]pyrimidin-4-amine 2-(6-oxa-3-azabicyclo[3.1.1]heptan-3-yl)-N-((2-(trifluoromethyl)pyridin-3-yl)methyl)pyrido[2,3-d]pyrimidin-4-amine 2-(2-oxa-5-azabicyclo[4.1.0]heptan-5-yl)-N-((2-(trifluoromethyl)pyridin-3-yl)methyl)pyrido[2,3-d]pyrimidin-4-amine 2-(2,2,6,6-tetrafluoromorpholino)-N-((2-(trifluoromethyl)pyridin-3-yl)methyl)pyrido[2,3-d]pyrimidin-4-amine 2-(4-azaspiro[2.5]octan-4-yl)-N-((2-(trifluoromethyl)pyridin-3-yl)methyl)pyrido[2,3-d]pyrimidin-4-amine 2-(3-(trifluoromethoxy)pyrrolidin-1-yl)-N-((2-(trifluoromethyl)pyridin-3-yl)methyl)pyrido[2,3-d]pyrimidin-4-amine 2-(5-azaspiro[3.4]octan-5-yl)-N-((2-(trifluoromethyl)pyridin-3-yl)methyl)pyrido[2,3-d]pyrimidin-4-amine 2-(2-((trifluoromethoxy)methyl)pyrrolidin-1-yl)-N-((2-(trifluoromethyl)pyridin-3-yl)methyl)pyrido[2,3-d]pyrimidin-4-amine 2-(6-oxa-3-azabicyclo[3.1.1]heptan-3-yl)-N-(2-(trifluoromethyl)benzyl)pyrido[2,3-d]pyrimidin-4-amine 2-(2-oxa-5-azabicyclo[4.1.0]heptan-5-yl)-N-(2-(trifluoromethyl)benzyl)pyrido[2,3-d]pyrimidin-4-amine 2-((3R)-3,5-dimethylmorpholino)-N-(2-(trifluoromethyl)benzyl)pyrido[2,3-d]pyrimidin-4-amine 6-fluoro-2-(3-methylmorpholino)-N-((2-(trifluoromethyl)pyridin-3-yl)methyl)pyrido[2,3-d]pyrimidin-4-amine 6-methoxy-2-(3-methylmorpholino)-N-((2-(trifluoromethyl)pyridin-3-yl)methyl)pyrido[2,3-d]pyrimidin-4-amine 7-methoxy-2-(3-methylmorpholino)-N-((2-(trifluoromethyl)pyridin-3-yl)methyl)pyrido[2,3-d]pyrimidin-4-amine 2-(3-methylmorpholino)-N-((2-(trifluoromethyl)pyridin-3-yl)methyl)pyrimido[4,5-d]pyrimidin-4-amine 2-(3-methylmorpholino)-N-(2-(trifluoromethyl)benzyl)pyrimido[4,5-d]pyrimidin-4-amine 5-methoxy-2-(3-methylmorpholino)-N-((2-(trifluoromethyl)pyridin-3-yl)methyl)pyrido[2,3-d]pyrimidin-4-amine 6,7-dimethoxy-2-(3-methylmorpholino)-N-((2-(trifluoromethyl)pyridin-3-yl)methyl)pyrido[2,3-d]pyrimidin-4-amine 2-(3-methylmorpholino)-N-((2-(trifluoromethyl)pyridin-3-yl)methyl)pteridin-4-amine 2-(3-methylmorpholino)-N-(2-(trifluoromethyl)benzyl)pteridin-4-amine 2-(3-methylmorpholino)-7-(2-morpholinoethoxy)-N-((2-(trifluoromethyl)pyridin-3-yl)methyl)pyrido[2,3-d]pyrimidin-4-amine 2-(3-methylmorpholino)-7-(2-morpholinoethoxy)-N-((2-(trifluoromethyl)pyridin-3-yl)methyl) quinazolin-4-amine.

77. A compound, or salt or solvate thereof, according to paragraph 76 selected from:

(3R)-3-methyl-4-(4-(2-(2-(trifluoromethyl)pyridin-3-yl)azetidin-1-yl)pyrido[2,3-d]pyrimidin-2-yl)morpholine 2-(3-(difluoromethyl)azetidin-1-yl)-N-((2-(trifluoromethyl)pyridin-3-yl)methyl)pyrido[2,3-d]pyrimidin-4-amine 2-((2R,3R)-2,3-dimethylmorpholino)-N-((2-(trifluoromethyl)pyridin-3-yl)methyl)pyrido[2,3-d]pyrimidin-4-amine 2-(3-isopropylmorpholino)-N-((2-(trifluoromethyl)pyridin-3-yl)methyl)pyrido[2,3-d]pyrimidin-4-amine N-(2-(trifluoromethyl)benzyl)-2-(3-(trifluoromethyl)pyrrolidin-1-yl)pyrido[2,3-d]pyrimidin-4-amine 2-(2,2-difluoro-7-azaspiro[3.5]nonan-7-yl)-N-(2-(trifluoromethyl)benzyl)pyrido[2,3-d]pyrimidin-4-amine 2-(2-oxa-5-azabicyclo[2.2.1]heptan-5-yl)-N-((2-(trifluoromethyl)pyridin-3-yl)methyl)pyrido[2,3-d]pyrimidin-4-amine 2-(3-cyclopropylmorpholino)-N-((2-(trifluoromethyl)pyridin-3-yl)methyl)pyrido[2,3-d]pyrimidin-4-amine 1-(4-(((2-(trifluoromethyl)pyridin-3-yl)methyl)amino)pyrido[2,3-d]pyrimidin-2-yl)piperidine-3-carbonitrile 1-(4-((2-(trifluoromethyl)benzyl)amino)pyrido[2,3-d]pyrimidin-2-yl)azetidine-3-carbonitrile 2-(4,4-dimethylpiperidin-1-yl)-N-(2-(trifluoromethyl)benzyl)pyrido[2,3-d]pyrimidin-4-amine 2-(3-fluoropyrrolidin-1-yl)-N-((2-(trifluoromethyl)pyridin-3-yl)methyl)pyrido[2,3-d]pyrimidin-4-amine 1-(4-(((2-(trifluoromethyl)pyridin-3-yl)methyl)amino)pyrido[2,3-d]pyrimidin-2-yl)piperidine-4-carbonitrile 2-(3-(trifluoromethyl)azetidin-1-yl)-4-(2-(2-(trifluoromethyl)pyridin-3-yl)azetidin-1-yl)pyrido[2,3-d]pyrimidine 3-methyl-4-(4-(2-(2-(trifluoromethyl)pyridin-3-yl)azetidin-1-yl)pyrido[2,3-d]pyrimidin-2-yl)morpholine (S)-2-(3-methylmorpholino)-N-((2-(trifluoromethyl)pyridin-3-yl)methyl)pyrido[2,3-d]pyrimidin-4-amine 2-(3-(trifluoromethyl)azetidin-1-yl)-N-((2-(trifluoromethyl)pyridin-3-yl)methyl)pyrido[2,3-d]pyrimidin-4-amine 2-(4-chloropiperidin-1-yl)-N-((2-(trifluoromethyl)pyridin-3-yl)methyl)pyrido[2,3-d]pyrimidin-4-amine 2-(4-chloropiperidin-1-yl)-N-(2-(trifluoromethyl)benzyl)pyrido[2,3-d]pyrimidin-4-amine $N^2$-isopropyl-$N^4$-((2-(trifluoromethyl)pyridin-3-yl)methyl)pyrido[2,3-d]pyrimidine-2,4-diamine methanesulfonate 2-(4,4-difluoropiperidin-1-yl)-N-((2-(trifluoromethyl)pyridin-3-yl)methyl)pyrido[2,3-d]pyrimidin-4-amine 2-(4-fluoropiperidin-1-yl)-N-((2-(trifluoromethyl)pyridin-3-yl)methyl)pyrido[2,3-d]pyrimidin-4-amine 2-(3,3-difluoropyrrolidin-1-yl)-N-((2-(trifluoromethyl)pyridin-3-yl)methyl)pyrido[2,3-d]pyrimidin-4-amine methanesulfonate 2-(3,3-difluoropyrrolidin-1-yl)-N-((2-(trifluoromethyl)pyridin-3-yl)methyl)pyrido[2,3-d]pyrimidin-4-amine 2-(3-methylmorpholino)-N-((2-(trifluoromethyl)pyridin-3-yl)methyl)pyrido[2,3-d]pyrimidin-4-amine methanesulfonate 2-(3-methylmorpholino)-N-((2-(trifluoromethyl)pyridin-3-yl)methyl)pyrido[2,3-d]pyrimidin-4-amine N-isopropyl-4-(2-(2-(trifluoromethyl)phenyl)azetidin-1-yl)pyrido[2,3-d]pyrimidin-2-amine $N^2$-cyclopropyl-$N^2$-methyl-N4-((2-(trifluoromethyl)pyridin-3-yl)methyl)pyrido[2,3-d]pyrimidine-2,4-diamine 2-(2,2-dimethylazetidin-1-yl)-N-((2-(trifluoromethyl)pyridin-3-yl)methyl)pyrido[2,3-d]pyrimidin-4-amine $N^2$-(tert-butyl)-$N^4$-((2-(trifluoromethyl)pyridin-3-yl)methyl)pyrido[2,3-d]pyrimidine-2,4-diamine $N^2$-isopropyl-$N^2$,$N^4$-dimethyl-N4-((2-(trifluoromethyl)pyridin-3-yl)methyl)pyrido[2,3-d]pyrimidine-2,4-diamine $N^2$-cyclopropyl-$N^4$-((2-(trifluoromethyl)pyridin-3-yl)methyl)pyrido[2,3-d]pyrimidine-2,4-diamine methanesulfonate $N^2$-cyclopropyl-$N^4$-((2-(trifluoromethyl)pyridin-3-yl)methyl)pyrido[2,3-d]pyrimidine-2,4-diamine $N^2$-cyclopropyl-$N^4$-(2-(trifluoromethyl)benzyl)pyrido[2,3-d]pyrimidine-2,4-diamine N,2-dimethyl-N-(1-(2-(trifluoromethyl)phenyl)ethyl)thieno[3,2-d]pyrimidin-4-amine N-ethyl-N-(2-(trifluoromethyl)benzyl)thieno[3,2-d]pyrimidin-4-amine $N^2$-isopropyl-$N^4$-(1-(2-(trifluoromethyl)phenyl)ethyl)thieno[3,2-d]pyrimidine-2,4-diamine 2-chloro-N-methyl-N-(2-(trifluoromethyl)benzyl)thieno[3,2-d]pyrimidin-4-amine $N^2$-isopropyl-$N^4$-(2-(trifluoromethyl)benzyl)pyrido[2,3-d]pyrimidine-2,4-diamine methanesulfonate $N^2$-isopropyl-$N^4$-(2-(trifluoromethyl)benzyl)pyrido[2,3-d]pyrimidine-2,4-diamine $N^2$-isopropyl-$N^2$-methyl-$N^4$-((2-(trifluoromethyl)pyridin-3-yl)methyl)pyrido[2,3-d]pyrimidine-2,4-diamine $N^2$-isopropyl-$N^2$-methyl-$N^4$-((2-(trifluoromethyl)pyridin-3-yl)methyl)pyrido[2,3-d]pyrimidine-2,4-diamine methanesulfonate $N^4$-(2-fluoro-6-(trifluoromethyl)benzyl)-$N^2$-isopropylpyrido[2,3-d]pyrimidine-2,4-diamine 2-(2-methylazetidin-1-yl)-N-((2-(trifluoromethyl)pyridin-3-yl)methyl)pyrido[2,3-d]pyrimidin-4-amine 2-(pyrrolidin-1-yl)-N-((2-(trifluoromethyl)pyridin-3-yl)methyl)pyrido[2,3-d]pyrimidin-4-amine
N-isopropyl-N-methyl-4-(2-(2-(trifluoromethyl)phenyl)azetidin-1-yl)pyrido[2,3-d]pyrimidin-2-amine
2-(4,4-difluoropiperidin-1-yl)-N-(2-(trifluoromethyl)benzyl)pyrido[2,3-d]pyrimidin-4-amine
3-methyl-4-(4-(2-(2-(trifluoromethyl)phenyl)azetidin-1-yl)pyrido[2,3-d]pyrimidin-2-yl)morpholine
2-(4,4-difluoropiperidin-1-yl)-4-(2-(2-(trifluoromethyl)pyridin-3-yl)azetidin-1-yl)pyrido[2,3-d]pyrimidine
2-(3,3-difluoropyrrolidin-1-yl)-4-(2-(2-(trifluoromethyl)pyridin-3-yl)azetidin-1-yl)pyrido[2,3-d]pyrimidine
2-(4-(trifluoromethyl)piperidin-1-yl)-N-((2-(trifluoromethyl)pyridin-3-yl)methyl)pyrido[2,3-d]pyr-imidin-4-amine
2-(2,2-dimethylmorpholino)-N-((2-(trifluoromethyl)pyridin-3-yl)methyl)pyrido[2,3-d]pyrimidin-4-amine
2-(3,3-dimethylmorpholino)-N-((2-(trifluoromethyl)pyridin-3-yl)methyl)pyrido[2,3-d]pyrimidin-4-amine
2-(2-methylmorpholino)-N-((2-(trifluoromethyl)pyridin-3-yl)methyl)pyrido[2,3-d]pyrimidin-4-amine
2-(2-methylmorpholino)-N-(2-(trifluoromethyl)benzyl)pyrido[2,3-d]pyrimidin-4-amine
4-methyl-1-(4-(((2-(trifluoromethyl)pyridin-3-yl)methyl)amino)pyrido[2,3-d]pyrimidin-2-yl)piperidine-4-carbonitrile
2-(2,2-difluoro-7-azaspiro[3.5]nonan-7-yl)-N-((2-(trifluoromethyl)pyridin-3-yl)methyl)pyrido[2,3-d]pyrimidin-4-amine
2-(2,2-difluoro-7-azaspiro[3.5]nonan-7-yl)-N-((2-(trifluoromethyl)pyridin-3-yl)methyl)pyrido[2,3-d]pyrimidin-4-amine methanesulfonate
2-(2-(trifluoromethyl)piperidin-1-yl)-N-((2-(trifluoromethyl)pyridin-3-yl)methyl)pyrido[2,3-d]pyrimidin-4-amine
2-(2,2-difluoro-7-azaspiro[3.5]nonan-7-yl)-N-(2-(trifluoromethyl)benzyl)pyrido[2,3-d]pyrimidin-4-amine
1-(4-((2-(trifluoromethyl)benzyl)amino)pyrido[2,3-d]pyrimidin-2-yl)piperidine-3-carbonitrile
2-((2S,5R)-2,5-dimethylmorpholino)-N-((2-(trifluoromethyl)pyridin-3-yl)methyl)pyrido[2,3-d]pyrimidin-4-amine
2-(6-oxa-9-azaspiro[4.5]decan-9-yl)-N-((2-(trifluoromethyl)pyridin-3-yl)methyl)pyrido[2,3-d]pyrimidin-4-amine
2-((3R)-3,5-dimethylmorpholino)-N-((2-(trifluoromethyl)pyridin-3-yl)methyl)pyrido[2,3-d]pyrimidin-4-amine
2-(2-cyclopropylmorpholino)-N-((2-(trifluoromethyl)pyridin-3-yl)methyl)pyrido[2,3-d]pyrimidin-4-amine
2-((2S,5S)-2,5-dimethylmorpholino)-N-((2-(trifluoromethyl)pyridin-3-yl)methyl)pyrido[2,3-d]pyrimidin-4-amine
(R)-2-(3-(difluoromethoxy)pyrrolidin-1-yl)-N-((2-(trifluoromethyl)pyridin-3-yl)methyl)pyrido[2,3-d]pyrimidin-4-amine
(S)-2-(3-(difluoromethoxy)pyrrolidin-1-yl)-N-((2-(trifluoromethyl)pyridin-3-yl)methyl)pyrido[2,3-d]pyrimidin-4-amine
2-(2-(difluoromethyl)morpholino)-N-((2-(trifluoromethyl)pyridin-3-yl)methyl)pyrido[2,3-d]pyrimidin-4-amine
4-(4-((2-(trifluoromethyl)benzyl)amino)pyrido[2,3-d]pyrimidin-2-yl)morpholine-2-carbonitrile
2-((2R,3S)-2,3-dimethylmorpholino)-N-((2-(trifluoromethyl)pyridin-3-yl)methyl)pyrido[2,3-d]pyrimidin-4-amine
(3S)-3-methyl-4-(4-(2-(2-(trifluoromethyl)pyridin-3-yl)azetidin-1-yl)pyrido[2,3-d]pyrimidin-2-yl)morpholine
(3R)-3-methyl-4-(4-(2-(2-(trifluoromethyl)phenyl)azetidin-1-yl)pyrido[2,3-d]pyrimidin-2-yl)morpholine
(3S)-3-methyl-4-(4-(2-(2-(trifluoromethyl)phenyl)azetidin-1-yl)pyrido[2,3-d]pyrimidin-2-yl)morpholine
2-(2-oxa-5-azabicyclo[4.1.0]heptan-5-yl)-N-((2-(trifluoromethyl)pyridin-3-yl)methyl)pyrido[2,3-d]pyrimidin-4-amine
2-(2-oxa-5-azabicyclo[4.1.0]heptan-5-yl)-N-(2-(trifluoromethyl)benzyl)pyrido[2,3-d]pyrimidin-4-amine
(S)-2-(3-methylmorpholino)-N-(2-(trifluoromethyl)benzyl)pyrido[2,3-d]pyrimidin-4-amine
(S)-2-(3-methylmorpholino)-N-(2-(trifluoromethyl)benzyl)pyrido[2,3-d]pyrimidin-4-amine methanesulfonate
2-(4-chloropiperidin-1-yl)-4-(2-(2-(trifluoromethyl)pyridin-3-yl)azetidin-1-yl)pyrido[2,3-d]pyrimidine
N-((2-(trifluoromethyl)pyridin-3-yl)methyl)-2-(3-(trifluoromethyl)pyrrolidin-1-yl)pyrido[2,3-d]pyrimidin-4-amine
2-(2,2-dimethylmorpholino)-N-(2-(trifluoromethyl)benzyl)pyrido[2,3-d]pyrimidin-4-amine
2-(4-oxa-7-azaspiro[2.5]octan-7-yl)-N-((2-(trifluoromethyl)pyridin-3-yl)methyl)pyrido[2,3-d]pyrimidin-4-amine
2-(3-(fluoromethyl)piperidin-1-yl)-N-((2-(trifluoromethyl)pyridin-3-yl)methyl)pyrido[2,3-d]pyri-midin-4-amine
(2-(trifluoromethyl)pyridin-3-yl)metha 4-methyl-1-(4-((2-(trifluoromethyl)benzyl)amino)pyrido[2,3-d]pyrimidin-2-yl)piperidine-4-carbonitrile
N-((2-(trifluoromethyl)pyridin-3-yl)methyl)-2-(2-(trifluoromethyl)pyrrolidin-1-yl)pyrido[2,3-d]pyrimidin-4-amine
2-(3-chloropyrrolidin-1-yl)-N-((2-(trifluoromethyl)pyridin-3-yl)methyl)pyrido[2,3-d]pyrimidin-4-amine
2-(2-oxa-5-azabicyclo[2.2.1]heptan-5-yl)-N-(2-(trifluoromethyl)benzyl)pyrido[2,3-d]pyrimidin-4-amine
2-(4-(trifluoromethoxy)piperidin-1-yl)-N-((2-(trifluoromethyl)pyridin-3-yl)methyl)pyrido[2,3-d]pyrimidin-4-amine
2-(4-(trifluoromethoxy)piperidin-1-yl)-N-((2-(trifluoromethyl)pyridin-3-yl)methyl)pyrido[2,3-d]pyrimidin-4-amine methanesulfonate
2-(3-(difluoromethyl)azetidin-1-yl)-N-(2-(trifluoromethyl)benzyl)pyrido[2,3-d]pyrimidin-4-amine
2-(2-(difluoromethyl)morpholino)-N-(2-(trifluoromethyl)benzyl)pyrido[2,3-d]pyrimidin-4-amine
2-(4-azaspiro[2.5]octan-4-yl)-N-((2-(trifluoromethyl)pyridin-3-yl)methyl)pyrido[2,3-d]pyrimidin-4-amine
2-(3-(trifluoromethoxy)pyrrolidin-1-yl)-N-((2-(trifluoromethyl)pyridin-3-yl)methyl)pyrido[2,3-d]pyrimidin-4-amine
2-(5-azaspiro[3.4]octan-5-yl)-N-((2-(trifluoromethyl)pyridin-3-yl)methyl)pyrido[2,3-d]pyrimidin-4-amine
2-(2-((trifluoromethoxy)methyl)pyrrolidin-1-yl)-N-((2-(trifluoromethyl)pyridin-3-yl)methyl)pyrido[2,3-d]pyrimidin-4-amine
2-(6-oxa-3-azabicyclo[3.1.1]heptan-3-yl)-N-(2-(trifluoromethyl)benzyl)pyrido[2,3-d]pyrimidin-4-amine
2-((3R)-3,5-dimethylmorpholino)-N-(2-(trifluoromethyl)benzyl)pyrido[2,3-d]pyrimidin-4-amine.

78. A pharmaceutical composition comprising a compound according to paragraphs 1 to 77, or a pharmaceutically acceptable salt or solvate thereof, in admixture with a pharmaceutically acceptable diluent or carrier.

79. A compound according to any one of paragraphs 1 to 77, or a pharmaceutically acceptable salt or solvate thereof, for use in therapy.

80. A combination comprising a compound according to any one of paragraphs 1 to 77, or a pharmaceutically acceptable salt or solvate thereof, with one or more additional therapeutic agents.

81. A compound of Formula II:

(II)

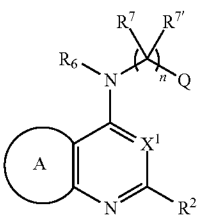

or a salt or solvate thereof, wherein,

A represents a fused aromatic ring selected from,

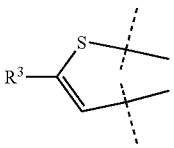

and

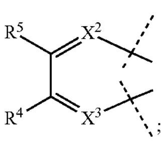

;

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3

$R^2$ is selected from hydrogen, hydroxyl, halogen, —CN, —C(═O)$R^d$, —C(═O)O$R^d$, —C(═O)N$R^cR^d$, —C(O)C(═O)$R^d$, —N$R^cR^d$, —N$R^o$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$; or a pharmaceutically acceptable salt or solvate thereof, for use in the treatment or prevention of a filarial worm infection.

82. A compound for use according to paragraph 81, wherein the infection is with one or more filarial worms selected from *Wuchereria bancrofti, Brugia malayi, Brugia timori* and *Onchocerca volvulus.*

83. A compound of Formula II:

(II)

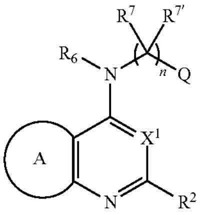

or a salt or solvate thereof, wherein,

A represents a fused aromatic ring selected from,

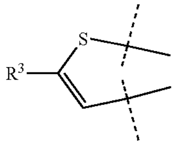

and

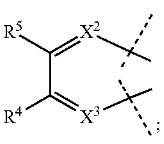

;

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7\prime}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7\prime}$, together with the carbon to which they are attached form a 3-7 membered cycloalkyl ring, optionally substituted with one or more $R^a$, or $R^7$ and $R^{7\prime}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3

$R^2$ is selected from hydrogen, hydroxyl, halogen, —CN, —C(═O)$R^d$, —C(═O)O$R^d$, —C(═O)N$R^cR^d$, —C(O)C(═O)$R^d$, —N$R^cR^d$, —N$R^o$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

or a pharmaceutically acceptable salt or solvate thereof, for use in the treatment or prevention of a disease or condition mediated by a filarial worm infection.

84. A compound for use according to paragraph 83, wherein the disease or condition is mediated by infection with one or more of *Wuchereria bancrofti, Brugia malayi, Brugia timori* and *Onchocerca volvulus.*

85. A compound for use according to paragraph 83, wherein the disease or condition is selected from onchocerciasis or lymphatic filariasis.

86. A compound of Formula II:

(II)

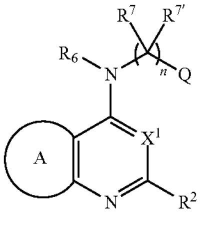

or a salt or solvate thereof, wherein,

A represents a fused aromatic ring selected from,

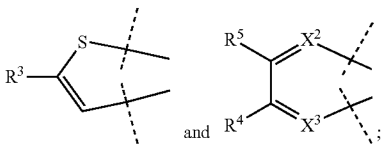

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7\prime}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7\prime}$, together with the carbon to which they are attached form a 3-7 membered cycloalkyl ring, optionally substituted with one or more $R^a$, or $R^7$ and $R^{7\prime}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3 $R^2$ is selected from hydrogen, hydroxyl, halogen, —CN, —C(=O)$R^d$, —C(=O)$OR^d$, —C(=O)$NR^cR^d$, —C(O)C(=O)$R^d$, —$NR^cR^d$, —$NR^c$($C_{1-6}$alkyl)$NR^cR^d$, —$NR^c$C(=O)$R^d$, —$NR^c$C(=O)$OR^d$, —$NR^c$C(=O)$NR^cR^d$, —$NR^c$S(=O)$_2R^d$, —$NR^c$S(=O)$_2NR^cR^d$, —$OR^d$, —$SR^d$—OC(=O)$R^d$, —OC(=O)$NR^cR^d$, —OC(=O)$OR^d$, —S(=O)$R^d$, —S(=O)$_2R^d$, —OS(=O)$R^d$, —OS(=O)$_2R^d$, —OS(=O)$_2OR^d$, —S(=O)$NR^cR^d$, —OS(=O)$_2NR^cR^d$, —S(=O)$_2NR^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(=O)$R^d$, —C(=O)$OR^d$, —C(=O)$NR^cR^d$, —C(O)C(=O)$R^d$, —$NR^cR^d$, —$NR^c$C(=O)$R^d$, —$NR^c$C(=O)$OR^d$, —$NR^c$C(=O)$NR^cR^d$, —$NR^c$S(=O)$_2R^d$, —$NR^c$S(=O)$_2NR^cR^d$, —$OR^d$, —$SR^d$, —OC(=O)$R^d$, —OC(=O)$NR^cR^d$, —OC(=O)$OR^d$, —S(=O)$_2R^d$, —S(=O)$R^d$, —OS(=O)$R^d$, —OS(=O)$_2R^d$, —OS(=O)$_2OR^d$, —S(=O)$NR^cR^d$, —OS(=O)$_2NR^cR^d$, and —S(=O)$_2NR^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

or a pharmaceutically acceptable salt or solvate thereof, for use in the treatment of a microbial infection.

87. A compound for use according to paragraph 86 wherein the microbial infection is a bacterial infection.

88. A compound for use according to paragraph 87 wherein the bacterial infection is *Wolbachia* infection.

89. A method of treating or preventing a filarial worm infection in a subject, said method comprising administering to a subject a therapeutically effective amount of a compound of Formula II:

(II)

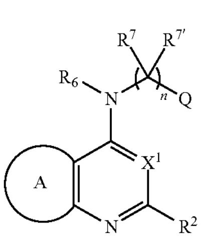

or a salt or solvate thereof, wherein,

A represents a fused aromatic ring selected from,

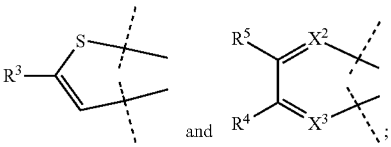

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3 $R^2$ is selected from hydrogen, hydroxyl, halogen, —CN, —C(═O)$R^d$, —C(═O)$OR^d$, —C(═O)$NR^cR^d$, —C(O)C(═O)$R^d$, —$NR^cR^d$, —$NR^c$($C_{1-6}$alkyl)$NR^cR^d$, —$NR^c$C(═O)$R^d$, —$NR^c$C(═O)$OR^d$, —$NR^c$C(═O)$NR^cR^d$, —$NR^c$S(═O)$_2R^d$, —$NR^c$S(═O)$_2NR^cR^d$, —$OR^d$, —$SR^d$—OC(═O)$R^d$, —OC(═O)$NR^cR^d$, —OC(═O)$OR^d$, —S(═O)$R^d$, —S(═O)$_2R^d$, —OS(═O)$R^d$, —OS(═O)$_2R^d$, —OS(═O)$_2OR^d$, —S(═O)$NR^cR^d$, —OS(═O)$_2NR^cR^d$, —S(═O)$_2NR^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)$OR^d$, —C(═O)$NR^cR^d$, —C(O)C(═O)$R^d$, —$NR^cR^d$, —$NR^c$C(═O)$R^d$, —$NR^c$C(═O)$OR^d$, —$NR^c$C(═O)$NR^cR^d$, —$NR^c$S(═O)$_2R^d$, —$NR^c$S(═O)$_2NR^cR^d$, —$OR^d$, —$SR^d$, —OC(═O)$R^d$, —OC(═O)$NR^cR^d$, —OC(═O)$OR^d$, —S(═O)$_2R^d$, —S(═O)$R^d$, —OS(═O)$R^d$, —OS(═O)$_2R^d$, —OS(═O)$_2OR^d$, —S(═O)$NR^cR^d$, —OS(═O)$_2NR^cR^d$, and —S(═O)$_2NR^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

or a pharmaceutically acceptable salt or solvate thereof.

90. A method according to paragraph 89 wherein the infection is with one or more filarial worms selected from *Wuchereria bancrofti, Brugia malayi, Brugia timori* and *Onchocerca volvulus*.

91. A method of treating or preventing a disease or condition mediated by a filarial worm infection, said method comprising administering to a subject in need thereof a therapeutically effective amount of a compound of Formula II:

(II)

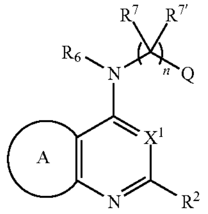

or a salt or solvate thereof, wherein,

A represents a fused aromatic ring selected from,

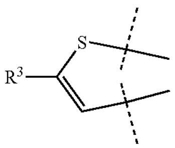

and

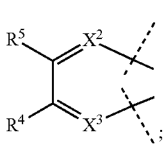

;

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7\prime}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7\prime}$, together with the carbon to which they are attached form a 3-7 membered cycloalkyl ring, optionally substituted with one or more $R^a$, or $R^7$ and $R^{7\prime}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3 $R^2$ is selected from hydrogen, hydroxyl, halogen, —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$ alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

or a pharmaceutically acceptable salt or solvate thereof.

92. A method according to paragraph 91 wherein the disease or condition is mediated by infection with one or more of *Wuchereria bancrofti, Brugia malayi, Brugia timori* and *Onchocerca volvulus.*

93. The method of any one of paragraphs 91 and 92, wherein the disease or condition is selected from onchocerciasis or lymphatic filariasis.

94. A method of treating a microbial infection, said method comprising administering to a subject in need thereof a therapeutically effective amount of a compound of Formula II:

(II)

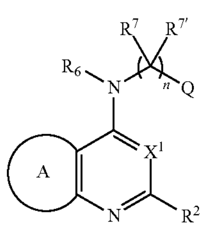

or a salt or solvate thereof, wherein,

A represents a fused aromatic ring selected from,

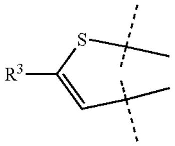

and

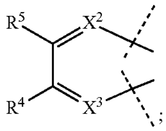

;

$X^1$, $X^2$ and $X^3$ are independently selected from N and CH;

Q is a group selected from an $C_{3-11}$cycloalkyl optionally substituted by one or more $R^b$, 3-15 membered heterocycloalkyl optionally substituted by one or more $R^b$, $C_{6-11}$ aryl group optionally substituted with by one or more $R^b$, 5-15 membered heteroaryl optionally substituted by one or more $R^b$;

$R^6$ is selected from hydrogen and $C_{1-6}$ alkyl;

$R^7$ and $R^{7\prime}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7\prime}$, together with the carbon to which they are attached form a 3-7 membered cycloalkyl ring, optionally substituted with one or more $R^a$, or $R^7$ and $R^{7\prime}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 0, 1, 2 and 3 $R^2$ is selected from hydrogen, hydroxyl, halogen, —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$ alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^e$, ($C_{7-16}$)alkylaryl optionally substituted by one or more $R^e$, $C_{3-11}$cycloalkyl optionally substituted by one or more $R^e$, ($C_{4-17}$)cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, =0, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$;

$R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

or a pharmaceutically acceptable salt or solvate thereof.

95. A method according to paragraph 94 wherein the microbial infection is a bacterial infection.

96. A method according to paragraph 95 wherein the bacterial infection is *Wolbachia* infection.

97. A compound for use according to paragraphs 81 to 88 or a method according to paragraphs 89 to 96 wherein in the compound of Formula II, or a salt or solvate thereof, A represents a fused aromatic ring selected from,

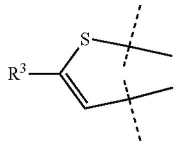

and

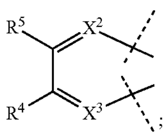

;

$X^1$, $X^2$ and $X^3$ are independently selected from N and CH;

Q is a group selected from an $C_{3-11}$cycloalkyl optionally substituted by 1-21 $R^b$, 3-15 membered heterocycloalkyl optionally substituted by 1-28 $R^b$, $C_{6-11}$ aryl group optionally substituted with by 1-11 $R^b$, 5-15 membered heteroaryl optionally substituted by 1-15 $R^b$;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 1, 2 and 3;

$R^2$ is selected from —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, ($C_{7-16}$)alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(=O)$R^d$, —C(=O)O$R^d$, —C(=O)N$R^cR^d$, —C(O)C(=O)$R^d$, —N$R^cR^d$, —N$R^c$C(=O)$R^d$, —N$R^c$C(=O)O$R^d$, —N$R^c$C(=O)N$R^cR^d$, —N$R^c$S(=O)$_2R^d$, —N$R^c$S(=O)$_2$N$R^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2$O$R^d$, —S(=O)N$R^cR^d$, —OS(=O)$_2$N$R^cR^d$, and —S(=O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^3$, $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$;

with the provisos that:

(i) when $X^1$ is N, $X^2$ and $X^3$ cannot both be CH;

(ii) when Q is phenyl, $R^b$ is not such that Q is a 3,4-di-O—$C_{1-6}$ alkyl phenyl, a 3,5-di-O—$C_{1-6}$ alkyl phenyl or a 3,4,5-tri-O—$C_{1-6}$ alkyl phenyl; and (iii) the compound of Formula (I) is not N-(4-fluorobenzyl)-2-(piperidinyl-1-yl)pyrido[2,3-d]pyrimidin-4-amine, N-(4-fluorobenzyl)-2-(piperidinyl-1-yl)pyrido[3,2-d]pyrimidin-4-amine, N-(4-fluorobenzyl)-2-(piperidinyl-1-yl)thieno[3,2-d]pyrimidin-4-amine.

98. A compound for use or a method according to any one of paragraphs 81 to 97 wherein A is,

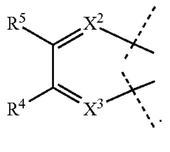

99. A compound for use or a method according to any one of paragraphs 81 to 98, wherein $X^1$ is N.

100. A compound for use or a method according to any one of paragraphs 81 to 99, wherein one of $X^2$ and $X^3$ is N and the other is CH.

101. A compound for use or a method according to any one of paragraphs 81 to 100, wherein $X^2$ is CH and $X^3$ is N.

102. A compound for use or a method according to any one of paragraphs 81 to 101, wherein $X^1$ is N and A is selected from

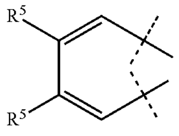 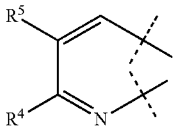 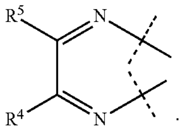 .

103. A compound for use or a method according to any one of paragraphs 81 to 97, wherein A is

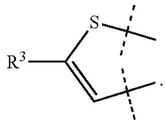 .

104. A compound for use or a method according to any one of paragraphs 81 to 103, wherein Q is a group selected from a 3-15 membered heterocycloalkyl optionally substituted by one or more $R^b$, $C_{6-11}$ aryl group optionally substituted with by one or more $R^b$, and a 5-15 membered heteroaryl optionally substituted by one or more $R^b$.

105. A compound for use or a method according to any one of paragraphs 81 to 104, wherein Q is a group selected from a 3-15 membered heterocycloalkyl optionally substituted by 1-28 $R^b$, $C_{6-11}$ aryl group optionally substituted with by 1-11 $R^b$, and a 5-15 membered heteroaryl optionally substituted by 1-15 $R^b$.

106. A compound for use or a method according to any one of paragraphs 81 to 105, wherein Q is a group selected from a $C_{6-11}$ aryl group optionally substituted with by 1-11 $R^b$ and a 5-15 membered heteroaryl optionally substituted by 1-15 $R^b$.

107. A compound for use or a method according to any one of paragraphs 81 to 106, wherein Q is a group selected from a $C_6$ aryl group optionally substituted with by one or more $R^b$ and a 5-6 membered heteroaryl optionally substituted by one or more $R^b$.

108. A compound for use or a method according to any one of paragraphs 81 to 107, wherein Q is selected from a phenyl or pyridyl group optionally substituted with 1-5 $R^b$.

109. A compound for use or a method according to any one of paragraphs 81 to 108, wherein Q is a group of Formula III (wherein the dotted line indicates the point of attachment):

(III)

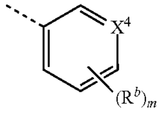

wherein $X^4$ is selected from CH and N;

m is selected from 0, 1 and 2; and $R^b$ is as previously defined.

110. A compound for use or a method according to any one of paragraphs 81 to 109, wherein Q is a group of Formula IIIa:

(IIIa)

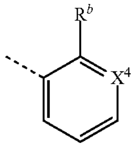

wherein $X^4$ is selected from CH and N; and $R^b$ is as previously defined.

111. A compound for use or a method according to any one of paragraphs 81 to 110, wherein each $R^b$ is independently selected from hydroxyl, =O, halogen, CN, $C_{1-6}$ haloalkyl, $C_{1-6}$ haloalkoxy, $C_{3-6}$ cycloalkyl, $C_{1-6}$ alkyl, O—$C_{1-6}$ alkyl, $C_{3-6}$ cycloalkyl, 3-7 membered heterocycloalkyl, —$NR^cR^d$, —$NR^cC(=O)R^d$, —$OR^d$, —$SR^d$, —$S(=O)_2R^d$, —$S(=O)R^d$, —$S(=O)NR^cR^d$, and —$S(=O)_2NR^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

112. A compound for use or a method according to any one of paragraphs 81 to 111, wherein each $R^b$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —$NR^cR^d$, and —$S(=O)_2R^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

113. A compound for use or a method according to any one of paragraphs 81 to 112, wherein each $R^b$ is independently selected from hydroxyl, halogen, CN, $C_{1-6}$ haloalkyl, $C_{1-6}$ haloalkoxy, $C_{1-6}$ alkyl and O—$C_{1-6}$ alkyl.

114. A compound for use or a method according to any one of paragraphs 81 to 113, wherein each $R^b$ is independently selected from fluoro, chloro, and $CF_3$.

115. A compound for use or a method according to any one of paragraphs 81 to 114, wherein Q is selected from:

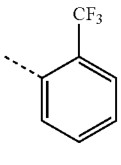

and

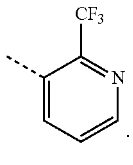

.

116. A compound for use or a method according to any one of paragraphs 81 to 115, wherein $R^6$ is selected from hydrogen, methyl and ethyl.

117. A compound for use or a method according to any one of paragraphs 81 to 116, wherein $R^6$ is selected from hydrogen and methyl.

118. A compound for use or a method according to any one of paragraphs 81 to 117, wherein $R^7$ and $R^{7'}$ are independently selected from hydrogen, methyl and cyclopropyl.

119. A compound for use or a method according to any one of paragraphs 81 to 118, wherein $R^7$ and $R^{7'}$ are independently selected from hydrogen and methyl.

120. A compound for use or a method according to any one of paragraphs 81 to 119, wherein $R^{7'}$ is hydrogen.

121. A compound for use or a method according to any one of paragraphs 81 to 117, wherein $R^7$ and $R^{7'}$, together with the atom to which they are attached form a $C_{3-7}$ cycloalkyl ring, optionally substituted by one or more $R^a$.

122. A compound for use or a method according to any one of paragraphs 81 to 117, wherein $R^7$ and $R^{7'}$, together with the atom to which they are attached form a cyclopropyl ring, optionally substituted by one or more $R^a$.

123. A compound for use or a method according to any one of paragraphs 81 to 120, wherein $R^6$ and $R^{7'}$ are both hydrogen.

124. A compound for use or a method according to any one of paragraphs 81 to 120, wherein $R^6$, $R^7$ and $R^{7'}$ are each hydrogen.

125. A compound for use or a method according to any one of paragraphs 81 to 115, wherein $R^6$ and $R^7$ together with the atoms to which they are attached form an azetidinyl, pyrrolidinyl, piperidinyl or morpholinyl ring.

126. A compound for use or a method according to any one of paragraphs 81 to 125, wherein n is 1 or 2.

127. A compound for use or a method according to any one of paragraphs 81 to 126, wherein n is 1.

128. A compound for use or a method according to any one of paragraphs 81 to 127, wherein $R^2$ is selected from —CN, —$C(=O)R^d$, —$C(=O)OR^d$, —$C(=O)NR^cR^d$, —$C(O)C(=O)R^d$, —$NR^cR^d$, —$NR^c(C_{1-6}alkyl)NR^cR^d$, —$NR^cC(=O)R^d$, —$NR^cC(=O)OR^d$, —$NR^cC(=O)NR^cR^d$, —$NR^cS(=O)_2R^d$, —$NR^cS(=O)_2NR^cR^d$, —$OR^d$, —$SR^d$—$OC(=O)R^d$, —$OC(=O)NR^cR^d$, —$OC(=O)OR^d$, —$S(=O)R^d$, —$S(=O)_2R^d$, —$OS(=O)R^d$, —$OS(=O)_2R^d$, —$OS(=O)_2OR^d$, —$S(=O)NR^cR^d$, —$OS(=O)_2NR^cR^d$, —$S(=O)_2NR^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, $(C_{7-16})$alkylaryl optionally substituted by 1-9 $R^e$, $C_{3-11}$cycloalkyl optionally substituted by 1-21 $R^e$, $(C_{4-17})$cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

129. A compound for use or a method according to any one of paragraphs 81 to 128, wherein $R^2$ is selected from —CN, —$C(=O)R^d$, —$C(=O)OR^d$, —$C(=O)NR^cR^d$, —$C(O)C(=O)R^d$, —$NR^cR^d$, —$NR^c(C_{1-6}alkyl)NR^cR^d$, —$NR^cC(=O)R^d$, —$NR^cC(=O)OR^d$, —$NR^cC(=O)NR^cR^d$, —$NR^cS(=O)_2R^d$, —$NR^cS(=O)_2NR^cR^d$, —$OR^d$, —$SR^d$—$OC(=O)R^d$, —$OC(=O)NR^cR^d$, —$OC(=O)OR^d$, —$S(=O)R^d$, —$S(=O)_2R^d$, —$OS(=O)R^d$, —$OS(=O)_2R^d$, —$OS(=O)_2OR^d$, —$S(=O)NR^cR^d$, —$OS(=O)_2NR^cR^d$, —$S(=O)_2NR^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, $(C_{7-16})$alkylaryl optionally substituted by 1-9 $R^e$, $C_{3-11}$cycloalkyl optionally substituted by 1-21 $R^e$, $(C_{4-17})$cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

130. A compound for use or a method according to any one of paragraphs 81 to 129, wherein $R^2$ is selected from —CN, —C(═O)$R^d$, —C(═O)O$R^d$, —C(═O)N$R^cR^d$, —N$R^cR^d$, —N$R^c$($C_{1-6}$ alkyl)N$R^cR^d$, —N$R^c$C(═O)$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by 1-13 $R^e$, $C_{6-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

131. A compound for use or a method according to any one of paragraphs 81 to 130, wherein $R^2$ is selected from —CN, —C(═O)$R^d$, C(═O)N$R^cR^d$, —N$R^cR^d$, —N$R^o$($C_{1-6}$alkyl)N$R^cR^d$, —N$R^c$C(═O)N$R^cR^d$, —O$R^d$, —S$R^d$, —S(═O)$_2R^d$, $C_{1-10}$ haloalkyl, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

132. A compound for use or a method according to any one of paragraphs 81 to 131, wherein $R^2$ is selected from N$R^cR^d$, —N$R^c$($C_{1-6}$alkyl)N$R^cR^d$, —N$R^c$C(═O)N$R^cR^d$, —O$R^d$, —S$R^d$, $C_{1-10}$haloalkyl, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

133. A compound for use or a method according to any one of paragraphs 81 to 132, wherein $R^2$ is selected from N$R^cR^d$, —N$R^c$($C_{1-6}$alkyl)N$R^cR^d$, $C_{1-10}$alkyl optionally substituted by 1-13 $R^e$, $C_{1-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$.

134. A compound for use or a method according to any one of paragraphs 81 to 133, wherein $R^2$ is selected from N$R^cR^d$, —N$R^c$($C_{1-6}$alkyl)N$R^cR^d$, $C_{1-10}$alkyl optionally substituted by 1-13 $R^e$, and 3-15 membered heterocycloalkyl optionally substituted by 1-28 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

135. A compound for use or a method according to any one of paragraphs 81 to 134, wherein $R^2$ is selected from N$R^cR^d$ and a 3-15 membered heterocycloalkyl optionally substituted by 1-28 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

136. A compound for use or a method according to any one of paragraphs 81 to 135, wherein $R^2$ is selected from N$R^cR^d$ and a 5-10 membered heterocycloalkyl optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

137. A compound for use or a method according to any one of paragraphs 81 to 136, wherein $R^2$ is selected from N$R^cR^d$ and a 5-7 membered heterocycloalkyl optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

138. A compound for use or a method according to any one of paragraphs 81 to 137, wherein $R^2$ is selected from N$R^cR^d$, azetidinyl, pyrrolidinyl, piperidinyl, piperazinyl and morpholinyl, wherein said azetidinyl, pyrrolidinyl, piperidinyl, piperazinyl and morpholinyl are optionally substituted by one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

139. A compound for use or a method according to any one of paragraphs 81 to 138, wherein $R^2$ is selected from N$R^cR^d$; and

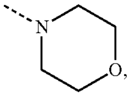 , 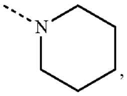 , 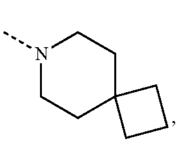 , 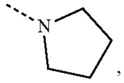 , and 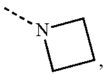 , each of which may optionally be substituted with one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

140. A compound according to any one of paragraphs 81 to 139, or a salt or solvate thereof, wherein $R^2$ is selected from

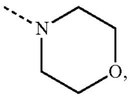 , 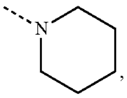 , 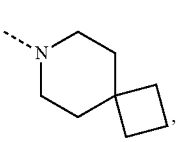 , 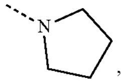 , and 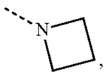 , each of which may optionally be substituted with one or more $R^e$.

141. A compound according to any one of paragraphs 81 to 140, or a salt or solvate thereof, wherein $R^2$ is selected from

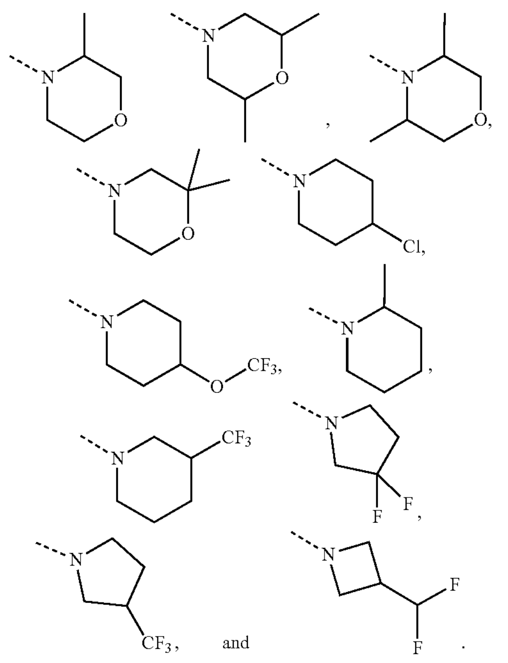

and

142. A compound for use or a method according to any one of paragraphs 81 to 141, wherein $R^e$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —$NR^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl.

143. A compound for use or a method according to any one of paragraphs 81 to 142, wherein $R^e$ is independently selected from hydroxyl, =O, halogen, CN, $C_{1-6}$ haloalkyl, $C_{1-6}$ haloalkoxy, $C_{1-6}$ alkyl and O—$C_{1-6}$ alkyl.

144. A compound for use or a method according to any one of paragraphs 81 to 143, wherein $R^e$ is independently selected from halogen, CN, $C_{1-6}$ haloalkyl, $C_{1-6}$ haloalkoxy, $C_{1-6}$ alkyl and O—$C_{1-6}$ alkyl.

145. A compound for use or a method according to any one of paragraphs 81 to 144, wherein $R^e$ is independently selected from halogen, CN, $C_{1-3}$ haloalkyl, $C_{1-3}$ haloalkoxy, $C_{1-3}$ alkyl and O—$C_{1-3}$ alkyl.

146. A compound for use or a method according to any one of paragraphs 81 to 145, wherein $R^e$ is independently selected from fluoro, chloro, CN, $CF_3$, $OCF_3$ and $C_{1-3}$ alkyl.

147. A compound for use or a method according to any one of paragraphs 81 to 146, wherein each $R^e$ is independently selected from fluoro, chloro, CN, $CF_3$, $OCF_3$, and methyl.

148. A compound for use or a method according any one of paragraphs 81 to 147, wherein each $R^c$ is independently selected from hydrogen, hydroxyl, $C_{1-6}$ haloalkyl, $C_{3-6}$ cycloalkyl, $C_{1-6}$ alkyl and O—$C_{1-6}$ alkyl;

149. A compound for use or a method according to any one of paragraphs 81 to 148, wherein each $R^c$ is independently selected from hydrogen and $C_{1-6}$ alkyl, suitably $C_{1-6}$ alkyl.

150. A compound for use or a method according to any one of paragraphs 81 to 149, wherein each $R^c$ is independently selected from hydrogen and $C_{1-3}$ alkyl, suitably $C_{1-3}$ alkyl.

151. A compound for use or a method according to any one of paragraphs 81 to 150, wherein each $R^d$ is independently selected from hydrogen, 3-7 membered heterocycloalkyl, $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

152. A compound for use or a method according to any one of paragraphs 81 to 151, wherein each $R^d$ is independently selected from 3-7 membered heterocycloalkyl, $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

153. A compound for use or a method according to any one of paragraphs 81 to 152, wherein each $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

154. A compound for use or a method according to any one of paragraphs 81 to 153, wherein $R^c$ and $R^d$ are independently selected from $C_{1-6}$ alkyl.

155. A compound for use or a method according to any one of paragraphs 81 to 154, wherein $R^3$, $R^4$ and $R^5$ are independently selected from hydrogen, halogen and $C_{1-6}$ alkyl.

156. A compound for use or a method according to any one of paragraphs 81 to 155, wherein $R^3$ is H.

157. A compound for use or a method according to any one of paragraphs 81 to 156, wherein $R^4$ is H.

158. A compound for use or a method according to any one of paragraphs 81 to 157, wherein $R^5$ is H.

159. A compound for use or a method according to any one of paragraphs 81 to 159, wherein $R^4$ and $R^5$ are H.

160. A compound for use or a method according to any one of paragraphs 81 to 159, wherein $R^3$, $R^4$ and $R^5$ are H.

161. A compound for use or a method according to any one of paragraphs 97, which is a sub-Formula IIa:

(IIa)

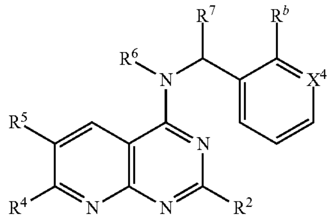

wherein, $R^6$ is selected from hydrogen and $C_{1-6}$ alkyl;

$R^7$ is selected from hydrogen, =O, $C_{3-6}$ cycloalkyl, $C_{1-6}$ alkyl, where said $C_{3-6}$ cycloalkyl, $C_{1-6}$ alkyl are optionally substituted by one or more $R^a$; or $R^6$ and $R^7$, together with the atoms to which they are attached form a 3-7 membered heterocyclic ring, optionally substituted with one or more $R^a$;

$X^4$ is selected from CH and N;

$R^2$ is selected from —CN, —C(═O)$R^d$, —C(═O)O$R^d$, —C(═O)N$R^cR^d$, —C(O)C(═O)$R^d$, —N$R^cR^d$, —N$R^c$($C_{1-6}$alkyl)N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{1-11}$aryl optionally substituted by 1-11 $R^e$, ($C_{7-16}$)alkylaryl optionally substituted by 1-9 $R^e$, $C_{3-11}$cycloalkyl optionally substituted by 1-21 $R^e$, ($C_{4-17}$)cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl, 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

each $R^b$ and $R^e$ is independently selected from hydroxyl, ═O, halogen, CN, $C_{1-6}$ haloalkyl, $C_{1-6}$ haloalkoxy, $C_{3-6}$ cycloalkyl, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl and O—$C_{1-6}$ alkyl, $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, ═O, halogen, CN, $C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-7 membered ring, optionally substituted with one or more $R^a$; and $R^4$ and $R^5$ are independently selected from hydrogen, hydroxyl, halogen, CN, $C_{1-6}$ haloalkyl, $C_{1-6}$ haloalkoxy, and $C_{1-6}$ alkyl, optionally substituted by one or more $R^a$.

162. A compound for use or a method according to paragraph 161, wherein $R^4$ and $R^5$ are hydrogen.

163. A compound for use or a method according to any one of paragraphs 161 to 162, wherein each $R^b$ is independently selected from fluoro, chloro, and $CF_3$.

164. A compound for use or a method according to any one of paragraphs 161 to 163, wherein $R^6$ and $R^7$ are both hydrogen.

165. A compound for use or a method according to any one of paragraphs 161 to 164, wherein $R^2$ is selected from —CN, —C(═O)$R^d$, C(═O)N$R^cR^d$, —N$R^cR^d$, —N$R^c$($C_{1-6}$alkyl)N$R^cR^d$, —N$R^c$C(═O)N$R^cR^d$, —O$R^d$, —S$R^d$, —S(═O)$_2R^d$, $C_{1-10}$ haloalkyl, $C_{1-10}$ alkyl optionally substituted by 1-13 $R^e$, $C_{6-11}$aryl optionally substituted by 1-11 $R^e$, $C_{3-11}$cycloalkyl optionally substituted by 1-21 $R^e$, 3-15 membered heterocycloalkyl optionally substituted by 1-28 $R^e$, and 5-15 membered heteroaryl optionally substituted by 1-15 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

166. A compound for use or a method according to any one of paragraphs 161 to 165, wherein $R^2$ is selected from N$R^cR^d$, $C_{1-10}$ alkyl optionally substituted by 1-13 $R^e$, and 3-15 membered heterocycloalkyl optionally substituted by 1-28 $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

167. A compound for use or a method according to any one of paragraphs 161 to 166, wherein $R^2$ is selected from N$R^cR^d$; and

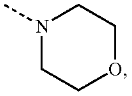,
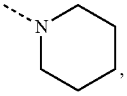,
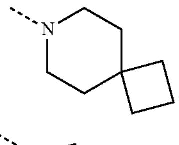,
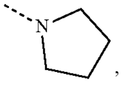, and
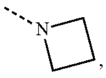, each of which may optionally be substituted with one or more $R^e$. Suitably, $R^c$ is $C_{1-6}$ alkyl, and $R^d$ is independently selected from $C_{3-6}$ cycloalkyl, $C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl.

168. A compound according to any one of paragraphs 161 to 167, or a salt or solvate thereof, wherein $R^2$ is selected from

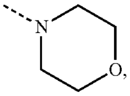 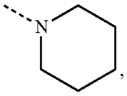, 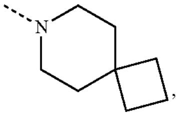,
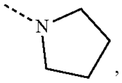, and 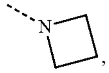, each of which may optionally be substituted with one or more $R^e$.

169. A compound according to any one of paragraphs 161 to 168, or a salt or solvate thereof, wherein $R^2$ is selected from

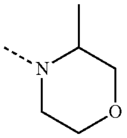 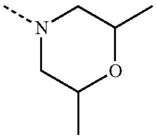, 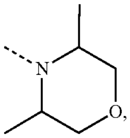
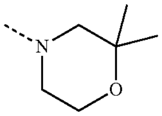 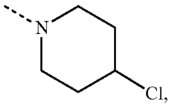
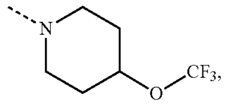 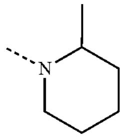,
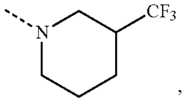, 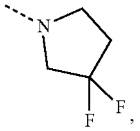,
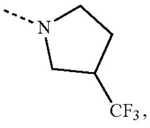 and 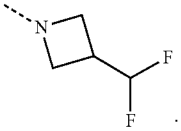.

170. A compound for use or a method according to any one of paragraphs 161 to 169, wherein each $R^e$ is independently selected from fluoro, chloro, CN, $CF_3$, $OCF_3$, and methyl.

171. A compound for use or a method according to any one of paragraphs 161 to 170, wherein $R^c$ and $R^d$ are independently selected from $C_{1-6}$ alkyl.

172. A compound for use or a method according to any one of paragraphs 161 to 171, wherein the compound is selected from:

(3R)-3-methyl-4-(4-(2-(2-(trifluoromethyl)pyridin-3-yl)azetidin-1-yl)pyrido[2,3-d]pyrimidin-2-yl)morpholine 2-(3-(difluoromethyl)azetidin-1-yl)-N-((2-(trifluoromethyl)pyridin-3-yl)methyl)pyrido[2,3-d]pyrimidin-4-amine 2-((2R,3R)-2,3-dimethylmorpholino)-N-((2-(trifluoromethyl)pyridin-3-yl)methyl)pyrido[2,3-d]pyrimidin-4-amine 2-(3-isopropylmorpholino)-N-((2-(trifluoromethyl)pyridin-3-yl)methyl)pyrido[2,3-d]pyrimidin-4-amine N-(2-(trifluoromethyl)benzyl)-2-(3-(trifluoromethyl)pyrrolidin-1-yl)pyrido[2,3-d]pyrimidin-4-amine 2-(2,2-difluoro-7-azaspiro[3.5]nonan-7-yl)-N-(2-(trifluoromethyl)benzyl)pyrido[2,3-d]pyrimidin-4-amine 2-(2-oxa-5-azabicyclo[2.2.1]heptan-5-yl)-N-((2-(trifluoromethyl)pyridin-3-yl)methyl)pyrido[2,3-d]pyrimidin-4-amine 2-(3-cyclopropylmorpholino)-N-((2-(trifluoromethyl)pyridin-3-yl)methyl)pyrido[2,3-d]pyrimidin-4-amine 1-(4-(((2-(trifluoromethyl)pyridin-3-yl)methyl)amino)pyrido[2,3-d]pyrimidin-2-yl)piperidine-3-carbonitrile 1-(4-((2-(trifluoromethyl)benzyl)amino)pyrido[2,3-d]pyrimidin-2-yl)azetidine-3-carbonitrile 2-(4,4-dimethylpiperidin-1-yl)-N-(2-(trifluoromethyl)benzyl)pyrido[2,3-d]pyrimidin-4-amine 2-(3-fluoropyrrolidin-1-yl)-N-((2-(trifluoromethyl)pyridin-3-yl)methyl)pyrido[2,3-d]pyrimidin-4-amine 1-(4-(((2-(trifluoromethyl)pyridin-3-yl)methyl)amino)pyrido[2,3-d]pyrimidin-2-yl)piperidine-4-carbonitrile 2-(3-(trifluoromethyl)azetidin-1-yl)-4-(2-(2-(trifluoromethyl)pyridin-3-yl)azetidin-1-yl)pyrido[2,3-d]pyrimidine 3-methyl-4-(4-(2-(2-(trifluoromethyl)pyridin-3-yl)azetidin-1-yl)pyrido[2,3-d]pyrimidin-2-yl)morpholine (S)-2-(3-methylmorpholino)-N-((2-(trifluoromethyl)pyridin-3-yl)methyl)pyrido[2,3-d]pyrimidin-4-amine 2-(3-(trifluoromethyl)azetidin-1-yl)-N-((2-(trifluoromethyl)pyridin-3-yl)methyl)pyrido[2,3-d]pyrimidin-4-amine 2-(4-chloropiperidin-1-yl)-N-((2-(trifluoromethyl)pyridin-3-yl)methyl)pyrido[2,3-d]pyrimidin-4-amine 2-(4-chloropiperidin-1-yl)-N-(2-(trifluoromethyl)benzyl)pyrido[2,3-d]pyrimidin-4-amine $N^2$-isopropyl-$N^4$-((2-(trifluoromethyl)pyridin-3-yl)methyl)pyrido[2,3-d]pyrimidine-2,4-diamine methanesulfonate 2-(4,4-difluoropiperidin-1-yl)-N-((2-(trifluoromethyl)pyridin-3-yl)methyl)pyrido[2,3-d]pyrimidin-4-amine 2-(4-fluoropiperidin-1-yl)-N-((2-(trifluoromethyl)pyridin-3-yl)methyl)pyrido[2,3-d]pyrimidin-4-amine 2-(3,3-difluoropyrrolidin-1-yl)-N-((2-(trifluoromethyl)pyridin-3-yl)methyl)pyrido[2,3-d]pyrimidin-4-amine methanesulfonate 2-(3,3-difluoropyrrolidin-1-yl)-N-((2-(trifluoromethyl)pyridin-3-yl)methyl)pyrido[2,3-d]pyrimidin-4-amine 2-(3-methylmorpholino)-N-((2-(trifluoromethyl)pyridin-3-yl)methyl)pyrido[2,3-d]pyrimidin-4-amine methanesulfonate 2-(3-methylmorpholino)-N-((2-(trifluoromethyl)pyridin-3-yl)methyl)pyrido[2,3-d]pyrimidin-4-amine N-isopropyl-4-(2-(2-(trifluoromethyl)phenyl)azetidin-1-yl)pyrido[2,3-d]pyrimidin-2-amine $N^2$-cyclopropyl-$N^2$-methyl-$N^4$-((2-(trifluoromethyl)pyridin-3-yl)methyl)pyrido[2,3-d]pyrimidine-2,4-diamine 2-(2,2-dimethylazetidin-1-yl)-N-((2-(trifluoromethyl)pyridin-3-yl)methyl)pyrido[2,3-d]pyrimidin-4-amine $N^2$-(tert-butyl)-$N^4$-((2-(trifluoromethyl)pyridin-3-yl)methyl)pyrido[2,3-d]pyrimidine-2,4-diamine $N^2$-isopropyl-$N^2$,$N^4$-dimethyl-$N^4$-((2-(trifluoromethyl)pyridin-3-yl)methyl)pyrido[2,3-d]pyrimidine-2,4-diamine $N^2$-cyclopropyl-$N^4$-((2-(trifluoromethyl)pyridin-3-yl)methyl)pyrido[2,3-d]pyrimidine-2,4-diamine methanesulfonate $N^2$-cyclopropyl-$N^4$-((2-(trifluoromethyl)pyridin-3-yl)methyl)pyrido[2,3-d]pyrimidine-2,4-diamine $N^2$-cyclopropyl-$N^4$-(2-(trifluoromethyl)benzyl)pyrido[2,3-d]pyrimidine-2,4-diamine N,2-dimethyl-N-(1-(2-(trifluoromethyl)phenyl)ethyl)thieno[3,2-d]pyrimidin-4-amine N-ethyl-N-(2-(trifluoromethyl)benzyl)thieno[3,2-d]pyrimidin-4-amine $N^2$-isopropyl-N4-(1-(2-(trifluoromethyl)phenyl)ethyl)thieno[3,2-d]pyrimidine-2,4-diamine 2-chloro-N-methyl-N-(2-(trifluoromethyl)benzyl)thieno[3,2-d]pyrimidin-4-amine
$N^2$-isopropyl-$N^4$-(2-(trifluoromethyl)benzyl)pyrido[2,3-d]pyrimidine-2,4-diamine methanesulfonate
$N^2$-isopropyl-$N^4$-(2-(trifluoromethyl)benzyl)pyrido[2,3-d]pyrimidine-2,4-diamine
$N^2$-isopropyl-$N^2$-methyl-$N^4$-((2-(trifluoromethyl)pyridin-3-yl)methyl)pyrido[2,3-d]pyrimidine-2,4-diamine
$N^2$-isopropyl-$N^2$-methyl-$N^4$-((2-(trifluoromethyl)pyridin-3-yl)methyl)pyrido[2,3-d]pyrimidine-2,4-diamine methanesulfonate
$N^4$-(2-fluoro-6-(trifluoromethyl)benzyl)-$N^2$-isopropylpyrido[2,3-d]pyrimidine-2,4-diamine
2-(2-methylazetidin-1-yl)-N-((2-(trifluoromethyl)pyridin-3-yl)methyl)pyrido[2,3-d]pyrimidin-4-amine
2-(pyrrolidin-1-yl)-N-((2-(trifluoromethyl)pyridin-3-yl)methyl)pyrido[2,3-d]pyrimidin-4-amine
N-isopropyl-N-methyl-4-(2-(2-(trifluoromethyl)phenyl)azetidin-1-yl)pyrido[2,3-d]pyrimidin-2-amine
2-(4,4-difluoropiperidin-1-yl)-N-(2-(trifluoromethyl)benzyl)pyrido[2,3-d]pyrimidin-4-amine
3-methyl-4-(4-(2-(2-(trifluoromethyl)phenyl)azetidin-1-yl)pyrido[2,3-d]pyrimidin-2-yl)morpholine
2-(4,4-difluoropiperidin-1-yl)-4-(2-(2-(trifluoromethyl)pyridin-3-yl)azetidin-1-yl)pyrido[2,3-d]pyrimidine
2-(3,3-difluoropyrrolidin-1-yl)-4-(2-(2-(trifluoromethyl)pyridin-3-yl)azetidin-1-yl)pyrido[2,3-d]pyrimidine
2-(4-(trifluoromethyl)piperidin-1-yl)-N-((2-(trifluoromethyl)pyridin-3-yl)methyl)pyrido[2,3-d]pyr-imidin-4-amine
2-(2,2-dimethylmorpholino)-N-((2-(trifluoromethyl)pyridin-3-yl)methyl)pyrido[2,3-d]pyrimidin-4-amine
2-(3,3-dimethylmorpholino)-N-((2-(trifluoromethyl)pyridin-3-yl)methyl)pyrido[2,3-d]pyrimidin-4-amine
2-(2-methylmorpholino)-N-((2-(trifluoromethyl)pyridin-3-yl)methyl)pyrido[2,3-d]pyrimidin-4-amine
2-(2-methylmorpholino)-N-(2-(trifluoromethyl)benzyl)pyrido[2,3-d]pyrimidin-4-amine
4-methyl-1-(4-(((2-(trifluoromethyl)pyridin-3-yl)methyl)amino)pyrido[2,3-d]pyrimidin-2-yl)piperidine-4-carbonitrile
2-(2,2-difluoro-7-azaspiro[3.5]nonan-7-yl)-N-((2-(trifluoromethyl)pyridin-3-yl)methyl)pyrido[2,3-d]pyrimidin-4-amine
2-(2,2-difluoro-7-azaspiro[3.5]nonan-7-yl)-N-((2-(trifluoromethyl)pyridin-3-yl)methyl)pyrido[2,3-d]pyrimidin-4-amine methanesulfonate
2-(2-(trifluoromethyl)piperidin-1-yl)-N-((2-(trifluoromethyl)pyridin-3-yl)methyl)pyrido[2,3-d]pyrimidin-4-amine
2-(2,2-difluoro-7-azaspiro[3.5]nonan-7-yl)-N-(2-(trifluoromethyl)benzyl)pyrido[2,3-d]pyrimidin-4-amine
1-(4-((2-(trifluoromethyl)benzyl)amino)pyrido[2,3-d]pyrimidin-2-yl)piperidine-3-carbonitrile
2-((2S,5R)-2,5-dimethylmorpholino)-N-((2-(trifluoromethyl)pyridin-3-yl)methyl)pyrido[2,3-d]pyrimidin-4-amine
2-(6-oxa-9-azaspiro[4.5]decan-9-yl)-N-((2-(trifluoromethyl)pyridin-3-yl)methyl)pyrido[2,3-d]pyrimidin-4-amine
2-((3R)-3,5-dimethylmorpholino)-N-((2-(trifluoromethyl)pyridin-3-yl)methyl)pyrido[2,3-d]pyrimidin-4-amine
2-(2-cyclopropylmorpholino)-N-((2-(trifluoromethyl)pyridin-3-yl)methyl)pyrido[2,3-d]pyrimidin-4-amine
2-((2S,5S)-2,5-dimethylmorpholino)-N-((2-(trifluoromethyl)pyridin-3-yl)methyl)pyrido[2,3-d]pyrimidin-4-amine
(R)-2-(3-(difluoromethoxy)pyrrolidin-1-yl)-N-((2-(trifluoromethyl)pyridin-3-yl)methyl)pyrido[2,3-d]pyrimidin-4-amine
(S)-2-(3-(difluoromethoxy)pyrrolidin-1-yl)-N-((2-(trifluoromethyl)pyridin-3-yl)methyl)pyrido[2,3-d]pyrimidin-4-amine
2-(2-(difluoromethyl)morpholino)-N-((2-(trifluoromethyl)pyridin-3-yl)methyl)pyrido[2,3-d]pyrimidin-4-amine
4-(4-((2-(trifluoromethyl)benzyl)amino)pyrido[2,3-d]pyrimidin-2-yl)morpholine-2-carbonitrile
2-((2R,3S)-2,3-dimethylmorpholino)-N-((2-(trifluoromethyl)pyridin-3-yl)methyl)pyrido[2,3-d]pyrimidin-4-amine
(3S)-3-methyl-4-(4-(2-(2-(trifluoromethyl)pyridin-3-yl)azetidin-1-yl)pyrido[2,3-d]pyrimidin-2-yl)morpholine
(3R)-3-methyl-4-(4-(2-(2-(trifluoromethyl)phenyl)azetidin-1-yl)pyrido[2,3-d]pyrimidin-2-yl)morpholine
(3S)-3-methyl-4-(4-(2-(2-(trifluoromethyl)phenyl)azetidin-1-yl)pyrido[2,3-d]pyrimidin-2-yl)morpholine
2-(2-oxa-5-azabicyclo[4.1.0]heptan-5-yl)-N-((2-(trifluoromethyl)pyridin-3-yl)methyl)pyrido[2,3-d]pyrimidin-4-amine
2-(2-oxa-5-azabicyclo[4.1.0]heptan-5-yl)-N-(2-(trifluoromethyl)benzyl)pyrido[2,3-d]pyrimidin-4-amine
(S)-2-(3-methylmorpholino)-N-(2-(trifluoromethyl)benzyl)pyrido[2,3-d]pyrimidin-4-amine
(S)-2-(3-methylmorpholino)-N-(2-(trifluoromethyl)benzyl)pyrido[2,3-d]pyrimidin-4-amine methanesulfonate
2-(4-chloropiperidin-1-yl)-4-(2-(2-(trifluoromethyl)pyridin-3-yl)azetidin-1-yl)pyrido[2,3-d]pyrimidine
N-((2-(trifluoromethyl)pyridin-3-yl)methyl)-2-(3-(trifluoromethyl)pyrrolidin-1-yl)pyrido[2,3-d]pyrimidin-4-amine
2-(2,2-dimethylmorpholino)-N-(2-(trifluoromethyl)benzyl)pyrido[2,3-d]pyrimidin-4-amine
2-(4-oxa-7-azaspiro[2.5]octan-7-yl)-N-((2-(trifluoromethyl)pyridin-3-yl)methyl)pyrido[2,3-d]pyrimidin-4-amine
2-(3-(fluoromethyl)piperidin-1-yl)-N-((2-(trifluoromethyl)pyridin-3-yl)methyl)pyrido[2,3-d]pyri-midin-4-amine
(2-(trifluoromethyl)pyridin-3-yl)metha 4-methyl-1-(4-((2-(trifluoromethyl)benzyl)amino)pyrido[2,3-d]pyrimidin-2-yl)piperidine-4-carbonitrile
N-((2-(trifluoromethyl)pyridin-3-yl)methyl)-2-(2-(trifluoromethyl)pyrrolidin-1-yl)pyrido[2,3-d]pyrimidin-4-amine
2-(3-chloropyrrolidin-1-yl)-N-((2-(trifluoromethyl)pyridin-3-yl)methyl)pyrido[2,3-d]pyrimidin-4-amine
2-(2-oxa-5-azabicyclo[2.2.1]heptan-5-yl)-N-(2-(trifluoromethyl)benzyl)pyrido[2,3-d]pyrimidin-4-amine
2-(4-(trifluoromethoxy)piperidin-1-yl)-N-((2-(trifluoromethyl)pyridin-3-yl)methyl)pyrido[2,3-d]pyrimidin-4-amine
2-(4-(trifluoromethoxy)piperidin-1-yl)-N-((2-(trifluoromethyl)pyridin-3-yl)methyl)pyrido[2,3-d]pyrimidin-4-amine methanesulfonate
2-(3-(difluoromethyl)azetidin-1-yl)-N-(2-(trifluoromethyl)benzyl)pyrido[2,3-d]pyrimidin-4-amine
2-(2-(difluoromethyl)morpholino)-N-(2-(trifluoromethyl)benzyl)pyrido[2,3-d]pyrimidin-4-amine
2-(4-azaspiro[2.5]octan-4-yl)-N-((2-(trifluoromethyl)pyridin-3-yl)methyl)pyrido[2,3-d]pyrimidin-4-amine
2-(3-(trifluoromethoxy)pyrrolidin-1-yl)-N-((2-(trifluoromethyl)pyridin-3-yl)methyl)pyrido[2,3-d]pyrimidin-4-amine
2-(5-azaspiro[3.4]octan-5-yl)-N-((2-(trifluoromethyl)pyridin-3-yl)methyl)pyrido[2,3-d]pyrimidin-4-amine 2-(2-((trifluoromethoxy)methyl)pyrrolidin-1-yl)-N-((2-(trifluoromethyl)pyridin-3-yl)methyl)pyrido[2,3-d]pyrimidin-4-amine 2-(6-oxa-3-azabicyclo[3.1.1]heptan-3-yl)-N-(2-(trifluoromethyl)benzyl)pyrido[2,3-d]pyrimidin-4-amine 2-((3R)-3,5-dimethylmorpholino)-N-(2-(trifluoromethyl)benzyl)pyrido[2,3-d]pyrimidin-4-amine.

173. A compound for use according to any one of paragraphs 81 to 88 when $X^1$, $X^2$ and $X^3$ are CH, $R^4$ is not Cl.

174. A method according to any one of paragraphs 89 to 96 wherein when $X^1$, $X^2$ and $X^3$ are CH, $R^4$ is not Cl.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and II are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I may exist in solvated as well as unsolvated forms such as, for example, hydrated forms. It is to be understood that the invention encompasses all such solvated forms that possess antiproliferative activity.

Polymorphs

It is also to be understood that certain compounds of the Formula I may exhibit polymorphism, and that the invention encompasses all such forms that possess antiproliferative activity.

N-Oxides

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I may exist in a number of different tautomeric forms and references to compounds of the Formula I include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

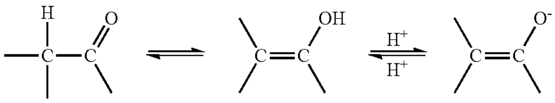

keto enol enolate

Isomers

Compounds that have the same molecular formula but differ in the nature or sequence of bonding of their atoms or the arrangement of their atoms in space are termed “isomers”. Isomers that differ in the arrangement of their atoms in space are termed “stereoisomers”. Stereoisomers that are not mirror images of one another are termed “diastereomers” and those that are non-superimposable mirror images of each other are termed “enantiomers”. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a “racemic mixture”.

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents: — a) *Methods in Enzymoloqy*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 “Design and Application of Pro-drugs”, by H. Bundgaard p. 113-191 (1991);
d) H. Bundgaard, *Advanced Drug Delivery Reviews,* 8, 1-38 (1992);
e) H. Bundgaard, et al., *Journal of Pharmaceutical Sciences,* 77, 285 (1988);
f) N. Kakeya, et al., *Chem. Pharm. Bull.,* 32, 692 (1984);
g) T. Higuchi and V. Stella, “Pro-Drugs as Novel Delivery Systems”, A.C.S. Symposium Series, Volume 14; and
h) E. Roche (editor), “Bioreversible Carriers in Drug Design”, Pergamon Press, 1987.

A suitable pharmaceutically acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I that possesses a carboxy group is, for example, an in vivo cleavable amide thereof, for example an amide formed with an amine such as ammonia, a $C_{1-4}$alkylamine such as methylamine, a $(C_{1-4}alkyl)_2$amine such as dimethylamine, N-ethyl-N-methylamine or diethylamine, a $C_{1-4}$ alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I may be exerted in part by one or more metabolites that are formed within the human or animal body after administration of a compound of the Formula 1. As stated hereinbefore, the in vivo effects of a compound of the Formula I may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In another aspect, the present invention provides a compound of Formula I or II as defined herein, or a pharmaceutically acceptable salt or solvate thereof, or a pharmaceutical composition as defined herein, for use in therapy.

In another aspect, the present invention provides a compound of Formula I or II as defined herein, or a pharmaceutically acceptable salt or solvate thereof, or a pharmaceutical composition as defined herein, for use in the treatment or prevention of a filarial worm infection.

In another aspect, the present invention provides a compound of Formula I or II as defined herein, or a pharmaceutically acceptable salt or solvate thereof, or a pharmaceutical composition as defined herein, for use in the treatment or prevention of a disease or condition mediated by a filarial worm infection.

In another aspect, the present invention provides a compound of Formula I or II as defined herein, or a pharmaceutically acceptable salt or solvate thereof, or a pharmaceutical composition as defined herein, for use in the treatment of a microbial infection.

In one embodiment, the present invention provides a compound of Formula I or II as defined herein, or a pharmaceutically acceptable salt or solvate thereof, or a pharmaceutical composition as defined herein, for use in the treatment of filariasis, suitably lymphatic filariasis, or onchocerciasis.

In another aspect, the present invention provides the use of a compound of Formula I or II as defined herein, or a pharmaceutically acceptable salt or solvate thereof, in the manufacture of a medicament for the treatment or prevention of a filarial worm infection.

In another aspect, the present invention provides the use of a compound of Formula I or II as defined herein, or a pharmaceutically acceptable salt or solvate thereof, in the manufacture of a medicament for the treatment or prevention of a disease or condition mediated by a filarial worm infection.

In another aspect, the present invention provides the use of a compound of Formula I or II as defined herein, or a pharmaceutically acceptable salt or solvate thereof, in the manufacture of a medicament for the treatment of a microbial infection.

In another aspect, the present invention provides a method of treating or preventing a filarial worm infection, said method comprising administering to a subject in need thereof an effective amount of a compound of Formula I or II as defined herein, or a pharmaceutically acceptable salt or solvate thereof.

In another aspect, the present invention provides a method of treating or preventing a disease mediated by a filarial worm infection, said method comprising administering to a subject in need thereof an effective amount of a compound of Formula I or II as defined herein, or a pharmaceutically acceptable salt or solvate thereof.

In another aspect, the present invention provides a method of treating a microbial infection, said method comprising administering to a subject in need thereof a therapeutically effective amount of a compound of Formula I or II as defined herein, or a pharmaceutically acceptable salt or solvate thereof, or a pharmaceutical composition as defined herein.

In each of the above aspects or embodiments, the subject or patient treated is suitably a carrier of a filarial worm infection. In each of the above aspects or embodiments, the subject or patient treated is suitably a human.

In another aspect, the present invention provides a combination comprising a compound of Formula I or II, or a pharmaceutically acceptable salt or solvate thereof, as defined herein, with one or more additional therapeutic agents.

In each of the above aspects, in one embodiment, the infection is with one or more filarial worms selected from *Wuchereria bancrofti, Brugia malayi, Brugia timori* and *Onchocerca volvulus.*

In each of the above aspects, in another embodiment, the infection is with one or more filarial worms selected from *Wuchereria bancrofti, Brugia malayi* and *Brugia timori.*

In each of the above aspects, in another embodiment, the infection is with one or more filarial worms selected from *Onchocerca volvulus.*

In each of the above aspects, in one embodiment, the disease or condition is mediated by a filarial worm infection with one or more filarial worms selected from *Wuchereria bancrofti, Brugia malayi, Brugia timori* and *Onchocerca volvulus.*

In each of the above aspects, in another embodiment, the disease or condition is mediated by a filarial worm infection with one or more filarial worms selected from *Wuchereria bancrofti, Brugia malayi* and *Brugia timori.*

In each of the above aspects, in another embodiment, the disease or condition is mediated by a filarial worm infection with one or more filarial worms selected from *Onchocerca volvulus.*

In each of the above aspects, in another embodiment, the disease or condition is filariasis, suitably lymphatic filariasis.

In each of the above aspects, in another embodiment, the disease or condition is selected from onchocerciasis or lymphatic filariasis.

In each of the above aspects, in one embodiment, the microbial infection is a bacterial infection.

In each of the above aspects, in another embodiment, the microbial infection is *Wolbachia* infection.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein.

These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Synthesis and Characterisation $^1H$ Nuclear Magnetic Resonance spectra were recorded on Bruker (300, 400 or 500 MHz) NMR spectrometers. Data analysis are reported as follows: chemical shift relative to TMS (δ, ppm), multiplicity (s=singlet, d=doublet, t=triplet, m=multiplet), coupling constant (J, Hz), integration.

High resolution mass spectrometry (HRMS) was recorded on a VG analytical 7070E machine and Fisons TRIO spectrometers using electron ionisation (EI) and chemical ionisation (CI). LCMS was performed and recorded on Agilent 1200\G6110A or 1100\G1956A (LC) and SHIMADZU LCMS-2020 (MS) using electron spread ionisation (ESI). Data was reported as follows: (ionization method) main peak shift.

General synthetic route 1 (Route 1)

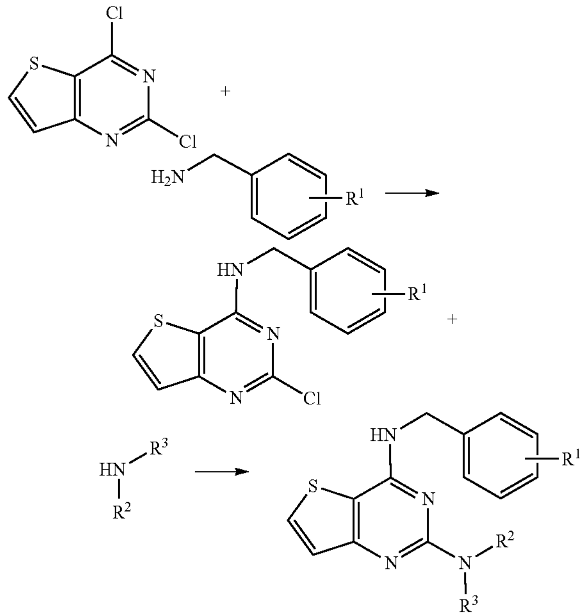

Example 1

Preparation of 2-chloro-N-(2-(trifluoromethyl)benzyl)thieno[3,2-d]pyrimidin-4-amine

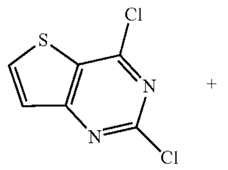

-continued

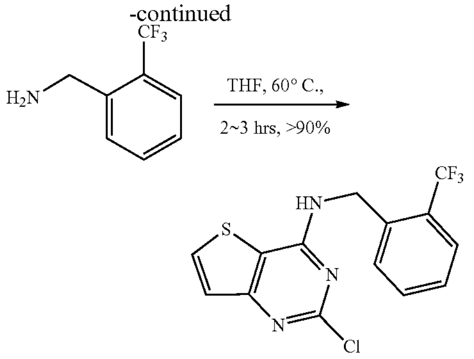

To a suspension of 2,4-dichlorothieno[3,2-d]pyrimidine (205 mg, 1.0 mmol) in THF (5 ml), 2-(trifluoromethyl)-benzylamine (214 mg, 0.17 ml, 1.2 mmol, 1.2 eq) and triethylamine (0.28 ml, 2.0 mmol, 2.0 eq) were added. The resulting mixture was heated to 6500 for 3 hours. After cooled down to room temperature, ice-water (50 ml) was added to the reaction mixture, and the resulting mixture was kept stirring for 5~10 min. The precipitation was collected by filtration, washed with water and redissolved with EtOAc. The solution was dried with $MgSO_4$, and concentrated under vacuum to give the product 2-chloro-N-(2-(trifluoromethyl)benzyl)thieno[3,2-d]pyrimidin-4-amine (330 mg, >95%) as a pale yellow solid. The product was used directly in the next step without any further purification.

Preparation of $N^2$-isopropyl-$N^4$-(2-(trifluoromethyl)benzyl)thieno[3,2-d]pyrimidine-2,4-diamine

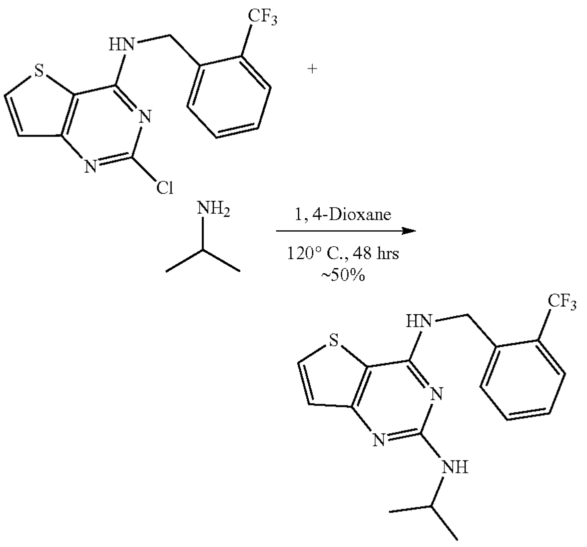

To the suspension of 2-chloro-N-(2-(trifluoromethyl)benzyl)thieno[3,2-d]pyrimidin-4-amine (330 mg) in 1,4-dioxane (5 ml), isopropylamine (0.60 g, 0.87 ml, 10 mmol, 10 eq.) was heated to 120° C. in seal-tube for 48 hours. After that, 1,4-dioxane and the excess isopropylamine was removed under vacuum. The residue was purified by flash column chromatograph eluting with 5-10% MeOH in DCM to give the product $N^2$-isopropyl-$N^4$-(2-(trifluoromethyl)benzyl)thieno[3,2-d]pyrimidine-2,4-diamine (175 mg, 48%) as an off-white solid.

General synthetic route 2 (Route 2)

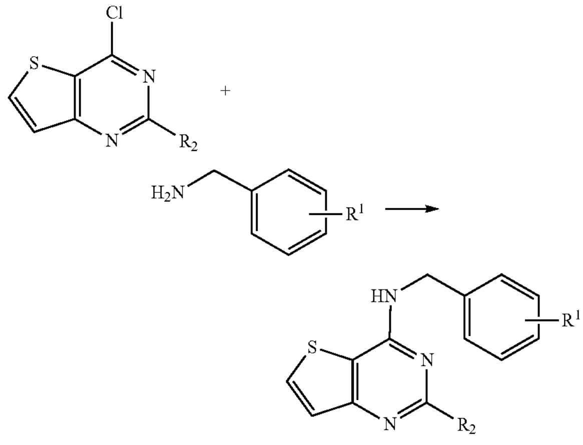

Example 2

Preparation of 2-methyl-N-(2-(trifluoromethyl)benzyl)thieno[3,2-d]pyrimidin-4-amine

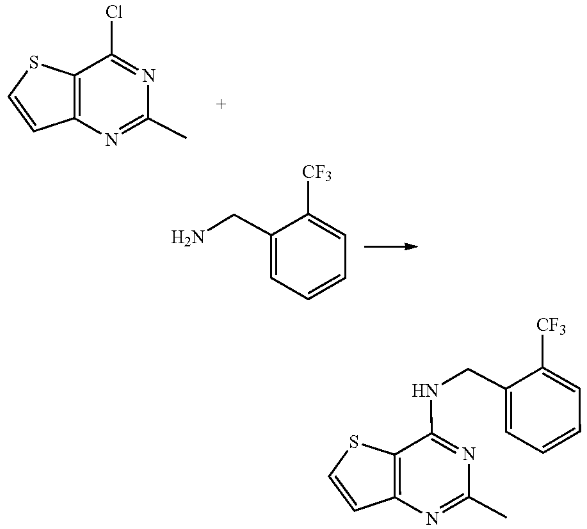

To a suspension of 4-chloro-2-methylthieno[3,2-d]pyrimidine (185 mg, 1.0 mmol) in THF (5 ml), 2-(trifluoromethyl)-benzylamine (214 mg, 0.17 ml, 1.2 mmol, 1.2 eq) and triethylamine (0.28 ml, 2.0 mmol, 2.0 eq) were added. The resulting mixture was heated to 75° C. for 36 hours. After cooled down to room temperature, ice-water (50 ml) was added to the reaction mixture, and the resulting mixture was kept stirring for 5-10 min. The precipitation was collected by filtration, washed with water and redissolved with EtOAc. The solution was dried with $MgSO_4$, and concentrated under vacuum to give the crude product. The crude was further purified by flash column chromatograph to give the product 2-methyl-N-(2-(trifluoromethyl)benzyl)thieno[3,2-d]pyrimidin-4-amine (150 mg, 46%) as a pale yellow solid.

General synthetic route 3 (Route 3)

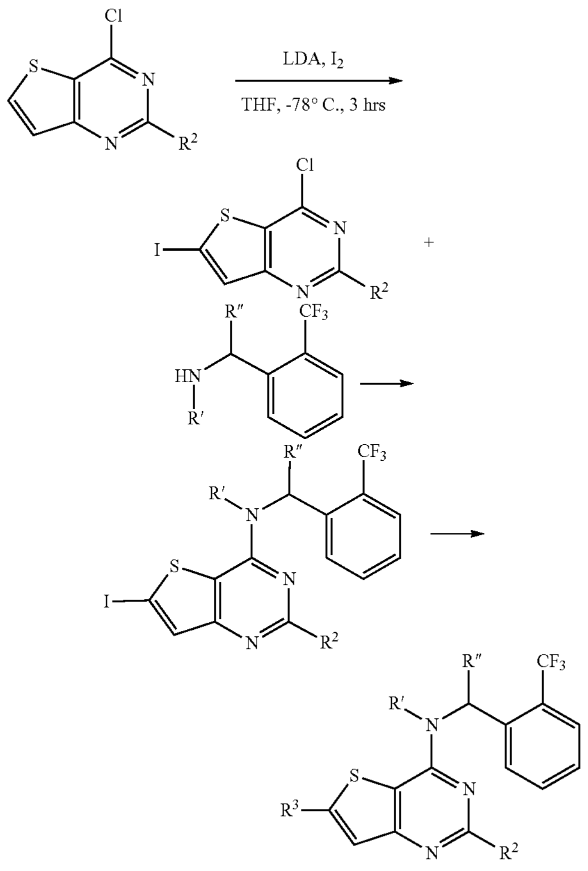

Example 3

Preparation of 4-chloro-6-iodothieno[3,2-d]pyrimidine

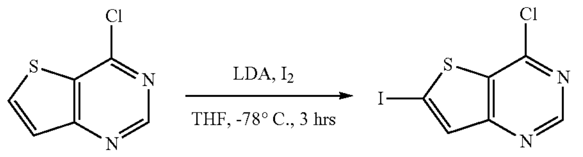 [SMILES: Clc1ncnc2ccsc12 ; Clc1ncnc2cc(I)sc12]

The reaction was performed in anhydrous conditions and under nitrogen. 4-chlorothieno[3,2-d]pyrimidine (5 mmol, 850 mg) was dissolved in anhydrous THF (25 ml) in a 100 ml round bottomed flask. The mixture was cooled with dry-ice/acetone bath for 10 minutes. LDA 2M (1.2 eq, 6 mmol, in THF) was added drop-wise to the mixture. The mixture was left to react for half an hour. $I_2$ (1.3 eq, 6.5 mmol) was dissolved in anhydrous THF (10 ml) and the mixture was slowly added to the reaction. After an hour the cold bath was removed and the mixture was left to stir for 2 more hours. Work up: $H_2O$ (2 ml) was added to quench the reaction. The solvent was removed to dryness. $H_2O$ (100 ml) was added to the residue and the mixture was stirred for 30 minutes. The precipitate was collected through filtration. The solid was washed with a $Na_2S_2O_3$ solution to remove the excess $I_2$. Purification: the product was dissolved in DCM and purified by silica filtration (5% EtOAc in DCM, 10% EtOAc in DCM). Product: 4-chloro-6-iodothieno[3,2-d]pyrimidine, 0.85 g, yield=57%, white solid. $^1$H NMR (400 MHz, DMSO) δ 8.97 (s, 1H), 8.14 (s, 1H).

Preparation of 6-iodo-N-(1-(2-(trifluoromethyl)phenyl)ethyl)thieno[3,2-d]pyrimidin-4-amine

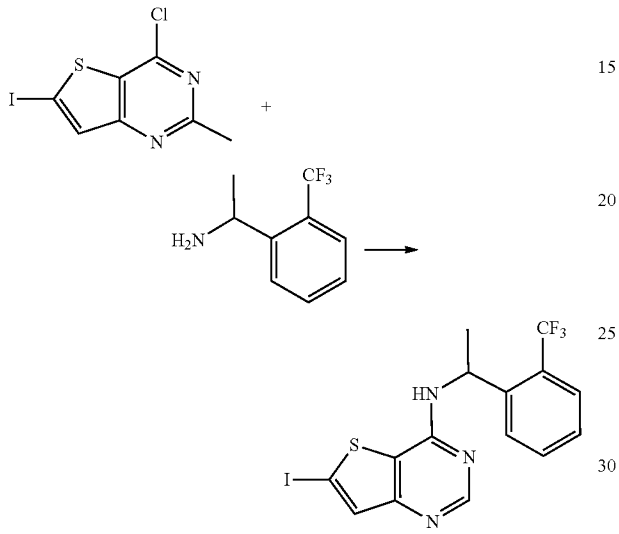

The reaction was performed under nitrogen atmosphere. 4-chloro-6-iodothieno[3,2-d]pyrimidine (2.7 mmol, 800 mg), diisopropylethylamine (2 eq, 0.94 ml), α-methyl-2-trifluoromethylbenzylamine (1.2 eq, 620 mg) and 1-butanol (15 ml) were placed in a sealed tube and heated to 110° C. overnight. The solvent was evaporated in vacuo. Purification: the product was purified by flash column chromatography (2% EtOAc in DCM). Product: 6-iodo-N-(1-(2-(trifluoromethyl)phenyl)ethyl)thieno[3,2-d]pyrimidin-4-amine, 1.00 g, yield=81%, pale yellow solid. $^1$H NMR (400 MHz, CDCl3) δ 8.46 (s, 1H), 7.69 (d, J=7.8 Hz, 1H), 7.60 (d, J=7.4 Hz, 2H), 7.54 (t, J=7.5 Hz, 1H), 7.38 (t, J=7.6 Hz, 1H), 5.81 (p, J=6.7 Hz, 1H), 4.95 (d, J=5.9 Hz, 1H), 1.65 (d, J=6.7 Hz, 3H).

Preparation of 6-phenyl-N-(1-(2-(trifluoromethyl)phenyl)ethyl)thieno[3,2-d]pyrimidin-4-amine

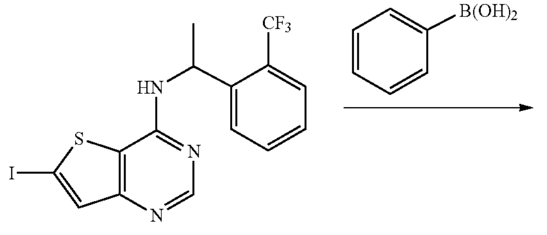

-continued

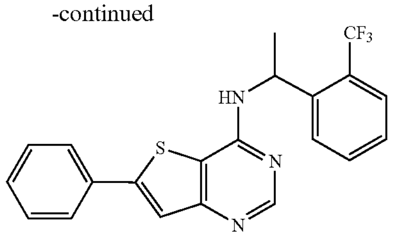

The reaction was performed in anhydrous conditions and under nitrogen atmosphere. 6-iodo-N-(1-(2-(trifluoromethyl)phenyl)ethyl)thieno[3,2-d]pyrimidin-4-amine (1 mmol, 450 mg), phenylboronic acid (1.5 eq, 180 mg), and $K_3PO_4$ (4 eq, 850 mg) were placed in a 50 ml flask. Anhydrous toluene (20 ml) was added. The reaction was degassed using a nitrogen-vacuum line and stirred. $Pd(PPh_3)_4$ (0.05 eq, 60 mg) was added to the mixture. After completion the reaction was left to cool down at room temperature. Purification: the product was purified by silica filtration (50% EtOAc in Hexane) and then by flash column chromatography (30% EtOAc in Hexane). Product: 6-phenyl-N-(1-(2-(trifluoromethyl)phenyl)ethyl)thieno[3,2-d]pyrimidin-4-amine, 0.28 g, yield=70%, pale yellow solid.

General synthetic route 4 (Route 4)

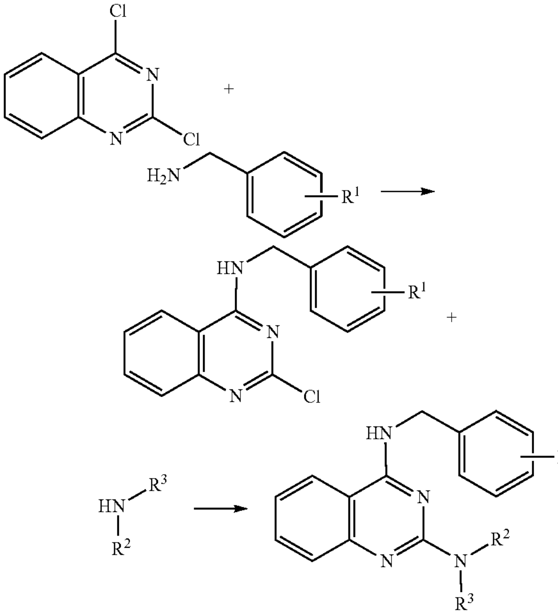

Example 4

Preparation of 2-chloro-N-((2-(trifluoromethyl)pyridin-3-yl)methyl)quinazolin-4-amine

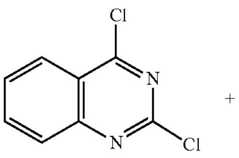

-continued

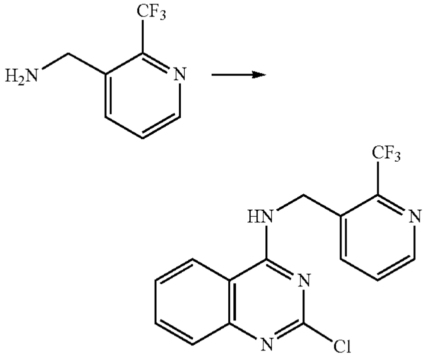

A mixture of [2-(trifluoromethyl)-3-pyridyl]methanamine (176 mg, 1.00 mmol, 1.00 eq), 2,4-dichloroquinazoline (200 mg, 1.00 mmol, 1.00 eq) and $Et_3N$ (202 mg, 2.00 mmol, 2.00 eq) in THF (10.00 mL) was stirred at 10-20° C. for 12 hours. LCMS showed all of 2,4-dichloroquinazoline was consumed and a new peak with desired MS. The mixture was concentrated to give a residue. The residue was triturated with EtOAc (2 mL). 2-chloro-N-[[2-(trifluoromethyl)-3-pyridyl]methyl]quinazolin-4-amine (110 mg, 195 umol, 19% yield, 60% purity) was obtained as a light yellow solid.

Preparation of $N^2$-isopropyl-$N^4$-((2-(trifluoromethyl)pyridin-3-yl)methyl)quinazoline-2,4-diamine

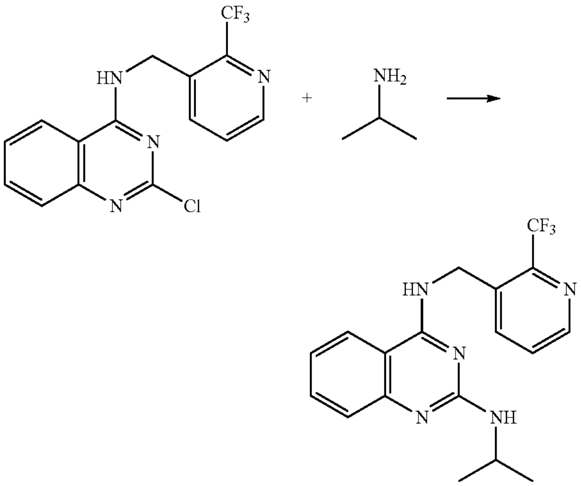

A mixture of propan-2-amine (31 mg, 530 umol, 2.99 eq), 2-chloro-N-[[2-(trifluoromethyl)-3-pyridyl]methyl]quinazolin-4-amine (100 mg, 177 umol, 1.00 eq) and TEA (54 mg, 531 umol, 3.00 eq) in DMSO (2.00 mL) was stirred at 110° C. for 12 hours. LCMS showed all of 2-chloro-N-[[2-(trifluoromethyl)-3-pyridyl]methyl]quinazolin-4-amine was consumed and a new peak with desired MS. TLC (EtOAc/MeOH=15/1) showed all of 2-chloro-N-[[2-(trifluoromethyl)-3-pyridyl]methyl]quinazolin-4-amine was consumed and a new spot. The mixture was diluted with water (10 mL) and extracted with EtOAc (20 mL*3). The organic layer was dried over $Na_2SO_4$ and concentrated to give a residue. The residue was purified by prep-TLC (EtOAc/MeOH=15/1). $N^2$-isopropyl-$N^4$-[[2-(trifluoromethyl)-3-pyridyl]methyl]quinazoline-2,4-diamine (20 mg, 54 umol, 30% yield, 98% purity) was obtained as a light yellow solid.

General synthetic route 5 (Route 5)

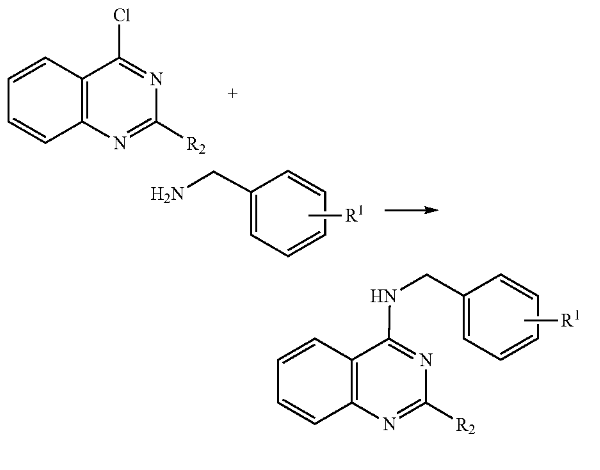

Example 5

Preparation of N-(4-fluoro-2-(trifluoromethyl)benzyl)-2-methylquinazolin-4-amine

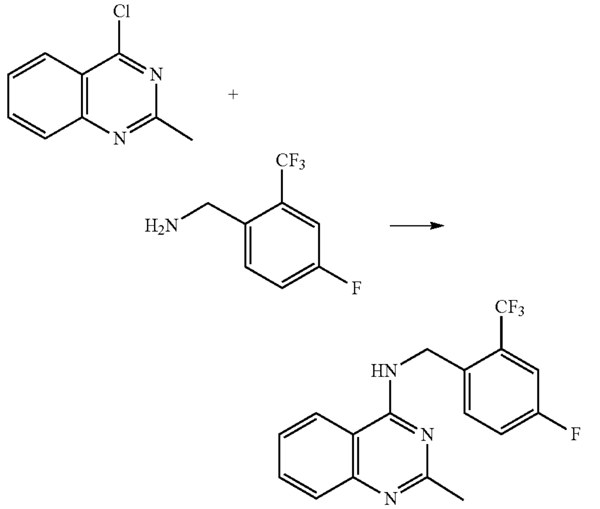

To a suspension of 4-chloro-2-methylquinazoline (188 mg, 1.0 mmol) in nBuOH (5 ml), 4-Fluoro-2-(trifluoromethyl)-benzylamine (239 mg, 1.2 mmol, 1.2 eq) and diisopropylethylamine (0.35 ml, 2.0 mmol, 2.0 eq) were added. The resulting mixture was heated to 120° C. for 12 hours. After cooled down to room temperature, ice-water (50 ml) was added to the reaction mixture, and the resulting mixture was kept stirring for 5-10 min. The precipitation was collected by filtration and dried to give the crude product. The crude was further purified by flash column chromatograph to give the product N-(4-fluoro-2-(trifluoromethyl)benzyl)-2-methylquinazolin-4-amine (170 mg, 50%) as an off-white solid.

General synthetic route 6 (Route 6)

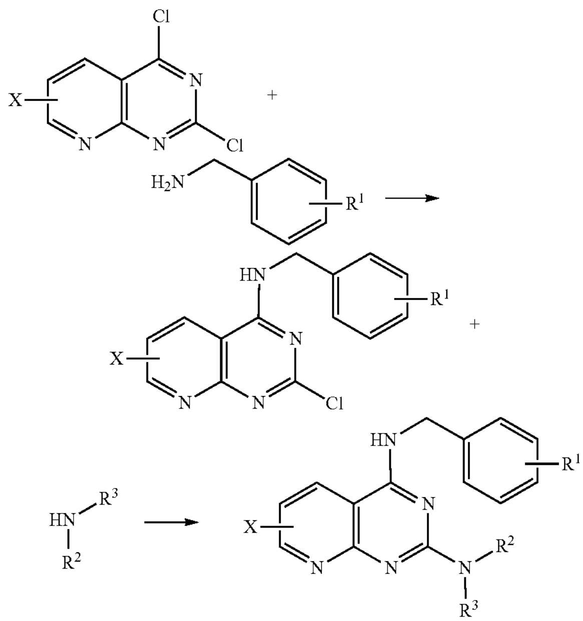

Example 6

Preparation of 2-chloro-N-((2-(trifluoromethyl)pyridin-3-yl)methyl)pyrido[2,3-d]pyrimidin-4-amine

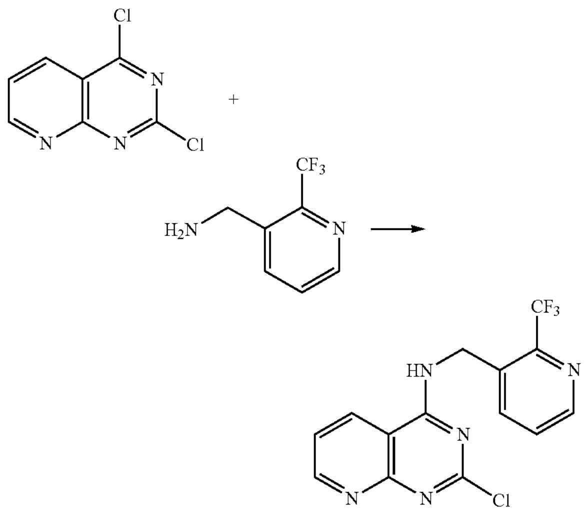

To a mixture of [2-(trifluoromethyl)-3-pyridyl]methanamine (118.00 g, 549.34 mmol, 1.00 eq) and 2,4-dichloropyrido[2,3-d]pyrimidine (109.88 g, 549.34 mmol, 1.00 eq) in THF (200.00 mL) was added TEA (111.17 g, 1.10 mol, 152.29 mL, 2.00 eq) at 0° C. The mixture was stirred at 20° C. for 3 h. TLC (Ethyl acetate:Petroleum ether=2:1) showed a major new spot. The mixture was concentrated to remove half of solvent. The resultant mixture was diluted with $H_2O$ (200 mL), then filtered to collected the yellow solid. The yellow solid was triturated from Ethyl acetate:Petroleum ether (2:1, 30 mL) and dried under high vacuum to give 2-chloro-N-[[2-(trifluoromethyl)-3-pyridyl]methyl]pyrido[2,3-d]pyrimidin-4-amine (161.00 g, 469.21 mmol, 85% yield, 99% purity) as a white solid. 1H NMR (400 MHz, DMSO-d6) δ ppm 9.62 (s, 1H), 9.02 (d, J=2.8 Hz, 1H), 8.78-8.80 (d, J=8.0 Hz, 1H), 8.65-8.66 (d, J=4.0 Hz, 1H), 8.04-8.06 (d, J=8.0 Hz, 1H), 7.61-7.70 (m, 2H), 4.94-4.95 (d, J=4.0 Hz, 1H).

Preparation of 2-(3-methylmorpholino)-N-((2-(trifluoromethyl)pyridin-3-yl)methyl)pyrido[2,3-d]pyrimidin-4-amine

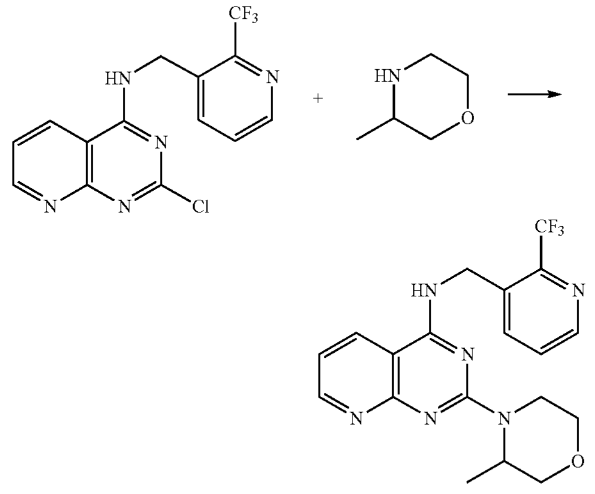

To a mixture of 2-chloro-N-[[2-(trifluoromethyl)-3-pyridyl]methyl]pyrido[2,3-d]pyrimidin-4-amine (14.35 g, 42.24 mmol, 1.00 eq) and DIEA (10.92 g, 84.48 mmol, 14.76 mL, 2.00 eq) in DMSO (150.00 mL) was added 3-methylmorpholine (5.12 g, 50.68 mmol, 1.2 eq). The mixture was stirred at 90° C. for 16 h. LCMS showed a major peak with desired mass. The mixture was diluted with $H_2O$ (300 mL) and the resulted mixture was stirred at 20° C. for 3 h. LCMS showed 88% of a major peak with desired mass. The mixture was filtered to collect the light yellow solid. The light yellow solid was trituration with Petroleum ether:Ethyl acetate (1:1, 50 mL), followed by filtration and the solid was dried under high vacuum to give crude product (16 g). Then the crude product was trituration with MeCN (120.00 mL) at 20° C. for 12 h. The mixture was filtered to collect the solid which was dried under high vacuum to give 2-(3-methylmorpholin-4-yl)-N-[[2-(trifluoromethyl)-3-pyridyl]methyl]pyrido[2,3-d]pyrimidin-4-amine (12.60 g, 30.78 mmol, 78% yield, 98.1% purity) as a light yellow solid.

General synthetic route 7 (Route 7)

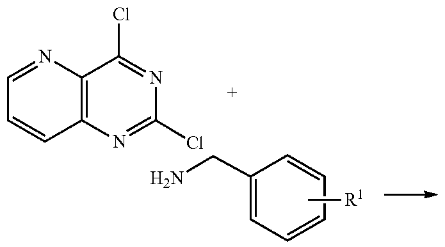

-continued

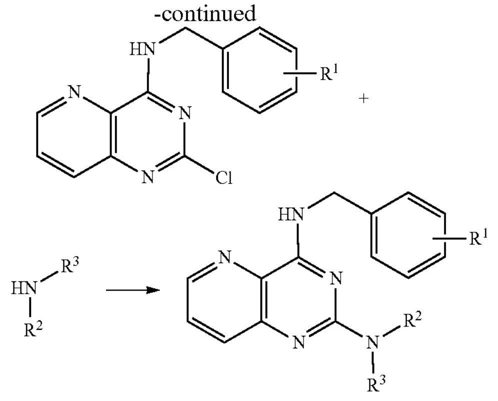

Example 7

Preparation of 2-chloro-N-((2-(trifluoromethyl)pyridin-3-yl)methyl)pyrido[3,2-d]pyrimidin-4-amine

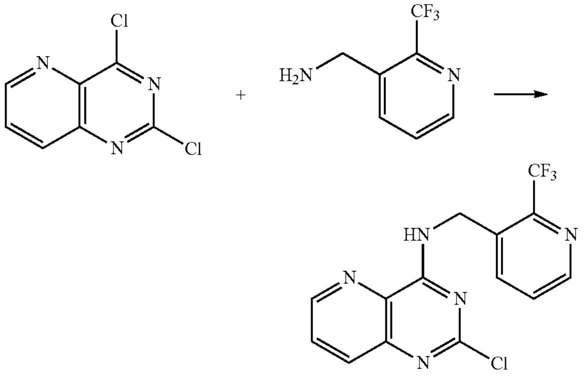

A mixture of [2-(trifluoromethyl)-3-pyridyl]methanamine (132 mg, 750 umol, 1.00 eq), 2,4-dichloropyrido[3,2-d]pyrimidine (150 mg, 750 umol, 1.00 eq) and $Et_3N$ (152 mg, 1.50 mmol, 2.00 eq) in THF (10.00 ml) was stirred at 10-20° C. for 12 hours. LCMS showed all of 2,4-dichloropyrido[3,2-d]pyrimidine was consumed and a new peak with desired MS. The mixture was concentrated to give a residue. The residue was triturated with EtOAc (2 mL). 2-chloro-N-[[2-(trifluoromethyl)-3-pyridyl]methyl]pyrido[3,2-d]pyrimidin-4-amine (120 mg, 177 umol, 23% yield, 50% purity) was obtained as an off-white solid.

Preparation of $N^2$-isopropyl-$N^4$-((2-(trifluoromethyl)pyridin-3-yl)methyl)pyrido[3,2-d]pyrimidine-2,4-diamine

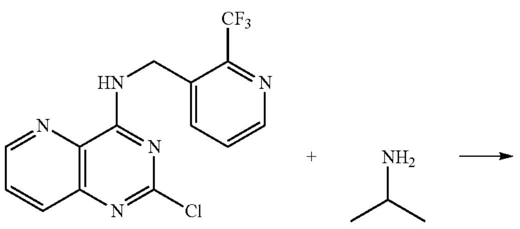

-continued

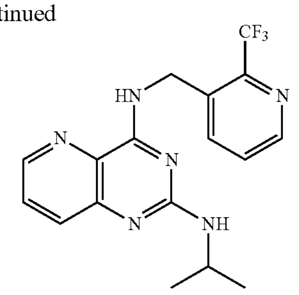

A mixture of propan-2-amine (31 mg, 530 umol, 3.00 eq), 2-chloro-N-[[2-(trifluoromethyl)-3-pyridyl]methyl]pyrido[3,2-d]pyrimidin-4-amine (120 mg, 177 umol, 1.00 eq) and TEA (54 mg, 530 umol, 3.00 eq) in DMSO (2.00 ml-) was stirred at 11000 for 5 hours. LCMS showed all of 2-chloro-N-[[2-(trifluoromethyl)-3-pyridyl]methyl]pyrido[3,2-d]pyrimidin-4-amine was consumed and a new major peak with desired MS. 2 mL water was added to the mixture and filtered. The precipitate was washed with 0.5 mL EtOAc and dried. $N^2$-isopropyl-$N^4$-[[2-(trifluoromethyl)-3-pyridyl]methyl]pyrido[3,2-d]pyrimidine-2,4-diamine (44 mg, 122 umol, 68% yield, 99.2% purity) was obtained as a light yellow solid.

General synthetic route 8 (Route 8)

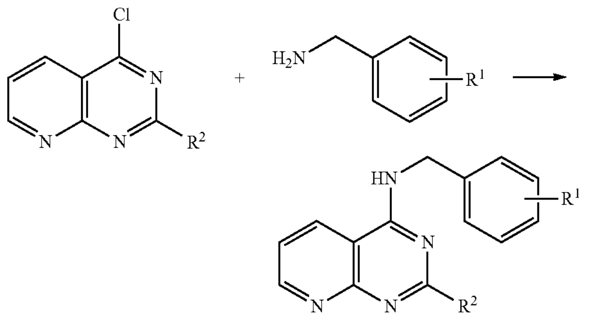

Example 8

Preparation of N-((2-(trifluoromethyl)pyridin-3-yl)methyl)pyrido[2,3-d]pyrimidin-4-amine

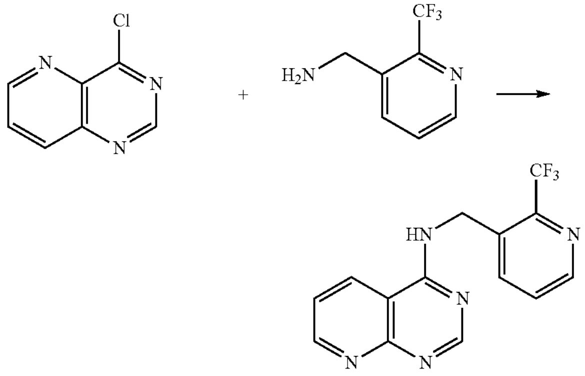

To a solution of 4-chloropyrido[2,3-d]pyrimidine (100 mg, 604 umol, 1.00 eq) and [2-(trifluoromethyl)-3-pyridyl]methanamine (160 mg, 906 umol, 1.50 eq) in THF (5.00 mL) was added TEA (122 mg, 1.21 mmol, 167 uL, 2.00 eq). The reaction mixture was stirred at 15° C. for 3 h. TLC (Dichloromethane:Methanol=10:1) showed 4-chloropyrido[2,3-d]pyrimidine was consumed completely and a new spot was formed. The mixture was diluted with water (5 mL) and a lot of white solid was precipitated out. The mixture was filtered and the filter cake was washed with water (15 mL) and dried in vacuo to give N-[[2-(trifluoromethyl)-3-pyridyl]methyl]pyrido[2,3-d]pyrimidin-4-amine (36 mg, 117 umol, 19% yield, 100% purity) as a white solid.

General synthetic route 9 (Route 9)

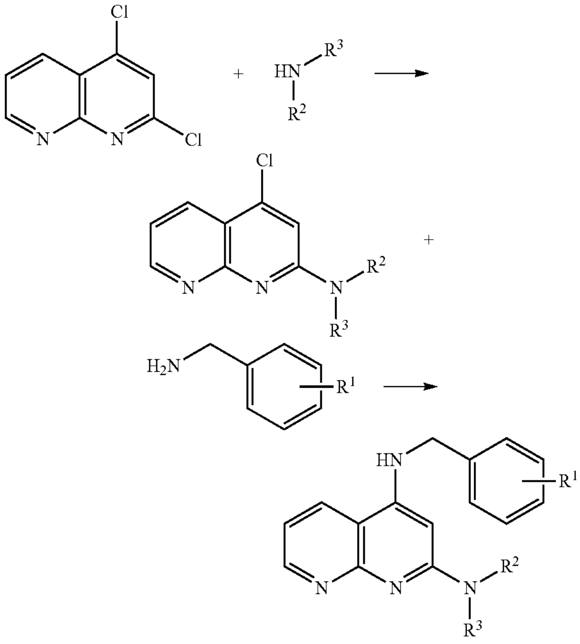

Example 9

Preparation of 4-chloro-N-isopropyl-1,8-naphthyridin-2-amine

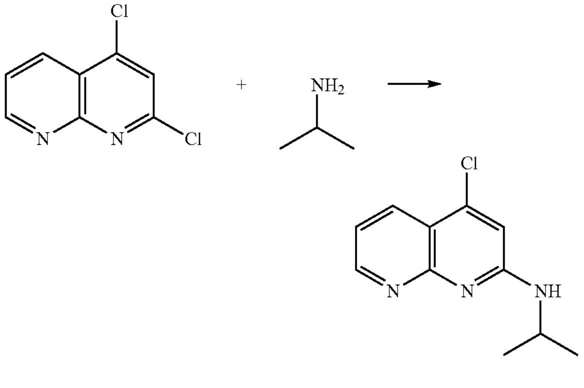

To a solution of 2,4-dichloro-1,8-naphthyridine (50 mg, 251 umol, 1 eq) and propan-2-amine (22 mg, 377 umol, 32 uL, 1.5 eq) in dioxane (6 mL) was added TEA (51 mg, 502 umol, 69 uL, 2 eq). The mixture was stirred at 90° C. for 16 hours. TLC (Petroleum ether:EtOAc=1:1) showed that 2,4-dichloro-1,8-naphthyridine was consumed completely and several new spots. LCMS showed that a major peak of desired product's MS was detected. The mixture was concentrated directly. The residue was purified by trituration from ($H_2O$:Petroleum ether:EtOAc=10:10:1) to obtain compound 4-chloro-N-isopropyl-1,8-naphthyridin-2-amine (35 mg, 158 umol, 63% yield) as a light brown solid. 1H NMR (400 MHz, CDCl3-d) δ ppm 8.83 (dd, J=4.4, 1.6 Hz, 1H), 8.28 (dd, J=8.0, 1.9 Hz, 1H), 7.20 (dd, J=8.0, 4.5 Hz, 1H), 6.76 (s, 1H), 4.95 (br. s., 1H), 4.44 (d, J=5.6 Hz, 1H), 1.29 (d, J=6.5 Hz, 6H).

Preparation of $N^2$-isopropyl-$N^4$-((2-(trifluoromethyl)pyridin-3-yl)methyl)-1,8-naphthyridine-2,4-diamine

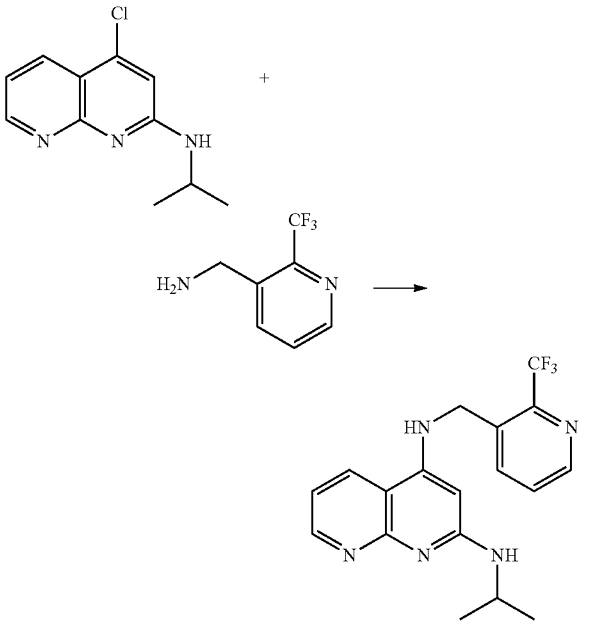

A mixture of 4-chloro-N-isopropyl-1,8-naphthyridin-2-amine (150 mg, 676.6 umol, 1 eq) and [2-(trifluoromethyl)-3-pyridyl]methanamine (1.2 g, 6.8 mmol, 10 eq) was stirred at 180° C. for 0.5 hour under microwave and $N_2$. TLC (EtOAc) showed that 4-chloro-N-isopropyl-1,8-naphthyridin-2-amine was consumed completely and several new spots. LCMS showed that several peaks and 20% of desired product. To the mixture was added water (40 mL) and extracted with EtOAc (40 mL*2). The organic layers were washed with brine (40 mL), dried over $Na_2SO_4$ and concentrated. The residue was purified by prep-TLC (EtOAc). Then the crude product was further purified by prep-HPLC (Column: Phenomenex Synergi C18 150*30 mm*4 um; Condition: water (0.225% FA)-ACN). The salt product was basified by strong basic anion exchange resin. Then the residue was purified by prep-TLC (Dichloromethane:Methanol=10:1) to obtain $N^2$-isopropyl-$N^4$-[[2-(trifluoromethyl)-3-pyridyl]methyl]-1,8-naphthyridine-2,4-diamine (5.4 mg, 15 umol, 2% yield) as a light yellow solid.

General synthetic route 10 (Route 10)

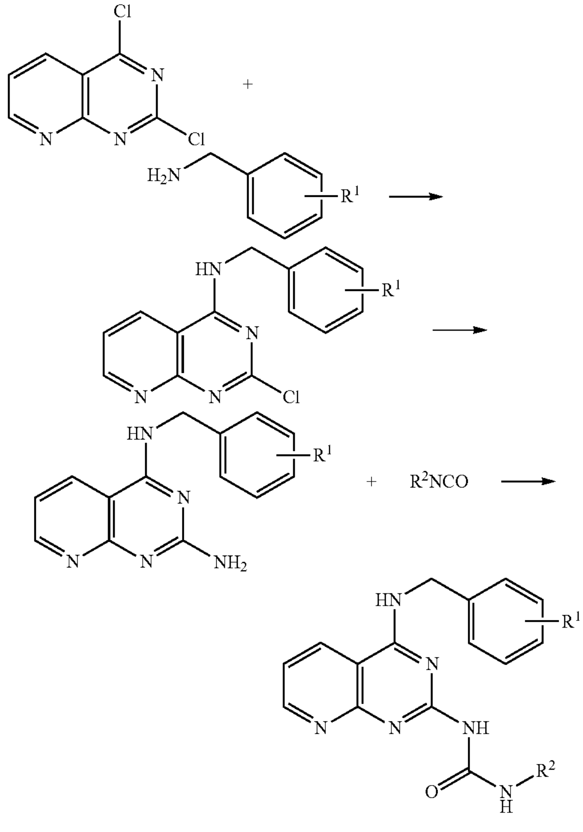

Example 10

Preparation of $N^4$-((2-(trifluoromethyl)pyridin-3-yl) methyl)pyrido[2,3-d]pyrimidine-2,4-diamine

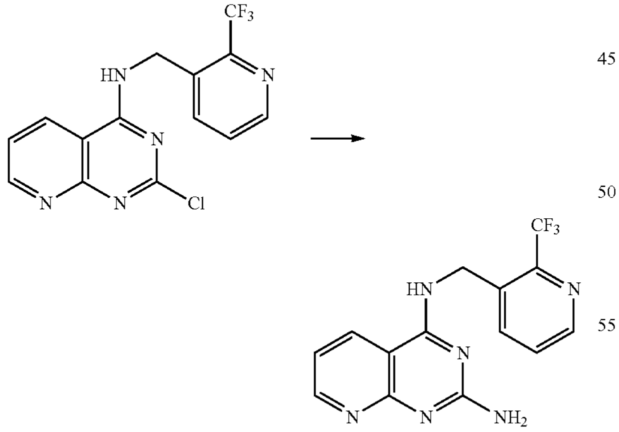

To a mixture of 2-chloro-N-[[2-(trifluoromethyl)-3-pyridyl]methyl]pyrido[2,3-d]pyrimidin-4-amine (50 mg, 147 umol, 1.00 eq) in DMSO (2.00 mL) was added $NH_3 \cdot H_2O$ (10 mg, 294 umol, 11 uL, 2.00 eq). The mixture was stirred at 95° C. for 12 h. TLC (Ethyl acetate) showed most of 2-chloro-N-[[2-(trifluoromethyl)-3-pyridyl]methyl] pyrido[2,3-d]pyrimidin-4-amine was consumed and a major new spot. The mixture was diluted with water (10 mL). The precipitate was collected by filtration and purified by triturated from EtOAc (1 mL) to give $N^4$-[[2-(trifluoromethyl)-3-pyridyl]methyl]pyrido[2,3-d]pyrimidine-2,4-diamine (20 mg, 62 umol, 42% yield) as a light yellow solid. $^1$H NMR (300 MHz, DMSO-d6) δ ppm 8.62-8.67 (m, 3H), 8.40-8.43 (dd, J=6.0 Hz, J=3.0 Hz, 1H), 7.96-7.99 (d, J=9.0 Hz, 1H), 7.65-7.70 (dd, J=6.0 Hz, J=3.0 Hz, 1H), 7.05-7.09 (dd, J=6.0 Hz, J=3.0 Hz, 1H), 6.44 (bs, 2H), 4.90-4.92 (d, J=6.0 Hz, 2H).

Preparation of 1-(4-fluorophenyl)-3-(4-(((2-(trifluoromethyl)pyridin-3-yl)methyl)amino)pyrido[2,3-d] pyrimidin-2-yl)urea

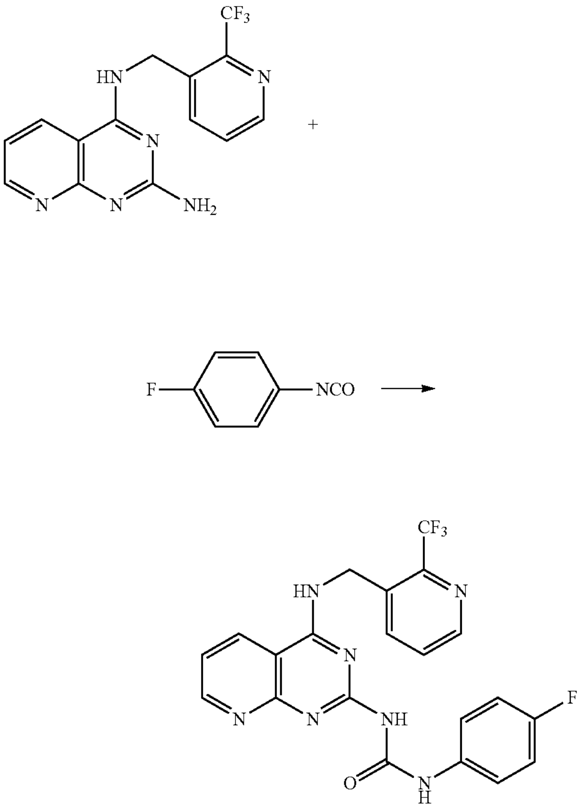

A mixture of $N^4$-[[2-(trifluoromethyl)-3-pyridyl]methyl] pyrido[2,3-d]pyrimidine-2,4-diamine (100 mg, 312 umol, 1.00 eq), 1-fluoro-4-isocyanato-benzene (128 mg, 937 umol, 105 uL, 3.00 eq) in dioxane (2.00 mL) was stirred at 120° C. under microwave for 30 min. TLC (Ethyl acetate:Petroleum ether=2:1) showed most of $N^4$-[[2-(trifluoromethyl)-3-pyridyl]methyl]pyrido[2,3-d]pyrimidine-2,4-diamine was consumed and two major new spots. The mixture was diluted with MeOH (5 mL). The precipitate was collected by filtration and purified by prep-HPLC (column: Phenomenex Synergi C18 150*30 mm*4 um; mobile phase: [water (0.225% FA)-ACN]; B %: 30%-60%,12 min), then adjust the pH=7-8 with anion resin, followed by lyophilization to give 1-(4-fluorophenyl)-3-[4-[[2-(trifluoromethyl)phenyl] methylamino]pyrido[2,3-d]pyrimidin-2-yl]urea (10.6 mg, 23 umol, 7% yield) as a white solid.

General synthetic route 11 (Route 11)

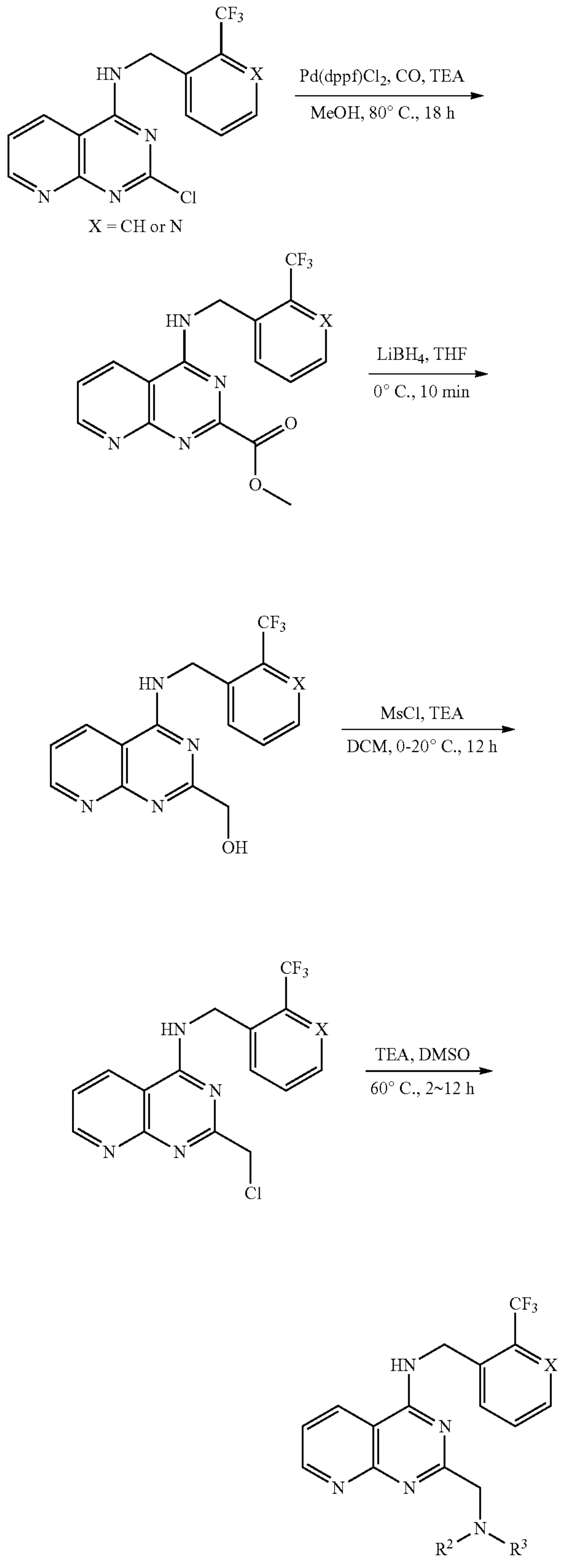

Example 11

Preparation of methyl 4-((2-(trifluoromethyl)benzyl) amino)pyrido[2,3-d]pyrimidine-2-carboxylate

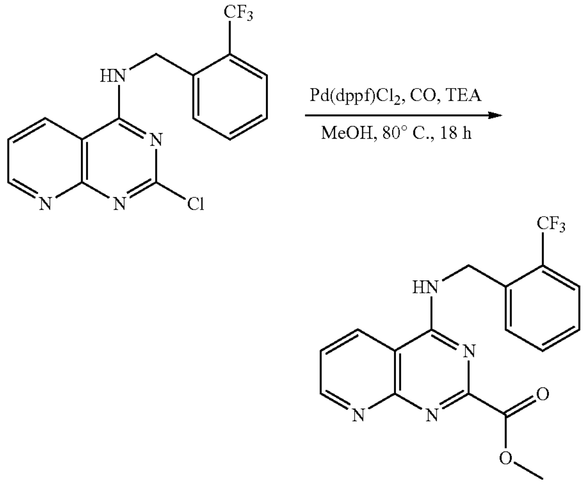

The mixture of 2-chloro-N-(2-(trifluoromethyl)benzyl) pyrido[2,3-d]pyrimidin-4-amine (3.00 g, 8.96 mmol, 1.00 eq), Pd(dppf)$Cl_2$ (131 mg, 179 umol, 0.15 eq), TEA (2.92 g, 28.86 mmol, 4.00 mL, 3.22 eq) in MeOH (30 mL) was stirred at 80° C. under CO (45 psi) for 18 h. TLC (Ethyl acetate:Methanol=20:1) showed most of the 2-chloro-N-(2-(trifluoromethyl)benzyl)pyrido[2,3-d]pyrimidin-4-amine was consumed and a new spot. The mixture was concentrated directly to remove the solvent. The residue was purified by chromatography (Ethyl acetate to Ethyl acetate: Methanol=20:1) to get methyl 4-((2-(trifluoromethyl)benzyl)amino)pyrido[2,3-d]pyrimidine-2-carboxylate (2.20 g, 5.10 mmol, 57% yield, 84% purity) as a light yellow solid.

Preparation of (4-((2-(trifluoromethyl)benzyl) amino)pyrido[2,3-d]pyrimidin-2-yl)methanol

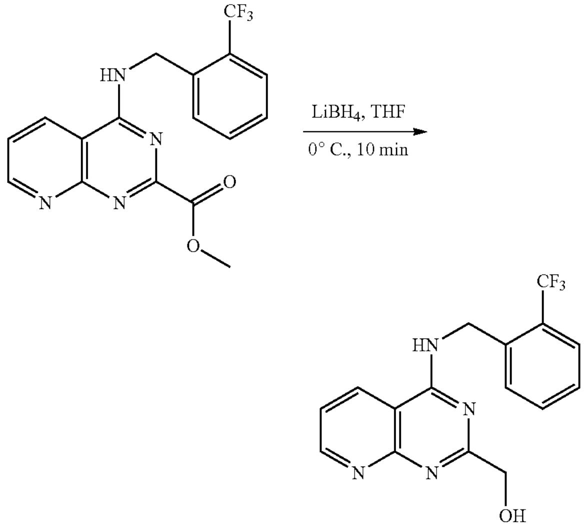

To a mixture of methyl 4-[[2-(trifluoromethyl)phenyl]methylamino]pyrido[2,3-d]pyrimidine-2-carboxylate (2.20 g, 6.07 mmol, 1.00 eq) in THF (30.00 mL) was added $LiBH_4$ (265 mg, 12.14 mmol, 2.00 eq) at 0° C. The mixture was stirred at 0° C. for 10 min. TLC (Ethyl acetate:Methanol=10:1) showed methyl 4-[[2-(trifluoromethyl)phenyl]methylamino]pyrido[2,3-d]pyrimidine-2-carboxylate was consumed completely and three new spots. The mixture was diluted with $H_2O$ (100 mL), then the resultant mixture was extracted with ethyl acetate (100 mL*3). The combined organic layers were washed with saturated brine (40 mL), dried with anhydrous $Na_2SO_4$, filtered and concentrated in vacuo. The residue was purified by chromatography (Ethyl acetate:Methanol=10:1) to give (4-((2-(trifluoromethyl)benzyl)amino)pyrido[2,3-d]pyrimidin-2-yl)methanol (1.20 g, 2.58 mmol, 43% yield, 72% purity) as a yellow solid.

Preparation of 2-(chloromethyl)-N-(2-(trifluoromethyl)benzyl)pyrido[2,3-d]pyrimidin-4-amine

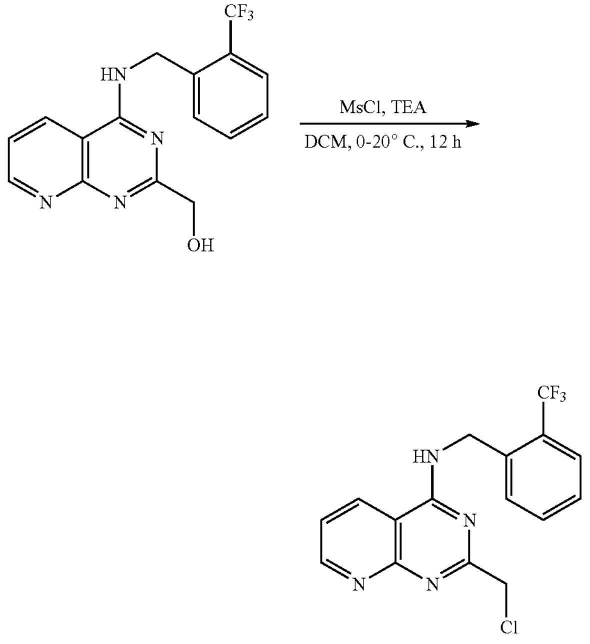

To a mixture of [4-[[2-(trifluoromethyl)phenyl]methylamino]pyrido[2,3-d]pyrimidin-2-yl]methanol (80 mg, 239 umol, 1.00 eq) and TEA (85 mg, 838 umol, 116 uL, 3.50 eq) in DCM (2.00 mL) was added MsCl (41 mg, 359 umol, 28 uL, 1.50 eq) at 0° C. Then the mixture was stirred at 20° C. for 12 h. TLC (EtOAc) showed little of [4-[[2-(trifluoromethyl)phenyl]methylamino]pyrido[2,3-d]pyrimidin-2-yl] methanol remained and a major new spot. The mixture was purified by prep-TLC (EtOAc) to give 2-(chloromethyl)-N-(2-(trifluoromethyl)benzyl)pyrido[2,3-d]pyrimidin-4-amine (30 mg, 83 umol, 34% yield, 97% purity) was obtained as a light yellow solid. $^1H$ NMR (400 MHz, DMSO-d6) δ ppm 9.25-9.27 (t, J=4.0 Hz, 1H), 9.03-9.04 (dd, J=4.0, 1.6 Hz, 1H), 8.79-8.82 (dd, J=8.0, 4.0 Hz, 1H), 7.75-7.77 (d, J=8.0 Hz, 1H), 7.57-7.64 (m, 3H), 7.47-7.51 (d, J=8.0 Hz, 1H), 4.99-5.00 (d, J=8.0 Hz, 1H), 4.58 (s, 2H).

Preparation of 2-((4-chloropiperidin-1-yl)methyl)-N-((2-(trifluoromethyl)pyridin-3-yl)methyl)pyrido[2,3-d]pyrimidin-4-amine

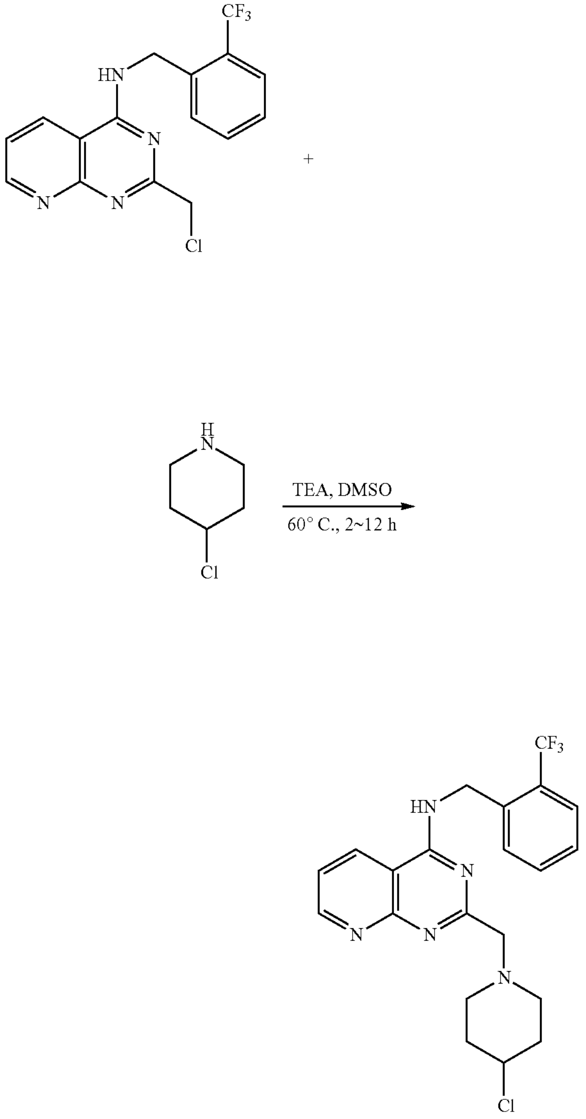

To a solution of 2-(chloromethyl)-N-[[2-(trifluoromethyl)phenyl]methyl]pyrido[2,3-d]pyrimidin-4-amine (85 mg, 241 umol, 1 eq) and 4-chloropiperidine (45 mg, 289 umol, 1.2 eq, HCl salt) in DMSO (2 mL) was added TEA (97 mg, 964 umol, 133 uL, 4 eq). The mixture was stirred at 60° C. for 2 hour. LCMS showed the starting material was consumed completely and a major peak with desired product mass. The residue was purified by prep-HPLC (column: Gemini 150*25 5u; mobile phase: [water (0.05% ammonia hydroxide v/v)-ACN]; B %: 36%-66%,12 min), followed by lyophilisation to give 2-((4-chloropiperidin-1-yl)methyl)-N-((2-(trifluoromethyl)pyridin-3-yl)methyl)pyrido[2,3-d]pyrimidin-4-amine (32.4 mg, 70 umol, 29% yield, 94.6% purity) as a light yellow solid.

The compounds of Table 1 were prepared using the general methodology outlined above:

TABLE 1

| | |
|---|---|
| 4 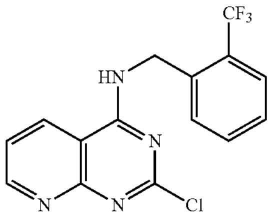 [SMILES: FC(F)(F)c1ccccc1CNc1nc(Cl)nc2ncccc12] | 2-chloro-N-(2-(trifluoromethyl)benzyl)pyrido[2,3-d]pyrimidin-4-amine<br>Synthesised via Route 6<br>$^{1}$H NMR (400 MHz, DMSO-$d_6$) δ (ppm) 9.61 (t, J = 5.33 Hz, 1H), 9.03 (dd, J = 1.76, 4.39 Hz, 1H), 8.82 (dd, J = 1.76, 8.28 Hz, 1H), 7.79 (d, J = 7.53 Hz, 1H), 7.61-7.67 (m, 2H), 7.48-7.60 (m, 2H), 4.94 (d, J = 5.27 Hz, 2H).<br>LCMS (ES) $C_{15}H_{11}N_4F3Cl$ $[M + H]^+$ 339.1. |
| 5 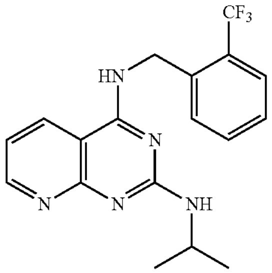 [SMILES: CC(C)Nc1nc(NCc2ccccc2C(F)(F)F)c2cccnc2n1] | $N^2$-isopropyl-$N^4$-(2-(trifluoromethyl)benzyl)pyrido[2,3-d]pyrimidine-2,4-diamine<br>Synthesised via Route 6<br>$^{1}$H NMR (400 MHz, DMSO-d6) δ (ppm) 10.04 (br. s., 1H), 8.48-8.95 (m, 2H), 7.77 (d, J = 7.78 Hz, 2H), 7.44-7.68 (m, 3H), 7.00-7.38 (m, 1H), 4.94 (d, J = 4.89 Hz, 2H), 3.83-4.22 (m, 1H), 0.91-1.22 (m, 6H).<br>LCMS (ES) $C_{18}H_{19}N_5F3$ $[M + H]^+$ 362.2. |
| 5_S 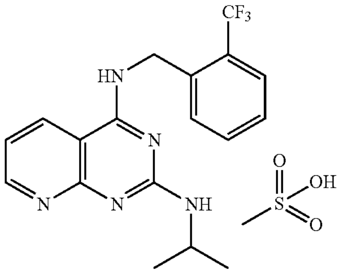 | $N^2$-isopropyl-$N^4$-(2-(trifluoromethyl)benzyl)pyrido[2,3-d]pyrimidine-2,4-diamine methanesulfonate<br>Synthesised via Route 6<br>$^{1}$H NMR (400 MHz, DMSO-$d_6$) δ (ppm) 12.55 (br. s., 1H), 10.33 (br. s., 1H), 8.69-8.85 (m, 2H), 8.02 (d, J = 7.4 Hz, 1H), 7.79 (d, J = 7.7 Hz, 1H), 7.46-7.67 (m, 4H), 4.99 (d, J = 4.3 Hz, 2H), 3.96 (qd, J = 6.5, 13.3 Hz, 1H), 2.37 (s, 3H), 0.96-1.22 (m, 6H).<br>LCMS (ES) $C_{18}H_{19}N_5F3$ $[M + H]^+$ 362.2. |
| 10 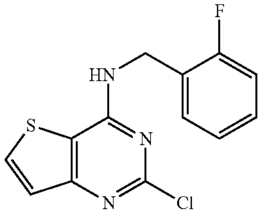 [SMILES: Fc1ccccc1CNc1nc(Cl)nc2ccsc12] | 2-chloro-N-(2-fluorobenzyl)thieno[3,2-d]pyrimidin-4-amine<br>Synthesised via Route 1<br>$^{1}$H NMR (400 MHz, $CDCl_3$) δ (ppm) 7.73 (d, J = 5.4 Hz, 1H), 7.49 (td, J = 7.6, 1.6 Hz, 1H), 7.35 (d, J = 5.3 Hz, 1H), 7.34-7.27 (m, 1H), 7.14 (td, J = 7.5, 1.1 Hz, 1H), 7.12-7.05 (m, 1H), 5.47 (br. s, 1H), 4.91 (d, J = 5.6 Hz, 2H).<br>HRMS (ES) $C_{13}H_{10}N_3FClS$ $[M + H]^+$ 294.0260. |
| 11 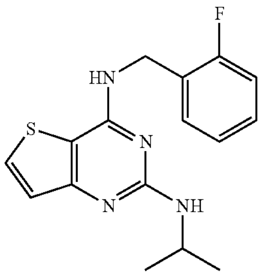 [SMILES: CC(C)Nc1nc(NCc2ccccc2F)c2sccc2n1] | $N^4$-(2-fluorobenzyl)-$N^2$-isopropylthieno[3,2-d]pyrimidine-2,4-diamine<br>Synthesised via Route 1<br>$^{1}$H NMR (400 MHz, $CDCl_3$) δ (ppm) 7.54 (d, J = 5.3 Hz, 1H), 7.42 (td, J = 7.5, 1.5 Hz, 1H), 7.33-7.21 (m, 1H), 7.17-7.01 (m, 3H), 5.12 (br. s, 1H), 5.08 (br. s, 1H), 4.85 (d, J = 5.8 Hz, 2H), 4.28-4.04 (m, 1H), 1.23 (d, J = 6.5 Hz, 6H).<br>HRMS (ES) $C_{16}H_{18}N_4FS$ $[M + H]^+$ 317.1225. |

TABLE 1-continued

| | |
|---|---|
| 12 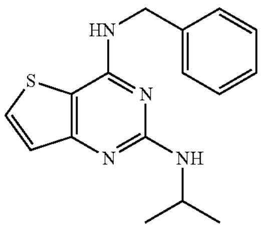 [SMILES: CC(C)Nc1nc(NCc2ccccc2)c2sccc2n1] | $N^4$-benzyl-$N^2$-isopropylthieno[3,2-d]pyrimidine-2,4-diamine<br>Synthesised via Route 1<br>$^1H$ NMR (400 MHz, $CDCl_3$) δ (ppm) 7.54 (d, J = 5.3 Hz, 1H), 7.42-7.27 (m, 5H), 7.12 (d, J = 5.3 Hz, 1H), 5.26 (br. s, 1H), 5.16 (br. s, 1H), 4.80 (d, J = 5.6 Hz, 2H), 4.26-4.12 (m, 1H), 1.23 (d, J = 6.5 Hz, 6H).<br>HRMS (ES) $C_{16}H_{19}N_4S$ $[M + H]^+$ 299.1329. |
| 13 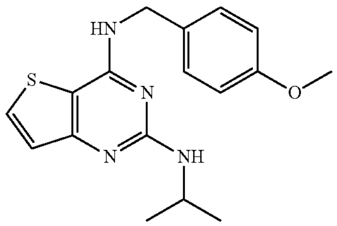 [SMILES: COc1ccc(CNc2nc(NC(C)C)nc3ccsc23)cc1] | $N^2$-isopropyl-$N^4$-(4-methoxybenzyl)thieno[3,2-d]pyrimidine-2,4-diamine<br>Synthesised via Route 1<br>$^1H$ NMR (400 MHz, $CDCl_3$) δ (ppm) 7.52 (d, J = 5.3 Hz, 1H), 7.34-7.28 (m, 2H), 7.11 (d, J = 5.3 Hz, 1H), 6.91-6.86 (m, 2H), 4.98 (br. s, 1H), 4.92 (br. s, 1H), 4.72 (d, J = 5.5 Hz, 2H), 4.27-4.14 (m, 1H), 3.81 (s, 3H), 1.24 (d, J = 6.5 Hz, 6H).<br>HRMS (ES) $C_{17}H_{21}N_4OS$ $[M + H]^+$ 329.1431. |
| 14 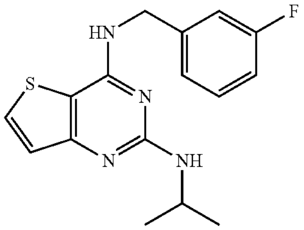 [SMILES: CC(C)Nc1nc(NCc2cccc(F)c2)c2sccc2n1] | $N^4$-(3-fluorobenzyl)-$N^2$-isopropylthieno[3,2-d]pyrimidine-2,4-diamine<br>Synthesised via Route 1<br>$^1H$ NMR (400 MHz, $CDCl_3$) δ (ppm) 7.55 (d, J = 5.3 Hz, 1H), 7.31 (td, J = 7.9, 5.9 Hz, 1H), 7.18-7.06 (m, 3H), 6.98 (td, J = 8.4, 2.6 Hz, 1H), 5.07 (br. s, 1H), 4.84 (br. s, 1H), 4.79 (d, J = 5.7 Hz, 2H), 4.20-4.09 (m, 1H), 1.21 (d, J = 6.5 Hz, 6H).<br>HRMS (ES) $C_{16}H_{18}N_4FS$ $[M + H]^+$ 317.1226. |
| 15 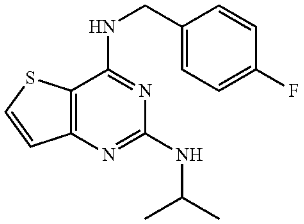 [SMILES: CC(C)Nc1nc(NCc2ccc(F)cc2)c2sccc2n1] | $N^4$-(4-fluorobenzyl)-$N^2$-isopropylthieno[3,2-d]pyrimidine-2,4-diamine<br>Synthesised via Route 1<br>$^1H$ NMR (400 MHz, $CDCl_3$) δ (ppm) 7.55 (d, J = 5.3 Hz, 1H), 7.38-7.32 (m, 2H), 7.12 (d, J = 5.3 Hz, 1H), 7.07-6.99 (m, 2H), 5.00 (br. s, 1H), 4.89 (br. s, 1H), 4.76 (d, J = 5.5 Hz, 2H), 4.23-4.10 (m, 1H), 1.23 (d, J = 6.5 Hz, 6H).<br>HRMS (ES) $C_{16}H_{18}N_4FS$ $[M + H]^+$ 317.1230. |
| 16 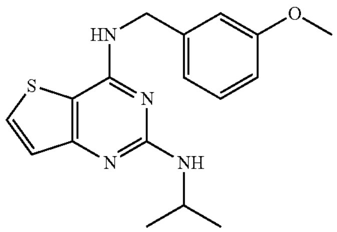 [SMILES: COc1cccc(CNc2nc(NC(C)C)nc3ccsc23)c1] | $N^2$-isopropyl-$N^4$-(3-methoxybenzyl)thieno[3,2-d]pyrimidine-2,4-diamine<br>Synthesised via Route 1<br>$^1H$ NMR (400 MHz, $CDCl_3$) δ (ppm) 7.53 (d, J = 5.3 Hz, 1H), 7.27 (t, J = 7.9 Hz, 1H), 7.11 (d, J = 5.3 Hz, 1H), 6.97 (d, J = 8.0 Hz, 1H), 6.94-6.91 (m, 1H), 6.84 (dd, J = 8.2, 2.1 Hz, 1H), 5.02 (br. s, 1H), 4.85 (br. s, 1H), 4.77 (d, J = 5.6 Hz, 2H), 4.24-4.13 (m, 1H), 3.80 (s, 3H), 1.23 (d, J = 6.5 Hz, 6H).<br>HRMS (ES) $C_{17}H_{21}N_4OS$ $[M + H]^+$ 329.1427. |

TABLE 1-continued

| | |
|---|---|
| 17 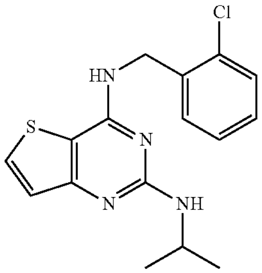 | $N^4$-(2-chlorobenzyl)-$N^2$-isopropylthieno[3,2-d]pyrimidine-2,4-diamine<br>Synthesised via Route 1<br>$^1H$ NMR (400 MHz, $CDCl_3$) δ (ppm) 7.55 (d, J = 5.3 Hz, 1H), 7.45 (dd, J = 5.6, 3.8 Hz, 1H), 7.39 (dd, J = 5.5, 3.8 Hz, 1H), 7.25-7.20 (m, 2H), 7.11 (d, J = 5.3 Hz, 1H), 5.16 (br. s, 1H), 4.89 (d, J = 5.9 Hz, 2H), 4.84 (br. s, 1H), 4.22-4.09 (m, 1H), 1.22 (d, J = 6.5 Hz, 6H).<br>HRMS (ES) $C_{16}H_{18}N_4S^{35}Cl$ $[M + H]^+$ 333.0934. |
| 18 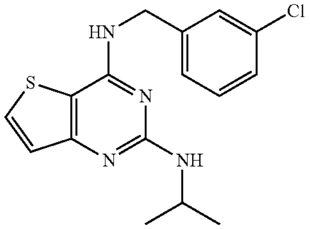 [SMILES: CC(C)Nc1nc(NCc2cccc(Cl)c2)c2sccc2n1] | $N^4$-(3-chlorobenzyl)-$N^2$-isopropyithieno[3,2-d]pyrimidine-2,4-diamine<br>Synthesised via Route 1<br>$^1H$ NMR (400 MHz, $CDCl_3$) δ (ppm) 7.56 (d, J = 5.3 Hz, 1H), 7.37 (s, 1H), 7.29-7.23 (m, 3H), 7.12 (d, J = 5.3 Hz, 1H), 5.09 (br. s, 1H), 4.91 (br. s, 1H), 4.77 (d, J = 5.6 Hz, 2H), 4.21-4.09 (m, 1H), 1.21 (d, J = 6.5 Hz, 6H).<br>HRMS (ES) $C_{16}H_{18}N_4S^{35}Cl$ $[M + H]^+$ 333.0930. |
| 19 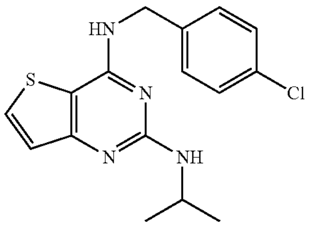 [SMILES: CC(C)Nc1nc(NCc2ccc(Cl)cc2)c2sccc2n1] | $N^4$-(4-chlorobenzyl)-$N^2$-isopropylthieno[3,2-d]pyrimidine-2,4-diamine<br>Synthesised via Route 1<br>$^1H$ NMR (400 MHz, $CDCl_3$) δ (ppm) 7.55 (d, J = 5.3 Hz, 1H), 7.31 (s, 4H), 7.12 (d, J = 5.3 Hz, 1H), 5.05 (br. s, 1H), 4.92 (br. s, 1H), 4.76 (d, J = 5.8 Hz, 2H), 4.22-4.08 (m, 1H), 1.22 (d, J = 6.5 Hz, 6H).<br>HRMS (ES) $C_{16}H_{18}N_4S^{35}Cl$ $[M + H]^+$ 333.0930. |
| 20 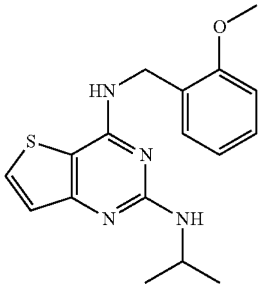 [SMILES: COc1ccccc1CNc1nc(NC(C)C)nc2ccsc12] | $N^2$-isopropyl-$N^4$-(2-methoxybenzyl)thieno[3,2-d]pyrimidine-2,4-diamine<br>Synthesised via Route 1<br>$^1H$ NMR (400 MHz, $CDCl_3$) δ (ppm) 7.53 (d, J = 5.3 Hz, 1H), 7.35 (dd, J = 7.3, 1.5 Hz, 1H), 7.32-7.27 (m, 1H), 7.10 (d, J = 5.3 Hz, 1H), 6.96-6.89 (m, 2H), 4.79 (d, J = 5.7 Hz, 2H), 4.29-4.17 (m, 1H), 3.90 (s, 3H), 1.26 (d, J = 6.5 Hz, 6H).<br>HRMS (ES) $C_{17}H_{21}N_4OS$ $[M + H]^+$ 329.1440. |
| 21 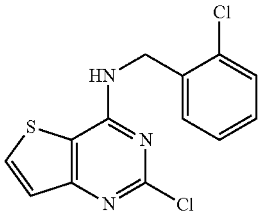 | 2-chloro-N-(2-chlorobenzyl)thieno[3,2-d]pyrimidin-4-amine<br>Synthesised via Route 1<br>$^1H$ NMR (400 MHz, $CDCl_3$) δ (ppm) 7.74 (d, J = 5.4 Hz, 1H), 7.57-7.51 (m, 1H), 7.45-7.38 (m, 1H), 7.36 (d, J = 5.4 Hz, 1H), 7.30-7.24 (m, 2H), 5.52 (br. s, 1H), 4.95 (d, J = 5.9 Hz, 2H).<br>HRMS (Cl) $C_{13}H_9N_3Cl_2S$ $[M + H]^+$ 309.9959. |

TABLE 1-continued

22

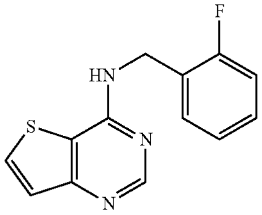 [SMILES: Fc1ccccc1CNc1ncnc2ccsc12]

N-(2-fluorobenzyl)thieno[3,2-d]pyrimidin-4-amine

Synthesised via Route 2
$^1$H NMR (400 MHz, $CDCl_3$) δ (ppm) 8.66 (s, 1H), 7.71 (d, J = 5.4 Hz, 1H), 7.49-7.40 (m, 2H), 7.33-7.24 (m, 1H), 7.15-7.04 (m, 2H), 5.40 (br. s, 1H), 4.94 (d, J = 5.7 Hz, 2H).
HRMS (Cl) $C_{13}H_{10}N_3FS$ $[M + H]^+$ 260.0660.

23

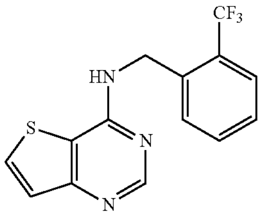

N-(2-(trifluoromethyl)benzyl)thieno[3,2-d]pyrimidin-4-amine

Synthesised via Route 2
$^1$H NMR (400 MHz, $CDCl_3$) δ (ppm) 8.68 (s, 1H), 7.73 (d, J = 5.4 Hz, 1H), 7.70 (d, J = 7.8 Hz, 1H), 7.67 (d, J = 7.8 Hz, 1H), 7.52 (t, J = 7.4 Hz, 1H), 7.46 (d, J = 5.4 Hz, 1H), 7.41 (t, J = 7.7 Hz, 1H), 5.29 (br. s, 1H), 5.10 (d, J = 5.6 Hz, 2H).
HRMS (Cl) $C_{14}H_{10}N_3F_3S$ $[M + H]^+$ 310.0618.

24

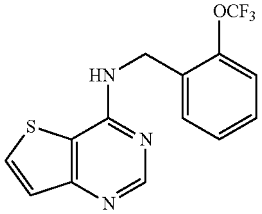 [SMILES: FC(F)(F)Oc1ccccc1CNc1ncnc2ccsc12]

N-(2-(trifluoromethoxy)benzyl)thieno[3,2-d]pyrimidin-4-amine

Synthesised via Route 2
$^1$H NMR (400 MHz, $CDCl_3$) δ (ppm) 8.66 (s, 1H), 7.73 (d, J = 5.4 Hz, 1H), 7.53 (dd, J = 7.5, 1.4 Hz, 1H), 7.45 (d, J = 5.4 Hz, 1H), 7.38-7.32 (m, 1H), 7.32-7.24 (m, 2H), 5.28 (br. s, 1H), 4.98 (d, J = 5.9 Hz, 2H).
HRMS (Cl) $C_{14}H_{10}N_3F_3OS$ $[M + H]^+$ 326.0568.

25

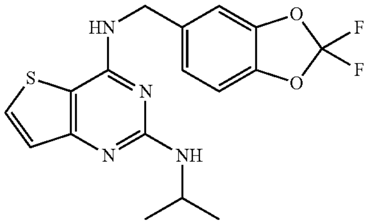 [SMILES: CC(C)Nc1nc(NCc2ccc3c(c2)OC(F)(F)O3)c2sccc2n1]

$N^4$-((2,2-difluorobenzo[d][1,3]dioxol-5-yl)methyl)-$N^2$-isopropylthieno[3,2-d]pyrimidine-2,4-diamine Synthesised via Route 1
$^1$H NMR (400 MHz, $CDCl_3$) δ (ppm) 7.58 (d, J = 5.3 Hz, 1H), 7.15-7.09 (m, 2H), 7.04 (t, J = 7.9 Hz, 1H), 6.98 (dd, J = 7.9, 1.3 Hz, 1H), 4.85 (d, J = 5.8 Hz, 2H), 4.43-4.08 (m, 1H), 1.20 (d, J = 6.5 Hz, 6H).
HRMS (Cl) $C_{17}H_{16}N_4F_2O_2S$ $[M + H]^+$ 379.1038.

26

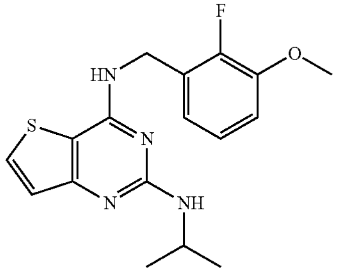 [SMILES: COc1cccc(CNc2nc(NC(C)C)nc3ccsc23)c1F]

$N^4$-(2-fluoro-3-methoxybenzyl)-$N^2$-isopropylthieno[3,2-d]pyrimidine-2,4-diamine Synthesised via Route 1
$^1$H NMR (400 MHz, $CDCl_3$) δ (ppm) 7.54 (d, J = 5.3 Hz, 1H), 7.11 (d, J = 5.3 Hz, 1H), 7.06-7.00 (m, 1H), 7.00-6.95 (m, 1H), 6.90 (td, J = 8.0, 1.8 Hz, 1H), 4.85 (d, J = 5.4 Hz, 2H), 4.24-4.14 (m, 1H), 3.89 (s, 3H), 1.23 (d, J = 6.5 Hz, 6H).
HRMS (Cl) $C_{17}H_{19}N_4FOS$ $[M + H]^+$ 347.1339.

TABLE 1-continued

| | |
|---|---|
| 27 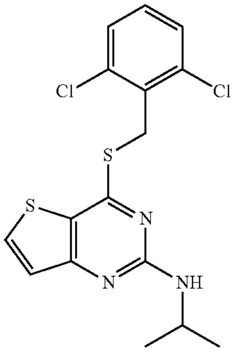 | $N^4$-(2,6-dichlorobenzyl)-N-isopropylthieno[3,2-d]pyrimidine-2,4-diamine<br>Synthesised via Route 1<br>$^1H$ NMR (400 MHz, $CDCl_3$) δ (ppm) 7.54 (d, J = 5.3 Hz, 1H), 7.36 (d, J = 8.1 Hz, 2H), 7.22 (dd, J = 8.6, 7.5 Hz, 1H), 7.12 (d, J = 5.3 Hz, 1H), 5.10 (d, J = 5.2 Hz, 2H), 4.34-4.23 (m, 1H), 1.27 (d, J = 6.5 Hz, 6H).<br>HRMS (Cl) $C_{16}H_{16}N_4Cl_2S$ $[M + H]^+$ 367.0538. |
| 28 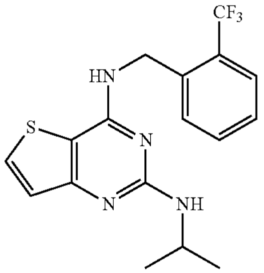 | $N^2$-isopropyl-$N^4$-(2-(trifluoromethyl)benzyl)thieno[3,2-d]pyrimidine-2,4-diamine<br>Synthesised via Route 1<br>$^1H$ NMR (400 MHz, $CDCl_3$) δ (ppm) 7.68 (d, J = 7.8 Hz, 1H), 7.61 (d, J = 7.8 Hz, 1H), 7.55 (d, J = 5.3 Hz, 1H), 7.50 (t, J = 7.6 Hz, 1H), 7.38 (t, J = 7.6 Hz, 1H), 7.11 (d, J = 5.3 Hz, 1H), 5.09 (br. s, 1H), 5.01 (d, J = 5.7 Hz, 2H), 4.79 (br. s, 1H), 4.20-4.06 (m, 1H), 1.18 (d, J = 6.5 Hz, 6H).<br>HRMS (Cl) $C_{17}H_{17}N_4F_3S$ $[M + H]^+$ 367.1196. |
| 29 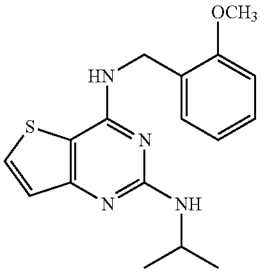 | $N^2$-isopropyl-$N^4$-(2-(trifluoromethoxy)benzyl)thieno[3,2-d]pyrimidine-2,4-diamine<br>Synthesised via Route 1<br>$^1H$ NMR (400 MHz, $CDCl_3$) δ (ppm) 7.5S (d, J = 5.3 Hz, 1H), 7.48 (dd, J = 7.4, 1.3 Hz, 1H), 7.35-7.23 (m, 3H), 7.11 (d, J = 5.3 Hz, 1H), 5.08 (br. s, 1H), 4.88 (d, J = 5.9 Hz, 2H), 4.83 (br. s, 1H), 4.22-4.07 (m, 1H), 1.20 (d, J = 6.5 Hz, 6H).<br>HRMS (Cl) $C_{17}H_{17}N_4F_3OS$ $[M + H]^+$ 383.1149. |
| 30 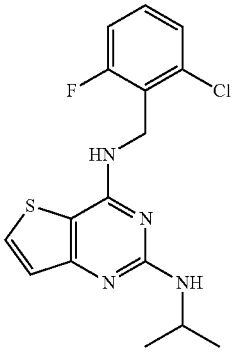 [SMILES: CC(C)Nc1nc(NCc2c(F)cccc2Cl)c2sccc2n1] | $N^4$-(2-chloro-6-fluorobenzyl)-$N^2$-isopropylthieno[3,2-d]pyrimidine-2,4-diamine<br>Synthesised via Route 1<br>$^1H$ NMR (400 MHz, $CDCl_3$) δ (ppm) 7.52 (d, J = 5.3 Hz, 1H), 7.25-7.19 (m, 2H), 7.08 (d, J = 5.3 Hz, 1H), 7.02 (ddd, J = 9.4, 6.7, 2.8 Hz, 1H), 5.11 (br, s, 1H), 4.97 (d, J = 5.7 Hz, 2H), 4.85 (d, J = 7.0 Hz, 1H), 4.34-4.21 (m, 1H), 1.25 (d, J = 6.5 Hz, 6H).<br>HRMS (Cl) $C_{16}H_{16}N_4FClS$ $[M + H]^+$ 351.0842. |

TABLE 1-continued

31

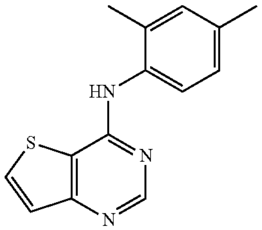 [SMILES: Cc1ccc(Nc2ncnc3ccsc23)c(C)c1]

N-(2,4-dimethylphenyl)thieno[3,2-d]pyrimidin-4-amine

Synthesised via Route 2

$^1$H NMR (400 MHz, $CDCl_3$) δ (ppm) 8.61 (s, 1H), 7.64 (d, J = 5.5 Hz, 1H), 7.37 (d, J = 5.5 Hz, 1H), 7.32 (d, J = 7.9 Hz, 1H), 7.16 (s, 1H), 7.11 (d, J = 7.9 Hz, 1H), 2.42 (s, 3H), 2.26 (s, 3H).

HRMS (Cl) $C_{14}H_{13}N_3S$ $[M + H]^+$ 256.0910.

32

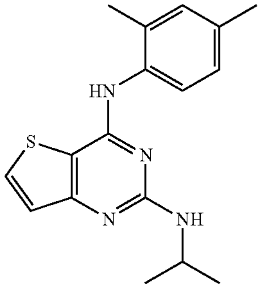 [SMILES: Cc1ccc(Nc2nc(NC(C)C)nc3ccsc23)c(C)c1]

$N^4$-(2,4-dimethylphenyl)-$N^2$-isopropylthieno[3,2-d]pyrimidine-2,4-diamine

Synthesised via Route 1

$^1$H NMR (400 MHz, $CDCl_3$) δ (ppm) 7.46 (d, J = 5.4 Hz, 1H), 7.36 (d, J = 7.9 Hz, 1H), 7.11 (s, 1H), 7.06 (dd, J = 6.5, 4.8 Hz, 2H), 4.65 (br. s, 1H), 4.23-4.11 (m, 1H), 2.38 (s, 3H), 2.25 (s, 3H), 1.21 (d, J = 6.4 Hz, 6H).

HRMS (Cl) $C_{17}H_{20}N_4S$ $[M + H]^+$ 313.1488.

33

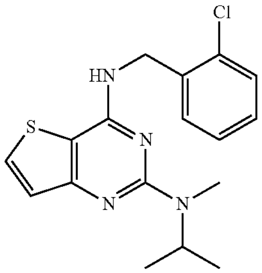 [SMILES: CC(C)N(C)c1nc(NCc2ccccc2Cl)c2sccc2n1]

$N^4$-(2-chlorobenzyl)-$N^2$-isopropyl-$N^2$-methylthieno[3,2-d]pyrimidine-2,4-diamine Synthesised via Route 1

$^1$H NMR (400 MHz, $CDCl_3$) δ (ppm) 7.52 (d, J = 5.3 Hz, 1H), 7.48-7.44 (m, 1H), 7.41-7.35 (m, 1H), 7.24-7.18 (m, 3H), 5.17-5.06 (m, 2H), 4.89 (d, J = 5.8 Hz, 2H), 2.99 (s, 3H), 1.14 (d, J = 6.8 Hz, 6H).

HRMS (Cl) $C_{17}H_{19}N_4ClS$ $[M + H]^+$ 347.1097.

34

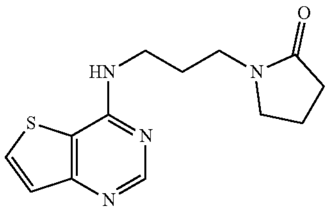 [SMILES: O=C1CCCN1CCCNc1ncnc2ccsc12]

1-(3-(thieno[3,2-d]pyrimidin-4-ylamino)propyl)pyrrolidin-2-one

Synthesised via Route 2

$^1$H NMR (400 MHz, $CDCl_3$) δ (ppm) 8.58 (s, 1H), 7.70 (d, J = 5.4 Hz, 1H), 7.39 (d, J = 5.4 Hz, 1H), 6.76 (t, J = 5.5 Hz, 1H), 3.64 (dd, J = 12.1, 6.2 Hz, 2H), 3.47-3.41 (m, 4H), 2.48 (t, J = 8.1 Hz, 2H), 2.14-2.01 (m, 2H), 1.91-1.82 (m, 2H).

HRMS (Cl) $C_{13}H_{16}N_4OS$ $[M + H]^+$ 277.1129.

35

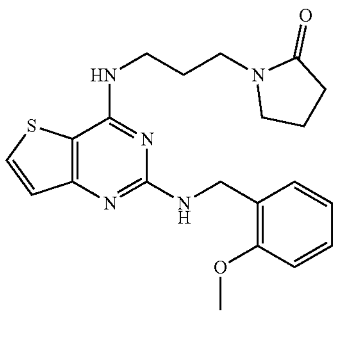 [SMILES: COc1ccccc1CNc1nc(NCCCN2CCCC2=O)c2sccc2n1]

1-(3-((2-((2-methoxybenzyl)amino)thieno[3,2-d]pyrimidin-4-yl)amino)propyl)pyrrolidin-2-one Synthesised via Route 1

$^1$H NMR (400 MHz, $CDCl_3$) δ (ppm) 7.54 (d, J-5.3 Hz, 1H), 7.35 (d, J = 7.1 Hz, 1H), 7.22 (td, J = 7.9, 1.7 Hz, 1H), 7.11 (d, J = 5.3 Hz, 1H), 6.91-6.84 (m, 2H), 6.51 (br. s, 1H), 5.90 (br. s, 1H), 4.66 (d, J = 6.2 Hz, 2H), 3.87 (s, 3H), 3.57 (dd, J = 12.1, 6.1 Hz, 2H), 3.39 (t, J = 6.9 Hz, 4H), 2.44 (t, J = 8.1 Hz, 2H), 2.10-1.99 (m, 2H), 1.84-1.72 (m, 2H).

HRMS (ES) $C_{21}H_{26}N_5O_2S$ $[M + H]^+$ 412.1797.

TABLE 1-continued

| | |
|---|---|
| 36 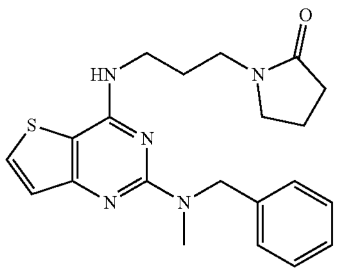 [SMILES: CN(Cc1ccccc1)c1nc(NCCCN2CCCC2=O)c2sccc2n1] | 1-(3-((2-(benzyl(methyl)amino)thieno[3,2-d]pyrimidin-4-yl)amino)propyl)pyrrolidin-2-one<br>Synthesised via Route 1<br>$^1$H NMR (400 MHz, $CDCl_3$) δ (ppm) 7.54 (d, J = 5.3 Hz, 1H), 7.32-7.27 (m, 4H), 7.25-7.13 (m, 2H), 6.06 (br. s, 1H), 4.94 (s, 2H), 3.54-3.47 (m, 2H), 3.38-3.30 (m, 4H), 3.18 (s, 3H), 2.41 (t, J = 8.1 Hz, 2H), 2.04-1.95 (m, 2H), 1.76-1.67 (m, 2H).<br>HRMS (Cl) $C_{21}H_{25}N_5OS$ [M + H]$^+$ 396.1868. |
| 37 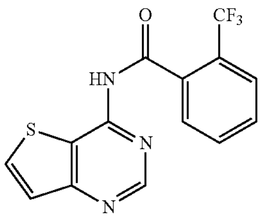 [SMILES: O=C(Nc1ncnc2ccsc12)c1ccccc1C(F)(F)F] | N-(thieno[3,2-d]pyrimidin-4-yl)-2-(trifluoromethyl)benzamide<br>Synthesised via Route 2<br>$^1$H NMR (400 MHz, $CDCl_3$) δ (ppm) 9.67 (br. s, 1H), 8.40 (s, 1H), 8.06 (d, J = 5.6 Hz, 1H), 7.81 (dd, J = 5.4, 3.7 Hz, 1H), 7.74 (dd, J = 5.1, 3.7 Hz, 1H), 7.71-7.65 (m, 2H), 7.53 (d, J = 5.6 Hz, 1H).<br>HRMS (Cl) $C_{14}H_8N_3F_3OS$ [M + H]$^+$ 324.0401. |
| 38 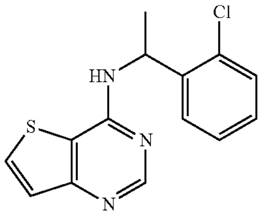 [SMILES: CC(Nc1ncnc2ccsc12)c1ccccc1Cl] | N-(1-(2-chlorophenyl)ethyl)thieno[3,2-d]pyrimidin-4-amine<br>Synthesised via Route 2<br>$^1$H NMR (400 MHz, $CDCl_3$) δ (ppm) 8.59 (s, 1H), 7.71 (d, J = 5.4 Hz, 1H), 7.46-7.36 (m, 3H), 7.26-7.18 (m, 2H), 5.83 (p, J = 6.9 Hz, 1H), 5.40 (d, J = 5.2 Hz, 1H), 1.68 (d, J = 6.9 Hz, 3H).<br>HRMS (Cl) $C_{14}H_{12}N_3ClS$ [M + H]$^+$ 290.0525. |
| 40 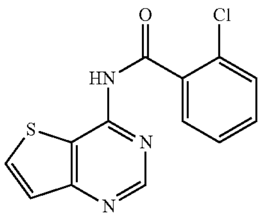 [SMILES: O=C(Nc1ncnc2ccsc12)c1ccccc1Cl] | 2-chloro-N-(thieno[3,2-d]pyrimidin-4-yl)benzamide<br>Synthesised via Route 2<br>$^1$H NMR (400 MHz, $CDCl_3$) δ (ppm) 9.89 (s, 1H), 8.50 (s, 1H), 8.05 (d, J = 5.6 Hz, 1H), 7.85-7.80 (m, 1H), 7.52 (d, J = 5.6 Hz, 1H), 7.50-7.46 (m, 2H), 7.42 (ddd, J = 7.6, 5.7, 2.9 Hz, 1H).<br>HRMS (Cl) $C_{13}H_8N_3OClS$ [M + H]$^+$ 290.0161. |
| 41 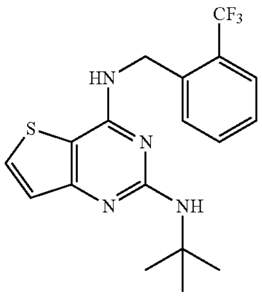 [SMILES: CC(C)(C)Nc1nc(NCc2ccccc2C(F)(F)F)c2sccc2n1] | $N^2$-(tert-butyl)-$N^4$-(2-(trifluoromethyl)benzyl)thieno[3,2-d]pyrimidine-2,4-diamine<br>Synthesised via Route 1<br>$^1$H NMR (400 MHz, $CDCl_3$) δ (ppm) 7.68 (d, J = 7.7 Hz, 1H), 7.61-7.43 (m, 3H), 7.37 (t, J = 7.0 Hz, 1H), 7.09 (d, J = 5.3 Hz, 1H), 5.44 (br. s, 1H), 5.30 (br. s, 1H), 5.04 (d, J = 5.5 Hz, 2H), 1.34 (s, 9H).<br>HRMS (Cl) $C_{18}H_{19}N_4F_3S$ [M + H]$^+$ 381.1339. |

TABLE 1-continued

| | |
|---|---|
| 42 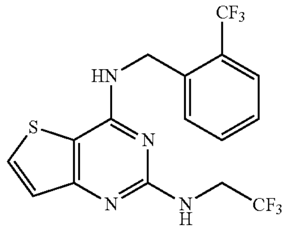 [SMILES: FC(F)(F)CNc1nc(NCc2ccccc2C(F)(F)F)c2sccc2n1] | $N^2$-(2,2,2-trifluoroethyl)-$N^4$-(2-(trifluoromethyl)benzyl)thieno[3,2-d]pyrimidine-2,4-diamine<br>Synthesised via Route 1<br>$^1H$ NMR (400 MHz, $CDCl_3$) δ (ppm) 7.69 (d, J = 7.7 Hz, 1H), 7.63-7.55 (m, 2H), 7.50 (t, J = 7.2 Hz, 1H), 7.39 (t, J = 7.5 Hz, 1H), 7.14 (d, J = 5.3 Hz, 1H), 5.32-5.10 (m, 2H), 5.00 (d, J = 5.7 Hz, 2H), 4.12 (qd, J = 9.2, 6.9 Hz, 2H).<br>HRMS (CI) $C_{16}H_{12}N_4F_6S$ $[M + H]^+$ 407.0744. |
| 43 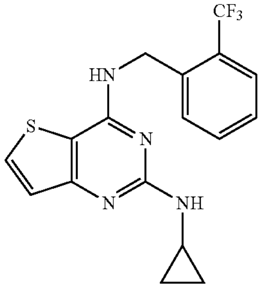 [SMILES: FC(F)(F)c1ccccc1CNc1nc(NC2CC2)nc2ccsc12] | $N^2$-cyclopropyl-$N^4$-(2-(trifluoromethyl)benzyl)thieno[3,2-d]pyrimidine-2,4-diamine<br>Synthesised via Route 1<br>$^1H$ NMR (500 MHz, $CDCl_3$) δ (ppm) 7.70 (d, J = 8.1 Hz, 2H), 7.59 (d, J = 5.3 Hz, 1H). 7.52 (t, J = 7.6 Hz, 1H), 7.41 (t, J = 7.6 Hz, 1H), 7.20 (d, J = 5.3 Hz, 1H), 5.42 (br. s, 1H), 5.20 (br. s, 1H), 5.05 (d, J = 5.9 Hz, 2H), 2.84-2.77 (m, 1H), 0.80-0.74 (m, 2H), 0.57-0.51 (m, 2H).<br>HRMS (CI) $C_{17}H_{15}N_4F_3S$ $[M + H]^+$ 365.1029. |
| 44 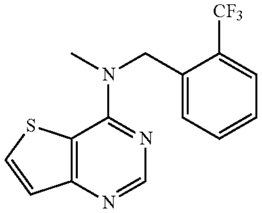 [SMILES: CN(Cc1ccccc1C(F)(F)F)c1ncnc2ccsc12] | N-methyl-N-(2-(trifluoromethyl)benzyl)thieno[3,2-d]pyrimidin-4-amine<br>Synthesised via Route 2<br>$^1H$ NMR (400 MHz, $CDCl_3$) δ (ppm) 8.58 (s, 1H), 7.76-7.70 (m, 2H), 7.48 (t, J = 7.6 Hz, 1H), 7.44 (d, J = 5.6 Hz, 1H), 7.39 (t, J = 7.5 Hz, 1H), 7.29 (d, J = 7.8 Hz, 1H), 5.30 (s, 2H), 3.47 (s, 3H).<br>HRMS (ES) $C_{15}H_{13}N_3F_3S$ $[M + H]^+$ 324.0792. |
| 45 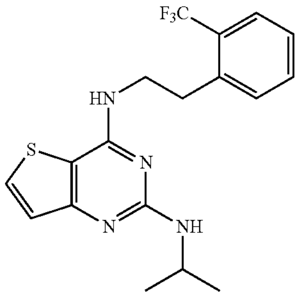 [SMILES: CC(C)Nc1nc(NCCc2ccccc2C(F)(F)F)c2sccc2n1] | $N^2$-isopropyl-$N^4$-(2-(trifluoromethyl)phenethyl)thieno(3,2-d]pyrimidine-2,4-diamine<br>Synthesised via Route 1<br>$^1H$ NMR (400 MHz, $CDCl_3$) δ (ppm) 7.67 (d, J = 7.8 Hz, 1H), 7.53 (d, J = 5.3 Hz, 1H), 7.48 (t, J = 7.5 Hz, 1H), 7.39-7.30 (m, 2H), 7.10 (d, J = 5.3 Hz, 1H), 4.98-4.71 (m, 2H), 4.30-4.17 (m, 1H), 3.84 (dd, J = 13.8, 6.6 Hz, 2H), 3.18 (t, J = 7.2 Hz, 2H), 1.27 (d, J = 6.5 Hz, 6H).<br>HRMS (CI) $C_{18}H_{19}N_4F_3S$ $[M + H]^+$ 381.1353. |
| 46 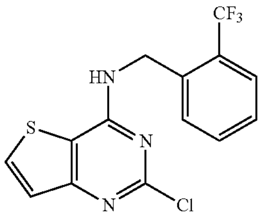 | 2-chloro-N-(2-(trifluoromethyl)benzyl)thieno[3,2-d]pyrimidin-4-amine<br>Synthesised via Route 1<br>$^1H$ NMR (400 MHz, $CDCl_3$) δ (ppm) 7.74 (d, J = 5.3 Hz, 1H), 7.70 (d, J = 7.8 Hz, 2H), 7.55 (t, J = 7.6 Hz, 1H), 7.43 (t, J = 7.6 Hz, 1H), 7.36 (d, J = 5.3 Hz, 1H), 5.46 (br. s, 1H), 5.06 (d, J = 5.7 Hz, 2H).<br>HRMS (CI) $C_{14}H_{10}N_3F_3Cl_2S$ $[M + H]^+$ 378.9921. |

TABLE 1-continued

47

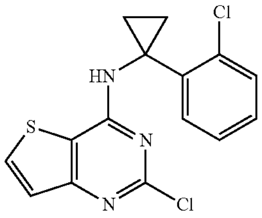 [SMILES: Clc1nc(NC2(c3ccccc3Cl)CC2)c2sccc2n1]

2-chloro-N-(1-(2-chlorophenyl)cyclopropyl)thieno[3,2-d]pyrimidine-4-diamine

Synthesised via Route 1

$^{1}$H NMR (400 MHz, $CDCl_3$) δ (ppm) 7.93 (d, J = 7.6 Hz, 1H), 7.70 (d, J = 5.3 Hz, 1H), 7.36-7.28 (m, 2H), 7.27-7.23 (m, 1H), 7.19 (td, J = 7.6, 1.7 Hz, 1H), 6.16 (br. s, 1H), 1.41 (d, J = 7.3 Hz, 4H).

HRMS (CI) $C_{15}H_{11}N_3Cl_2S$ $[M + H]^+$ 336.0118.

48

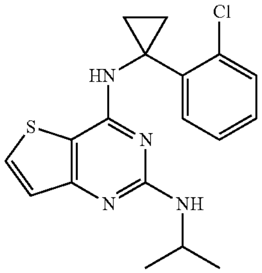 [SMILES: CC(C)Nc1nc(NC2(c3ccccc3Cl)CC2)c2sccc2n1]

$N^4$-(1-(2-chlorophenyl)cyclopropyl)-$N^2$-isopropylthieno[3,2-d]pyrimidine-2,4-diamine Synthesised via Route 1

$^{1}$H NMR (400 MHz, $CDCl_3$) δ (ppm) 7.78 (dd, J = 7.1, 2.2 Hz, 1H), 7.49 (d, J = 5.3 Hz, 1H), 7.32 (dd, J = 7.2, 1.9 Hz, 1H), 7.22-7.13 (m, 2H), 7.01 (d, J = 5.3 Hz, 1H), 5.81 (s, 1H), 4.77 (d, J = 6.5 Hz, 1H), 4.36-4.21 (m, 1H), 1.42-1.30 (m, 4H), 1.29 (d, J = 6.5 Hz, 6H).

HRMS (CI) $C_{18}H_{19}N_4ClS$ $[M + H]^+$ 359.1099.

49

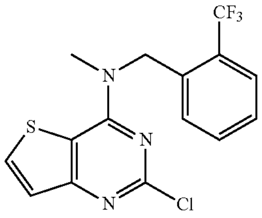 [SMILES: CN(Cc1ccccc1C(F)(F)F)c1nc(Cl)nc2ccsc12]

2-chloro-N-methyl-N-(2-(trifluoromethyl)benzyl)thieno[3,2-d]pyrimidin-4-amine

Synthesised via Route 1

$^{1}$H NMR (400 MHz, $CDCl_3$) δ (ppm) 7.78 - 7.70 (m, 2H), 7.50 (t, J = 7.4 Hz, 1H), 7.41 (t, J = 7.5 Hz, 1H), 7.37 (d, J = 5.5 Hz, 1H), 7.28 (d, J = 7.8 Hz, 1H), 5.28 (s, 2H), 3.44 (s, 3H).

HRMS (CI) $C_{15}H_{11}N_3F_3ClS$ $[M + H]^+$ 358.0397.

50

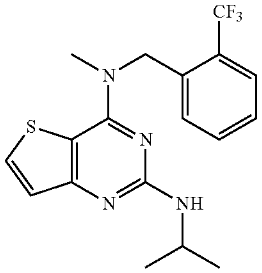 [SMILES: CC(C)Nc1nc(N(C)Cc2ccccc2C(F)(F)F)c2sccc2n1]

$N^2$-isopropyl-$N^4$-methyl-$N^4$-(2-(trifluoromethyl)benzyl)thieno[3,2-d]pyrimidine-2,4-diamine Synthesised via Route 1

$^{1}$H NMR (400 MHz, $CDCl_3$) δ (ppm) 7.70 (d, J = 7.7 Hz, 1H), 7.57 (d, J = 5.5 Hz, 1H), 7.46 (t, J = 7.5 Hz, 1H), 7.36 (t, J = 7.5 Hz, 1H), 7.30 (d, J = 7.8 Hz, 1H), 7.11 (d, J = 5.5 Hz, 1H), 5.20 (s, 2H), 4.67 (d, J = 7.0 Hz, 1H), 4.04 (dq, J = 13.4, 6.5 Hz, 1H), 3.43 (s, 3H), 1.13 (d, J = 6.4 Hz, 6H).

HRMS (ES) $C_{18}H_{20}N_4F_3S$ $[M + H]^+$ 381.1351.

51

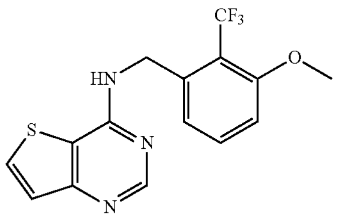 [SMILES: COc1cccc(CNc2ncnc3ccsc23)c1C(F)(F)F]

N-(3-methoxy-2-(trifluoromethyl)benzyl)thieno[3,2-d]pyrimidin-4-amine

Synthesised via Route 2

$^{1}$H NMR (400 MHz, DMSO) δ (ppm) 8.44-8.37 (m, 2H), 8.15 (d, J = 5.4 Hz, 1H), 7.51 (t, J = 8.1 Hz, 1H), 7.41 (d, J = 5.4 Hz, 1H), 7.17 (d, J = 8.4 Hz, 1H), 7.02 (d, J = 7.9 Hz, 1H), 4.87 (d, J = 2.7 Hz, 2H), 3.87 (s, 3H).

HRMS (ES) $C_{15}H_{13}N_3F_3OS$ $[M + H]^+$ 340.0728.

TABLE 1-continued

| | |
|---|---|
| 52<br>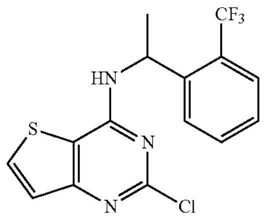 [SMILES: CC(Nc1nc(Cl)nc2ccsc12)c1ccccc1C(F)(F)F] | 2-chloro-N-(1-(2-(trifluoromethyl)phenyl)ethyl)thieno[3,2-d]pyrimidin-4-amine<br>Synthesised via Route 1<br>$^1$H NMR (400 MHz, DMSO) δ (ppm) 8.93 (d, J = 7.0 Hz, 1H), 8.21 (d, J = S.4 Hz, 1H), 7.81 (d, J = 7.9 Hz, 1H), 7.70 (d, J = 7.9 Hz, 1H), 7.65 (t, J = 7.7 Hz, 1H), 7.44 (t, J = 7.6 Hz, 1H), 7.33 (d, J = 5.4 Hz, 1H), 5.75-5.62 (m, 1H), 1.54 (d, J = 6.9 Hz, 3H).<br>HRMS (ES) $C_{15}H_{12}N_3F_3ClS$ $[M + H]^+$ 358.0391. |
| 53<br>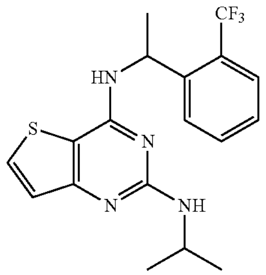 [SMILES: CC(C)Nc1nc(NC(C)c2ccccc2C(F)(F)F)c2sccc2n1] | $N^2$-isopropyl-$N^4$-(1-(2-(trifluoromethyl)phenyl)ethyl)thieno[3,2-d]pyrimidine-2,4-diamine<br>Synthesised via Route 1<br>$^1$H NMR (400 MHz, $CDCl_3$) δ (ppm) 7.66 (d, J = 7.8 Hz, 1H), 7.60 (d, J = 7.9 Hz, 1H), 7.54 (d, J = 5.3 Hz, 1H), 7.49 (t, J = 7.6 Hz, 1H), 7.33 (t, J = 7.6 Hz, 1H), 7.07 (d, J = 5.3 Hz, 1H), 5.71 (p, J = 6.5 Hz, 1H), 4.98 (br. s, 1H), 4.65 (br. s, 1H), 4.06-3.90 (m, 1H), 1.61 (d, J = 6.8 Hz, 3H), 1.15 (d, J = 6.5 Hz, 3H), 0.90 (d, J = 6.1 Hz, 3H).<br>HRMS (ES) $C_{15}H_{12}N_3F_3ClS$ $[M + H]^+$ 381.1356. |
| 54<br>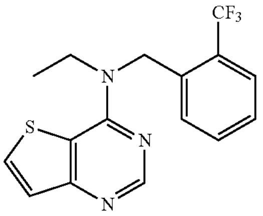 [SMILES: CCN(Cc1ccccc1C(F)(F)F)c1ncnc2ccsc12] | N-ethyl-N-(2-(trifluoromethyl)benzyl)thieno[3,2-d]pyrimidin-4-amine<br>Synthesised via Route 2<br>$^1$H NMR (400 MHz, $CDCl_3$) δ (ppm) 8.58 (s, 1H), 7.71 (dd, J = 6.8, 4.0 Hz, 2H), 7.49-7.41 (m, 2H), 7.38 (t, J = 7.5 Hz, 1H), 7.31 (d, J = 7.7 Hz, 1H), 5.29 (s, 2H), 3.85 (q, J = 7.1 Hz, 2H), 1.37 (t, J = 7.1 Hz, 3H).<br>HRMS (ES) $C_{16}H_{15}N_3F_3S$ $[M + H]^+$ 338.0930. |
| 55<br>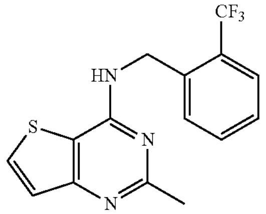 [SMILES: Cc1nc(NCc2ccccc2C(F)(F)F)c2sccc2n1] | 2-methyl-N-(2-(trifluoromethyl)benzyl)thieno[3,2-d]pyrimidin-4-amine<br>Synthesised via Route 2<br>$^1$H NMR (400 MHz, $CDCl_3$) δ (ppm) 7.75-7.63 (m, 3H), 7.52 (t, J = 7.5 Hz, 1H), 7.44-7.33 (m, 2H), 5.22 (br. s, 1H), 5.09 (d, J = 5.3 Hz, 2H), 2.66 (s, 3H).<br>HRMS (ES) $C_{15}H_{13}N_3F_3S$ $[M + H]^+$ 324.0780. |
| 56<br>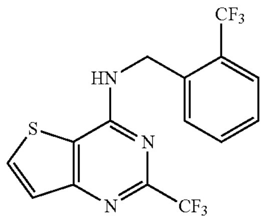 [SMILES: FC(F)(F)c1nc(NCc2ccccc2C(F)(F)F)c2sccc2n1] | 2-(trifluoromethyl)-N-(2-(trifluoromethyl)benzyl)thieno(3,2-d]pyrimidin-4-amine<br>Synthesised via Route 2<br>$^1$H NMR (400 MHz, $CDCl_3$) δ (ppm) 7.82 (d, J = 5.4 Hz, 1H), 7.79 (d, J = 7.7 Hz, 1H), 7.70 (d, J = 7.8 Hz, 1H), 7.54 (dd, J = 9.3, 3.9 Hz, 2H), 7.42 (t, J = 7.7 Hz, 1H), 5.49 (br. s, 1H), 5.10 (d, J = 5.9 Hz, 2H).<br>HRMS (ES) $C_{15}H_{10}N_3F_6S$ $[M + H]^+$ 378.0493. |
| 57<br>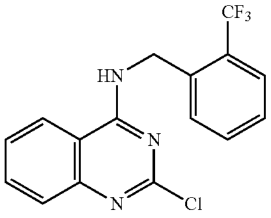 [SMILES: FC(F)(F)c1ccccc1CNc1nc(Cl)nc2ccccc12] | 2-chloro-N-(2-(trifluoromethyl)benzyl)quinazolin-4-amine<br>Synthesised via Route 4<br>$^1$H NMR (400 MHz, $CDCl_3$) δ (ppm) 7.80-7.62 (m, 5H), 7.55 (t, J = 7.5 Hz, 1H), 7.44 (dd, J = 16.4, 8.2 Hz, 2H), 6.28 (br. s, 1H), 5.07 (d, J = 5.1 Hz, 2H).<br>HRMS (ES) $C_{16}H_{12}N_3F_3Cl$ $[M + H]^+$ 338.0670. |

TABLE 1-continued

58

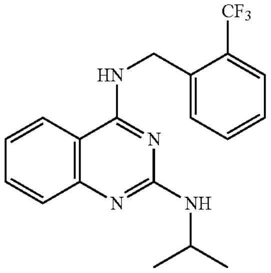 [SMILES: CC(C)Nc1nc(NCc2ccccc2C(F)(F)F)c2ccccc2n1]

N[2]-isopropyl-N[4]-(2-(trifluoromethyl)benzyl)quinazoline-2,4-diamine

Synthesised via Route 4

$^1$H NMR (400 MHz, CDCl3) δ (ppm) 13.42 (s, 1H), 8.30-8.11 (m, 1H), 7.93 (d, J = 8.4 Hz, 1H), 7.79-7.61 (m, 2H), 7.52 (dd, J = 14.7, 7.8 Hz, 2H), 7.43 (t, J = 7.5 Hz, 1H), 7.32 (m, 1H), 5.10 (d, J = 5.4 Hz, 2H), 4.20-4.05 (m, 1H), 1.57 (d, J = 6.6 Hz, 2H), 1.20 (d, J = 6.6 Hz, 4H).

HRMS (ES) $C_{19}H_{20}N_4F_3$ $[M + H]^+$ 361.1648.

59

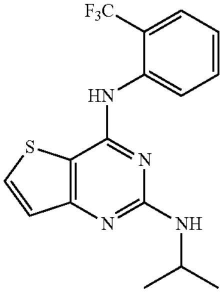 [SMILES: CC(C)Nc1nc(Nc2ccccc2C(F)(F)F)c2sccc2n1]

N[2]-isopropyl-N[4]-(2-(trifluoromethyl)phenyl)thieno[3,2-d]pyrimidin-2,4-amine

Synthesised via Route 1

$^1$H NMR (400 MHz, $CDCl_3$) δ (ppm) 8.21 (d, J = 8.2 Hz, 1H), 7.70 (d, J = 7.8 Hz, 1H), 7.61 (dd, J = 16.5, 6.7 Hz, 2H), 7.30 (dd, J = 9.8, 4.0 Hz, 1H), 7.17 (d, J = 5.3 Hz, 1H), 6.82 (br. s, 1H), 4.92 (br. s, 1H), 4.27-4.07 (m, 1H), 1.27 (d, J = 6.6 Hz, 6H).

HRMS (ES) $C_{16}H_{16}N_4F_3S$ $[M + H]^+$ 353.1039.

60

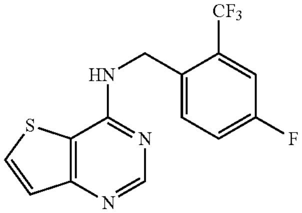 [SMILES: Fc1ccc(CNc2ncnc3ccsc23)c(C(F)(F)F)c1]

N-(4-fluoro-2-(trifluoromethyl)benzyl)thieno[3,2-d]pyrimidin-4-amine

Synthesised via Route 2

$^1$H NMR (400 MHz, $CDCl_3$) δ (ppm) 8.69 (s, 1H), 7.76 (d, J = 5.4 Hz, 1H), 7.71 (dd, J = 8.6, 5.5 Hz, 1H), 7.49 (d, J = 5.4 Hz, 1H), 7.42 (dd, J = 8.9, 2.7 Hz, 1H), 7.23 (td, J = 8.2, 2.7 Hz, 1H), 5.34 (br. s, 1H), 5.08 (d, J = 5.7 Hz, 2H).

HRMS (ES) $C_{14}H_{10}N_3F_4S$ $[M + H]^+$ 328.0527.

61

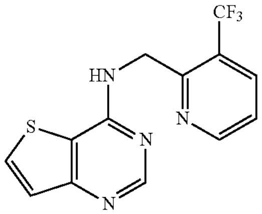 [SMILES: FC(F)(F)c1cccnc1CNc1ncnc2ccsc12]

N-((3-(trifluoromethyl)pyridin-2-yl)methyl)thieno[3,2-d]pyrimidin-4-amine

Synthesised via Route 2

$^1$H NMR (400 MHz, $CDCl_3$) δ (ppm) 8.81 (d, J = 4.4 Hz, 1H), 8.70 (s, 1H), 8.04 (d, J = 7.9 Hz, 1H), 7.76 (d, J = 5.4 Hz, 1H), 7.47 (d, J = 5.4 Hz, 1H), 7.43 (dd, J = 7.5, 5.2 Hz, 1H), 7.02 (br. s, 1H), 5.14 (d, J = 3.8 Hz, 2H).

HRMS (ES) $C_{13}H_{10}N_4F_3S$ $[M + H]^+$ 311.0572.

62

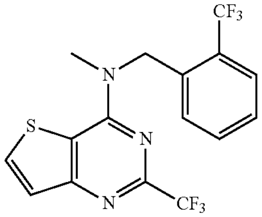 [SMILES: CN(Cc1ccccc1C(F)(F)F)c1nc(C(F)(F)F)nc2ccsc12]

N-methyl-2-(trifluoromethyl)-N-(2-(trifluoromethyl)benzyl)thieno[3,2-d]pyrimidin-4-amine Synthesised via Route 2

$^1$H NMR (400 MHz, $CDCl_3$) δ (ppm) 7.83 (d, J = 5.6 Hz, 1H), 7.74 (d, J = 7.7 Hz, 1H), 7.55 (d, J = 5.6 Hz, 1H), 7.49 (t, J = 7.5 Hz, 1H), 7.41 (t, J = 7.5 Hz, 1H), 7.30 (d, J = 7.7 Hz, 1H), 5.32 (s, 2H), 3.51 (s, 3H).

HRMS (ES) $C_{16}H_{12}N_3F_6S$ $[M + H]^+$ 392.0651.

TABLE 1-continued

63

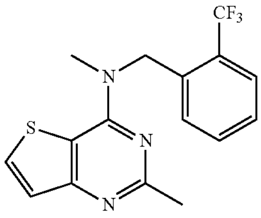 [SMILES: Cc1nc(N(C)Cc2ccccc2C(F)(F)F)c2sccc2n1]

N,2-dimethyl-N-(2-(trifluoromethyl)benzyl)thieno[3,2-d]pyrimidin-4-amine

Synthesised via Route 2
$^1$H NMR (400 MHz, $CDCl_3$) δ (ppm) 7.72 (d, J = 7.7 Hz, 1H), 7.68 (d, J = 5.2 Hz, 1H), 7.47 (t, J = 7.6 Hz. 1H), 7.38 (t, J = 6.7 Hz, 2H), 7.29 (d, J = 7.7 Hz, 1H), 5.29 (s, 2H), 3.45 (s, 3H), 2.59 (s, 3H).
HRMS (ES) $C_{16}H_{15}N_3F_3S$ [M + H]$^+$ 338.0935.

64

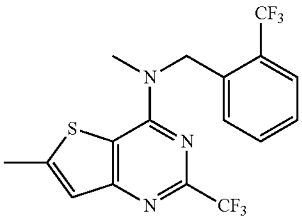 [SMILES: Cc1cc2nc(C(F)(F)F)nc(N(C)Cc3ccccc3C(F)(F)F)c2s1]

N,6-dimethyl-2-(trifluoromethyl)-N-(2-(trifluoromethyl)benzyl)thieno[3,2-d]pyrimidin-4-amine Synthesised via Route 2
$^1$H NMR (400 MHz, $CDCl_3$) δ (ppm) 7.73 (d, J = 7.7 Hz, 1H), 7.49 (t, J = 7.5 Hz, 1H), 7.40 (t, J = 7.4 Hz, 1H), 7.30 (d, J = 7.6 Hz, 1H), 7.20 (s, 1H), 5.27 (s, 2H), 3.44 (s, 3H), 2.59 (s, 3H).
HRMS (ES) $C_{17}H_{14}N_3F_6S$ [M + H]$^+$ 406.0808.

65

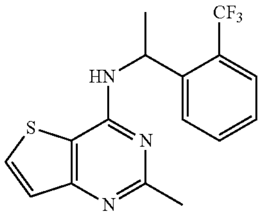 [SMILES: Cc1nc(NC(C)c2ccccc2C(F)(F)F)c2sccc2n1]

2-methyl-N-(1-(2-(trifluoromethyl)phenyl)ethyl)thieno[3,2-d]pyrimidin-4-amine

Synthesised via Route 2
$^1$H NMR (400 MHz, $CDCl_3$) δ (ppm) 7.72-7.63 (m, 2H), 7.60 (d, J = 7.8 Hz, 1H), 7.49 (t, J = 7.6 Hz, 1H), 7.35 (d, J = 7.8 Hz, 1H), 7.33 (d, J = 5.4 Hz, 1H), 5.83 (p, J = 6.6 Hz, 1H), 5.19 (d, J = 5.7 Hz, 1H), 2.50 (s, 3H), 1.63 (d, J = 6.8 Hz, 3H).
HRMS (ES) $C_{16}H_{15}N_3F_3S$ [M + H]$^+$ 338.0933.

66

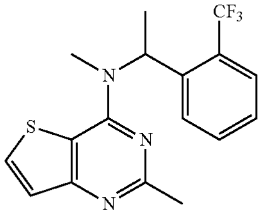 [SMILES: Cc1nc(N(C)C(C)c2ccccc2C(F)(F)F)c2sccc2n1]

N,2-dimethyl-N-(1-(2-(trifluoromethyl)phenyl)ethyl)thieno[3,2-d]pyrimidin-4-amine Synthesised via Route 2
$^1$H NMR (400 MHz, $CDCl_3$) δ (ppm) 7.70 (d, J = 7.8 Hz, 1H), 7.66 (d, J = 5.5 Hz, 1H), 7.63 (d, J = 7.8 Hz, 1H), 7.57 (t, J = 7.5 Hz, 1H), 7.42 (t, J = 7.6 Hz, 1H), 7.34 (d, J = 5.5 Hz, 1H), 6.62 (q, J = 6.8 Hz, 1H), 3.20 (s, 3H), 2.57 (s, 3H), 1.67 (d, J = 6.9 Hz, 3H).
HRMS (ES) $C_{17}H_{17}N_3F_3S$ [M + H]$^+$ 352.1091.

68

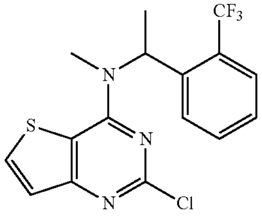 [SMILES: CC(c1ccccc1C(F)(F)F)N(C)c1nc(Cl)nc2ccsc12]

2-chloro-N-methyl-N-(1-(2-(trifluoromethyl)phenyl)ethyl)thieno[3,2-d]pyrimidin-4-amine Synthesised via Route 1
$^1$H NMR (400 MHz, $CDCl_3$) δ (ppm) 7.74 (d, J = 5.6 Hz, 1H), 7.72 (d, J = 8.4 Hz, 1H), 7.69-7.58 (m, 2H), 7.46 (t, J = 7.5 Hz, 1H), 7.35 (d, J = 5.5 Hz, 1H), 6.54 (q, J = 6.8 Hz, 1H), 3.11 (s, 3H), 1.70 (d, J = 6.8 Hz, 3H).
HRMS (ES) $C_{16}H_{14}N_3F_3ClS$ [M + H]$^+$ 372.0541.

TABLE 1-continued

68

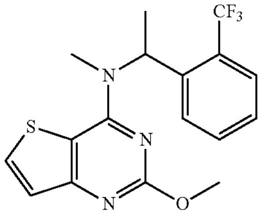 [SMILES: COc1nc(N(C)C(C)c2ccccc2C(F)(F)F)c2sccc2n1]

2-methoxy-N-methyl-N-(1-(2-(trifluoromethyl)phenyl)ethyl)thieno[3,2-d]pyrimidin-4-amine Synthesised via Route 2
$^1$H NMR (400 MHz, $CDCl_3$) δ (ppm) 7.72 (d, J = 7.8 Hz, 1H), 7.67 (dd, J = 6.6, 4.4 Hz, 2H), 7.62 (t, J = 7.6 Hz, 1H), 7.46 (t, J = 7.6 Hz, 1H), 7.28 (s, 1H), 6.66 (q, J = 6.8 Hz, 1H), 4.00 (s, 3H), 3.08 (s, 3H), 1.69 (d, J = 6.8 Hz, 3H).
HRMS (ES) $C_{17}H_{17}N_3F_3OS$ $[M + H]^+$ 368.1037.

69

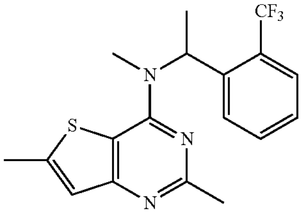 [SMILES: Cc1nc(N(C)C(C)c2ccccc2C(F)(F)F)c2sc(C)cc2n1]

N,2,6-trimethyl-N-(1-(2-(trifluoromethyl)phenyl)ethyl)thieno[3,2-d]pyrimidin-4-amine Synthesised via Route 2
$^1$H NMR (400 MHz, $CDCl_3$) δ (ppm) 7.70 (d, J = 7.8 Hz, 1H), 7.63 (d, J = 7.8 Hz, 1H), 7.57 (t, J = 7.5 Hz, 1H), 7.41 (t, J = 7.6 Hz, 1H), 7.01 (s, 1H), 6.56 (q, J = 6.8 Hz, 1H), 3.14 (s, 3H), 2.56 (d, J = 0.7 Hz, 3H), 2.54 (s, 3H), 1.66 (d, J = 6.8 Hz, 3H).
HRMS (ES) $C_{18}H_{19}N_3F_3S$ $[M + H]^+$ 366.1247.

70

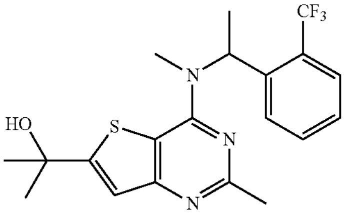 [SMILES: Cc1nc(N(C)C(C)c2ccccc2C(F)(F)F)c2sc(C(C)(C)O)cc2n1]

2-(2-methyl-4-(methyl(1-(2-(trifluoromethyl)phenyl)ethyl)amino)thieno[3,2-d]pyrimidin-6-yl)propan-2-ol Synthesised via Route 3
$^1$H NMR (400 MHz, $CDCl_3$) δ (ppm) 7.70 (d, J = 7.8 Hz, 1H), 7.63 (d, J = 7.8 Hz, 1H), 7.57 (t, J = 7.5 Hz, 1H), 7.42 (t, J = 7.5 Hz, 1H), 7.14 (s, 1H), 6.60 (q, J = 6.8 Hz, 1H), 3.19 (s, 3H), 2.55 (s, 3H), 1.69 (s, 6H), 1.66 (d, J = 6.9 Hz, 3H).
HRMS (ES) $C_{20}H_{23}N_3F_3OS$ $[M + H]^+$ 410.1505.

72

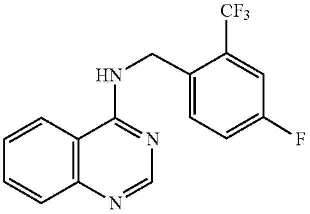 [SMILES: Fc1ccc(CNc2ncnc3ccccc23)c(C(F)(F)F)c1]

N-(4-fluoro-2-(trifluoromethyl)benzyl)quinazolin-4-amine

Synthesised via Route 5
$^1$H NMR (400 MHz, $CDCl_3$) δ (ppm) 8.70 (s, 1H), 7.88 (d, J = 8.3 Hz, 1H), 7.80-7.73 (m, 1H), 7.73-7.66 (m, 2H), 7.52-7.46 (m, 1H), 7.40 (dd, J = 8.9, 2.6 Hz, 1H), 7.20 (td, J = 8.3, 2.6 Hz, 1H), 6.14 (br. s, 1H), 5.07 (d, J = 5.7 Hz, 2H).
HRMS (ES) $C_{16}H_{12}N_3F_4$ $[M + H]^+$ 322.0869.

73

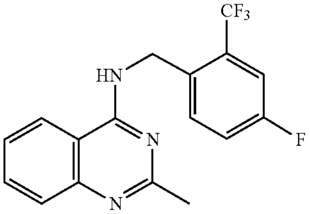 [SMILES: Cc1nc(NCc2ccc(F)cc2C(F)(F)F)c2ccccc2n1]

N-(4-fluoro-2-(trifluoromethyl)benzyl)-2-methylquinazolin-4-amine

Synthesised via Route 5
$^1$H NMR (400 MHz, DMSO) δ (ppm) 8.75 (t, J = 5.7 Hz, 1H), 8.28 (d, J = 7.8 Hz, 1H), 7.75 (t, J = 8.2 Hz, 1H), 7.68-7.61 (m, 2H), 7.58 (dd, J = 8.6, 5.7 Hz, 1H), 7.52-7.44 (m, 2H), 4.93 (d, J = 5.4 Hz, 2H), 2.39 (s, 3H).
HRMS (ES) $C_{17}H_{14}N_3F_4$ $[M + H]^+$ 336.1127.

TABLE 1-continued

| | | |
|---|---|---|
| 74 | 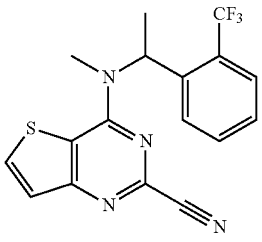 [SMILES: CC(c1ccccc1C(F)(F)F)N(C)c1nc(C#N)nc2ccsc12] | 4-(methyl(1-(2-(trifluoromethyl)phenyl)ethyl)amino)thieno[3,2-d]pyrimidine-2-carbonitrile<br>Synthesised via Route 2<br>$^1$H NMR (400 MHz, DMSO) δ (ppm) 8.41 (d, J = 5.6 Hz, 1H), 7.87 (d, J = 7.8 Hz, 1H), 7.82-7.72 (m, 2H), 7.59 (t, J = 7.6 Hz, 1H), 7.55 (d, J = 5.6 Hz, 1H), 6.37 (q, J = 6.8 Hz, 1H), 3.24 (s, 3H), 1.68 (d, J = 6.9 Hz, 3H).<br>HRMS (ES) $C_{17}H_{14}N_4F_3S$ [M + H]$^+$ 363.0888. |
| 75 | 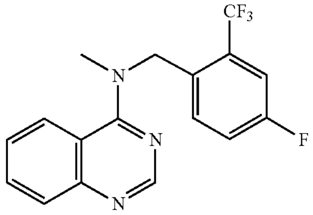 [SMILES: CN(Cc1ccc(F)cc1C(F)(F)F)c1ncnc2ccccc12] | N-(4-fluoro-2-(trifluoromethyl)benzyl)-N-methylquinazolin-4-amine<br>Synthesised via Route 5<br>$^1$H NMR (400 MHz, $CDCl_3$) δ (ppm) 8.70 (s, 1H), 7.92 (d, J = 8.4 Hz, 1H), 7.85 (d, J = 8.5 Hz, 1H), 7.78-7.69 (m, 1H), 7.59 (dd, J = 8.4, 5.5 Hz, 1H), 7.48 (dd, J = 8.8, 2.5 Hz, 1H), 7.41-7.33 (m, 1H), 7.31-7.22 (m, 1H), 5.13 (s, 2H), 3.33 (s, 4H).<br>HRMS (ES) $C_{17}H_{14}N_3F_4$ [M + H]$^+$ 336.1126. |
| 88 | 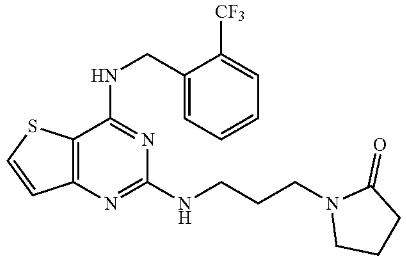 [SMILES: O=C1CCCN1CCCNc1nc(NCc2ccccc2C(F)(F)F)c2sccc2n1] | 1-(3-((4-((2-(trifluoromethyl)benzyl)amino)thieno[3,2-d]pyrimidin-2-yl)amino)propyl)pyrrolidin-2-one<br>Synthesised via Route 1<br>1H NMR (400 MHz, Chloroform-d) δ (ppm) 7.68 (d, J = 7.8 Hz, 1H), 7.63 (d, J = 7.8 Hz, 1H), 7.55 (dd, J = 5.3, 1.0 Hz, 1H), 7.50 (t, J = 7.6 Hz, 1H), 7.38 (t, J = 7.6 Hz, 1H), 7.12 (dd, J = 5.3,1.0 Hz, 1H), 5.22 (m, 1H), 5.11 (br.s, 1H), 5.00 (d, J = 6.0 Hz, 2H), 3.41 (q, J = 6.5 Hz, 2H), 3.35 (td, J = 7.0, 3.2 Hz, 4H), 2.38 (t, J = 8.1 Hz, 2H), 2.07-1.93 (m, 2H), 1.76 (p, J = 6.8 Hz, 2H).<br>HRMS (Cl+) C21H22$F_3$N5OS [M + H]$^+$ 450.1582. |
| 89 | 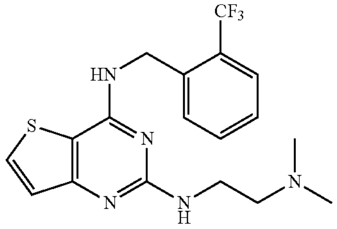 [SMILES: CN(C)CCNc1nc(NCc2ccccc2C(F)(F)F)c2sccc2n1] | N$^2$-(2-(dimethylamino)ethyl)-N$^4$-(2-(trifluoromethyl)benzyl)thieno[3,2-d]pyrimidine-2,4-diamine<br>Synthesised via Route 1<br>1H NMR (400 MHz, CDCl3) δ (ppm) 7.68 (d,J = 7.8 Hz, 1H), 7.62 (d, J-7.7 Hz, 1H), 7.54 (d, J = 5.3 Hz, 1H), 7.50 (t, J = 7.5 Hz, 1H), 7.37 (t, J = 7.6 Hz, 1H), 7.13 (d, J = 5.3 Hz, 1H), 5.30 (t, J = 4.7 Hz, 1H), 5.05 (d, J = 5.0 Hz, 1H), 5.01 (d, J = 5.5 Hz, 2H), 3.49 (dd, 1 = 11.6, 5.9 Hz, 2H), 2.49 (t, J = 6.1 Hz, 2H), 2.24 (s, 7H).<br>HRMS (ES+) C18H20F3N5S [M + H]$^+$ 396.1460 |
| 90 | 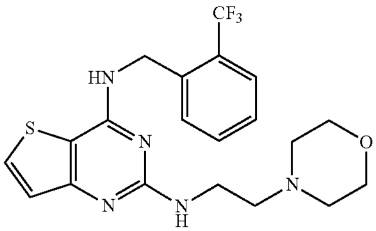 [SMILES: FC(F)(F)c1ccccc1CNc1nc(NCCN2CCOCC2)nc2ccsc12] | N$^2$-(2-morpholinoethyl)-N$^4$-(2-(trifluoromethyl)benzyl)thieno[3,2-d]pyrimidine-2,4-diamine<br>Synthesised via Route 1<br>1H NMR (400 MHz, CDCl3) δ (ppm) 7.68 (d, J = 7.8 Hz, 1H), 7.61 (d, J = 7.7 Hz, 1H), 7.56 (d, J = 5.3 Hz, 1H), 7.50 (t, J = 7.5 Hz, 1H), 7.37 (dd, J = 17.4, 9.9 Hz, 1H), 7.13 (d, J = 5.3 Hz, 1H), 5.38 (s, 1H), 5.16 (s, 1H), 5.02 (d, J = 5.9 Hz, 2H), 3.84-3.61 (m, 5H), 3.50 (dd, J = 10.1, 4.3 Hz, 2H), 2.54 (dd, J = 11.2, 5.1 Hz, 2H), 2.45 (s, 4H).<br>HRMS (Cl+) C20H22F3N5OS [M + H]$^+$ 438.1583 |

TABLE 1-continued

| | |
|---|---|
| 91 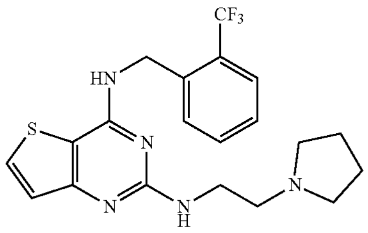 [SMILES: FC(F)(F)c1ccccc1CNc1nc(NCCN2CCCC2)nc2ccsc12] | $N^2$-(2-(pyrrolidin-1-yl)ethyl)-$N^4$-(2-(trifluoromethyl)benzyl)thieno[3,2-d]pyrimidine-2,4-diamine<br>Synthesised via Route 1<br>1H NMR (400 MHz, CDCl3) δ (ppm) 7.68 (d, J = 7.8 Hz, 1H), 7.62 (s, 1H), 7.55 (d, J = 5.3 Hz, 1H), 7.50 (t, J = 7.6 Hz, 1H), 7.38 (t, J = 7.6 Hz, 1H), 7.12 (d, J = 5.3 Hz, 1H), 5.40 (t, J = 4.9 Hz, 1H), 5.06 (d, J = 4.9 Hz, 1H), 5.01 (d, J = 5.6 Hz, 2H), 3.57 (dd, J = 11.8, 6.0 Hz, 2H), 2.74 (t, J = 6.0 Hz, 2H), 2.62 (s, 4H).<br>HRMS (ES+) C20H22F3N5S $[M + H]^+$ 422.1612 |
| 92 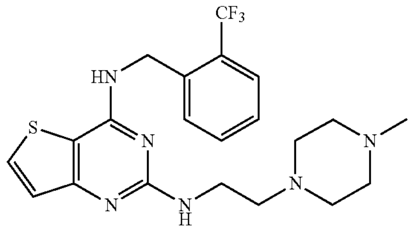 [SMILES: CN1CCN(CCNc2nc(NCc3ccccc3C(F)(F)F)c3sccc3n2)CC1] | $N^2$-(2-(4-methyipiperazin-1-yl)ethyl)-$N^4$-(2-(trifluoromethyl)benzyl)thieno[3,2-d]pyrimidine-2,4-diamine<br>Synthesised via Route 1<br>1H NMR (400 MHz, CDCl3) δ (ppm) 7.60 (d, J = 7.8 Hz, 1H), 7.54 (d, J = 7.7 Hz, 1H), 7.47 (t, J = 4.9 Hz, 1H), 7.42 (t, J = 7.5 Hz, 1H), 7.30 (t, J = 7.6 Hz, 1H), 7.04 (d, J = 5.3 Hz, 1H), 5.37 (s, 1H), 5.16 (s, 1H), 4.94 (d, J = 5.9 Hz, 2H), 3.41 (dd, J = 11.5, 5.9 Hz, 2H), 2.47 (dd, J = 12.0, 5.9 Hz, 3H), 2.41 (dd, J = 13.8, 7.7 Hz, 5H), 1.18 (t, J = 7.1 Hz, 1H).<br>HRMS (Cl+) C21H25F3N6S $[M + H]^+$ 451.1892 |
| 93 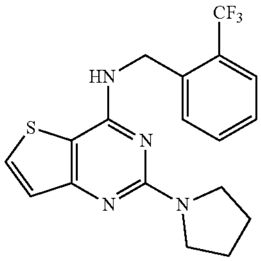 [SMILES: FC(F)(F)c1ccccc1CNc1nc(N2CCCC2)nc2ccsc12] | 2-(pyrrolidin-1-yl)-N-(2-(trifluoromethyl)benzyl)thieno[3,2-d]pyrimidin-4-amine<br>Synthesised via Route 1<br>1H NMR (400 MHz, CDCl3) δ (ppm) 8.58 (s, 1H), 7.73 (d, J = 5.6 Hz, 2H), 7.48 (t, J = 7.5 Hz, 1H), 7.43 (d, J = 5.6 Hz, 1H), 7.39 (t, J = 7.5 Hz, 1H), 7.29 (d, J = 7.7 Hz, 1H), 3.47 (s, 3H), 1.64 (s, 2H).<br>HRMS (ES+) C18H17F3N4S $[M + H]^+$ 379.1196 |
| 94 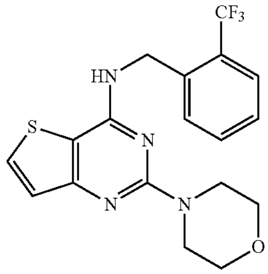 [SMILES: FC(F)(F)c1ccccc1CNc1nc(N2CCOCC2)nc2ccsc12] | 2-morpholino-N-(2-(trifluoromethyl)benzyl)thieno[3,2-d]pyrimidin-4-amine<br>Synthesised via Route 1<br>1H NMR (400 MHz, CDCl3) δ (ppm) 7.67 (t, J = 8.4 Hz, 1H), 7.60 (d, J = 7.5 Hz, 1H), 7.57 (d, J = 5.5 Hz, 1H), 7.49 (q, J = 7.5 Hz, 1H), 7.38 (t, J = 7.6 Hz, 1H), 7.16 (d, J = 5.3 Hz, 1H), 5.10 (t, J = 5.6 Hz, 1H), 5.00 (d, J = 5.9 Hz, 2H), 3.83-3.67 (m, 8H).<br>HRMS (ES+) C18H17F3N4OS $[M + H]^+$ 395.1161 |
| 95 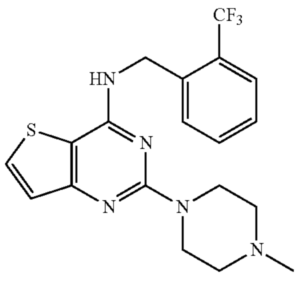 [SMILES: CN1CCN(c2nc(NCc3ccccc3C(F)(F)F)c3sccc3n2)CC1] | 2-(4-methylpiperazin-1-yl)-N-(2-(trifluoromethyl)benzyl)thieno[3,2-d]pyrimidin-4-amine<br>Synthesised via Route 1<br>1H NMR (400 MHz, CDCl3) δ (ppm) 7.68 (d, J = 7.8 Hz, 1H), 7.61 (d, J = 7.7 Hz, 1H), 7.56 (d, J = 5.3 Hz, 1H), 7.49 (t, J = 7.5 Hz, 1H), 7.38 (t, J = 7.6 Hz, 1H), 7.15 (d, J = 5.3 Hz, 1H), 5.09-5.03 (m, 1H), 5.00 (d, J = 5.8 Hz, 2H), 3.90-3.77 (m, 4H), 2.52-2.41 (m, 4H), 2.33 (s, 3H).<br>HRMS (Cl+) C19H20F3N5S $[M + H]^+$ 408.1475 |

TABLE 1-continued

| | |
|---|---|
| 96 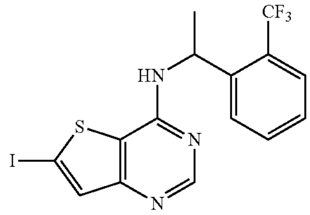 [SMILES: CC(Nc1ncnc2cc(I)sc12)c1ccccc1C(F)(F)F] | 6-iodo-N-(1-(2-(trifluoromethyl)phenyl)ethyl)thieno[3,2-d]pyrimidin-4-amine<br>Synthesised via Route 3<br>1H NMR (400 MHz, CDCl3) δ (ppm) 8.46 (s, 1H), 7.69 (d, J = 7.8 Hz, 1H), 7.60 (d, J = 7.4 Hz, 2H), 7.54 (t, J = 7.5 Hz, 1H), 7.38 (t, J = 7.6 Hz, 1H), 5.81 (p, J = 6.7 Hz, 1H), 4.95 (d, J = 5.9 Hz, 1H), 1.65 (d, J = 6.7 Hz, 3H).<br>HRMS (Cl+) C15H11F3IN3S $[M + H]^+$ 449.9759 |
| 97 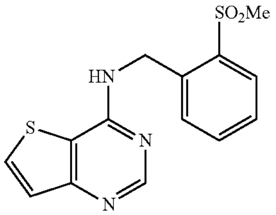 [SMILES: CS(=O)(=O)c1ccccc1CNc1ncnc2ccsc12] | N-(2-(methylsulfonyl)benzyl)thieno[3,2-d]pyrimidin-4-amine<br>Synthesised via Route 2<br>1H NMR (400 MHz, CDCl3) δ (ppm) 8.62 (s, 1H), 8.05 (dd, J = 7.9, 1.2 Hz, 1H), 7.85 (d, J = 7.7 Hz, 1H), 7.70 (d, J = 5.4 Hz, 1H), 7.61 (td, J = 7.6,1.3 Hz, 1H), 7.50 (td, J = 7.8, 1.2 Hz, 1H), 7.40 (d, J = 5.4 Hz, 1H), 6.05 (t, J = 5.9 Hz, 1H), 5.19 (d, J = 6.4 Hz, 2H), 3.24 (s, 3H).<br>HRMS (Cl+) C14H13N3O2S2 $[M + H]^+$ 320.0533 |
| 98 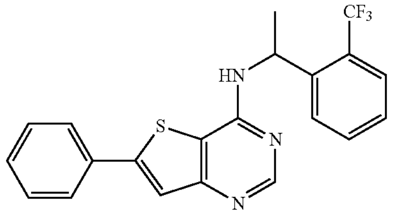 [SMILES: CC(Nc1ncnc2cc(-c3ccccc3)sc12)c1ccccc1C(F)(F)F] | 6-phenyl-N-(1-(2-(trifluoromethyl)phenyl)ethyl)thieno[3,2-d]pyrimidin-4-amine<br>Synthesised via Route 3<br>1H NMR (400 MHz, CDCl3) δ (ppm) 8.55 (s, 1H), 7.76-7.68 (m, 3H), 7.66 (d, J = 7.9 Hz, 1H), 7.58 (s, 1H), 7.55 (t, J = 7.8 Hz, 1H), 7.50-7.42 (m, 3H), 7.39 (t, J = 7.5 Hz, 1H), 5.86 (p, J = 6.7 Hz, 1H), 5.08 (d, J = 6.0 Hz, 1H), 1.68 (d, J = 6.7 Hz, 3H).<br>HRMS (Cl+) C21H16F3N3S $[M + H]^+$ 400.1104 |
| 99 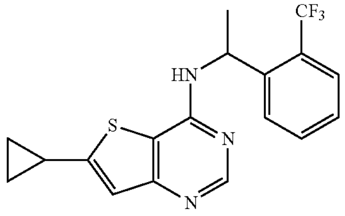 [SMILES: CC(Nc1ncnc2cc(C3CC3)sc12)c1ccccc1C(F)(F)F] | 6-cyclopropyl-N-(1-(2-(trifluoromethyl)phenyl)ethyl)thieno[3,2-d]pyrimidin-4-amine<br>Synthesised via Route 3<br>1H NMR (400 MHz, CDCl3) δ (ppm) 8.49 (s, 1H), 7.73-7.63 (m, 1H), 7.61 (d, J = 7.8 Hz, 1H), 7.51 (dd, J = 18.3, 10.5 Hz, 1H), 7.41-7.32 (m, 1H), 7.03 (s, 1H), 5.89-5.75 (m, 1H), 5.00 (d, J = 5.7 Hz, 1H), 2.26-2.16 (m, 1H), 1.31-1.19 (m, 1H), 1.20-1.11 (m, 2H), 0.87 (tt, J = 14.7, 7.2 Hz, 2H).<br>HRMS (Cl+) C18H16F3N3S $[M + H]^+$ 364.1094 |
| 102 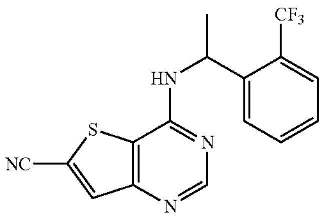 [SMILES: CC(Nc1ncnc2cc(C#N)sc12)c1ccccc1C(F)(F)F] | 4-((1-(2-(trifluoromethyl)phenyl)ethyl)amino)thieno[3,2-d]pyrimidine-6-carbonitrile<br>Synthesised via Route 3<br>1H NMR (400 MHz, CDCl3) δ (ppm) 8.63 (s, 1H), 7.93 (d, J = 2.4 Hz, 1H), 7.69 (t, J = 10.1 Hz, 1H), 7.63 (d, J = 7.8 Hz, 1H), 7.55 (t, J = 7.6 Hz, 1H), 7.40 (t, J = 7.5 Hz, 1H), 5.96-5.80 (m, 1H), 5.46 (s, 1H), 1.70 (d, J = 6.7 Hz, 3H), 1.26 (d, J = 7.6 Hz, 1H).<br>HRMS (Cl+) C16H11F3N4S $[M + H]^+$ 349.074 |
| 103 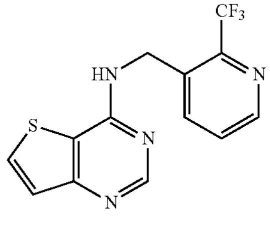 [SMILES: FC(F)(F)c1ncccc1CNc1ncnc2ccsc12] | N-((2-(trifluoromethyl)pyridin-3-yl)methyl)thieno[3,2-d]pyrimidin-4-amine<br>Synthesised via Route 2<br>1H NMR (400 MHz, CDCl3) δ (ppm) 8.58 (s, 1H), 8.54 (d, J = 4.3 Hz, 1H), 7.99 (d, J = 7.9 Hz, 1H), 7.68 (d, J = 5.4 Hz, 1H), 7.39 (dd, J = 10.1, 5.0 Hz, 2H), 5.41 (d, J = 5.2 Hz, 1H), 5.05 (d, J = 6.1 Hz, 2H).<br>HRMS (ES+) C13H9F3N4S $[M + H]^+$ 311.0575 |

TABLE 1-continued

104

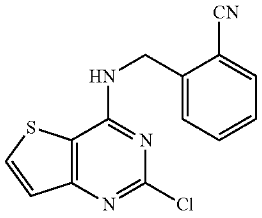 [SMILES: N#Cc1ccccc1CNc1nc(Cl)nc2ccsc12]

2-(((2-chlorothieno[3,2-d]pyrimidin-4-yl)amino)methyl)benzonitrile

Synthesised via Route 1
1H NMR (400 MHz, CDCl3) δ (ppm) 7.77 (d, J = 5.4 Hz, 1H), 7.73-7.66 (m, 2H), 7.60 (t, J = 7.6 Hz, 1H), 7.41 (t, J = 7.7 Hz, 1H), 7.37 (d, J = 5.4 Hz, 1H), 5.88 (b, 1H), 5.04 (d, J = 6.2 Hz, 2H).
HRMS (Cl+) C14H9ClN4S $[M + H]^+$ 301.0322

105

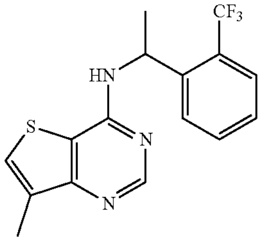 [SMILES: Cc1csc2c(NC(C)c3ccccc3C(F)(F)F)ncnc12]

7-methyl-N-(1-(2-(trifluoromethyl)phenyl)ethyl)thieno[3,2-d]pyrimidin-4-amine

Synthesised via Route 2
1H NMR (400 MHz, CDCl3) δ (ppm) 8.61 (s, 1H), 7.64 (d, 1H, J = 7.9 Hz), 7.65 (d, 1H, J = 7.8 Hz), 7.52 (t, 1H, J = 7.9 Hz), 7.38 (t, 1H, J = 7.8 Hz), 7.32 (s, 1H), 5.86 (m, 1H, J = 6.6 Hz)), 5.07 (s, 1H), 2.44 (s, 3H), 1.67 (d, 3H, J = 6.6 Hz).
HRMS: (Cl+, NH3) C16H15F3N3S $[M + H]^+$ 338.0945

106

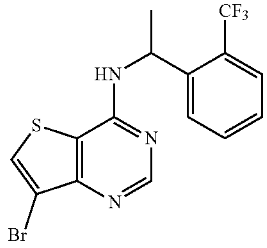 [SMILES: CC(Nc1ncnc2c(Br)csc12)c1ccccc1C(F)(F)F]

7-bromo-N-(1-(2-(trifluoromethyl)phenyl)ethyl)thieno[3,2-d]pyrimidin-4-amine

Synthesised via Route 2
1H NMR (400 MHz, CDCl3) δ (ppm) 8.68 (s, 1H), 7.72 (s, 1H), 7.71 (d, 1H, J = 8.8 Hz), 7.64 (d, 1H, J = 7.8 Hz), 7.59 (t, 1H, J = 8.8 Hz), 7.54 (t, 1H, J = 7.8 Hz), 5.86 (m , 1H), 5.14 (s, 1H), 1.68 (s, 3H).
HRMS: (Cl+, NH3) C15H11BrF3N3S $[M + H]^+$ 401.9896.

108

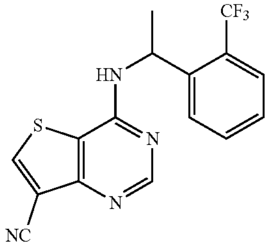 [SMILES: CC(Nc1ncnc2c(C#N)csc12)c1ccccc1C(F)(F)F]

4-((1-(2-(trifluoromethyl)phenyl)ethyl)amino)thieno[3,2-d]pyrimidine-7-carbonitrile Synthesised via Route 2
1H NMR (400 MHz, CDCl3) δ (ppm) 8.68 (s, 1H), 8.31 (s, 1H), 7.70 (d, 1H, J = 7.8 Hz), 7.60 (d, 1H, J = 7.7 Hz), 7.55 (t, 1H, J = 7.7 Hz), 7.41 (t, 1H, J = 7.8 Hz), 5.85 (m, 1H), 5.24 (s, 1H), 1.68 (d, 3H).
HRMS: (Cl+, CH4) C16H11F3N4S $[M + H]^+$ 349.0739.

109

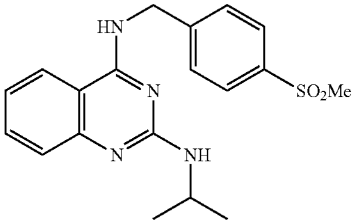

$N^2$-isopropyl-$N^4$-(4-(trifluoromethyl)benzyl)thieno[3,2-d]pyrimidine-2,4-diamine Synthesised via Route 1
1H NMR (400 MHz, MeOD) δ (ppm) 7.53 (d, J = 8.2 Hz, 2H), 7.50 (d, J = 5.3 Hz, 1H), 7.43 (d, J = 8.1 Hz, 2H), 7.07 (d, J = 5.3 Hz, 1H), 5.97 (s, 1H), 5.14 (s, 1H), 4.81 (d, J = 5.6 Hz, 2H), 4.09 (dq, J = 13.2, 6.5 Hz, 1H), 1.15 (d, J = 6.5 Hz, 6H).
HRMS: (ES) C17H18F3N4S $[M + H]^+$ 367.1203.

TABLE 1-continued

110

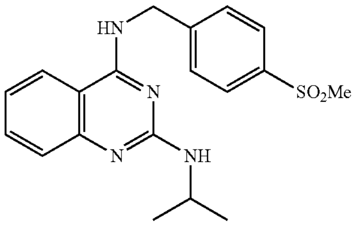 [SMILES: CC(C)Nc1nc(NCc2ccc(S(C)(=O)=O)cc2)c2ccccc2n1]

$N^2$-isopropyl-$N^4$-(4-(methylsulfonyl)benzyl)quinazoline-2,4-diamine

Synthesised via Route 4
1H NMR (400 MHz, CDCl3) δ (ppm) 8.01 (d, J = 6.9 Hz, 1H), 7.73 (d, J = 8.3 Hz, 2H), 7.50-7.47 (m, 2H), 7.47-7.44 (m, 1H), 7.32 (d, J = 8.3 Hz, 1H), 7.07 (t, J = 7.6 Hz, 1H), 4.85 (s, 2H), 4.13-4.01 (m, 1H), 2.97 (s, 3H), 1.109 (d, J = 6.4 Hz 6H).
HRMS: (ES) C19H23N4O2S $[M + H]^+$ 371.1539.

111

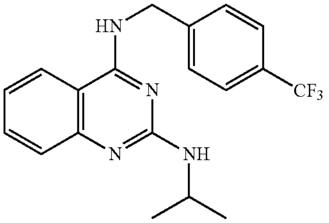 [SMILES: CC(C)Nc1nc(NCc2ccc(C(F)(F)F)cc2)c2ccccc2n1]

$N^2$-isopropyl-$N^4$-(4-(trifluoromethyl)benzyl)quinazoline-2,4-diamine

Synthesised via Route 4
1H NMR (400 MHz, CDCl3) δ (ppm) 7.65 (d, J = 8.0 Hz, 1H), 7.52 (t, J = 5.6 Hz, 2H), 7.48 (dd, J = 6.9, 1.2 Hz, 1H), 7.42 (d, J = 4.5 Hz, 2H), 7.41 (s, 1H), 7.07-7.00 (m, 1H), 6.62 (s, 1H), 4.82 (d, J = 5.0 Hz, 3H), 4.17 (dd, J = 12.4, 6.1 Hz, 1H), 1.14 (d, J = 6.5 Hz, 6H).
HRMS: (ES) C19H20F3N4 $[M + H]^+$ 361.1639.

112

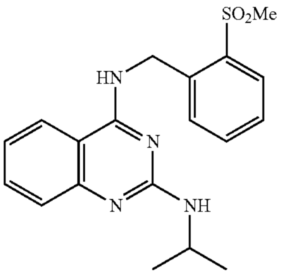 [SMILES: CC(C)Nc1nc(NCc2ccccc2S(C)(=O)=O)c2ccccc2n1]

$N^2$-isopropyl-$N^4$-(2-(methylsulfonyl)benzyl)quinazoline-2,4-diamine

Synthesised via Route 4
1H NMR (400 MHz, CDCl3) δ (ppm) 8.04 (dd, J = 7.9, 1.3 Hz, 1H), 7.71 (dd, J = 7.6, 0.8 Hz, 1H), 7.64-7.56 (m, 2H), 7.55-7.47 (m, 2H), 7.39 (d, J = 8.0 Hz, 1H), 7.14-7.08 (m, 1H), 5.15 (d, J = 5.6 Hz, 2H), 4.29 (dq, J = 13.3, 6.5 Hz, 1H), 3.18 (s, 3H), 1.27 (d, J = 6.5 Hz, 6H).
HRMS: (ES) C19H23N4O2S $[M + H]^+$ 371.1540.

114

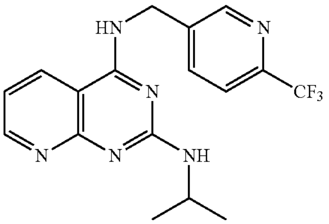

$N^2$-isopropyl-$N^4$-((6-(trifluoromethyl)pyridin-3-yl)methyl)quinazoline-2,4-diamine Synthesised via Route 4
1H NMR (400 MHz, MeOD) δ (ppm) 8.78 (s, 1H), 8.08 (d, J = 6.3 Hz, 1H), 8.07 (s, 1H), 7.79 (d, J = 8.1 Hz, 1H), 7.70 (t, J = 7.7 Hz, 1H), 7.43 (d, J = 8.1 Hz, 1H), 7.33 (t, J = 7.7 Hz, 1H), 4.95 (s, 2H), 4.12 (dq, J = 12.5, 6.3 Hz, 1H), 1.17 (d, J = 6.4 Hz, 6H).
HRMS: (ES) C19H20F3N4 $[M + H]^+$ 362.1590.

116

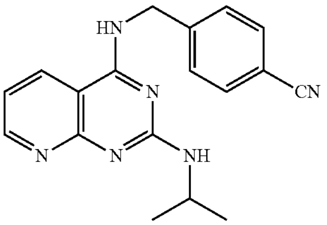 [SMILES: CC(C)Nc1nc(NCc2ccc(C#N)cc2)c2cccnc2n1]

$N^4$-(4-cyanobenzyl)-$N^2$-isopropylthieno[3,2-d]pyrimidine-2,4-diamine

Synthesised via Route 1
1H NMR (400 MHz, CDCl3) δ (ppm) 7.63-7.58 (m, 2H), 7.56 (d, J = 5.3 Hz, 1H), 7.46 (d, J = 8.4 Hz, 2H), 7.11 (d, J = 5.3 Hz, 1H), 5.43 (s, 1H), 4.96 (s, 1H), 4.84 (d, J = 5.8 Hz, 2H), 4.07 (tt, J = 13.1, 6.7 Hz, 1H), 1.16 (d, J = 6.5 Hz, 6H).
HRMS: (ES) C17H17N5S $[M + H]^+$ 324.1281.

TABLE 1-continued

| | |
|---|---|
| 117 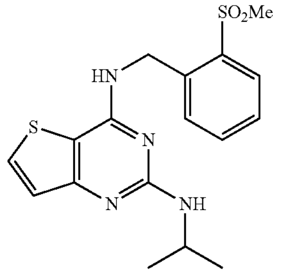 [SMILES: CC(C)Nc1nc(NCc2ccccc2S(C)(=O)=O)c2sccc2n1] | $N^2$-isopropyl-$N^4$-(2-(methylsuifonyl)benzyl)thieno[3,2-d]pyrimidine-2,4-diamine<br>Synthesised via Route 1<br>1H NMR (400 MHz, CDCl3) δ (ppm) 8.03-7.99 (m, 1H), 7.72 (d, J = 7.5 Hz, 1H), 7.56 (t, J = 7.4 Hz, 1H), 7.50 (d, J = 5.3 Hz, 1H), 7.44 (t, J = 7.6 Hz, 1H), 7.04 (d, J = 5.3 Hz, 1H), 5.88 (s, 1H), 5.10 (d, J = 6.3 Hz, 2H), 4.70 (d, J = 8.0 Hz, 1H), 4.17 (dq, J = 13.0, 6.5 Hz, 1H), 3.14 (s, 3H), 1.20 (d, J = 6.5 Hz, 6H).<br>HRMS: (ES) C17H20N2NaO2S2 $[M + Na]^+$ 399.0925. |
| 118 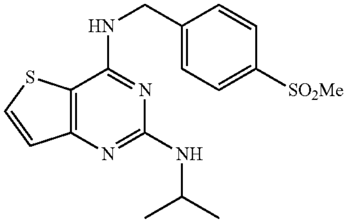 [SMILES: CC(C)Nc1nc(NCc2ccc(S(C)(=O)=O)cc2)c2sccc2n1] | $N^2$-isopropyl-$N^4$-(4-(methylsuifonyl)benzyl)thieno[3,2-d]pyrimidine-2,4-diamine<br>Synthesised via Route 1<br>1H NMR (400 MHz, CDCl3) δ (ppm) 7.80 (d, J = 8.3 Hz, 2H), 7.52 (d, J = 5.3 Hz, 1H), 7.49 (d, J = 8.2 Hz, 2H), 7.07 (d, J = 5.3 Hz, 1H), 5.82 (s, 1H), 4.82 (d, J = 5.9 Hz, 2H), 4.75 (d, J = 7.9 Hz, 1H), 4.05 (dq, J = 13.1, 6.5 Hz, 1H), 3.00 (s, 3H), 1.12 (d, J = 6.5 Hz, 6H).<br>HRMS: (ES) C17H20N2NaO2S2 $[M + Na]^+$ 399.0924. |
| 119 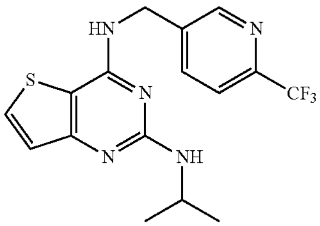 [SMILES: CC(C)Nc1nc(NCc2ccc(C(F)(F)F)nc2)c2sccc2n1] | $N^2$-isopropyl-$N^4$-((6-(trifluoromethyl)pyridin-3-yl)methyl)thieno[3,2-d]pyrimidine-2,4-diamine<br>Synthesised via Route 1<br>1H NMR (400 MHz, CDCl3) δ (ppm) 8.71 (s, 1H), 7.85 (d, J = 7.1 Hz, 1H), 7.60 (d, J = 8.1 Hz, 1H), 7.53 (d, J = 5.3 Hz, 1H), 7.08 (d, J = 5.3 Hz, 1H), 5.69 (s, 1H), 4.84 (d, J = 5.7 Hz, 2H), 4.77 (d, J = 7.6 Hz, 1H), 4.05 (m, 1H), 1.14 (d, J = 6.5 Hz, 6H).<br>HRMS: (ES) C16H16F3N5NaS $[M + Na]^+$ 390.0973. |
| 120 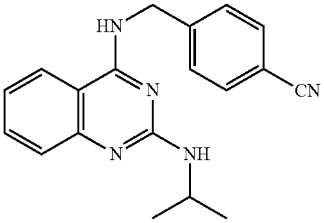 [SMILES: CC(C)Nc1nc(NCc2ccc(C#N)cc2)c2ccccc2n1] | $N^4$-(4-cyanobenzyl)-$N^2$-isopropylquinazoline-2,4-diamine<br>Synthesised via Route 4<br>1H NMR (400 MHz, DMSO) δ (ppm) 10.35 (s, 1H), 8.38 (s, 1H), 7.80 (d, J = 8.3 Hz, 2H), 7.78-7.72 (m, 1H), 7.59 (d, J = 8.2 Hz, 2H), 7.37 (s, 1H), 4.84 (d, J = 5.5 Hz, 2H), 4.06 (s, 1H), 1.08 (s, 6H).<br>HRMS: (ES) C19H20N5 $[M + H]^+$ 318.1719. |
| 121 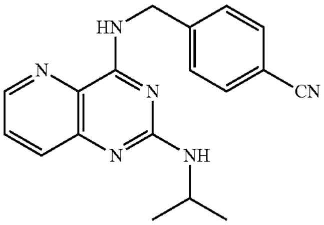 [SMILES: CC(C)Nc1nc(NCc2ccc(C#N)cc2)c2ncccc2n1] | $N^4$-(4-cyanobenzyl)-$N^2$-isopropylpyrido[3,2-d]pyrimidine-2,4-diamine<br>Synthesised via Route 7<br>1H NMR (400 MHz, CDCl3) δ (ppm) 8.28 (d, J = 3.4 Hz, 1H), 7.68 (d, J = 7.5 Hz, 1H), 7.57 (d, J = 7.9 Hz, 2H), 7.43 (d, J = 7.0 Hz, 2H), 7.40 (s, 1H), 5.19 (s, 1H), 4.80 (d, J = 5.9 Hz, 2H), 4.17 (m, 1H), 1.18 (d, J = 5.8 Hz, 6H).<br>HRMS: (ES) C18H19N6 $[M + H]^+$ 319.1669. |

TABLE 1-continued

| | |
|---|---|
| 122 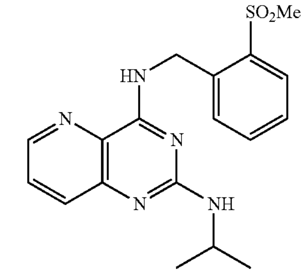 [SMILES: CC(C)Nc1nc(NCc2ccccc2S(C)(=O)=O)c2ncccc2n1] | $N^2$-isopropyl-$N^4$-(2-(methylsulfonyl)benzyl)pyrido[3,2-d]pyrimidine-2,4-diamine<br>Synthesised via Route 7<br>1H NMR (400 MHz, CDCl3) δ (ppm) 8.30 (d, J = 4.2 Hz, 1H), 8.05 (d, J = 7.9 Hz, 1H), 7.75 (d, J = 8.4 Hz, 1H), 7.72 (d, J = 7.7 Hz, 1H), 7.65 (d, J = 8.4 Hz, 1H), 7.59 (t, J = 7.5 Hz, 1H), 7.48 (t, J = 7.6 Hz, 1H), 7.41 (dd, J = 8.5, 4.2 Hz, 1H), 5.17 (d, J = 6.5 Hz, 2H), 4.91 (s, 1H), 4.28-4.18 (m, 1H), 3.17 (s, 3H), 1.24 (d, J = 6.5 Hz, 6H).<br>HRMS: (ES) C18H22N5O2S $[M + H]^+$ 372.1495. |
| 123 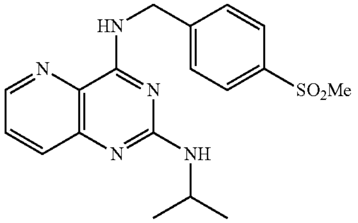 | $N^2$-isopropyl-$N^4$-(4-(methylsulfonyl)benzyl)pyrido[3,2-d]pyrimidine-2,4-diamine<br>Synthesised via Route 7<br>1H NMR (400 MHz, CDCl3) δ (ppm) 8.32-8.28 (m, 1H), 7.90 (d, J = 8.3 Hz, 2H), 7.70 (d, J = 8.4 Hz, 1H), 7.58 (d, J = 8.1 Hz, 2.H), 7.44 (dd, J = 8.5, 4.2 Hz, 2.H), 4.87 (d, J = 6.2 Hz, 2H), 4.18 (dt, J = 13.4, 6.7 Hz, 1H), 3.03 (s, 3H), 1.21 (d, J = 6.5 Hz, 6H).<br>HRMS: (ES) C18H22N5O2S $[M + H]^+$ 372.1491. |
| 124 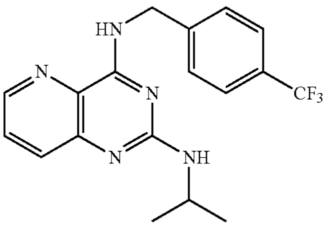 [SMILES: CC(C)Nc1nc(NCc2ccc(C(F)(F)F)cc2)c2ncccc2n1] | $N^2$-isopropyl-$N^4$-(4-(trifluoromethyl)benzyl)pyrido[3,2-d]pyrimidine-2,4-diamine<br>Synthesised via Route 7<br>1H NMR (400 MHz, CDCl3) δ (ppm) 8.31 (d, J = 4.2 Hz, 1H), 7.72 (d, J = 8.5 Hz, 1H), 7.60 (d, J = 8.1 Hz, 2H), 7.50 (d, J = 8.0 Hz, 2H), 7.45 (dd, J = 8.5, 4.2 Hz, 1H), 4.85 (d, J = 6.1 Hz, 2H), 4.21 (dq, J = 13.4, 6.7 Hz, 1H), 1.23 (d, J = 6.5 Hz, 6H).<br>HRMS: (ES) C18H19F3N5 $[M + H]^+$ 362.1595. |
| 125 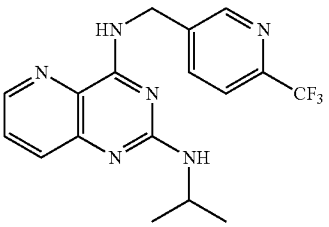 | $N^2$-isopropyl-$N^4$-((6-(trifluoromethyl)pyridin-3-yl)methyl)pyrido[3,2-d]pyrimidine-2,4-diamine<br>Synthesised via Route 7<br>1H NMR (400 MHz, CDCl3) δ (ppm) 8.77 (s, 1H), 8.28 (dd, J = 4.2, 1.1 Hz, 1H), 7.88 (d, J = 7.9 Hz, 1H), 7.68 (d, J = 8.4 Hz, 1H), 7.63 (d, J = 8.1 Hz, 1H), 7.43 (dd, J = 8.5, 4.2 Hz, 1H), 4.94 (s, 1H), 4.85 (d, J = 6.2 Hz, 2H), 4.17 (d, J = 6.3 Hz, 1H), 1.20 (d, J = 6.4 Hz, 6H).<br>HRMS: (ES) C17H18F3N6 $[M + H]^+$ 363.1546. |
| 126 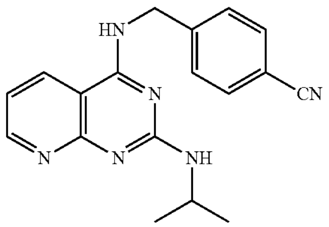 [SMILES: CC(C)Nc1nc(NCc2ccc(C#N)cc2)c2cccnc2n1] | $N^4$-(4-cyanobenzyl)-$N^2$-isopropylpyrido[2,3-d]pyrimidine-2,4-diamine<br>Synthesised via Route 6<br>1H NMR (400 MHz, MeOD) δ (ppm) 8.53 (dd, J = 4.5, 1.6 Hz, 1H), 8.27 (d, J = 7.7 Hz, 1H), 7.59 (d, J = 8.1 Hz, 2H), 7.47 (d, J = 8.2 Hz, 2H), 7.00 (dd, J = 8.0, 4.6 Hz, 1H), 4.77 (s, 2H), 4.11 (s, 1H), 3.28-3.26 (m, 1H), 1.12 (d, J = 23.6 Hz, 6H).<br>HRMS: (ES) C18H18N6Na $[M + Na]^+$ 341.1489. |

TABLE 1-continued

127

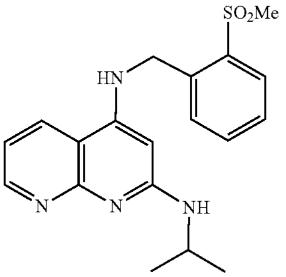 [SMILES: CC(C)Nc1cc(NCc2ccccc2S(C)(=O)=O)c2cccnc2n1]

$N^2$-isopropyl-$N^4$-(2-(methylsulfonyl)benzyl)pyrido[2,3-d]pyrimidine-2,4-diamine Synthesised via Route 6

1H NMR (400 MHz, MeOD) δ (ppm) 8.64-8.60 (m, 1H), 8.34 (d, J = 7.5 Hz, 1H), 8.05 (d, J = 7.8 Hz, 1H), 7.63 (d, J = 5.5 Hz, 2.H), 7.51 (dd, J = 10.9, 5.5 Hz, 1H), 7.10 (dd, J = 7.9, 4.6 Hz, 1H), 5.22 (s, 2H), 4.18 (s, 1H), 3.31 (s, 3H), 1.12 (s, 6H).

HRMS: (ES) C18H21NaN5O2S $[M + Na]^+$ 394.1313.

128

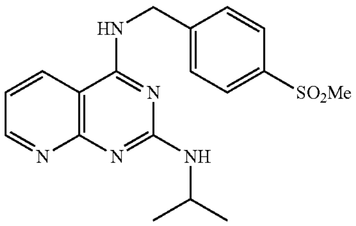 [SMILES: CC(C)Nc1nc(NCc2ccc(S(C)(=O)=O)cc2)c2cccnc2n1]

$N^2$-isopropyl-$N^4$-(4-(methylsulfonyl)benzyl)pyrido[2,3-d]pyrimidine-2,4-diamine Synthesised via Route 6

1H NMR (400 MHz, MeOD) δ (ppm) 8.56 (dd, J = 4.6, 1.6 Hz, 1H), 8.30 (d, J = 7.7 Hz, 1H), 7.84 (d, J = 8.3 Hz, 2H), 7.57 (d, J = 8.3 Hz, 2H), 7.02 (dd, J = 8.0, 4.6 Hz, 1H), 4.82 (s, 2H), 3.30-3.27 (m, 1H), 3.04 (s, 3H), 1.14 (d, J = 34.1 Hz, 6H).

HRMS: (ES) C18H21NaN5O2S $[M + Na]^+$ 394.1311.

129

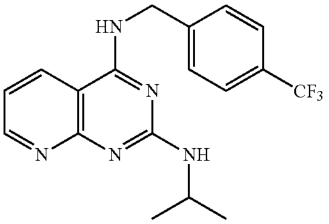 [SMILES: CC(C)Nc1nc(NCc2ccc(C(F)(F)F)cc2)c2cccnc2n1]

$N^2$-isopropyl-$N^4$-(4-(trifluoromethyl)benzyl)pyrido[2,3-d]pyrimidine-2,4-diamine Synthesised via Route 6

1H NMR (400 MHz, DMSO) δ (ppm) 8.72-8.44 (m, 1H), 8.44 (d, J = 42.8 Hz, 1H), 7.62 (d, J = 8.1 Hz, 2H), 7.52 (d, J = 7.9 Hz, 2H), 7.05 (d, J = 35.0 Hz, 1H), 4.74 (d, J = 4.3 Hz, 2H), 4.14-3.88 (m, 1H), 1.01 (dd, J = 23.4, 16.7 Hz, 6H).

HRMS: (ES) C18H18F3N5Na $[M + Na]^+$ 384.1410.

130

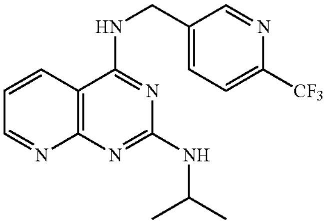 [SMILES: CC(C)Nc1nc(NCc2ccc(C(F)(F)F)nc2)c2cccnc2n1]

$N^2$-isopropyl-$N^4$-((6-(trifluoromethyl)pyridin-3-yl)methyl)pyrido[2,3-d]pyrimidine-2,4-diamine Synthesised via Route 6

1H NMR (400 MHz, MeOD) δ (ppm) 8.76 (s, 1H), 8.64 (s, 1H), 8.39 (s, 1H), 8.06 (d, J = 8.0 Hz, 1H), 7.78 (d, J = 8.1 Hz, 1H), 7.17 (s, 1H), 4.90 (d, J = 2.4 Hz, 2H), 4.18 (d, J = 8.2 Hz, 1H), 1.15 (s, 6H).

HRMS: (ES) C17H17F3N6Na $[M + Na]^+$ 385.1366.

131

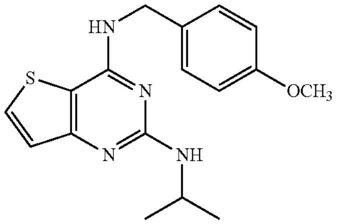 [SMILES: COc1ccc(CNc2nc(NC(C)C)nc3ccsc23)cc1]

$N^2$-isopropyl-$N^4$-(4-methoxybenzyl)thieno[3,2-d]pyrimidine-2,4-diamine

Synthesised via Route 1

1H NMR (400 MHz, CDCl3) δ (ppm) 7.49 (d, J = 5.3 Hz, 1H), 7.29 (d, J = 8.5 Hz, 2H), 7.09 (d, J = 5.3 Hz, 1H), 6.86 (d, J = 8.6 Hz, 2H), 5.17 (s, 1H), 4.77 (d, J = 7.8 Hz, 1H), 4.70 (d, J = 5.5 Hz, 2H), 4.20 (m, 1H), 3.79 (s, 3H), 1.22 (d, J = 6.5 Hz, 6H).

HRMS: (ES) C17H21N4OS $[M + H]^+$ 329.1432.

TABLE 1-continued

| | |
|---|---|
| 132 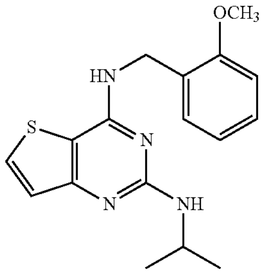 [SMILES: COc1ccccc1CNc1nc(NC(C)C)nc2ccsc12] | $N^2$-isopropyl-$N^4$-(2-methoxybenzyl)thieno[3,2-d]pyrimidine-2,4-diamine<br>Synthesised via Route 1<br>1H NMR (400 MHz, CDCl3) δ (ppm) 7.47 (d, J = 5.3 Hz, 1H), 7.34 (dd, J = 7.4, 1.3 Hz, 1H), 7.28-7.22 (m, 1H), 7.07 (d, J = 5.3 Hz, 1H), 6.90 (dd, J = 14.2, 7.7 Hz, 2H), 5.42 (s, 1H), 4.82 (d, J = 7.8 Hz, 1H), 4.78 (d, J = 5.8 Hz, 2H), 4.22 (m, 1H), 3.86 (s, 3H), 1.23 (d, J = 6.5 Hz, 6H).<br>HRMS: (ES) C17H21N4OS $[M + H]^+$ 329.1434. |
| 133 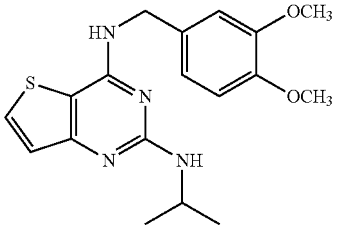 [SMILES: COc1ccc(CNc2nc(NC(C)C)nc3ccsc23)cc1OC] | $N^4$-(3,4-dimethoxybenzyl)-$N^2$-isopropylthieno[3,2-d]pyrimidine-2,4-diamine<br>Synthesised via Route 1<br>1H NMR (400 MHz, CDCl3) δ (ppm) 7.52 (d, J = 5.3 Hz, 1H), 7.10 (d, J = 5.3 Hz, 1H), 6.92 (d, J = 4.6 Hz, 2H), 6.86-6.81 {m, 1H), 5.05 (s, 1H), 4.83 (s, 1H), 4.71 (d, J = 5.4 Hz, 2H), 4.21 (td, J = 13.1, 6.5 Hz, 1H), 3.87 (d, J = 3.2 Hz, 3H), 3.85 (s, 3H), 1.24 (d, J = 6.5 Hz, 6H).<br>HRMS: (ES) C18H23N4O2S $[M + H]^+$ 359.1542. |
| 134 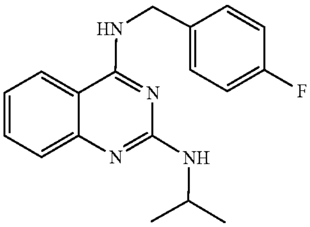 [SMILES: CC(C)Nc1nc(NCc2ccc(F)cc2)c2ccccc2n1] | $N^4$-(4-fluorobenzyl)-$N^2$-isopropylquinazoline-2,4-diamine<br>Synthesised via Route 4<br>1H NMR (400 MHz, CDCl3) δ (ppm) 9.71 (s, NH), 8.49 (s, 1H), 7.47 (t, J = 7.7 Hz, 1H), 7.37 (dd, J = 8.3, 5.5 Hz, 2H), 7.25 (d, J = 5.7 Hz, 1H), 7.14 (t, J = 7.6 Hz, 1H), 6.87 (t, J = 8.6 Hz, 2H), 4.80 (s, 2H), 4.17 (dd, J = 12.6, 6.3 Hz, 1H), 1.18 (d, J = 6.5 Hz, 6H).<br>HRMS: (ES) C18H20N4 $[M + H]^+$ 311.1669. |
| 135 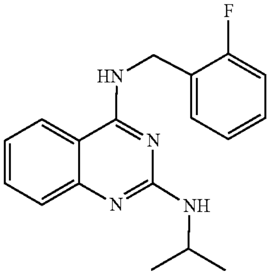 [SMILES: CC(C)Nc1nc(NCc2ccccc2F)c2ccccc2n1] | $N^4$-(2-fluorobenzyl)-$N^2$-isopropylquinazoline-2,4-diamine<br>Synthesised via Route 4<br>1H NMR (400 MHz, CDCl3) δ (ppm) 8.04 (d, J = 5.6 Hz, 1H), 7.51 (t, J = 7.7 Hz, 1H), 7.36 (t, J = 7.1 Hz, 2H), 7.19 (d, J = 7.8 Hz, 1H), 7.17 (dd, J = 4.7, 2.8 Hz, 1H), 7.05-7.00 (m, 1H), 6.98 (d, J = 10.0 Hz, 1H), 4.86 (d, J = 3.5 Hz, 2H), 4.14 (m, 3H), 1.15 (d, J = 6.7 Hz, 6H).<br>HRMS: (ES) C18H20N4 $[M + H]^+$ 311.1669. |
| 136 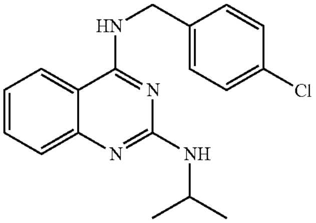 [SMILES: CC(C)Nc1nc(NCc2ccc(Cl)cc2)c2ccccc2n1] | $N^4$-(4-chlorobenzyl)-$N^2$-isopropylquinazoline-2,4-diamine<br>Synthesised via Route 4<br>1H NMR (400 MHz, CDCl3) δ (ppm) 8.09 (d, J = 7.7 Hz, 1H), 7.49 (t, J = 7.7 Hz, 1H), 7.35 (d, J = 8.3 Hz, 1H), 7.29 (d, J = 8.4 Hz, 2H), 7.22 (d, J = 8.4 Hz, 2H), 7.14 (t, J = 7.5 Hz, 1H), 6.21-6.09 (m, 2H), 4.76 (s, 2H), 4.14 (dt, J = 11.4, 5.0 Hz, 1H), 1.19 (d, J = 6.5 Hz, 6H).<br>HRMS: (ES) C18H20ClN4 $[M + H]^+$ 327.1373. |

TABLE 1-continued

137

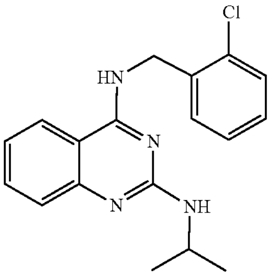 [SMILES: CC(C)Nc1nc(NCc2ccccc2Cl)c2ccccc2n1]

$N^4$-(2-chlorobenzyl)-$N^2$-isopropylquinazoline-2,4-diamine
Synthesised via Route 4
1H NMR (400 MHz, CDCl3) δ (ppm) 8.19-8.13 (m, 1H), 7.58 (td, J = 7.2, 3.2 Hz, 1H), 7.42 (d, J = 7.0 Hz, 1H), 7.37-7.27 (m, 3H), 7.21-7.15 (m, 2H), 4.90 (d, J = 2.3 Hz, 2H), 4.13 (m, 1H), 1.14 (d, J = 6.5 Hz 6H).
HRMS: (ES) C18H20ClN4 $[M + H]^+$ 327.1374.

138

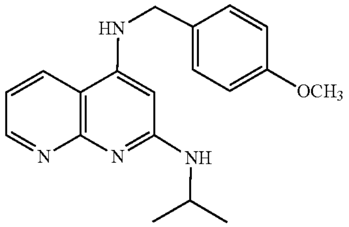 [SMILES: COc1ccc(CNc2cc(NC(C)C)nc3ncccc23)cc1]

$N^2$-isopropyl-$N^4$-(4-methoxybenzyl)quinazoline-2,4-diamine
Synthesised via Route 4
1H NMR (400 MHz, CDCl3) δ (ppm) 8.29 (s, 1H), 7.45 (t, J = 7.7 Hz, 1H), 7.35 (d, J = 8.6 Hz, 2H), 7.27 (d, J = 10.2 Hz, 1H), 7.13 (t, J = 7.6 Hz, 1H), 6.77 (d, J = 8.4 Hz, 2H), 4.78 (d, J = 4.2 Hz, 2H), 4.24 (m, 1H), 3.73 (s, 3H), 1.24 (d, J = 6.5 Hz, 6H).
HRMS: (ES) C19H23N4O $[M + H]^+$ 323.1869.

139

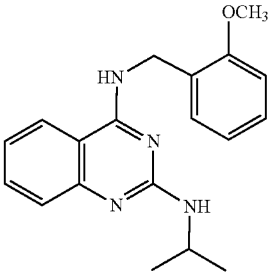 [SMILES: COc1ccccc1CNc1nc(NC(C)C)nc2ccccc12]

$N^2$-isopropyl-$N^4$-(2-methoxybenzyl)quinazoline-2,4-diamine
Synthesised via Route 4
1H NMR (400 MHz, CDCl3) δ (ppm) 7.87 (d, J = 7.4 Hz, 1H), 7.51 (t, J = 7.7 Hz, 1H), 7.38 (d, J = 8.2 Hz, 1H), 7.30-7.26 (m, 1H), 7.23 (d, J = 7.8 Hz, 1H), 7.18 (t, J = 7.6 Hz, 1H), 6.87 (d, J = 6.6 Hz, 1H), 6.85 (d, J = 6.6 Hz, 1H), 4.84 (d, J = 5.0 Hz, 2H), 4.23 (m, 1H), 3.88 (s, 3H), 1.25 (d, J = 6.5 Hz, 6H).
HRMS: (ES) C19H23N4O $[M + H]^+$ 323.1870.

140

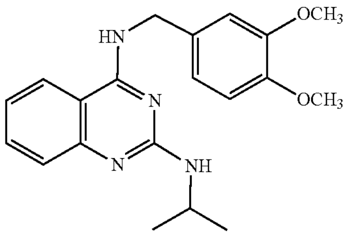 [SMILES: COc1ccc(CNc2nc(NC(C)C)nc3ccccc23)cc1OC]

$N^4$-(3,4-dimethoxybenzyl)-$N^2$-isopropylquinazoline-2,4-diamine
Synthesised via Route 4
1H NMR (400 MHz, CDCl3) δ (ppm) 8.24 (s, 1H), 7.44 (t, J = 7.7 Hz, 1H), 7.27 (d, J = 10.7 Hz, 1H), 7.11 (t, J = 7.6 Hz, 1H), 7.04 (d, J = 1.3 Hz, 1H), 6.95 (dd, J = 8.2, 1.4 Hz, 1H), 6.74 (d, J = 8.2 Hz, 1H), 4.77 (s, 2H), 4.25 (dd, J = 11.9, 5.8 Hz, 1H), 3.81 (s, 3H), 3.80 (s, 3H), 1.24 (d, J = 6.4 Hz, 6H).
HRMS: (ES) C20H25N4O2 $[M + H]^+$ 353.1976.

141

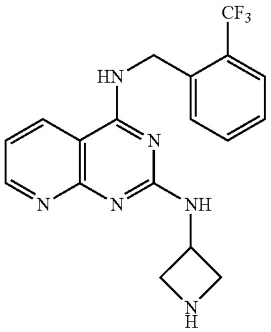 [SMILES: FC(F)(F)c1ccccc1CNc1nc(NC2CNC2)nc2ncccc12]

$N^2$-(azetidin-3-yl)-$N^4$-(2-(trifluoromethyl)benzyl)pyrido[2,3-d]pyrimidine-2,4-diamine
Synthesised via Route 6
$^1H$ NMR (400 MHz, DMSO-d6) δ (ppm) 8.93-8.67 (m, 2H), 8.48 (d, 1H), 7.75 (d, 1H), 7.62-7.43 (m, 4H), 7.10 (s, 1H), 4.92 (brs, 2H), 3.75-3.30 (m,5H).
LCMS (ES) $C_{18}H_{18}N_6F_3$ $[M + H]^+$ 375.0.

TABLE 1-continued

| | | |
|---|---|---|
| 142 | 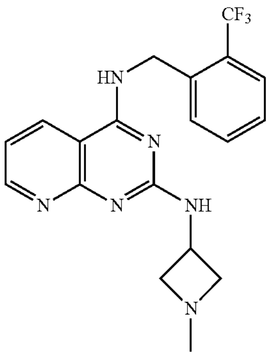 [SMILES: CN1CC(Nc2nc(NCc3ccccc3C(F)(F)F)c3cccnc3n2)C1] | $N^2$-(1-methylazetidin-3-yl)-$N^4$-(2-(trifluoromethyl)benzyl)pyrido[2,3-d]pyrimidine-2,4-diamine<br>Synthesised via Route 6<br>$^1$H NMR (400 MHz, DMSO-$d_6$) δ (ppm) 8.59-8.41 (m, 2H), 7.88 (d, J = 7.7 Hz, 1H), 7.68 (d, J = 7.6 Hz, 1H), 7.61 (t, J = 7.4 Hz, 1H), 7.41 (t, J = 7.5 Hz, 1H), 7.24 (dd, J = 7.5, 4.9 Hz, 1H), 5.00-4.77 (m, 2H), 4.26 (dd, J = 12.3, 3.3 Hz, 1H), 3.79 (dd, J = 12.6, 7.3 Hz, 1H), 3.57-3.15 (m, 3H), 3.10 (s, 3H).<br>LCMS (ES) $C_{19}H_{20}N_6F_3$ $[M + H]^+$ 389.0. |
| 143 | 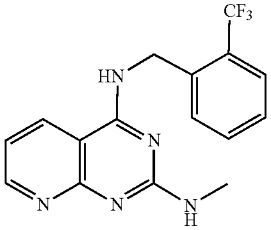 [SMILES: CNc1nc(NCc2ccccc2C(F)(F)F)c2cccnc2n1] | $N^2$-methyl-$N^4$-(2-(trifluoromethyl)benzyl)pyrido[2,3-d]pyrimidine-2,4-diamine<br>Synthesised via Route 6<br>$^1$H NMR (400 MHz, DMSO-$d_6$) δ (ppm) 8.83-8.41 (m, 3H), 7.76 (d, J = 7.7 Hz, 1H), 7.63 (t, J = 7.6 Hz, 1H), 7.59-7.41 (m, 2H), 7.32-6.85 (m, 2H), 5.02-4.85 (m, 2H), 2.74 (d, J = 52.1 Hz, 3H).<br>LCMS (ES) $C_{16}H_{15}N_5F_3$ $[M + H]^+$ 334.0. |
| 144 | 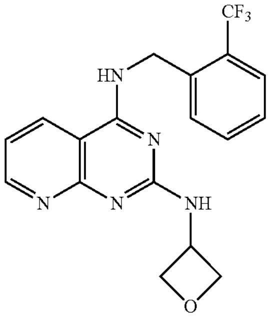 [SMILES: FC(F)(F)c1ccccc1CNc1nc(NC2COC2)nc2ncccc12] | $N^2$-(oxetan-3-yl)-$N^4$-(2-(trifluoromethyl)benzyl)pyrido[2,3-d]pyrimidine-2,4-diamine<br>Synthesised via Route 6<br>$^1$H NMR (400 MHz, DMSO-d6) δ (ppm) 9.41-7.91 (m, 4H), 7.78 (d, J = 8.0 Hz, 1H), 7.63 (t, J = 6.6 Hz, 1H), 7.50 (dd, J = 15.9, 8.6 Hz, 2H), 7.30-7.08 (m, 1H), 5.05-4.84 (m, 2H), 4.80-4.67 (m, 2H), 4.57-4.47 (m, 1H), 4.46-4.18 (m, 2H).<br>LCMS (ES) $C_{18}H_{17}N_5F_3O$ $[M + H]^+$ 376.0. |
| 145 | 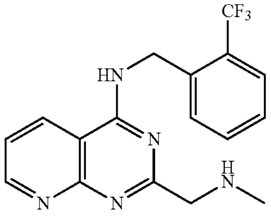 [SMILES: CNCc1nc(NCc2ccccc2C(F)(F)F)c2cccnc2n1] | 2-((methylamino)methyl)-N-(2-(trifluoromethyl)benzyl)pyrido[2,3-d]pyrimidin-4-amine<br>Synthesised via Route 8<br>$^1$H NMR (400 MHz, DMSO-d6) δ (ppm) 8.99-9.00 (d, J = 4.0 Hz, 1H), 8.70-8.72 (d, J = 8.0 Hz, J = 4.0 Hz, 1H), 7.74-7.76 (d, J = 8.0 Hz, 1H) 7.53-7.60 (m, 3H), 7.43-7.47 (m, 1H), 5.09 (s, 2H), 3.86 (s, 2H), 2.39 (s, 3H). LCMS (ES) $C_{17}H_{17}N_5F_3$ $[M + H]^+$ 348.2. |
| 146 | 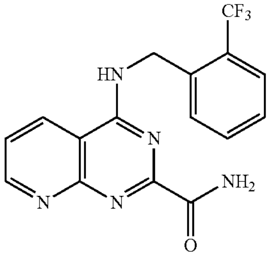 [SMILES: NC(=O)c1nc(NCc2ccccc2C(F)(F)F)c2cccnc2n1] | 4-((2-(trifluoromethyl)benzyl)amino)pyrido[2,3-d]pyrimidine-2-carboxamide<br>Synthesised via Route 8<br>$^1$H NMR (400 MHz, $CDCl_3$) δ (ppm) 9.12 (dd, J = 8.0 Hz, J = 4.0 Hz, 1H), 8.15 (d, J = 8.0 Hz, 1H), 8.06 (s, 1H), 7.92 (d, J = 8.0 Hz, 1H), 7.71 (d, J = 8.0 Hz, 1H), 7.57 (t, J = 8.0 Hz, 1H), 7.51-7.48 (dd, J = 8.0 Hz, J = 4.0 Hz, 1H), 7.45 (t, J = 8.0 Hz, 1H), 6.37 (s, 1H), 5.73 (s, 1H), 5.21 (d, J = 4.0 Hz, 2H).<br>LCMS (ES) $C_{16}H_{13}N_5F_3O$ $[M + H]^+$ 348.0. |

TABLE 1-continued

| | |
|---|---|
| 147 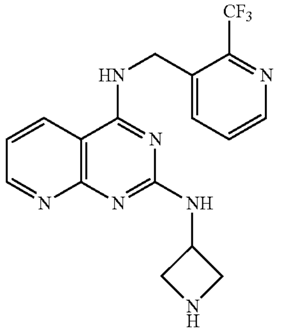 [SMILES: FC(F)(F)c1ncccc1CNc1nc(NC2CNC2)nc2ncccc12] | $N^2$-(azetidin-3-yl)-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.76-8.75 (dd, J = 4.0 Hz, J = 1.6 Hz, 1H), 8.61-8.60 (d, J = 4.0 Hz, 1H), 7.97-7.93 (t, J = 8.0 Hz, 2H), 7.47-7.44 (dd, J = 8.0 Hz, J = 4.0 Hz, 1H), 7.04-7.01 (dd, J = 8.0 Hz, J = 4.0 Hz, 1H), 6.40 (s, 0.4H), 5.53 (s, 0.8H), 5.03-5.01 (d, J = 8.0 Hz, 2H), 3.97 (s, 1H), 3.55-3.52 (t, J = 8.0 Hz, 2H), 1.78 (s, 2H).<br>LCMS (ES) $C_{17}H_{17}N_7F_3$ $[M + H]^+$ 376.2. |
| 148 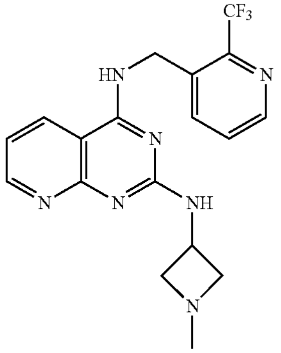 [SMILES: CN1CC(Nc2nc(NCc3cccnc3C(F)(F)F)c3cccnc3n2)C1] | $N^2$-(1-methylazetidin-3-yl)-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.55-8.54 (d, J = 4.0 Hz, 1H), 8.47-8.43 (m, 2H), 8.34-8.32 (d, J = 8.0 Hz, 1H), 7.64-7.62 (dd, J = 8.0 Hz, J = 4.0 Hz, 1H), 7.22-7.19 (dd, J = 8.0 Hz, J = 4.0 Hz, 1H), 4.83 (s, 2H), 4.27-4.23 (dd, J = 12.0 Hz, J = 4.0 Hz, 1H), 3.78-3.73 (dd, J = 12.0 Hz, J = 8.0 Hz, 1H), 3.52-3.49 (dd, J = 8.0 Hz, J = 4.0 Hz, 1H), 3.34 (s, 1H), 3.19-3.15 (dd, J = 12.0 Hz, J = 4.0 Hz, 1H), 3.09 (s, 3H).<br>LCMS (ES) $C_{18}H_{19}N_7F_3$ $[M + H]^+$ 390.0. |
| 149 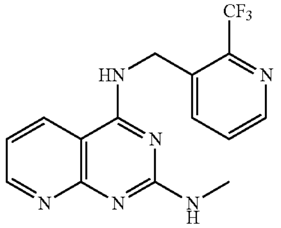 [SMILES: CNc1nc(NCc2cccnc2C(F)(F)F)c2cccnc2n1] | $N^2$-methyl-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.78-8.77 (d, J = 4.0 Hz, 1H), 8.69-8.67 (d, J = 8.0 Hz, 1H), 8.62-8.61 (d, J = 4.0 Hz, 1H), 8.09-8.08 (d, J = 4.0 Hz, 1H), 7.67-7.63 (dd, J = 8.0 Hz, J = 4.0 Hz, 1H), 7.52-7.49 (dd, J = 8.0 Hz, J = 4.0 Hz, 1H), 5.14 (s, 2H), 2.90 (s, 2H).<br>LCMS (ES) $C_{15}H_{14}N_6F_3$ $[M + H]^+$ 335.0. |
| 150 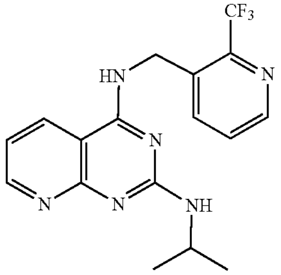 [SMILES: CC(C)Nc1nc(NCc2cccnc2C(F)(F)F)c2cccnc2n1] | $N^2$-isopropyl-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.92 (s, 0.4H), 8.65-8.61 (m, 2.6H), 8.42 (s, 1H), 7.94 (s, 1H), 7.66 (s, 1H), 7.07-7.05 (dd, J = 8.0 Hz, J = 4.0 Hz, 1H), 6.85-6.64 (d, 1H), 4.90 (s, 2H), 4.15 (s, 0.5H), 3.76 (s, 0.4H), 1.13-0.83 (d, 6H).<br>LCMS (ES) $C_{17}H_{18}N_6F_3$ $[M + H]^+$ 363.0. |

TABLE 1-continued

150_S

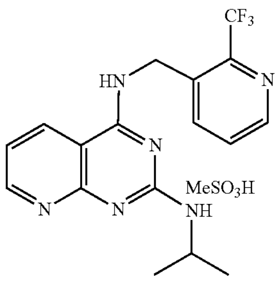 [SMILES: "MeSO3H" ; CC(C)Nc1nc(NCc2cccnc2C(F)(F)F)c2cccnc2n1]

$N^2$-isopropyl-$N^4$-((2-(trifluoromethyl)pyridin-3-yl)methyl)pyrido[2,3-d]pyrimidine-2,4-diamine methanesulfonate Synthesised via Route $^1$H NMR (400 MHz, DMSO-d6) δ (ppm) 10.37 (s, 0.87H), 8.76-8.80 (m, 2H), 8.64-8.67 (m, 1H), 8.00-8.08 (m, 2H), 7.66-7.69 (m, 1H), 7.53-7.56 (dd, J = 8.0 Hz, J = 4.0 Hz, 1H), 4.98-4.99 (d, J = 4.0 Hz, 2H), 3.87-3.95 (m, 1H), 2.36-2.38 (d, J = 8.0 Hz, 3H), 1.19-1.20 (d, J = 4.0 Hz, 1H), 0.96-0.97 (d, J = 4.0 Hz, 1H).

LCMS (ES) $C_{17}H_{18}N_6F_3$ $[M + H]^+$ 363.2.

151

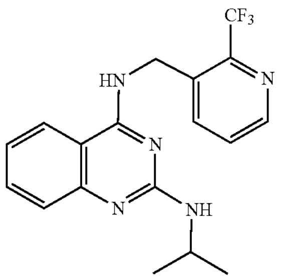 [SMILES: CC(C)Nc1nc(NCc2cccnc2C(F)(F)F)c2ccccc2n1]

$N^2$-isopropyl-$N^4$-((2-(trifluoromethyl)pyridin-3-yl)methyl)quinazoline-2,4-diamine Synthesised via Route 4

$^1$H NMR (400 MHz, DMSO-d6) δ (ppm) 12.06-12.48 (m, 1H), 9.89-10.32 (m, 1H), 8.65 (d, J = 4.14 Hz, 1H), 8.34 (brs, 1H), 8.00 (d, J = 7.78 Hz, 1H), 7.62-7.90 (m, 3H), 7.41 (brs, 1H), 4.98 (d, J = 3.64 Hz, 2H), 3.90 (brs, 1H), 0.96 (brs, 6H).

LCMS (ES) $C_{18}H_{19}N_5F_3$ $[M + H]^+$ 362.2.

152

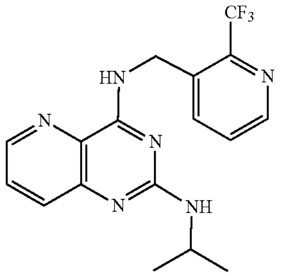 [SMILES: CC(C)Nc1nc(NCc2cccnc2C(F)(F)F)c2ncccc2n1]

$N^2$-isopropyl-$N^4$-((2-(trifluoromethyl)pyridin-3-yl)methyl)pyrido[3,2-d]pyrimidine-2,4-diamine Synthesised via Route 7

$^1$H NMR (400 MHz, DMSO-d6) δ (ppm) 8.49-9.02 (m, 2H), 8.37 (d, J = 3.51 Hz, 1H), 7.90 (d, J = 8.03 Hz, 1H), 7.51-7.74 (m, 3H), 6.55 (brs, 1H), 4.90 (d, J = 4.02 Hz, 2H), 3.59-4.24 (m, 1H), 0.62-1.27 (m, 6H).

LCMS (ES) $C_{17}H_{18}N_6F_3$ $[M + H]^+$ 363.2.

153

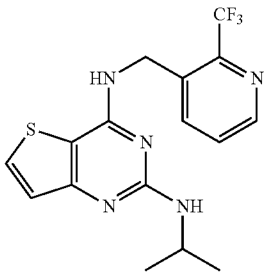 [SMILES: CC(C)Nc1nc(NCc2cccnc2C(F)(F)F)c2sccc2n1]

$N^2$-isopropyl-$N^4$-((2-(trifluoromethyl)pyridin-3-yl)methyl)thieno[3,2-d]pyrimidine-2,4-diamine Synthesised via Route 1

$^1$H NMR (400 MHz, DMSO-d6) δ (ppm) 8.60 (d, J = 4.27 Hz, 1H), 8.05(brs, 1H), 7.87-7.95 (m, 2H), 7.67 (dd, J = 8.03, 4.64 Hz, 1H), 7.03 (d, J = 5.14 Hz, 1H), 6.11 (d, J = 7.78 Hz, 1H), 4.85 (d, J = 5.14 Hz, 2H), 3.73-4.01 (m, 1H), 0.74-1.16 (m, 6H).

LCMS (ES) $C_{16}H_{17}N_5F_3S$ $[M + H]^+$ 368.2.

154

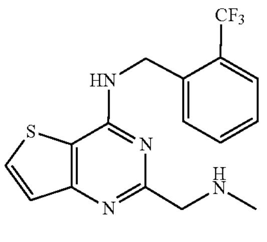 [SMILES: CNCc1nc(NCc2ccccc2C(F)(F)F)c2sccc2n1]

2-((methylamino)methyl)-N-(2-(trifluoromethyl)benzyl)thieno[3,2-d]pyrimidin-4-amine Synthesised via Route 2

$^1$H NMR (400 MHz, DMSO-d6) δ (ppm) 8.55 (s, 1H), 8.12-8.13 (d, J = 4.0 Hz, 1H), 7.73-7.75 (d, J = 8.0 Hz, 1H), 7.57-7.61 (t, J = 8.0 Hz, 1H), 7.51-7.53 (d, J = 8.0 Hz, 1H), 7.43-7.47 (t, J = 8.0 Hz, 1H), 7.36-7.37 (d, J = 4.0 Hz, 1H), 4.90-4.91 (d, J = 4.0 Hz, 2H), 3.55 (s, 2H), 3.16 (s, 1H), 2.13 (s, 3H).

LCMS (ES) $C_{16}H_{16}N_4F_3S$ $[M + H]^+$ 353.2.

TABLE 1-continued

| | |
|---|---|
| 155 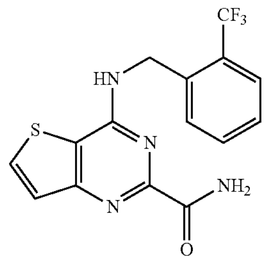 [SMILES: NC(=O)c1nc(NCc2ccccc2C(F)(F)F)c2sccc2n1] | 4-((2-(trifluoromethyl)benzyl)amino)thieno[3,2-d]pyrimidine-2-carboxamide<br>Synthesised via Route 2<br>$^1$H NMR (400 MHz, MeOD) δ (ppm) 8.08-8.10 (d, J = 8.0 Hz, 1H), 7.72-7.74 (d, J = 8.0 Hz, 1H), 7.51-7.60 (m, 3H), 7.41-7.45 (d, J = 8.0 Hz, 1H), 5.08 (s, 2H).<br>LCMS (ES) $C_{15}H_{12}N_4F_3OS$ $[M + H]^+$ 353.0. |
| 156 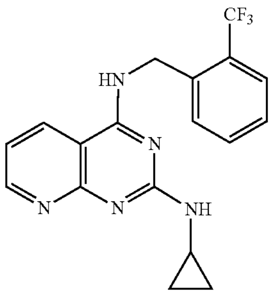 [SMILES: FC(F)(F)c1ccccc1CNc1nc(NC2CC2)nc2ncccc12] | $N^2$-cyclopropyl-$N^4$-(2-(trifluoromethyl)benzyl)pyrido[2,3-d]pyrimidine-2,4-diamine<br>Synthesised via Route 6<br>$^1$H NMR (400 MHz, DMSO-d6) δ (ppm) 9.05-8.53 (m, 2H), 8.47 (d, J = 7.5 Hz, 1H), 7.75 (d, J = 7.8 Hz, 1H), 7.62 (t, J = 7.6 Hz, 1H), 7.56-7.40 (m, 2H), 7.21-6.92 (m, 2H), 4.93 (b, 2H), 2.92-2.63 (m, 1H), 0.86-0.04 (m, 4H).<br>LCMS (ES) $C_{18}H_{17}N_5F_3$ $[M + H]^+$ 360.2. |
| 156_B2_S 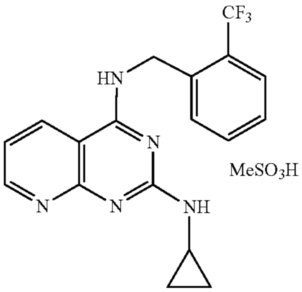 [SMILES: "MeSO3H" ; FC(F)(F)c1ccccc1CNc1nc(NC2CC2)nc2ncccc12] | $N^2$-cyclopropyl-$N^4$-(2-(trifluoromethyl)benzyl)pyrido[2,3-d]pyrimidine-2,4-diamine methanesulfonate<br>Synthesised via Route 6<br>$^1$H NMR (400 MHz, DMSO-d6) δ (ppm) 10.35-9.61 (m, 1H), 9.20-8.16 (m, 3H), 7.80 (d, J = 7.7 Hz, 1H), 7.71-7.46 (m, 4H), 5.02 (d, J = 26.4 Hz, 2H), 2.94-2.59 (m, 1H), 2.33 (s, 3H), 0.98-0.37 (m, 4H).<br>LCMS (ES) $C_{18}H_{17}N_5F_3$ $[M + H]^+$ 360.2. |
| 157 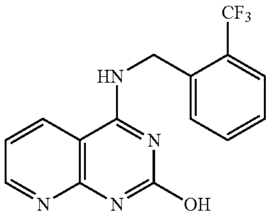 [SMILES: Oc1nc(NCc2ccccc2C(F)(F)F)c2cccnc2n1] | 4-((2-(trifluoromethyl)benzyl)amino)pyrido[2,3-d]pyrimidin-2-ol<br>Synthesised via Route 8<br>$^1$H NMR (400 MHz, DMSO-d6) δ (ppm) 11.22 (s, 1H), 9.03 (t, J = 5.5 Hz, 1H), 8.64-8.48 (m, 2H), 7.82-7.74 (m, 1H), 7.68-7.60 (m, 1H), 7.54-7.47 (m, 2H), 7.25 (dd, J = 4.7, 8.0 Hz, 1H), 4.89 (d, J = 5.1 Hz, 2H).<br>LCMS (ES) $C_{15}H_{12}N_4F_3O$ $[M + H]^+$ 321.2. |
| 158 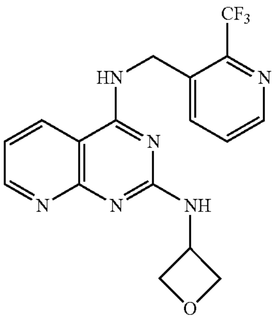 [SMILES: FC(F)(F)c1ncccc1CNc1nc(NC2COC2)nc2ncccc12] | $N^2$-(oxetan-3-yl)-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 9.0 (s, 0.37H), 8.62-8.68 (m, 2.48H), 8.46-8.48 (d, J = 8.0 Hz, 1H), 7.94 (s, 1H), 7.80 (s, 0.36H), 7.66 (s, 1H), 7.60 (s, 0.4H), 7.11-7.14 (dd, J = 8.0 Hz, J = 4.0 Hz, 1H), 4.20-5.08 (m, 7H).<br>LCMS (ES) $C_{17}H_{16}N_6F_3O$ $[M + H]^+$ 377.2. |

TABLE 1-continued

| | | |
|---|---|---|
| 159 | 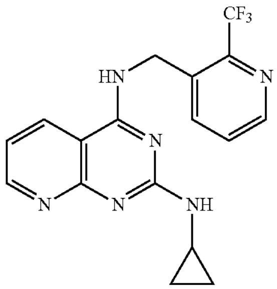 [SMILES: FC(F)(F)c1ncccc1CNc1nc(NC2CC2)nc2ncccc12] | $N^2$-cyclopropyl-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.79-8.11 (m, 4H), 7.72 (d, J = 7.8 Hz, 1H), 7.42 (dd, J = 7.8, 4.7 Hz, 1H), 7.09-6.65 (m, 2H), 4.67 (b, 2H), 2.70-2.34 (m, 1H), 0.54--0.39 (m, 4H).<br>LCMS (ES) $C_{17}H_{16}N_6F_3$ $[M + H]^+$ 361.2. |
| 159_S | 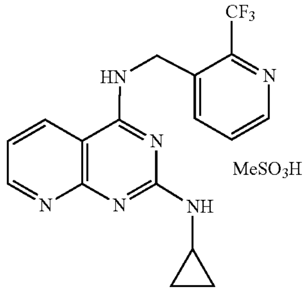 [SMILES: "MeSO3H" ; FC(F)(F)c1ncccc1CNc1nc(NC2CC2)nc2ncccc12] | $N^2$-cyclopropyl-$N^4$-((2-(trifluoromethyl)pyridin-3-yl)methyl)pyrido[2,3-d]pyrimidine-2,4-diamine methanesulfonate<br>Synthesised via Route 6<br>$^1$H NMR (400 MHz, DMSO-d6) δ (ppm) 10.46-9.78 (m, 1H), 9.28-8.41 (m, 4H), 8.08 (d, J = 7.8 Hz, 1H), 7.72 (t, J = 9.1 Hz, 1H), 7.64-7.49 (m, 1H), 5.03 (d, J = 26.1 Hz, 2H), 2.97-2.59 (m, 1H), 2.37 (s, 3H), 1.00-0.27 (m, 4H).<br>LCMS (ES) $C_{17}H_{16}N_6F_3$ $[M + H]^+$ 361.2. |
| 160 | 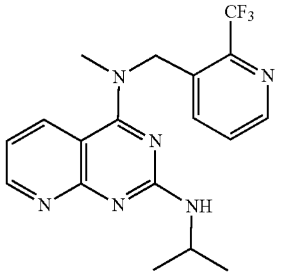 [SMILES: CC(C)Nc1nc(N(C)Cc2cccnc2C(F)(F)F)c2cccnc2n1] | $N^2$-isopropyl-$N^4$-methyl-N4-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.62-8.63 (dd, J = 4.0 Hz, 2.H), 7.65-8.39 (m, 3H), 6.97-7.00 (dd, J = 4.0 Hz, J = 8.0 Hz, 1H), 6.75-6.85 (m, 1H), 5.08 (s, 2H), 4.15 (s, 0.45), 3.49-3.67 (m, 2H), 3.27 (s, 1H), 0.81-1.15 (d, 6H)<br>LCMS (ES) $C_{18}H_{20}N_6F_3$ $[M + H]^+$ 377.1. |
| 161 | 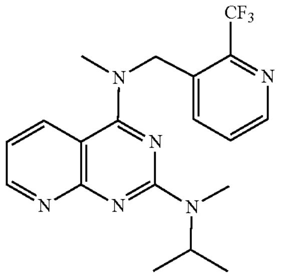 [SMILES: CC(C)N(C)c1nc(N(C)Cc2cccnc2C(F)(F)F)c2cccnc2n1] | $N^2$-isopropyl-$N^2$,$N^4$-dimethyl-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.61-8.64 (dd, J = 4.0 Hz, J = 8.0 Hz, 2H), 8.37-8.39 (d, J = 8.0 Hz, 1H), 7.82 (bs, 1H), 7.61-7.64 (m, 1H), 7.00-7.03 (dd, J = 4.0 Hz, J = 8.0 Hz, 1H), 5.06 (s, 2H), 3.54 (s, 3H), 3.33 (s, 1H), 2.78 (s, 3H), 0.84-1.06 (m, 6H).<br>LCMS (ES) $C_{19}H_{22}N_6F_3$ $[M + H]^+$ 391.0. |

TABLE 1-continued

162

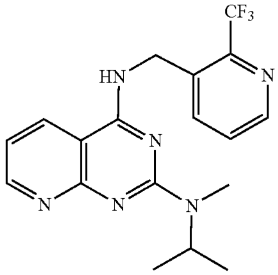 [SMILES: CC(C)N(C)c1nc(NCc2cccnc2C(F)(F)F)c2cccnc2n1]

$N^2$-isopropyl-$N^2$-methyl-$N^4$-((2-(trifluoromethyl)pyridin-3-yl)methyl)pyrido[2,3-d]pyrimidine-2,4-diamine
Synthesised via Route 6
$^1$H NMR (400 MHz, MeOD) δ (ppm) 8.65 (dd, J = 4.7, 1.9 Hz, 1H), 8.56 (d, J = 4.4 Hz, 1H), 8.42 (dd, J = 8.0, 1.9 Hz, 1H), 7.99 (d, J = 8.0 Hz, 1H), 7.58 (dd, J = 8.0, 4.7 Hz, 1H), 7.15 (dd, J = 7.9, 4.7 Hz, 1H), 4.99 (b, 2H), 4.73-4.43 (m, 1H), 2.93 (s, 3H), 1.01 (b, 6H).
LCMS (ES) $C_{18}H_{20}N_6F_3$ $[M + H]^+$ 377.2.

162_S

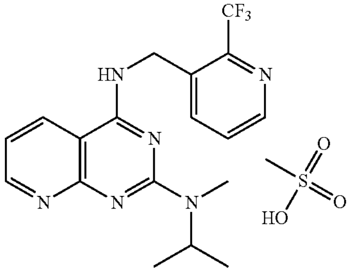

$N^2$-isopropyl-$N^2$-methyl-$N^4$-((2-(trifluoromethyl)pyridin-3-yl)methyl)pyrido[2,3-d]pyrimidine-2,4-diamine methanesulfonate
Synthesised via Route 6
$^1$H NMR (400 MHz, DMSO-d6) δ (ppm) 9.80 (s, 1H), 8.89 (dd, J = 8.0, 1.7 Hz, 1H), 8.75 (dd, J = 5.2, 1.6 Hz, 1H), 8.65 (d, J = 4.5 Hz, 1H), 8.05 (d, J = 8.0 Hz, 1H), 7.66 (dd, J = 8.0, 4.6 Hz, 1H), 7.49 (dd, J = 7.9, 5.3 Hz, 1H), 4.99 (d, J = 4.9 Hz, 2H), 4.89-4.75 (m, 1H), 3.00 (s, 3H), 2.34 (s, 3H), 1.06 (d, J = 6.5 Hz, 6H).
LCMS (ES) $C_{18}H_{20}N_6F_3$ $[M + H]^+$ 377.1.

163

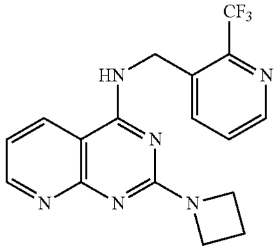 [SMILES: FC(F)(F)c1ncccc1CNc1nc(N2CCC2)nc2ncccc12]

2-(azetidin-1-yl)-N-((2-(trifluoromethyl)pyridin-3-yl)methyl)pyrido[2,3-d]pyrimidin-4-amine
Synthesised via Route 6
$^1$H NMR (400 MHz, DMSO-d6) δ (ppm) 8.91 (t, J = 5.33 Hz, 1 H), 8.68 (dd, J = 4.33, 1.69 Hz, 1 H), 8.61 (d, J = 4.39 Hz, 1 H), 8.48 (dd, J = 8.03, 1.76 Hz, 1 H), 7.99 (d, J = 7.91 Hz, 1 H), 7.65 (dd, J = 7.97, 4.58 Hz, 1 H), 7.12 (dd, J = 7.91, 4.39 Hz, 1 H), 4.86 (d, J = 4.77 Hz, 2 H), 3.87 (br. s., 4 H), 2.18 (m, 2 H).
LCMS (ES) $C_{17}H_{16}N_6F_3$ $[M + H]^+$ 361.1.

164

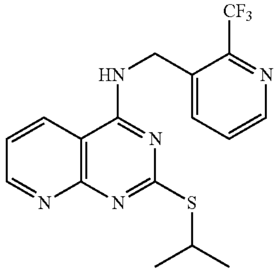 [SMILES: CC(C)Sc1nc(NCc2cccnc2C(F)(F)F)c2cccnc2n1]

2-(isopropylthio)-N-((2-(trifluoromethyl)pyridin-3-yl)methyl)pyrido[2,3-d]pyrimidin-4-amine
Synthesised via Route 8
$^1$H NMR (400 MHz, DMSO-d6) δ (ppm) 9.28 (t, J = 5.27 Hz, 1 H), 8.91 (dd, J = 4.39, 1.76 Hz, 1 H), 8.59-8.72 (m, 2 H), 7.98 (d, J = 7.91 Hz, 1 H), 7.66 (dd, J = 8.03, 4.64 Hz, 1 H), 7.48 (dd, J = 8.16, 4.39 Hz, 1 H), 4.93 (dd, J = 5.2 Hz, 2 H), 3.73 (m, 1 H), 1.18 (d, J = 6.78 Hz, 6 H).
LCMS (ES) $C_{17}H_{17}N_5F_3S$ $[M + H]^+$ 379.9.

165

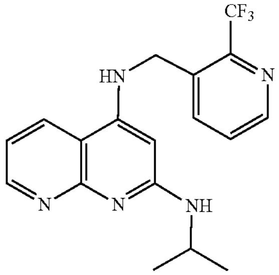 [SMILES: CC(C)Nc1cc(NCc2cccnc2C(F)(F)F)c2cccnc2n1]

$N^2$-isopropyl-$N^4$-((2-(trifluoromethyl)pyridin-3-yl)methyl)-1,8-naphthyridine-2,4-diamine
Synthesised via Route 9
$^1$H NMR (400 MHz, MeOD) δ (ppm) 8.70 (d, J = 3.3 Hz, 1H), 8.64 (d, J = 4.4 Hz, 1H), 8.57 (dd, J = 8.2, 1.6 Hz, 1H), 8.01 (d, J = 7.8 Hz, 1H), 7.65 (dd, J = 7.9, 4.8 Hz, 1H), 7.42 (dd, J = 8.1, 4.7 Hz, 1H), 5.59 (s, 1H), 4.60 (s, 2H), 3.98-4.19 (m, 1H), 1.22 (d, J = 6.0 Hz, 6H).
LCMS (ES) $C_{18}H_{19}N_5F_3$ $[M + H]^+$ 362.0.

TABLE 1-continued

| | |
|---|---|
| 166 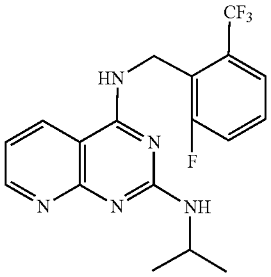 [SMILES: CC(C)Nc1nc(NCc2c(F)cccc2C(F)(F)F)c2cccnc2n1] | $N^4$-(2-fluoro-6-(trifluoromethyl)benzyl)-$N^2$-isopropylpyrido[2,3-d]pyrimidine-2,4-diamine<br>Synthesised via Route 6<br>$^1$H NMR (400 MHz, DMSO-d6) δ (ppm) 8.66 (m., 1H), 8.47 (m, 2H), 7.57-7.68 (m, 2H), 7.50 (t, J = 9.03 Hz, 1H), 7.25 (br. s., 1H), 4.98-5.10 (m, 2H), 4.30-4.67 (m, 1H), 1.29 (d, J = 6.53 Hz, 6H).<br>LCMS (ES) $C_{18}H_{18}N_5F_4$ [M + H]$^+$ 380.2. |
| 167 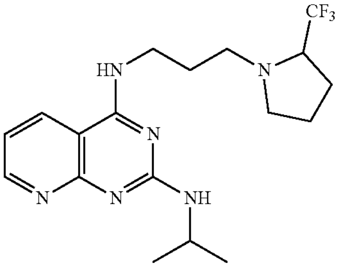 [SMILES: CC(C)Nc1nc(NCCCN2CCCC2C(F)(F)F)c2cccnc2n1] | 4-(6-chloro-5-methyl-7-((pyridin-2-ylmethyl)amino)pyrazolo[1,5-a]pyrimidin-3-yl)morpholin-3-one<br>Synthesised via Route 6<br>$^1$H NMR (400 MHz, DMSO-d6) δ (ppm) 8.57 (dd, J = 4.39, 1.76 Hz, 1H), 8.24-8.36 (m, 1H), 7.79-8.19 (m, 1H), 6.98 (br. s., 1H), 6.56 (br. s., 1H), 4.16 (dd, J = 13.68, 6.78 Hz, 1H), 3.43-3.57 (m, 2H), 3.27 (br. s., 1H), 3.11 (t, J = 7.40 Hz, 1H), 2.86 (dt, J = 12.05, 7.91 Hz, 1H), 2.61-2.68 (m, 1H), 2.33-2.39 (m, 1H), 1.93-2.06 (m, 1H), 1.67-1.85 (m, 5H), 1.15 (d, J = 6.53 Hz, 6H).<br>LCMS (ES) $C_{18}H_{26}N_6F_3$ [M + H]$^+$ 383.2. |
| 168 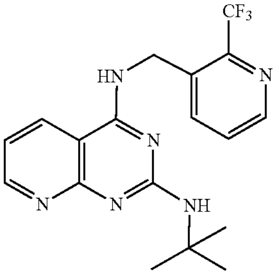 [SMILES: CC(C)(C)Nc1nc(NCc2cccnc2C(F)(F)F)c2cccnc2n1] | $N^2$-(tert-butyl)-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.61-8.68 (m, 2 H), 8.45 (d, J = 7.78 Hz, 1 H), 7.91 (br. s., 1 H), 7.66 (dd, J = 7.53, 4.89 Hz, 1 H), 7.08 (dd, J = 7.91, 4.39 Hz, 1 H), 4.93 (s., 2 H), 1.17 (br. s., 9 H).<br>LCMS (ES) $C_{18}H_{20}N_6F_3$ [M + H]$^+$ 377.0. |
| 169 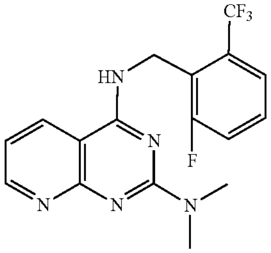 [SMILES: CN(C)c1nc(NCc2c(F)cccc2C(F)(F)F)c2cccnc2n1] | $N^4$-(2-fluoro-6-(trifluoromethyl)benzyl)-$N^2$,$N^2$-dimethylpyrido[2,3-d]pyrimidine-2,4-diamine<br>Synthesised via Route 6<br>$^1$H NMR (400 MHz, DMSO-d6) δ (ppm) 8.64 (d, J = 3.26 Hz, 1H), 8.48 (dd, J = 7.97, 1.57 Hz, 1H), 8.44 (m., 1H), 7.57-7.68 (m, 2H), 7.45-7.54 (m, 1H), 7.17 (dd, J = 8.03, 4.77 Hz, 1H), 5.01 (s, 2H), 3.30 (s, 6H).<br>LCMS (ES) $C_{17}H_{16}N_5F_3$ [M + H]$^+$ 366.1. |
| 170 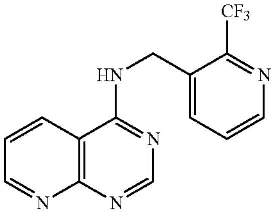 [SMILES: FC(F)(F)c1ncccc1CNc1ncnc2ncccc12] | N-((2-(trifluoromethyl)pyridin-3-yl)methyl)pyrido[2,3-d]pyrimidin-4-amine<br>Synthesised via Route 8<br>$^1$H NMR (400 MHz, DMSO-d6) δ (ppm) 9.18 (t, J = 5.5 Hz, 1H), 9.06 (dd, J = 1.8, 4.4 Hz, 1H), 8.79 (dd, J = 1.8, 8.3 Hz, 1H), 8.64 (d, J = 4.5 Hz, 1H), 8.60 (s, 1H), 7.99 (d, J = 8.0 Hz, 1H), 7.71-7.57 (m, 2H), 4.99 (d, J = 5.0 Hz, 2H).<br>LCMS (ES) $C_{14}H_{11}N_5F_3$ [M + H]$^+$ 306.1. |

TABLE 1-continued

| | |
|---|---|
| 171 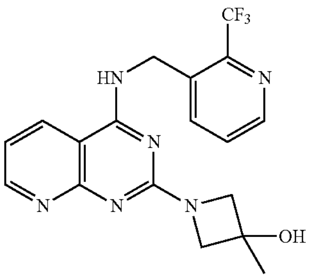 [SMILES: CC1(O)CN(c2nc(NCc3cccnc3C(F)(F)F)c3cccnc3n2)C1] | 3-methyl-1-(4-(((2-(trifluoromethyl)pyridin-3-yl)methyl)amino)pyrido[2,3-d]pyrimidin-2-yl)azetidin-3-ol<br>Synthesised via Route 6<br>$^1$H NMR (400 MHz, MeOD) δ (ppm) 8.68 (dd, J = 4.64, 1.88 Hz, 1H), 8.57 (d, J = 4.52 Hz, 1H), 8.41 (dd, J = 7.97, 1.82 Hz, 1H), 8.02 (d, J = 8.03 Hz, 1H), 7.60 (dd, J = 7.97, 4.71 Hz, 1H), 7.17 (dd, J = 8.03, 4.64 Hz, 1H), 4.98 (s, 2H), 3.89 (br. s., 4H), 1.47 (s, 3H).<br>LCMS (ES) $C_{18}H_{18}N_6F_3O$ $[M + H]^+$ 391.1. |
| 172 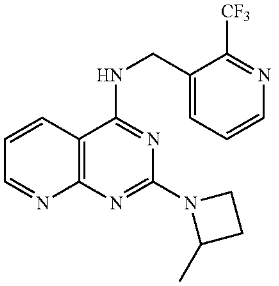 [SMILES: CC1CCN1c1nc(NCc2cccnc2C(F)(F)F)c2cccnc2n1] | 2-(2-methylazetidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.90 (br. s., 1H), 8.68 (br. s., 1H), 8.61 (br. s., 1H), 8.49 (d, J = 7.28 Hz, 1H), 7.93 (br. S., 1H), 7.65 (br. s., 1H), 7.13 (br. s., 1H), 4.87 (br. s., 2H), 3.82~4.18 (m, 3H), 2.30 (br. s., 1H), 1.80 (br. s., 1H), 1.15 (m, 3H).<br>LCMS (ES) $C_{18}H_{18}N_6F_3$ $[M + H]^+$ 375.1. |
| 173 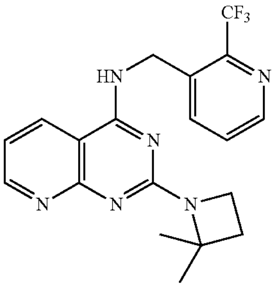 [SMILES: CC1(C)CCN1c1nc(NCc2cccnc2C(F)(F)F)c2cccnc2n1] | 2-(2,2-dimethylazetidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.55-8.78 (m, 3H), 8.47 (d, J = 8.03 Hz, 1H), 7.91 (br. s., 1 H), 7.62 (dd, J = 7.97, 4.58 Hz, 1H), 7.08 (dd, J = 7.78, 4.52 Hz, 1H), 4.92 (br. s., 2H), 3.83 (br. s., 2H), 1.98-2.02 (t, J = 7.60 Hz, 2H), 1.27 (br. s., 6H).<br>LCMS (ES) $C_{19}H_{20}N_6F_3$ $[M + H]^+$ 389.1. |
| 174 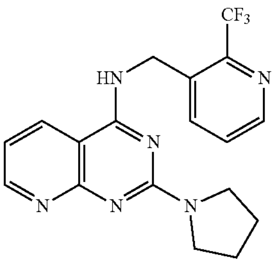 [SMILES: FC(F)(F)c1ncccc1CNc1nc(N2CCCC2)nc2ncccc12] | 2-(pyrrolidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.85 (br. s., 1H), 8.54-8.74 (m, 2H), 8.47 (br. s., 1H), 7.98 (br. s., 1H), 7.64 (br. s., 1H), 7.07 (br. s., 1H), 4.89 (br. s., 2H), 3.46 (s, 2H), 3.22 (s, 2H), 1.82 (br. s., 4H.).<br>LCMS (ES) $C_{18}H_{18}N_6F_3$ $[M + H]^+$ 375.1. |
| 175 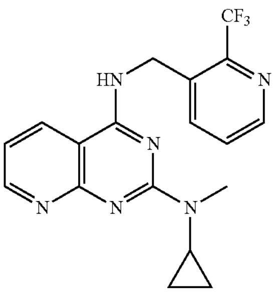 [SMILES: CN(c1nc(NCc2cccnc2C(F)(F)F)c2cccnc2n1)C1CC1] | $N^2$-cyclopropyl-$N^2$-methyl-$N^4$-((2-(trifluoromethyl)pyridin-3-yl)methyl)pyrido[2,3-d]pyrimidine-2,4-diamine<br>Synthesised via Route 6<br>$^1$H NMR (400 MHz, DMSO-d6) δ (ppm) 8.86 (br. s., 1H), 8.71 (br. s., 1H), 8.62 (br. s., 1H), 8.50 (d, J = 7.15 Hz, 1H), 7.93 (d, J = 7.28 Hz, 1H), 7.65 (br. s., 1H), 7.15 (br. s., 1H), 4.95 (br. s., 2H), 2.96 (br. s., 3H), 2.64 (br. s., 1H), 0.34-0.62 (m, 4H).<br>LCMS (ES) $C_{18}H_{18}N_6F_3$ $[M + H]^+$ 375.1. |

TABLE 1-continued

| | |
|---|---|
| 176<br>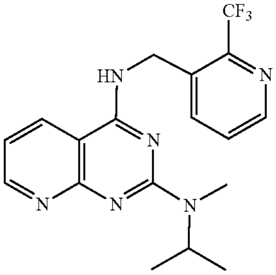 [SMILES: CC(C)N(C)c1nc(NCc2cccnc2C(F)(F)F)c2cccnc2n1] | $N^2$-isopropyl-$N^2$-methyl-$N^4$-((2-(trifluoromethyl)pyridin-3-yl)methyl)quinazoline-2,4-diamine<br>Synthesised via Route 4<br>$^1$H NMR (400 MHz, DMSO-d6) δ (ppm) 8.67 (t, J = 5.0 Hz, 1H), 8.58 (d, J = 4.3 Hz, 1H), 8.07 (d, J = 8.0 Hz, 1H), 7.91 (d, J = 8.0 Hz, 1H), 7.62 (dd, J = 8.0, 4.7 Hz, 1H), 7.52 (ddd, J = 8.3, 7.0, 1.4 Hz, 1H), 7.28 (d, J = 8.4 Hz, 1H), 7.06-7.13 (m, 1H), 4.86 (d, J = 4.4 Hz, 2H), 3.30-3.34 (m, 1H), 2.77 (br. s., 3H), 0.88 (br. s., 6 H).<br>LCMS (ES) $C_{19}H_{21}N_5F_3$ $[M + H]^+$ 376.2. |
| 177<br>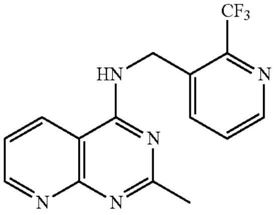 [SMILES: Cc1nc(NCc2cccnc2C(F)(F)F)c2cccnc2n1] | 2-methyl-N-((2-(trifluoromethyl)pyridin-3-yl)methyl)pyrido[2,3-d]pyrimidin-4-amine<br>Synthesised via Route 8<br>$^1$H NMR (400 MHz, DMSO-d6) δ (ppm) 9.08-9.11 (t, J = 8.0 Hz, 1H), 8.96-8.97 (dd, J = 4.0 Hz, 1H), 8.71-8.74 (dd, J = 4.0 Hz, J = 8.0 Hz, 1H), 8.62-8.63 (d, J = 8.0 Hz, 1H), 8.01-8.02 (d, J = 4.0 Hz, 1H), 7.65-7.68 (dd, J = 4.0 Hz, J = 8.0 Hz, 1H), 7.50-7.53 (dd, J = 4.0 Hz, J = 8.0 Hz, 1H), 4.95-4.96 (d, J = 4.0 Hz, 2H), 2.40 (s, 3H).<br>LCMS (ES) $C_{15}H_{13}N_5F_3$ $[M + H]^+$ 320.1. |
| 178<br>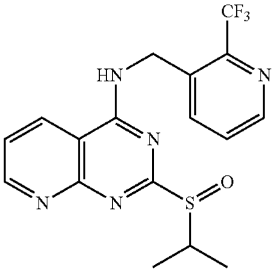 [SMILES: CC(C)S(=O)c1nc(NCc2cccnc2C(F)(F)F)c2cccnc2n1] | 2-(isopropylsulfinyl)-N-((2-(trifluoromethyl)pyridin-3-yl)methyl)pyrido[2,3-d]pyrimidin-4-amine<br>Synthesised via Route 8<br>$^1$H NMR (400 MHz, DMSO-d6) δ (ppm) 9.71 (br. s., 1H), 9.10 (d, J = 2.89 Hz, 1H), 8.85 (d, J = 8.16 Hz, 1H), 8.64 (d, J = 4.39 Hz, 1H), 8.06 (d, J = 7.91 Hz, 1H), 7.54-7.84 (m, 2H), 4.86-5.06 (m, 2H), 2.87-2.95 (m, 1H), 1.16 (d, J = 7.03 Hz, 3H), 0.81 (d, J = 6.78 Hz, 3H).<br>LCMS (ES) $C_{17}H_{17}N_5F_3OS$ $[M + H]^+$ 396.1. |
| 179<br>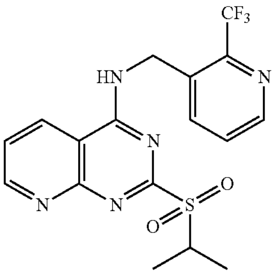 [SMILES: CC(C)S(=O)(=O)c1nc(NCc2cccnc2C(F)(F)F)c2cccnc2n1] | 2-(isopropylsulfonyl)-N-((2-(trifluoromethyl)pyridin-3-yl)methyl)pyrido[2,3-d]pyrimidin-4-amine<br>Synthesised via Route 8<br>$^1$H NMR (400 MHz, DMSO-d6) δ (ppm) 9.92 (t, J = 5.40 Hz, 1H), 9.17 (dd, J = 4.39, 1.76 Hz, 1H), 8.90 (dd, J = 8.34, 1.82 Hz, 1H), 8.65 (d, J = 4.39 Hz, 1H), 8.09 (d, J = 7.91 Hz, 1H), 7.79 (dd, J = 8.28, 4.39 Hz, 1H), 7.65 (dd, J = 7.97, 4.71 Hz, 1H), 4.99 (d, J = 4.89 Hz, 2H), 3.63-3.72 (m, 1H), 1.08 (d, J = 6.90 Hz, 6H).<br>LCMS (ES) $C_{17}H_{17}N_5F_3O_2S$ $[M + H]^+$ 412.1. |
| 182<br>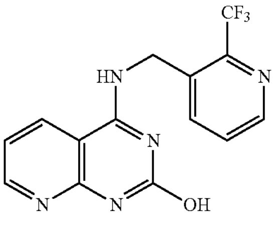 [SMILES: Oc1nc(NCc2cccnc2C(F)(F)F)c2cccnc2n1] | 4-(((2-(trifluoromethyl)pyridin-3-yl)methyl)amino)pyrido[2,3-d]pyrimldin-2-ol<br>Synthesised via Route 8<br>$^1$H NMR (400 MHz, DMSO-d6) δ (ppm) 11.23 (s, 1H), 9.02-9.05 (t, J = 8.0 Hz, 1H), 8.64-8.65 (d, J = 4.0 Hz, 1H), 8.57-8.59 (dd, J = 4.0 Hz, 1H), 8.49-8.51 (dd, J = 8.0 Hz, 1H), 7.96-7.98 (d, J = 8.0 Hz, 1H), 7.67-7.70 (dd, J = 8.0 Hz, J = 4.0 Hz, 1H), 7.23-7.26 (dd, J = 8.0 Hz, J = 4.0 Hz, 1H), 4.88-4.89 (d, J = 4.0 Hz, 2H).<br>LCMS (ES) $C_{14}H_{11}N_5F_3O$ $[M + H]^+$ 321.9. |

TABLE 1-continued

183

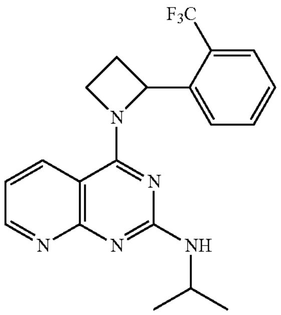 [SMILES: CC(C)Nc1nc(N2CCC2c2ccccc2C(F)(F)F)c2cccnc2n1]

N-isopropyl-4-(2-(2-(trifluoromethyl)phenyl)azetidin-1-yl)pyrido[2,3-d]pyrimidin-2-amine Synthesised via Route 6
$^1$H NMR (400 MHz, MeOD) δ (ppm) 8.62 (d, J = 3.0 Hz, 1H), 8.25 (br. s., 1H), 7.81 (d, J = 7.7 Hz, 1H), 7.75 (d, J = 7.8 Hz, 1H), 7.63 (t, J = 7.6 Hz, 1H), 7.43-7.50 (m, 1H), 7.06 (br. s., 1H), 6.11 (t, J = 7.4 Hz, 1H), 4.68 (br. s., 2H), 3.73 (br. s., 1H), 2.91-3.06 (m, 1H), 2.33 (br. s., 1H), 0.57-1.20 (m, 6H)
LCMS (ES) $C_{20}H_{21}N_5F_3$ [M + H]$^+$ 388.1.

184

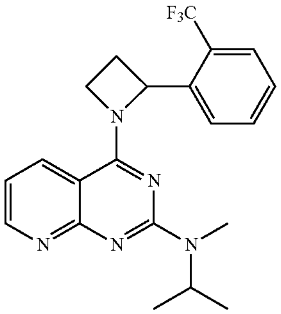 [SMILES: CC(C)N(C)c1nc(N2CCC2c2ccccc2C(F)(F)F)c2cccnc2n1]

N-isopropyl-N-methyl-4-(2-(2-(trifluoromethyl)phenyl)azetidin-1-yl)pyrido[2,3-d]pyrimidin-2-amine Synthesised via Route 6
$^1$H NMR (400 MHz, MeOD) δ (ppm) 8.62 (dd, J = 4.6, 1.8 Hz, 1H), 8.28 (d, J = 7.4 Hz, 1H), 7.84 (d, J = 7.8 Hz, 1H), 7.74 (d, J = 7.8 Hz, 1H), 7.62 (t, J = 7.6 Hz, 1H), 7.42-7.50 (m, 1H), 7.07 (dd, J = 8.0, 4.6 Hz, 1H), 6.06 (t, J = 7.7 Hz, 1H), 4.84 (br. s., 1H), 4.62-4.71 (m, 1H), 3.34 (br. s., 3H), 2.87-3.01 (m, 2H), 2.30-2.46 (m, 1H), 1.05 (d, J = 6.8 Hz, 6H).
LCMS (ES) $C_{21}H_{23}N_5F_3$ [M + H]$^+$ 402.2.

185

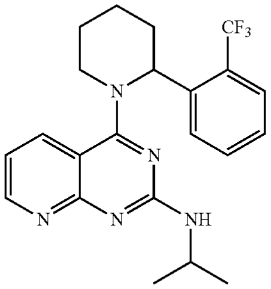 [SMILES: CC(C)Nc1nc(N2CCCCC2c2ccccc2C(F)(F)F)c2cccnc2n1]

N-isopropyl-4-(2-(2-(trifluoromethyl)phenyl)piperidin-1-yl)pyrido[2,3-d]pyrimidin-2-amine Synthesised via Route 6
$^1$H NMR (400 MHz, DMSO-d6) δ (ppm) 8.72 (d, J = 2.51 Hz, 1H), 8.36 (d, J = 7.78 Hz, 1H), 7.64 (m, 2H), 7.37 (t, J = 7.59 Hz, 1H), 7.29 (d, J = 8.00 Hz, 1H), 7.17 (br. s., 1H), 4.81 (d, J = 8.53 Hz, 1H), 3.82 (d, J = 12.42 Hz, 2H), 2.97-3.07 (m, 1H), 2.00 (br. s., 2H), 1.91 (d, J = 11.80 Hz, 1H), 1.79 (d, J = 12.42 Hz, 1H), 1.52-1.71 (m, 2H), 1.11-1.24 (m, 1H), 1.03 (d, J = 6.53 Hz, 3H), 0.52 (br. s., 2H).
LCMS (ES) $C_{22}H_{25}N_5F_3$ [M + H]$^+$ 416.3.

186

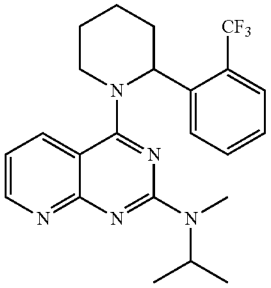 [SMILES: CC(C)N(C)c1nc(N2CCCCC2c2ccccc2C(F)(F)F)c2cccnc2n1]

N-isopropyl-N-methyl-4-(2-(2-(trifluoromethyl)phenyl)piperidin-1-yl)pyrido[2,3-d]pyrimidin-2-amine Synthesised via Route 6
$^1$H NMR (400 MHz, DMSO-d6) δ (ppm) 8.75 (br. s., 1H), 8.37 (br. s., 1H), 7.68 (br. s., 1H), 7.09-7.56 (m, 4H), 4.75 (br. s., 2H), 3.85 (br. s., 1H), 3.03 (br. s., 2H), 2.71-2.83 (m, 2H), 1.57-2.07 (m, 6H), 0.42-1.12 (m, 6H).
LCMS (ES) $C_{23}H_{27}N_5F_7$ [M + H]$^+$ 430.2.

TABLE 1-continued

| | |
|---|---|
| 187 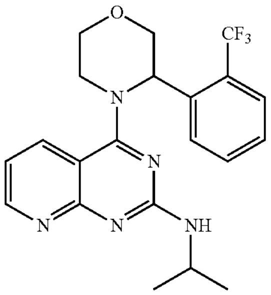 [SMILES: CC(C)Nc1nc(N2CCOCC2c2ccccc2C(F)(F)F)c2cccnc2n1] | N-isopropyl-4-(3-(2-(trifluoromethyl)phenyl)morpholino)pyrido[2,3-d]pyrimidin-2-amine<br>Synthesised via Route 6<br>$^1$H NMR (400 MHz, DMSO-d6) δ (ppm) 8.72-8.74 (dd, J = 4.0 Hz, 1H), 8.38-8.39 (d, J = 4.0 Hz, 1H), 7.69-7.71 (d, J = 8.0 Hz, 2H), 7.44-7.48 (t, J = 8.0 Hz, 1H), 7.36-7.39 (t, J = 8.0 Hz, 1H), 7.14-7.17 (dd, J = 8.0 Hz, J = 4.0 Hz, 1H), 5.03 (s, 2H), 3.77-4.06 (m, 6H), 3.17-3.22 (t, J = 8.0 Hz, 1H), 1.04-1.23 (m, 4H), 0.51 (bs, 2H).<br>LCMS (ES) $C_{21}H_{23}N_5F_3O$ [M + H]$^+$ 418.2. |
| 188 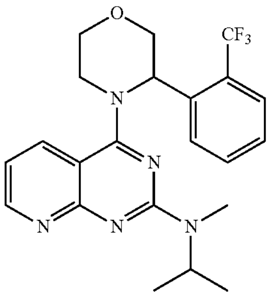 [SMILES: CC(C)N(C)c1nc(N2CCOCC2c2ccccc2C(F)(F)F)c2cccnc2n1] | N-isopropyl-N-methyl-4-(3-(2-(trifluoromethyl)phenyl)morpholino)pyrido[2,3-d]pyrimidin-2-amine<br>Synthesised via Route 6<br>$^1$H NMR (400 MHz, DMSO-d6) δ (ppm) 8.74-8.75 (dd, J = 4.0 Hz, 1H), 8.40-8.42 (d, J = 8.0 Hz, 1H), 7.72-7.74 (d, J = 8.0 Hz, 1H), 7.59-7.61 (d, J = 8.0 Hz, 1H), 7.41-7.45 (t, J = 8.0 Hz, 1H), 7.35-7.39 (t, J = 8.0 Hz, 1H), 7.16-7.19 (dd, J = 4.0 Hz, J = 8.0 Hz, 1H), 4.94 (bs, 1H), 4.64 (bs, 1H), 4.07-4.12 (t, J = 8.0 Hz, 1H), 3.92-3.98 (t, J = 12.0 Hz, 2H), 3.81-3.85 (t, J = 16.0 Hz, 1H), 3.55-3.60 (t, J = 12.0 Hz, 1H), 3.17-3.23 (t, J = 12.0 Hz, 1H), 2.77 (bs, 2H), 2.33 (bs, 1H), 1.02 (bs, 4H), 0.5 (bs, 2H).<br>LCMS (ES) $C_{22}H_{25}N_5F_3O$ [M + H]$^+$ 432.2. |
| 189 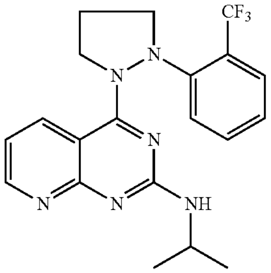 [SMILES: CC(C)Nc1nc(N2CCCN2c2ccccc2C(F)(F)F)c2cccnc2n1] | N-isopropyl-4-(2-(2-(trifluoromethyl)phenyl)pyrazolidin-1-yl)pyrido[2,3-d]pyrimidin-2-amine<br>Synthesised via Route 6<br>$^1$H NMR (400 MHz, DMSO-d6) δ (ppm) 8.69-8.72 (dd, J = 4.0 Hz, J = 8.0 Hz, 1H), 8.50-8.51 (dd, J = 4.0 Hz, 1H), 7.78-7.80 (d, J = 8.0 Hz, 1H), 7.53-7.56 (t, J = 8.0 Hz, 1H), 7.27-7.31 (t, J = 8.0 Hz, 1H), 7.22-7.24 (d, J = 8.0 Hz, 1H), 6.89 (bs, 1H), 6.74-6.76 (dd, J = 4.0 Hz, J = 8.0 Hz, 1H), 4.14-4.23 (m, 3H), 3.58 (m, 2 H), 2.07 (bs, 2H), 1.18-1.20 (d,J = 8.0 Hz, 6H).<br>LCMS (ES) $C_{20}H_{22}N_6F_3$ [M + H]$^+$ 403.0. |
| 190 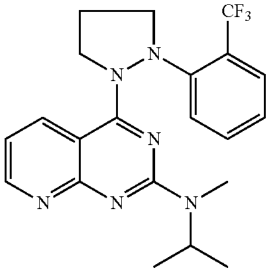 [SMILES: CC(C)N(C)c1nc(N2CCCN2c2ccccc2C(F)(F)F)c2cccnc2n1] | N-isopropyl-N-methyl-4-(2-(2-(trifluoromethyl)phenyl)pyrazolidin-1-yl)pyrido[2,3-d]pyrimidin-2-amine<br>Synthesised via Route 6<br>$^1$H NMR (400 MHz, DMSO-d6) δ (ppm) 8.69-8.72 (dd, J = 4.0 Hz, J = 8.0 Hz, 1H), 8.51-8.53 (dd, J = 4.0 Hz, 1H), 7.78-7.80 (d, J = 8.0 Hz, 1H), 7.52-7.55 (t, J = 8.0 Hz, 1H), 7.27-7.31 (t, J = 8.0 Hz, 1H), 7.21-7.23 (d, J = 8.0 Hz, 1H), 6.76-6.79 (dd, J = 4.0 Hz, J = 8.0 Hz, 1H), 5.13-5.16 (m, 1H), 4.16 (bs, 2H), 3.58-3.61 (t, J = 8.0 Hz, 2 H), 3.02 (s, 3H), 2.07 (bs, 2H), 1.16-1.18 (d, J = 8.0 Hz, 6H).<br>LCMS (ES) $C_{21}H_{24}N_6F_3$ [M + H]$^+$ 417.0. |
| 191 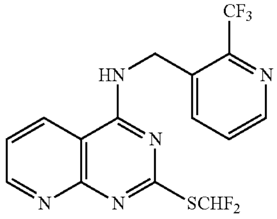 | 2-((difluoromethyl)thio)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 9.56 (br. s., 1H), 8.96-9.02 (m, 1H), 8.76 (dd, J = 8.16, 1.76 Hz, 1H), 8.65 (d, J = 4.27 Hz, 1H), 8.02 (d, J = 7.91 Hz, 1H), 7.71-8.00 (m, 1H), 7.67 (dd, J = 7.91, 4.64 Hz, 1H), 7.59 (dd, J = 8.16, 4.39 Hz, 1H), 4.95 (br. s., 2H).<br>LCMS (ES) $C_{15}H_{11}N_5F_5S$ [M + H]$^+$ 388.1. |

TABLE 1-continued

| | |
|---|---|
| 192<br>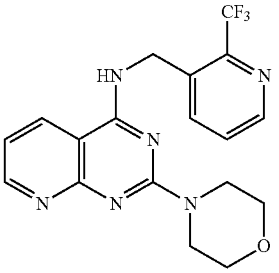 [SMILES: FC(F)(F)c1ncccc1CNc1nc(N2CCOCC2)nc2ncccc12] | 2-morpholino-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.97 (t,J = 5.46 Hz, 1H), 8.71 (dd, J = 4.39, 1.76 Hz, 1H), 8.62 (d, J = 4.14 Hz, 1H), 8.50 (dd, J = 8.03, 1.88 Hz, 1H), 7.98 (d, J = 8.03 Hz, 1H), 7.66 (dd, J = 7.91, 4.64 Hz, 1H), 7.15 (dd, J = 8.03, 4.52 Hz, 1H), 4.89 (d, J = 4.89 Hz, 2H), 3.44-3.69 (m, 8H).<br>LCMS (ES) $C_{18}H_{18}N_6F_3O$ [M + H]$^+$ 391.2. |
| 193<br>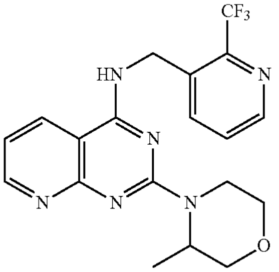 [SMILES: CC1COCCN1c1nc(NCc2cccnc2C(F)(F)F)c2cccnc2n1] | 2-(3-methylmorpholino)-N-((2-(trifluoromethyl)pyridin-3-yl)methyl)pyrido[2,3-d]pyrimidin-4-amine<br>Synthesised via Route 6<br>$^1$H NMR (400 MHz, CDCl3) δ (ppm) 8.80 (m, 1H), 8.64 (m, 1H), 7.94 (m, 2H), 7.52-7.38 (m, 1H), 7.05 (dd, J = 7.7, 4.3 Hz, 1H), 6.28 (m, 1H), 5.05 (dd, J = 44.6, 14.7 Hz, 2H), 4.86-4.67 (m, 1H), 4.51 (d, J = 6.3 Hz, 1H), 3.94 (d, J = 8.4 Hz, 1H), 3.68 (dd, J = 33.8, 11.9 Hz, 2H), 3.48 (t, J = 9.7 Hz, 1H), 3.26 (t, J = 12.0 Hz, 1H), 1.16 (b, 3H).<br>LCMS (ES) $C_{19}H_{20}N_6F_3O$ [M + H]$^+$ 405.3. |
| 193_S<br>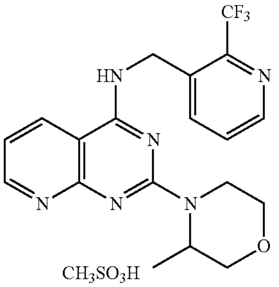 | 2-(3-methylmorpholino)-N-((2-(trifluoromethyl)pyridin-3-yl)methyl)pyrido[2,3-d]pyrimidin-4-amine methanesulfonate<br>Synthesised via Route 6<br>$^1$H NMR (400 MHz, MeOD) δ (ppm) 8.87-8.85 (m, 1H), 8.67-8.65 (m, 1H), 8.65-8.59 (m, 1H), 8.06-8.04 (m, 1H), 7.64-7.63 (m, 1H), 7.48-7.45 (m, 1H), 5.05-4.89 (m, 2H), 4.61 (b, 1H), 4.32 (d, 1H), 3.91 (d, 1H), 3.70 (d, 1H), 3.59 (dd, 1H), 3.45 (t, 1H), 3.32-3.30 (m, 1H), 2.70 (s, 3H), 1.14 (b, 3H).<br>LCMS (ES) $C_{19}H_{20}N_6F_3O$ [M + H]$^+$ 405.3. |
| 194<br>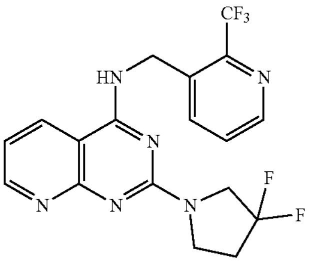 [SMILES: FC1(F)CCN(c2nc(NCc3cccnc3C(F)(F)F)c3cccnc3n2)C1] | 2-(3,3-difluoropyrrolidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, MeOD) δ (ppm) 8.72 (dd, J = 4.6, 1.9 Hz, 1H), 8.58 (d, J = 4.3 Hz, 1H), 8.46 (dd, J = 8.0, 1.9 Hz, 1H), 8.02 (d, J = 8.0 Hz, 1H), 7.60 (dd, J = 8.0, 4.7 Hz, 1H), 7.21 (dd, J = 8.0, 4.6 Hz, 1H), 5.02 (s, 2H), 4.08-3.49 (m, 4H), 2.52-2.31 (m, 2H).<br>LCMS (ES) $C_{18}H_{16}N_6F_5$ [M + H]$^+$ 411.2. |
| 194_S<br>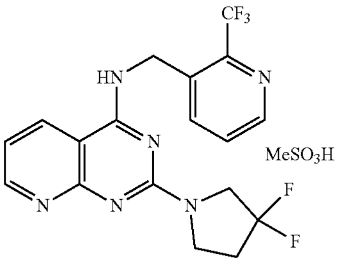 [SMILES: "MeSO3H" ; FC1(F)CCN(c2nc(NCc3cccnc3C(F)(F)F)c3cccnc3n2)C1] | 2-(3,3-difluoropyrrolidin-1-yl)-N-((2-(trifluoromethyl)pyridin-3-yl)methyl)pyrido[2,3-d]pyrimidin-4-amine methanesulfonate<br>Synthesised via Route 6<br>$^1$H NMR (400 MHz, MeOD) δ (ppm) 8.87-8.68 (m, 2H), 8.63 (d, J = 4.5 Hz, 1H). 8.08 (d, J = 7.8 Hz, 1H), 7.65 (dd, J = 7.7, 4.6 Hz, 1H), 7.57-7.45 (m, 1H), 5.11 (b, 2H), 4.16-3.68 (m, 4H), 2.72 (s, 3H), 2.63-2.38 (m, 2H).<br>LCMS (ES) $C_{18}H_{16}N_6F_5$ [M + H]$^+$ 411.1. |

TABLE 1-continued

195

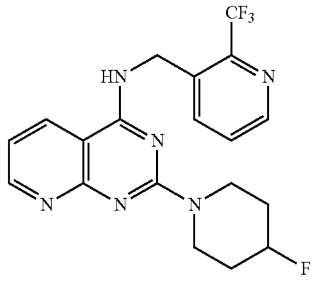 [SMILES: FC1CCN(c2nc(NCc3cccnc3C(F)(F)F)c3cccnc3n2)CC1]

2-(4-fluoropiperidin-1-yl)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.97 (t, J = 5.27 Hz, 1H), 8.70 (dd, J = 4.39, 1.88 Hz, 1H), 8.61 (d, J = 3.89 Hz, 1H), 8.49 (dd, J = 7.97, 1.82 Hz, 1H), 7.97 (d, J = 7.91 Hz, 1H), 7.65 (dd, J = 7.97, 4.58 Hz, 1H), 7.14 (dd, J = 7.97, 4.45 Hz, 1H), 4.74-4.94 (m, 3H), 3.83 (br. s., 2H), 3.56 (br. s., 2H), 1.71 (br. s., 2H), 1.46 (br. s., 2H).
LCMS (ES) $C_{19}H_{19}N_6F_4$ $[M + H]^+$ 407.3.

196

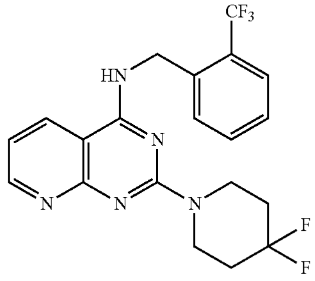 [SMILES: FC1(F)CCN(c2nc(NCc3ccccc3C(F)(F)F)c3cccnc3n2)CC1]

2-(4,4-difluoropiperidin-1-yl)-N-(2-(trifluoromethyl)benzyl)pyrido[2,3-d]pyrimidin-4-amine Synthesised via Route 6
$^1$H NMR (400 MHz, DMSO-d6) δ (ppm) 9.01 (t, J = 5.52 Hz, 1H), 8.72 (dd, J = 4.39, 1.76 Hz, 1H), 8.54 (dd, J = 8.03, 1.63 Hz, 1 H), 7.76 (d, J = 7.78 Hz, 1H), 7.58-7.63 (m, 1H), 7.51-7.56 (m, 1H), 7.43-7.50 (m, 1H), 7.18 (dd, J = 7.97, 4.45 Hz, 1H), 4.88 (d, J = 4.89 Hz, 2H), 3.79 (br. s., 4H), 1.78 (br. s., 4H).
LCMS (ES) $C_{20}H_{29}N_5F_5$ $[M + H]^+$ 424.3.

197

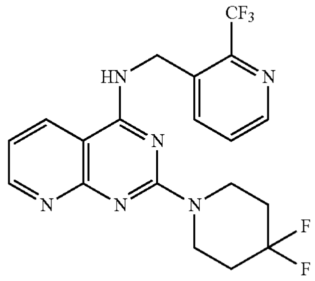 [SMILES: FC1(F)CCN(c2nc(NCc3cccnc3C(F)(F)F)c3cccnc3n2)CC1]

2-(4,4-difluoropiperidin-1-yl)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 9.03 (t, J = 5.2 Hz, 1H), 8.78-8.69 (m, 1H), 8.62 (d, J = 4.3 Hz, 1H), 8.57-8.47 (m, 1H), 7.98 (d, J = 8.0 Hz, 1H), 7.65 (dd, J = 7.9, 4.6 Hz, 1H), 7.18 (dd, J = 7.9, 4.4 Hz, 1H), 4.88 (d, J = 4.4 Hz, 2H), 3.91-3.64 (m, 4H), 1.99-1.61 (m, 4H).
LCMS (ES) $C_{19}H_{18}N_6F_5$ $[M + H]^+$ 425.1.

197_S

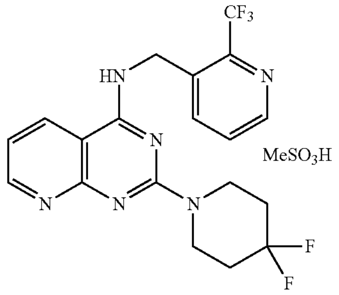 [SMILES: "MeSO3H" ; FC1(F)CCN(c2nc(NCc3cccnc3C(F)(F)F)c3cccnc3n2)CC1]

$N^2$-isopropyl-$N^4$-((2-(trifluoromethyl)pyridin-3-yl)methyl)pyrido[2,3-d]pyrimidine-2,4-diamine methanesulfonate Synthesised via Route 6
$^1$H NMR (400 MHz, MeOD) δ (ppm) 8.88 (d, J = 6.6 Hz, 1H), 8.68 (d, J = 4.2 Hz, 1H), 8.63 (d, J = 4.1 Hz, 1H), 8.07 (d, J = 7.7 Hz, 1H), 7.65 (dd, J = 7.9, 4.7 Hz, 1H), 7.49 (dd, J = 7.9, 5.7 Hz, 1H), 5.07 (s, 2H), 4.16-3.78 (m, 4H), 2.72 (s, 3H), 2.21-1.77 (m, 4H).
LCMS (ES) $C_{19}H_{18}N_6F_5$ $[M + H]^+$ 425.0.

TABLE 1-continued

| | |
|---|---|
| 198 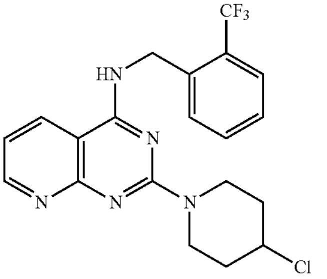 [SMILES: FC(F)(F)c1ccccc1CNc1nc(N2CCC(Cl)CC2)nc2ncccc12] | 2-(4-chloropiperidin-1-yl)-N-(2-(trifluoromethyl)benzyl)pyrido[2,3-d]pyrimidin-4-amine<br>Synthesised via Route 6<br>$^1$H NMR (400 MHz, DMSO-d6) δ (ppm) 8.96 (br. s., 1H), 8.69 (dd, J = 4.39, 1.76 Hz, 1H), 8.52 (dd, J = 8.03, 1.76 Hz, 1H), 7.75 (d, J = 7.53 Hz, 1H), 7.56-7.64 (m, 1H), 7.50-7.56 (m, 1H), 7.43-7.50 (m, 1H), 7.14 (dd, J = 7.97, 4.45 Hz, 1H), 4.86 (br. s., 2H), 4.32-4.44 (m, 1H), 4.07 (br. s., 2H), 3.40 (m, 2H), 1.91 (br. s., 2H), 1.51 (br. s., 2H).<br>LCMS (ES) $C_{20}H_{20}N_5F_3Cl$ $[M + H]^+$ 422.1. |
| 199 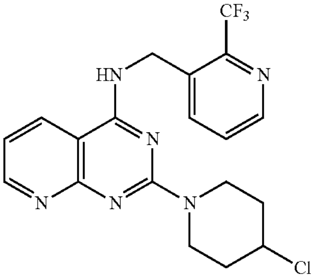 [SMILES: FC(F)(F)c1ncccc1CNc1nc(N2CCC(Cl)CC2)nc2ncccc12] | 2-(4-chloropiperidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.99 (t, J = 5.27 Hz, 1H), 8.70 (br. s., 1H), 8.61 (d, J = 4.39 Hz, 1H), 8.50 (d, J = 7.78 Hz, 1H), 7.97 (d, J = 8.03 Hz, 1H), 7.65 (dd, J = 7.97, 4.58 Hz, 1H), 7.15 (dd, J = 7.65, 4.39 Hz, 1H), 4.86 (d, J = 4.39 Hz, 2H), 4.38 (m, 1H), 4.04 (br. s., 2H), 3.03-3.25 (m, 2H), 1.89 (br. s., 2H), 1.49 (br. s., 2H).<br>LCMS (ES) $C_{19}H_{19}N_6F_3Cl$ $[M + H]^+$ 423.1. |
| 200 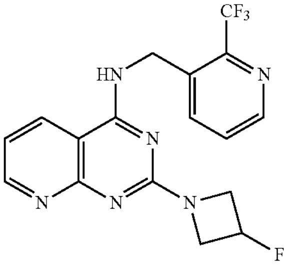 [SMILES: FC1CN(c2nc(NCc3cccnc3C(F)(F)F)c3cccnc3n2)C1] | 2-(3-fluoroazetidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 9.05 (t, J = 5.14 Hz, 1H), 8.72 (d, J = 3.14 Hz, 1H), 8.62 (d, J = 4.39 Hz, 1H), 8.53 (d, J = 6.65 Hz, 1H), 8.01 (d, J = 7.78 Hz, 1H), 7.67 (dd, J = 7.91, 4.64 Hz, 1H), 7.18 (dd, J = 7.91, 4.52 Hz, 1H), 5.29-5.51 (m, 1H), 4.87 (d, J = 4.77 Hz, 2H), 4.20 (m, 2H), 3.90 (m, 2H).<br>LCMS (ES) $C_{17}H_{15}N_6F_4$ $[M + H]^+$ 379.3. |
| 201 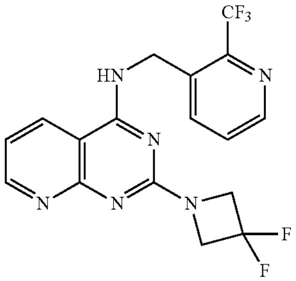 [SMILES: FC1(F)CN(c2nc(NCc3cccnc3C(F)(F)F)c3cccnc3n2)C1] | 2-(3,3-difluoroazetidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 9.12-9.13 (t, J = 4.0 Hz, 1H), 8.76-8.77 (dd, J = 4.0 Hz, 1H), 8.62-8.63 (d, J = 4.0 Hz, 1H), 8.55-8.58 (dd, J = 4.0 Hz, J = 8.0 Hz, 1H), 8.01-8.02 (d, J = 4.0 Hz, 1H), 7.65-7.68 (dd, J = 4.0 Hz, J = 8.0 Hz, 1H), 7.23-7.26 (dd, J = 4.0 Hz, J = 8.0 Hz, 1H), 4.88-4.89 (d, J = 4.0 Hz, 2H), 4.25-4.32 (t, J = 12.0 Hz, 4H).<br>LCMS (ES) $C_{17}H_{14}N_6F_5$ $[M + H]^+$ 397.1. |
| 202 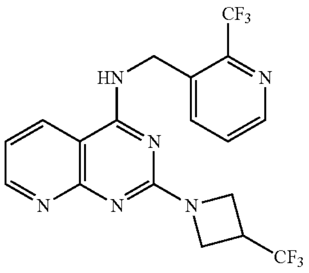 [SMILES: FC(F)(F)c1ncccc1CNc1nc(N2CC(C(F)(F)F)C2)nc2ncccc12] | 2-(3-(trifluoromethyl)azetidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 9.08 (t, J = 5.08 Hz, 1H), 8.74 (dd, J = 4.27, 1.63 Hz, 1H), 8.62 (d, J = 4.52 Hz, 1H), 8.54 (dd, J = 8.09, 1.69 Hz, 1H), 8.01 (d, J = 7.78 Hz, 1H), 7.66 (dd, J = 7.91, 4.52 Hz, 1H), 7.20 (dd, J = 7.97, 4.45 Hz, 1H), 4.88 (d, J = 4.64 Hz, 2H), 4.10 (br. s., 2H), 3.84 (br. s., 2H), 3.57-3.65 (m, 1H).<br>LCMS (ES) $C_{18}H_{15}N_6F_6$ $[M + H]^+$ 429.0. |

TABLE 1-continued

| | |
|---|---|
| 203 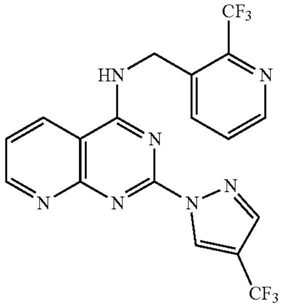 [SMILES: FC(F)(F)c1cnn(-c2nc(NCc3cccnc3C(F)(F)F)c3cccnc3n2)c1] | 2-(4-(trifluoromethyl)-1H-pyrazol-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 9.68 (br. s., 1H), 9.06 (dd, J = 4.39, 1.76 Hz, 1H), 9.00 (s, 1H), 8.83 (dd, J = 8.28, 1.76 Hz, 1H), 8.65 (d, J = 4.14 Hz, 1H), 8.27 (s, 1H), 8.16 (d, J = 7.91 Hz, 1H), 7.65 (ddd, J = 16.94, 8.03, 4.52 Hz, 2H), 5.09 (s, 2H).<br>LCMS (ES) $C_{18}H_{12}N_7F_6$ [M + H]$^+$ 440.0. |
| 204 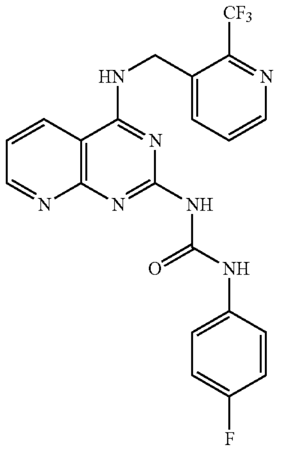 [SMILES: O=C(Nc1ccc(F)cc1)Nc1nc(NCc2cccnc2C(F)(F)F)c2cccnc2n1] | 1-(4-fluorophenyl)-3-(4-(((2-(trifluoromethyl)pyridin-3-yl)methyl)amino)pyrido[2,3-d]pyrimidin-2-yl)urea<br>Synthesised via Route 10<br>$^1$H NMR (400 MHz, DMSO-d6) δ (ppm) 12.61 (s, 1H), 9.78 (s, 1H), 9.24 (s, 1H), 8.92-8.93 (d, J = 4.0 Hz, 1H), 8.64-8.68 (m, 2.H), 8.13-8.15 (d, J = 8.0 Hz, 1H), 7.67-7.70 (dd, J = 4.0 Hz, J = 8.0 Hz, 1H), 7.52-7.55 (dd, J = 4.0 Hz, J = 8.0 Hz, 2H), 7.43-7.47 (dd, J = 4.0 Hz, J = 8.0 Hz, 1H), 7.17-7.21 (t, J = 8.0 Hz, 2H), 4.99 (s, 2H).<br>LCMS (ES) $C_{21}H_{16}N_7F_4O$ [M + H]$^+$ 458.0. |
| 205 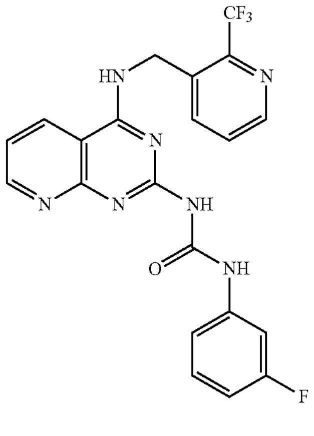 [SMILES: O=C(Nc1cccc(F)c1)Nc1nc(NCc2cccnc2C(F)(F)F)c2cccnc2n1] | 1-(3-fluorophenyl)-3-(4-(((2-(trifluoromethyl)pyridin-3-yl)methyl)amino)pyrido[2,3-d]pyrimidin-2-yl)urea<br>Synthesised via Route 10<br>$^1$H NMR (400 MHz, DMSO-d6) δ (ppm) 12.84 (s, 1H), 9.91 (s, 1H), 9.36 (s, 1H), 8.93-8.94 (d, J = 4.0 Hz, 1H), 8.64-8.90 (m, 2H), 8.11-8.13 (d, J = 8.0 Hz, 1H), 7.57-7.60 (m, 2H), 7.44-7.46 (dd, J = 4.0 Hz, J = 8.0 Hz, 1H), 7.37-7.39 (d, J = 8.0 Hz, 1H), 7.14-7.16 (d, J = 8.0 Hz, 1H), 6.88 (m, 1H), 5.00 (s, 2H).<br>LCMS (ES) $C_{21}H_{16}N_7F_4O$ [M + H]$^+$ 458.0. |

TABLE 1-continued

| | |
|---|---|
| 206 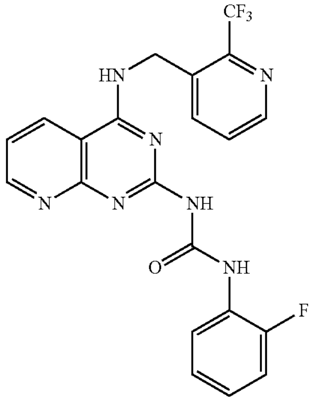 [SMILES: O=C(Nc1nc(NCc2cccnc2C(F)(F)F)c2cccnc2n1)Nc1ccccc1F] | 1-(2-fluorophenyl)-3-(4-(((2-(trifluoromethyl)pyridin-3-yl)methyl)amino)pyrido[2,3-d]pyrimidin-2-yl)urea<br>Synthesised via Route 10<br>$^1$H NMR (400 MHz, DMSO-d6) δ (ppm) 12.67 (s, 1H), 9.93 (s, 1H), 9.23-9.26 (t, J = 8.0 Hz, 1H), 8.92-8.93 (d, J = 4.0 Hz, 1H), 8.64-8.68 (m, 2H), 8.20-8.24 (d, J = 8.0 Hz, 1H), 8.12-8.14 (d, J = 8.0 Hz, 1H), 7.67-7.70 (dd, J = 4.0 Hz, J = 8.0 Hz, 1H), 7.43-7.46 (dd, J = 4.0 Hz, J = 8.0 Hz, 1H), 7.26-7.31 (t, J = 8.0 Hz, 1H), 7.15-7.19 (t, J = 8.0 Hz, 1H), 7.07-7.10 (m, 1H), 5.00 (s, 2H).<br>LCMS (ES) $C_{21}H_{16}N_7F_4O$ [M + H]$^+$ 458.0. |
| 207 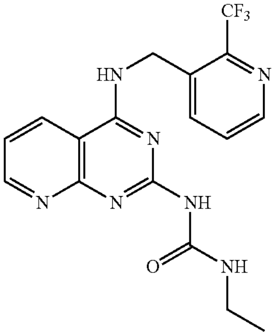 [SMILES: CCNC(=O)Nc1nc(NCc2cccnc2C(F)(F)F)c2cccnc2n1] | 1-ethyl-3-(4-(((2-(trifluoromethyl)pyridin-3-yl)methyl)amino)pyrido[2,3-d]pyrimidin-2-yl)urea<br>Synthesised via Route 10<br>$^1$H NMR (400 MHz, DMSO-d6) δ (ppm) 9.64 (t, 1H), 9.22 (s, 1H), 9.16 (bs, 1H), 8.85-8.86 (d, J = 4.0 Hz, 1H), 8.61-8.65 (m, 2H), 8.09-8.11 (d, J = 8.0 Hz, 1H), 7.66-7.69 (dd, J = 4.0 Hz, J = 8.0 Hz, 1H), 7.37-7.40 (dd, J = 4.0 Hz, J = 8.0 Hz 1H), 4.95 (bs, 2H), 3.18-3.22 (m, 2H), 1.05-1.08 (t, J = 8.0 Hz, 3H).<br>LCMS (ES) $C_{17}H_{17}N_7F_3O$ [M + H]$^+$ 392.0. |
| 208 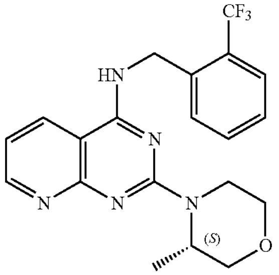 | (S)-2-(3-methylmorpholino)-N-(2-(trifluoromethyl)benzyl)pyrido[2,3-d]pyrimidin-4-amine<br>Synthesised via Route 6<br>$^1$H NMR (400 MHz, DMSO-d6) δ (ppm) 8.95 (s, 1H), 8.70 (d, J = 3.0 Hz, 1H), 8.52 (d, J = 7.9 Hz, 1H), 7.74 (d, J = 7.8 Hz, 1H), 7.60 (t, J = 7.5 Hz, 1H), 7.51 (d, J = 7.7 Hz, 1H), 7.45 (t, J = 7.5 Hz, 1H), 7.14 (dd, J = 7.9, 4.4 Hz, 1H), 4.87 (ddd, J = 57.1, 16.1, 4.6 Hz, 2H), 4.51 (b, 1H), 4.25 (d, J = 13.6 Hz, 1H), 3.82 (d, J = 8.9 Hz, 1H), 3.59 (d, J = 11.2 Hz, 1H), 3.45 (d, J = 8.6 Hz, 1H), 3.37-3.24 (m, 1H), 3.01 (td, J = 13.0, 3.2 Hz, 1H), 0.91 (b, 3H).<br>LCMS (ES) $C_{20}H_{21}N_5F_3O$ [M + H]$^+$ 404.1. |
| 208_S 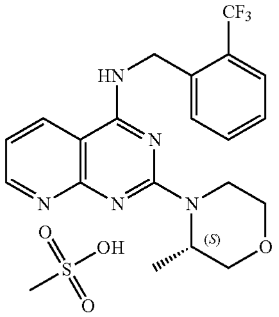 | (S)-2-(3-methylmorpholino)-N-(2-(trifluoromethyl)benzyl)pyrido[2,3-d]pyrimidin-4-amine methanesulfonate<br>Synthesised via Route 6<br>$^1$H NMR (400 MHz, DMSO-d6) δ (ppm) 9.98 (s, 1H), 9.01 (d, J = 7.9 Hz, 1H), 8.77 (dd, J = 5.4, 1.2 Hz, 1H), 7.78 (d, J = 7.8 Hz, 1H), 7.70-7.45 (m, 4H), 5.05-4.82 (m, 2H), 4.55 (b, 1H), 4.28 (d, J = 13.1 Hz, 1H), 3.89 (d, J = 10.1 Hz, 1H), 3.66 (d, J = 11.3 Hz, 1H), 3.49 (d, J = 10.9 Hz, 1H), 3.34 (d, J = 11.0 Hz, 1H), 3.30-3.18 (m, 1H), 2.35 (s, 3H), 1.05 (b, 3H).<br>LCMS (ES) $C_{20}H_{21}N_5F_3O$ [M + H]$^+$ 403.9. |

TABLE 1-continued

209

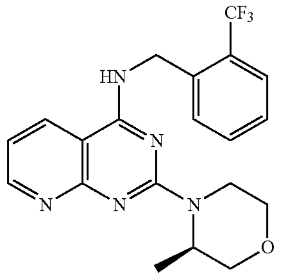 [SMILES: C[C@@H]1COCCN1c1nc(NCc2ccccc2C(F)(F)F)c2cccnc2n1]

(R)-2-(3-methylmorpholino)-N-(2-(trifluoromethyl)benzyl)pyrido[2,3-d]pyrimidin-4-amine Synthesised via Route 6
$^1$H NMR (400 MHz, DMSO-d6) δ (ppm) 8.96 (t, J = 4.8 Hz, 1H), 8.68 (dd, J = 4.4, 1.6 Hz, 1H), 8.52 (dd, J = 8.0, 1.6 Hz, 1H), 7.73 (d, J = 7.6 Hz, 1H), 7.59 (t, J = 7.6 Hz, 1H), 7.50 (d, J = 8.0 Hz, 1H), 7.44 (t, J = 7.6 Hz, 1H), 7.13 (dd, J = 7.6, 4.4 Hz, 1H), 4.76-4.96 (m, 2H), 4.50 (br s, 1H), 4.24 (d, J = 13.2 Hz, 1H), 3.81 (d, J = 8.4 Hz, 1H), 3.58 (d, J = 11.2 Hz, 1H), 3.42-3.46 (m, 1H), 3.26-3.29 (m, 1H), 2.96-3.03 (m, 1H), 0.91 (s, 3H).
LCMS (ES) $C_{20}H_{21}N_5F_3O$ $[M + H]^+$ 404.1.

210

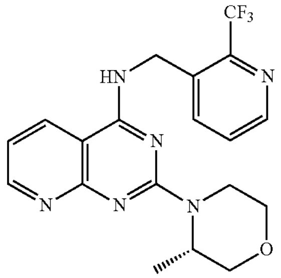 [SMILES: C[C@H]1COCCN1c1nc(NCc2cccnc2C(F)(F)F)c2cccnc2n1]

(S)-2-(3-methylmorpholino)-N-((2-(trifluoromethyl)pyridin-3-yl)methyl)pyrido[2,3-d]pyrimidin-4-amine Synthesised via Route 6
$^1$H NMR (400 MHz, DMSO-$d_6$) δ (ppm) 8.99 (t, J = 4.9 Hz, 1H), 8.70 (dd, J = 4.4,1.7 Hz, 1H), 8.61 (d, J = 4.2 Hz, 1H), 8.51 (dd, J = 8.0, 1.7 Hz, 1H), 7.95 (d, J = 7.9 Hz, 1H), 7.64 (dd, J = 7.9, 4.7 Hz, 1H), 7.15 (dd, J = 8.0, 4.5 Hz, 1H), 4.87 (ddd, J = 57.3, 16.4, 4.3 Hz, 2H), 4.46 (m, 1H), 4.22 (d, J = 13.1 Hz, 1H), 3.82 (d, J = 8.9 Hz, 1H), 3.58 (d, J = 11.2 Hz, 1H), 3.44 (dd, J = 11.3, 2.7 Hz, 1H), 3.36-3.22 (m, 1H), 3.00 (td, J = 13.2, 3.5 Hz, 1H), 0.88 (b, 3H).
LCMS (ES) $C_{19}H_{20}N_6F_3O$ $[M + H]^+$ 405.1.

211

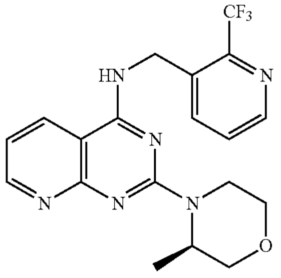 [SMILES: C[C@@H]1COCCN1c1nc(NCc2cccnc2C(F)(F)F)c2cccnc2n1]

(R)-2-(3-methylmorpholino)-N-((2-(trifluoromethyl)pyridin-3-yl)methyl)pyrido[2,3-d]pyrimidin-4-amine Synthesised via Route 6
$^1$H NMR (400 MHz, DMSO) δ (ppm) 8.99 (t, J = 4.9 Hz, 1H), 8.70 (dd, J = 4.4,1.7 Hz, 1H), 8.61 (d, J = 4.2 Hz, 1H), 8.51 (dd, J = 8.0, 1.7 Hz, 1H), 7.95 (d, J = 7.9 Hz, 1H), 7.64 (dd, J = 7.9, 4.7 Hz, 1H), 7.15 (dd, J = 8.0, 4.5 Hz, 1H), 4.87 (ddd, J = 57.3, 16.4, 4.3 Hz, 2H), 4.46 (m, 1H), 4.22 (d, J = 13.1 Hz, 1H), 3.82 (d, J = 8.9 Hz, 1H), 3.58 (d, J = 11.2 Hz, 1H), 3.44 (dd, J = 11.3, 2.7 Hz, 1H), 3.36-3.22 (m, 1H), 3.00 (td, J = 13.2, 3.5 Hz, 1H), 0.88 (b, 3H).
LCMS (ES) $C_{19}H_{20}N_6F_3O$ $[M + H]^+$ 405.0.

212

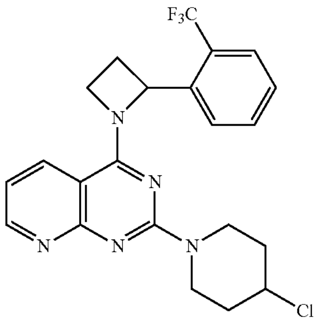 [SMILES: FC(F)(F)c1ccccc1C1CCN1c1nc(N2CCC(Cl)CC2)nc2ncccc12]

2-(4-chloropiperidin-1-yl)-4-(2-(2-(trifluoromethyl)phenyl)azetidin-1-yl)pyrido[2,3-d]pyrimidine Synthesised via Route 6
$^1$H NMR (400 MHz, $CDCl_3$) δ (ppm) 8.67 (d, J = 3.3 Hz, 1 H), 8.33 (s, 1 H), 7.83 (d, J = 7.9 Hz, 1 H), 7.75 (d, J = 7.9 Hz, 1 H), 7.63 (t, J = 7.7 Hz, 1 H), 7.45-7.52 (m, 1 H), 7.15 (s, 1 H), 6.05 (t, J = 7.7 Hz, 1 H), 4.70 (q, J = 8.0 Hz, 1 H), 4.19 (s, 1 H), 3.97 (s, 2 H), 3.37 (s, 1 H), 3.17-3.32 (m, 2 H), 2.90-3.02 (m, 1 H), 2.27-2.44 (m, 1 H), 1.81 (s, 2 H), 1.32-1.61 (m, 2 H)
LCMS (ES) $C_{22}H_{22}N_5F_3Cl$ $[M + H]^+$ 448.1.

TABLE 1-continued

213

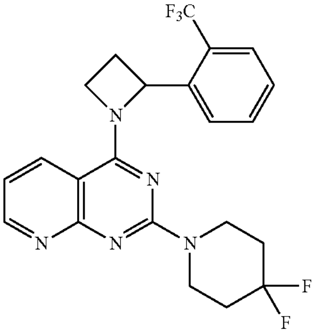

2-(4,4-difluoropiperidin-1-yl)-4-(2-(2-(trifluoromethyl)phenyl)azetidin-1-yl)pyrido[2,3-d]pyrimidine Synthesised via Route 6

$^1$H NMR (400 MHz, DMSO-d6) δ (ppm) 8.72 (dd, J = 4.3, 1.6 Hz, 1H), 8.26 (S, 1H), 7.83 (d, J = 7.8 Hz, 1H), 7.77 (d, J = 7.8 Hz, 1H), 7.67 (t, J = 7.5 Hz, 1H), 7.47-7.54 (m, 1H), 7.13 (dd, J = 7.8, 4.4 Hz, 1H), 5.91 (t, J = 7.3 Hz, 1H), 4.88 (d, J = 3.6 Hz, 1H), 4.65 (q, J = 8.2 Hz, 1H), 3.87-3.46 (m, 4H), 2.79-2.92 (m, 1H), 2.19-2.31 (m, 1H), 1.38-1.91 (m, 4H).

LCMS (ES) $C_{22}H_{21}N_5F_5$ $[M + H]^+$ 450.1.

214

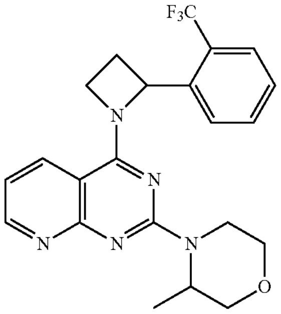 [SMILES: CC1COCCN1c1nc(N2CCC2c2ccccc2C(F)(F)F)c2cccnc2n1]

3-methyl-4-(4-(2-(2-(trifluoromethyl)phenyl)azetidin-1-yl)pyrido[2,3-d]pyrimidin-2-yl)morpholine Synthesised via Route 6

$^1$H NMR (400 MHz, DMSO-d6) δ (ppm) 8.68-8.69 (m, 1H), 8.22 (m, 1H), 7.82 (dd, J = 12.0, 8.0 Hz, 1H), 7.74 (d, J = 8.0 Hz, 1H), 7.65 (q, J = 8.0 Hz, 1H), 7.46-7.51 (m, 1H), 7.07-7.11 (m, 1H), 5.89-5.91 (m, 1H), 4.85 (m, 1H), 4.59-4.65 (m, 1H), 4.11 (s, 2H), 3.74 (d, J = 8.0 Hz, 1H), 3.39- 3.51 (m, 2H), 3.22-3.28 (m, 1H), 2.84-2.97 (m, 2H), 2.21-2.27 (m, 1H), 1.07 (d, J = 8.0 Hz, 1.7H), 0.58 (br s, 1.3H).

LCMS (ES) $C_{22}H_{23}N_5F_3O$ $[M + H]^+$ 430.1.

215

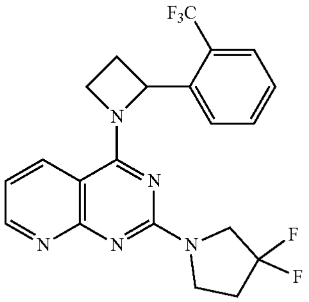 [SMILES: FC1(F)CCN(c2nc(N3CCC3c3ccccc3C(F)(F)F)c3cccnc3n2)C1]

2-(3,3-difluoropyrrolidin-1-yl)-4-(2-(2-(trifluoromethyl)phenyl)azetidin-1-yl)pyrido(2,3-d]pyrimidine Synthesised via Route 6

$^1$H NMR (400 MHz, DMSO-d6) δ (ppm) 8.72 (dd, J = 4.3, 1.6 Hz, 1H), 8.27 (s, 1H), 7.84 (d, J = 7.8 Hz, 1H), 7.77 (d, J = 7.8 Hz, 1H), 7.67 (t, J = 7.6 Hz, 1H), 7.47-7.54 (m, 1H), 7.13 (dd, J = 7.7, 4.3 Hz, 1H), 5.94 (s, 1H), 4.90 (s, 1H), 4.64 (q, J = 8.0 Hz, 1H), 3.38-4.04 (m, 4H), 2.86 (dd, J = 9.3, 4.4 Hz, 1H), 2.30-2.44 (m, 2H), 2.18-2.29 (m, 1H).

LCMS (ES) $C_{21}H_{19}N_5F_5$ $[M + H]^+$ 436.1.

216

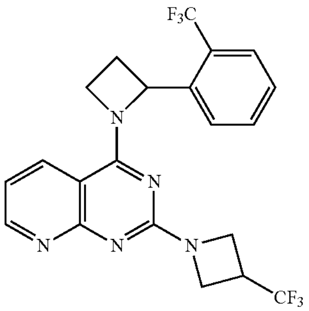 [SMILES: FC(F)(F)c1ccccc1C1CCN1c1nc(N2CC(C(F)(F)F)C2)nc2ncccc12]

2-(3-(trifluoromethyl)azetidin-1-yl)-4-(2-(2-(trifluoromethyl)phenyl)azetidin-1-yl)pyrido[2,3-d]pyrimidine Synthesised via Route 6

$^1$H NMR (400 MHz, DMSO-d6) δ (ppm) 8.73 (dd, J = 4.4, 1.6 Hz, 1H), 8.26 (s, 1H), 7.85 (d, J = 7.8 Hz, 1H), 7.76 (d, J = 7.7 Hz, 1H), 7.67 (t, J = 7.6 Hz, 1H), 7.46-7.54 (m, 1H), 7.16 (dd, J = 7.7, 4.3 Hz, 1H), 5.93 (s, 1H), 4.90 (s, 1H), 4.56-4.72 (m, 1H), 4.05 (s, 1H), 3.80 (s, 1H), 3.57 (s, 3H), 2.79-2.93 (m, 1H), 2.16-2.31 (m, 1H).

LCMS (ES) $C_{21}H_{18}N_5F_6$ $[M + H]^+$ 454.1.

TABLE 1-continued

217

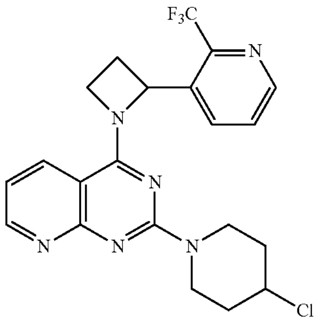 [SMILES: FC(F)(F)c1ncccc1C1CCN1c1nc(N2CCC(Cl)CC2)nc2ncccc12]

2-(4-chloropiperidin-1-yl)-4-(2-(2-(trifluoromethyl)pyridin-3-yl)azetidin-1-yl)pyrido[2,3-d]pyrimidine Synthesised via Route 6

$^1$H NMR (400 MHz, MeOD) δ (ppm) 8.67 (dd, J = 4.6, 1.8 Hz, 1 H), 8.62 (dd, J = 4.7, 1.2 Hz, 1 H), 8.34 (br d, J = 6.9 Hz, 1 H), 8.27 (d, J = 8.0 Hz, 1 H), 7.68 (dd, J = 8.0, 4.7 Hz, 1 H), 7.15 (dd, J = 8.0, 4.6 Hz, 1 H), 6.05 (br t, J = 7.9 Hz, 1 H), 4.73 (q, J = 8.3 Hz, 1 H), 4.19-4.26 (m, 1 H), 3.99 (br s, 2 H), 3.37 (br s, 1 H), 3.20-3.32 (m, 2 H), 2.94-3.04 (m, 1 H), 2.45 (ddt, J = 11.2, 9.3, 7.1, 7.1 Hz, 1 H), 1.86 (br s, 2 H), 1.35-1.65 (m, 2 H).

LCMS (ES) $C_{21}H_{21}N_6F_3Cl$ $[M + H]^+$ 449.1.

218

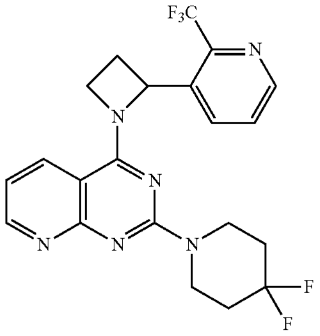 [SMILES: FC1(F)CCN(c2nc(N3CCC3c3cccnc3C(F)(F)F)c3cccnc3n2)CC1]

2-(4,4-difluoropiperidin-1-yl)-4-(2-(2-(trifluoromethyl)pyridin-3-yl)azetidin-1-yl)pyrido[2,3-d]pyrimidine Synthesised via Route 6

$^1$H NMR (400 MHz, DMSO-d6) δ (ppm) 8.73 (dd, J = 4.4, 1.8 Hz, 1H), 8.66 (d, J = 3.6 Hz, 1H), 8.18-8.39 (m, 2H), 7.72 (dd, J = 7.9, 4.6 Hz, 1H), 7.15 (dd, J = 8.0, 4.5 Hz, 1H), 5.91 (t, J = 7.5 Hz, 1H), 4.89 (d, J = 4.0 Hz, 1H), 4.67 (q, J = 8.0 Hz, 1H), 3.56 (s, 4H), 2.79-2.93 (m, 1H), 2.29-2.40 (m, 1H), 1.70 (s, 4H)

LCMS (ES) $C_{21}H_{20}N_6F_5$ $[M + H]^+$ 451.1.

219

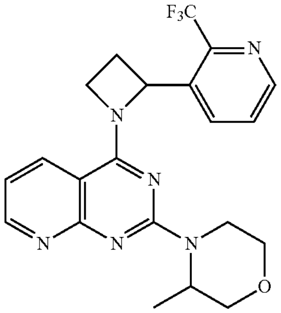 [SMILES: CC1COCCN1c1nc(N2CCC2c2cccnc2C(F)(F)F)c2cccnc2n1]

3-methyl-4-(4-(2-(2-(trifluoromethyl)pyridin-3-yl)azetidin-1-yl)pyrido[2,3-d]pyrimidin-2-yl)morpholine Synthesised via Route 6

$^1$H NMR (400 MHz, DMSO-d6) δ (ppm) 8.70 (d, J = 4.0 Hz, 1H), 8.64 (s, 1H), 8.24 (t, J = 8.0 Hz, 2H), 7.68-7.72 (m, 1H), 7.09-7.13 (m, 1H), 5.90 (t, J = 8.0 Hz, 1H), 4.85-4.88 (m, 1H), 4.62-4.67 (m, 1H), 4.07 (m, 2H), 3.74 (d, J = 12.0 Hz 1H), 3.38-3.51 (m, 2H), 3.21-3.27 (m, 1H), 2.67-2.74 (m, 2H), 2.31-2.36 (m, 1H), 1.06 (d, J = 4.0 Hz, 1.7H), 0.57 (br s, 1.3H)

LCMS (ES) $C_{21}H_{22}N_6F_3O$ $[M + H]^+$ 431.3.

220

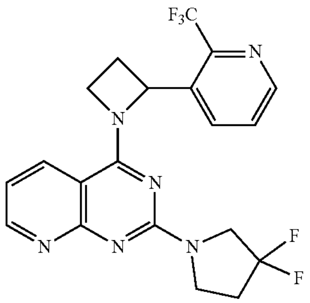 [SMILES: FC1(F)CCN(c2nc(N3CCC3c3cccnc3C(F)(F)F)c3cccnc3n2)C1]

2-(3,3-difluoropyrrolidin-1-yl)-4-(2-(2-(trifluoromethyl)pyridin-3-yl)azetidin-1-yl)pyrido[2,3-d]pyrimidine Synthesised via Route 6

$^1$H NMR (400 MHz, DMSO-d6) δ (ppm) 8.73 (dd, J = 4.4, 1.7 Hz, 1H), 8.66 (d, J = 4.2 Hz, 1H), 8.20-8.34 (m, 2H), 7.72 (dd, J = 8.0, 4.6 Hz, 1H), 7.15 (dd, J = 8.0, 4.4 Hz, 1H), 5.94 (t, J = 7.1 Hz, 1H), 4.84-4.99 (m, 1H), 4.66 (q, J = 8.2 Hz, 1H), 3.36-4.06 (m, 4H), 2.88 (dd, J = 10.0, 4.6 Hz, 1H), 2.29-2.44 (m, 3H).

LCMS (ES) $C_{20}H_{18}N_6F_5$ $[M + H]^+$ 437.1.

TABLE 1-continued

| | | |
|---|---|---|
| 221 | 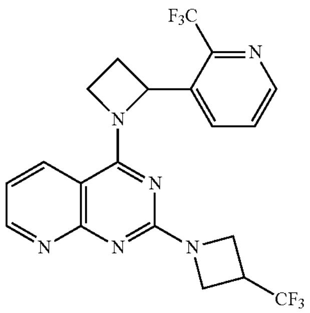 [SMILES: FC(F)(F)c1ncccc1C1CCN1c1nc(N2CC(C(F)(F)F)C2)nc2ncccc12] | 2-(3-(trifluoromethyl)azetidin-1-yl)-4-(2-(2-(trifluoromethyl)pyridin-3-yl)azetidin-1-yl)pyrido[2,3-d]pyrimidine<br>Synthesised via Route 6<br>$^1$H NMR (400 MHz, DMSO-d6) δ (ppm) 8.74 (d, J = 2.8 Hz, 1H), 8.65 (d, J = 4.0 Hz, 1H), 8.27 (d, J = 7.7 Hz, 2H), 7.72 (dd, J = 8.0, 4.6 Hz, 1H), 7.17 (dd, J = 8.0, 4.6 Hz, 1H), 5.92 (s, 1H), 4.91 (d, J = 4.4 Hz, 1H), 4.67 (q, J = 8.2 Hz, 1H), 4.03 (s, 1H), 3.77 (s, 1H), 3.56 (s, 3H), 2.87 (d, J = 5.40 Hz, 1H), 2.28-2.39 (m, 1H)<br>LCMS (ES) $C_{20}H_{17}N_6F_6$ [M + H]$^+$ 455.1. |
| 222 | 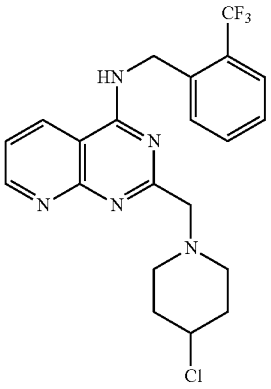 [SMILES: FC(F)(F)c1ccccc1CNc1nc(CN2CCC(Cl)CC2)nc2ncccc12] | 2-((4-chloropiperidin-1-yl)methyl)-N-((2-(trifluoromethyl)pyridin-3-yl)methyl)pyrido[2,3-d]pyrimidin-4-amine<br>Synthesised via Route 11<br>$^1$H NMR (400 MHz, $CDCl_3$) δ (ppm) 9.05 (dd, J = 4.3, 1.7 Hz, 1H), 8.09 (dd, J = 8.2, 1.7 Hz, 1H), 7.71 (t, J = 7.0 Hz, 2H), 7.52 (t, J = 7.5 Hz, 1H), 7.35-7.46 (m, 2H), 6.22 (br s, 1H), 5.12 (d, J = 4.9 Hz, 2H), 4.00 (br s, 1H), 3.86 (s, 2H), 3.04 (dd, J = 12.6, 6.7 Hz, 2H), 2.47-2.64 (m, 2H), 2.05-2.15 (m, 2H), 1.88-2.00 (m, 2H).<br>LCMS (ES) $C_{21}H_{22}N_5F_3Cl$ [M + H]$^+$ 436.1. |
| 223 | 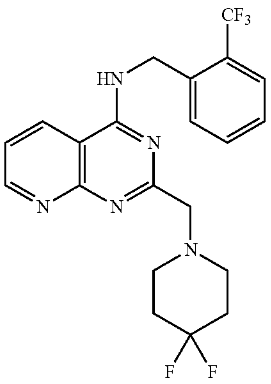 [SMILES: FC1(F)CCN(Cc2nc(NCc3ccccc3C(F)(F)F)c3cccnc3n2)CC1] | 2-((4,4-difluoropiperidin-1-yl)methyl)-N-((2-(trifluoromethyl)pyridin-3-yl)methyl)pyrido[2,3-d]pyrimidin-4-amine<br>Synthesised via Route 11<br>$^1$H NMR (400 MHz, DMSO-d6) δ (ppm) 9.04-9.05 (dd, J = 4.0, 1.6 Hz 1H), 8.07-8.09 (dd, J = 8.0, 1.6 Hz, 1H), 7.70-7.20 (d, J = 8.0 Hz, 1H), 7.68-7.66 (d, J = 8.0 Hz, 1H), 7.49-7.52 (t, J = 8.0 Hz, 1H), 7.37-7.44 (m, 2H), 6.20 (s, 1H), 5.10-5.11 (d, J = 4.0 Hz, 2H), 3.89 (s, 2H), 2.81-2.83 (t, J = 4.0 Hz, 4H), 1.95-2.05 (m, 4H).<br>LCMS (ES) $C_{21}H_{21}N_5F_5$ [M + H]$^+$ 438.1. |

TABLE 1-continued

224

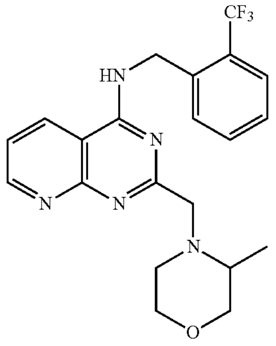 [SMILES: CC1COCCN1Cc1nc(NCc2ccccc2C(F)(F)F)c2cccnc2n1]

2-((3-methylmorpholino)methyl)-N-((2-(trifluoromethyl)pyridin-3-yl)methyl)pyrido[2,3-d]pyrimidin-4-amine Synthesised via Route 11

$^1$H NMR (400 MHz, MeOD) δ (ppm) 9.14-9.16 (t, J = 4.0 Hz, 1H), 8.99-9.01 (dd, J = 4.0, 1.6 Hz, 1H), 8.77-8.79 (dd, J = 8.0, 4.0 Hz, 1H), 7.74-7.76 (d, J = 8.0 Hz, 1H), 7.55-7.59 (m, 2H), 7.44-7.51 (m, 2H), 4.95-4.98 (m, 2H), 3.63-5.73 (q, J = 12.0 Hz, 2H), 3.44-3.47 (m, 1H), 3.37-3.40 (m, 1H), 3.25-3.31 (m, 1H), 2.89-2.94 (t, J = 12.0 Hz, 1H), 2.54-2.57 (m, 1H), 2.39-2.46 (m, 2H), 0.82-0.84 (d, J = 8.0 Hz, 3H).

LCMS (ES) $C_{21}H_{23}N_5F_3O$ $[M + H]^+$ 418.1.

225

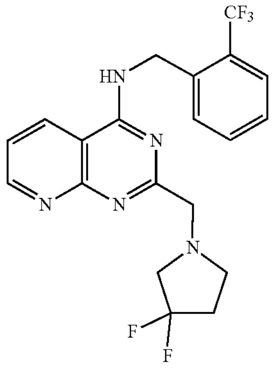 [SMILES: FC1(F)CCN(Cc2nc(NCc3ccccc3C(F)(F)F)c3cccnc3n2)C1]

2-((3,3-difluoropyrrolidin-1-yl)methyl)-N-((2-(trifluoromethyl)pyridin-3-yl)methyl)pyrido[2,3-d]pyrimidin-4-amine Synthesised via Route 11

$^1$H NMR (400 MHz, $CDCl_3$) δ (ppm) 9.05 (dd, J = 4.3, 1.8 Hz, 1H), 8.09 (dd, J = 8.2, 1.7 Hz, 1H), 7.71 (t, J = 7.9 Hz, 2H), 7.53 (t, J = 7.5 Hz, 1H), 7.29-7.46 (m, 2H), 6.25 (br s, 1H), 5.11 (d, J = 4.5 Hz, 2H), 3.97 (s, 2H), 3.19 (t, J = 13.6 Hz, 2H), 3.03 (t, J = 7.0 Hz, 2.H), 2.29 (m, 2H).

LCMS (ES) $C_{20}H_{19}N_5F_5$ $[M + H]^+$ 424.1.

226

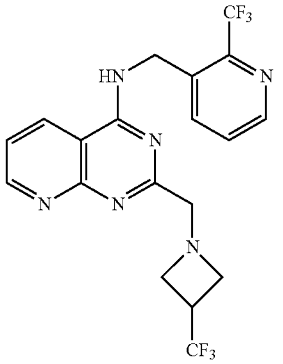 [SMILES: FC(F)(F)c1ncccc1CNc1nc(CN2CC(C(F)(F)F)C2)nc2ncccc12]

2-((3-(trifluoromethyl)azetidin-1-yl)methyl)-N-((2-(trifluoromethyl)pyridin-3-yl)methyl)pyrido[2,3-d]pyrimidin-4-amine Synthesised via Route 11

$^1$H NMR (400 MHz, MeOD) δ (ppm) 9.01-9.04 (dd, J = 4.0, 1.6 Hz, 1H), 8.09-8.12 (dd, J = 8.0, 1.6 Hz, 1H), 7.69-7.71 (d, J = 8.0 Hz, 1H), 7.62-7.64 (d, J = 8.0 Hz, 1H), 7.49-7.53 (t, J = 8.0 Hz, 1H), 7.40-7.43 (t, J = 8.0 Hz, 1H), 7.35-7.38 (dd, J = 8.0, 4.0 Hz, 1H), 6.31 (m, 1H), 5.08-5.10 (d, J = 8.0 Hz, 2H), 3.87 (s, 2H), 3.69-3.73 (t, J = 8.0 Hz, 2H), 3.44-3.48 (t, J = 8.0 Hz, 2H), 3.16-3.22 (m, 1H).

LCMS (ES) $C_{20}H_{18}N_5F_6$ $[M + H]^+$ 442.1.

TABLE 1-continued

| | |
|---|---|
| 227 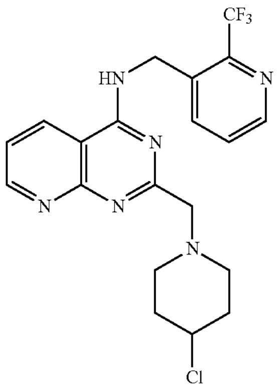 [SMILES: FC(F)(F)c1ncccc1CNc1nc(CN2CCC(Cl)CC2)nc2ncccc12] | 2-((4-chloropiperidin-1-yl)methyl)-N-((2-(trifluoromethyl)pyridin-3-yl)methyl)pyrido[2,3-d]pyrimidin-4-amine<br>Synthesised via Route 11<br>$^1$H NMR (400 MHz, DMSO-d6) δ (ppm) 9.32 (br s, 1H), 9.03 (br d, J = 3.1 Hz, 1H), 8.80 (br d, J = 8.2 Hz, 1H), 8.63 (d, J = 4.3 Hz, 1H), 8.01 (br d, J = 7.8 Hz, 1H), 7.65 (br dd, J = 4.6, 8.0 Hz, 2H), 4.98 (br d, J = 3.8 Hz, 2H), 4.05 (br s, 1H), 3.67 (br s, 2H), 2.79 (br s, 2H), 2.48-2.35 (m, 2H), 2.09-1.56 (m, 4H).<br>LCMS (ES) $C_{20}H_{21}N_6F_3Cl$ $[M + H]^+$ 437.0. |
| 228 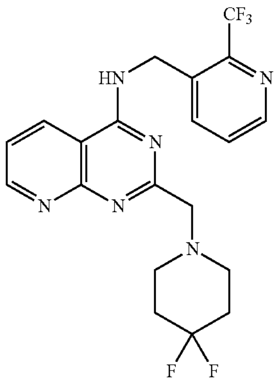 [SMILES: FC1(F)CCN(Cc2nc(NCc3cccnc3C(F)(F)F)c3cccnc3n2)CC1] | 2-((4,4-difluoropiperidin-1-yl)methyl)-N-((2-(trifluoromethyl)pyridin-3-yl)methyl)pyrido[2,3-d]pyrimidin-4-amine<br>Synthesised via Route 11<br>$^1$H NMR (400 MHz, DMSO-d6) δ (ppm) 9.34 (br s, 1H), 9.02 (dd, J = 1.6, 4.4 Hz, 1H), 8.78 (dd, J = 1.6, 8.2 Hz, 1H), 8.62 (d, J = 4.1 Hz, 1H), 8.00 (br d, J = 7.9 Hz, 1H), 7.69-7.56 (m, 2H), 4.97 (br d, J = 4.8 Hz, 2H), 3.66 (br s, 2H), 2.57 (m, 4H), 1.84 (br s, 4H).<br>LCMS (ES) $C_{20}H_{20}N_6F_5$ $[M + H]^+$ 439.2. |
| 229 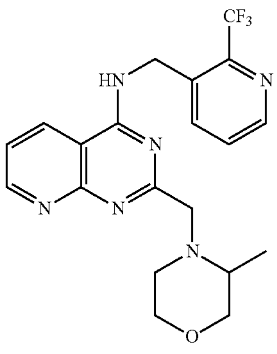 [SMILES: CC1COCCN1Cc1nc(NCc2cccnc2C(F)(F)F)c2cccnc2n1] | 2-((3-methylmorpholino)methyl)-N-((2-(trifluoromethyl)pyridin-3-yl)methyl)pyrido[2,3-d]pyrimidin-4-amine<br>Synthesised via Route 11<br>$^1$H NMR (400 MHz, DMSO-d6) δ (ppm) 9.28 (br s, 1H), 9.02 (dd, J = 1.6, 4.3 Hz, 1H), 8.78 (dd, J = 1.6, 8.2 Hz, 1H), 8.62 (d, J = 4.3 Hz, 1H), 7.98 (br d, J = 7.9 Hz, 1H), 7.62 (dt, J = 4.5, 8.8 Hz, 2H), 4.97 (br s, 2H), 3.75-3.46 (m, 4H), 2.99 (br s, 1H), 2.66-2.55 (m, 2H), 2.44 (m, 2H), 0.82 (d, J = 6.2 Hz, 3H).<br>LCMS (ES) $C_{20}H_{22}N_6F_3O$ $[M + H]^+$ 419.1. |

TABLE 1-continued

230

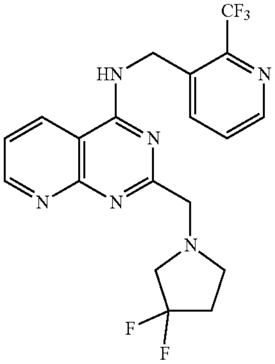 [SMILES: FC1(F)CCN(Cc2nc(NCc3cccnc3C(F)(F)F)c3cccnc3n2)C1]

2-((3,3-difluoropyrrolidin-1-yl)methyl)-N-((2-(trifluoromethyl)pyridin-3-yl)methyl)pyrido[2,3-d]pyrimidin-4-amine Synthesised via Route 11

$^1$H NMR (400 MHz, $CDCl_3$) δ (ppm) 9.04 (dd, J = 1.6, 4.4 Hz, 1H), 8.63 (d, J = 4.3 Hz, 1H), 8.24 (d, J = 8.5 Hz, 1H), 8.17 (d, J = 7.8 Hz, 1H), 7.47 (dd, J = 4.7, 7.8 Hz, 1H), 7.42 (dd, J = 4.4, 8.3 Hz, 1H), 6.74 (br s, 1H), 5.14 (br d, J = 5.5 Hz, 2H), 3.92 (s, 2H), 3.13 (t, J = 13.4 Hz, 2H), 2.98 (t, J = 7.0 Hz, 2H), 2.28 (tt, J = 7.1, 14.6 Hz, 2H).

LCMS (ES) $C_{19}H_{18}N_5F_6$ $[M + H]^+$ 425.1.

231

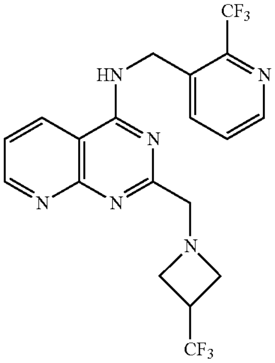 [SMILES: FC(F)(F)c1ncccc1CNc1nc(CN2CC(C(F)(F)F)C2)nc2ncccc12]

2-((3-(trifluoromethyl)azetidin-1-yl)methyl)-N-((2-(trifluoromethyl)pyridin-3-yl)methyl)pyrido[2,3-d]pyrimidin-4-amine Synthesised via Route 11

$^1$H NMR (400 MHz, DMSO-d6) δ (ppm) 9.32 (br s, 1H), 9.01 (dd, J = 1.9, 4.4 Hz, 1H), 8.81 (dd, J = 1.7, 8.2 Hz, 1H), 8.61 (d, J = 4.3 Hz, 1H), 7.97 (d, J = 7.9 Hz, 1H), 7.66-7.62 (m, 1H), 7.59-7.56 (m, 1H), 4.96 (br d, J = 5.0 Hz, 2H), 3.56 (s, 2H), 3.39 (m, 3H), 3.22 (br d, J = 5.9 Hz, 2H).

LCMS (ES) $C_{19}H_{17}N_6F_6$ $[M + H]^+$ 443.0.

232

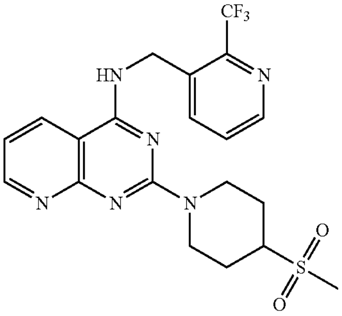 [SMILES: CS(=O)(=O)C1CCN(c2nc(NCc3cccnc3C(F)(F)F)c3cccnc3n2)CC1]

2-(4-(methylsulfonyl)piperidin-1-yl)-N-((2-(trifluoromethyl)pyridin-3-yl)methyl)pyrido[2,3-d]pyrimidin-4-amine Synthesised via Route 6

$^1$H NMR (400 MHz, $CDCl_3$) δ (ppm) 8.78 (dd, J = 1.7, 4.5 Hz, 1H), 8.63 (d, J = 4.3 Hz, 1H), 8.07 (d, J = 6.8 Hz, 1H), 7.93 (d, J = 7.8 Hz, 1H), 7.46 (dd, J = 4.7, 8.0 Hz, 1H), 7.06 (dd, J = 4.5, 7.9 Hz, 1H), 6.70 (s, 1H), 5.03 (d, J = 5.4 Hz, 4H), 3.15-3.04 (m, 1H), 2.90-2.84 (m, 5H), 2.11 (d, J = 12.3 Hz, 2H), 1.69 (s, 2H).

LCMS (ES) $C_{20}H_{22}N_6F_3O_2S$ $[M + H]^+$ 467.1.

233

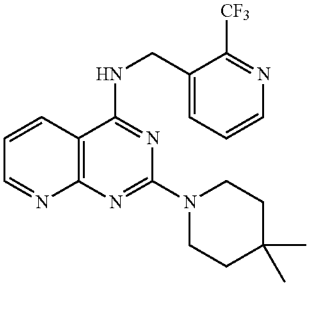 [SMILES: CC1(C)CCN(c2nc(NCc3cccnc3C(F)(F)F)c3cccnc3n2)CC1]

2-(4,4-dimethyipiperidin-1-yl)-N-((2-(trifluoromethyl)pyridin-3-yl)methyl)pyrido[2,3-d]pyrimidin-4-amine Synthesised via Route 6

$^1$H NMR (400 MHz, $CDCl_3$) δ (ppm) 8.73 (dd, J = 4.4, 1.6 Hz, 1H), 8.60 (d, J = 4.4 Hz, 1H) 7.94 (d, J = 8.0 Hz, 1H), 7.89 (dd, J = 8.0, 1.6 Hz, 1H), 7.43 (dd, J = 8.0, 4.8 Hz, 1H), 6.95 (dd, J = 7.6, 4.4 Hz, 1H), 6.23 (br s, 1H), 5.02 (d, J = 4.8 Hz, 2H), 3.82 (br s, 4H), 1.31 (br s, 4H), 0.96 (s, 6H). LCMS (ES) $C_{21}H_{24}N_6F_3$ $[M + H]^+$ 417.1.

TABLE 1-continued

234

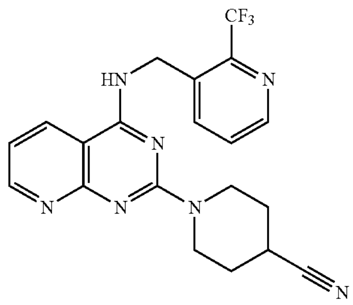 [SMILES: N#CC1CCN(c2nc(NCc3cccnc3C(F)(F)F)c3cccnc3n2)CC1]

1-(4-(((2-(trifluoromethyl)pyridin-3-yl)methyl)amino)pyrido[2,3-d]pyrimidin-2-yl)piperidine-4-carbonitrile Synthesised via Route 6
$^1$H NMR (400 MHz, $CDCl_3$) δ (ppm) 8.78 (dd, J = 4.0, 2.0 Hz, 1H), 8.62 (d, J = 4.0 Hz, 1H), 7.94 (dd, J = 8.0, 2.0 Hz, 1H), 7.90 (d, J = 8.0 Hz, 1H), 7.46 (dd, J = 8.0, 4.0 Hz, 1H), 7.04 (dd, J = 8.0, 4.0 Hz, 1H), 6.28 (t, J = 8.0 Hz, 1H), 5.02 (d, J = 4.0 Hz, 2H), 4.16 (br s, 2H), 3.72 (br s, 2H), 2.82-2.88 (m, 1H) 1.78-1.86 (m, 4H).
LCMS (ES) $C_{20}H_{19}N_7F_3$ $[M + H]^+$ 414.0.

235

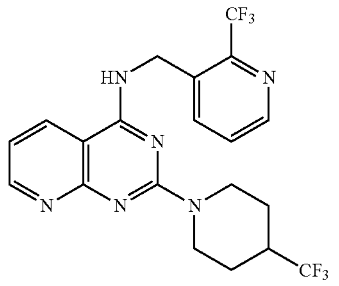 [SMILES: FC(F)(F)c1ncccc1CNc1nc(N2CCC(C(F)(F)F)CC2)nc2ncccc12]

2-(4-(trifluoromethyl)piperidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.80 (dd, J = 4.5, 1.8 Hz, 1H), 8.63 (d, J = 4.4 Hz, 1H), 7.84-8.00 (m, 2H), 7.46 (dd, J = 7.9, 4.7 Hz, 1H), 7.04 (dd, J = 7.9, 4.5 Hz, 1H), 6.19 (t, J = 5.3 Hz, 1H), 5.04 (d, J = 5.7 Hz, 4H), 2.82 (t, J = 12.1 Hz, 2H), 2.19-2.36 (m, 1H), 1.87 (d, J = 12.8 Hz, 2H), 1.46 (m, 2H).
LCMS (ES) $C_{20}H_{19}N_6F_6$ $[M + H]^+$ 457.1.

236

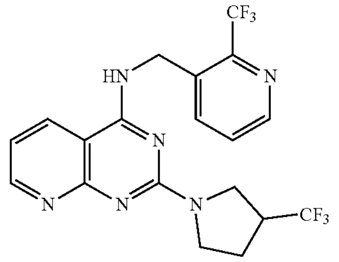 [SMILES: FC(F)(F)c1ncccc1CNc1nc(N2CCC(C(F)(F)F)C2)nc2ncccc12]

N-((2-(trifluoromethyl)pyridin-3-yl)methyl)-2-(3-(trifluoromethyl)pyrrolidin-1-yl)pyrido[2,3-d]pyrimidin-4-amine Synthesised via Route 6
$^1$H NMR (400 MHz, $CDCl_3$) δ (ppm) 8.72-8.84 (m, 1H), 8.58-8.67 (m, 1H), 7.96 (t, J = 8.2 Hz, 2H), 7.45 (dd, J = 7.4, 4.7 Hz, 1H), 7.02 (dd, J = 7.7, 4.4 Hz, 1H), 6.34 (s, 1H), 5.05 (d, J = 5.3 Hz, 2H), 3.53-4.04 (m, 4H), 2.99 (dd, J = 15.0, 7.5 Hz, 1H), 2.01-2.27 (m, 2H).
LCMS (ES) $C_{19}H_{17}N_6F_6$ $[M + H]^+$ 443.0.

237

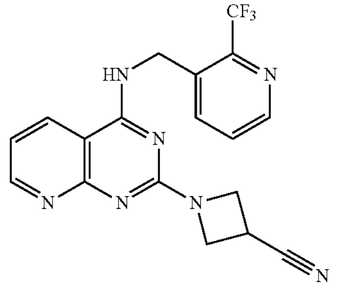 [SMILES: N#CC1CN(c2nc(NCc3cccnc3C(F)(F)F)c3cccnc3n2)C1]

1-(4-(((2-(trifluoromethyl)pyridin-3-yl)methyl)amino)pyrido[2,3-d]pyrimidin-2-yl)azetidine-3-carbonitrile Synthesised via Route 6
$^1$H NMR (400 MHz, $CDCl_3$) δ (ppm) 8.84 (dd, J = 4.4, 1.8 Hz, 1H), 8.65 (d, J = 4.0 Hz, 1H), 7.95 (m, J = 5.3, 2.4 Hz, 2H), 7.43-7.55 (m, 1H), 7.11 (dd, J = 8.1, 4.5 Hz, 1H), 6.29 (t, J = 5.4 Hz, 1H), 5.03 (d, J = 6.0 Hz, 2H), 4.25-4.53 (m, 4H), 3.45-3.58 (m, 1H).
LCMS (ES) $C_{18}H_{15}N_7F_3$ $[M + H]^+$ 386.0.

TABLE 1-continued

| | |
|---|---|
| 238 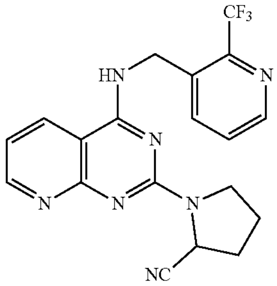 [SMILES: N#CC1CCCN1c1nc(NCc2cccnc2C(F)(F)F)c2cccnc2n1] | 1-(4-(((2-(trifluoromethyl)pyridin-3-yl)methyl)amino)pyrido[2,3-d]pyrimidin-2-yl)pyrrolidine-2-carbonitrile<br>Synthesised via Route 6<br>$^1$H NMR (400 MHz, $CDCl_3$) δ (ppm) 8.79 (dd, J = 1.9, 4.5 Hz, 1H), 8.63 (d, J = 4.3 Hz, 1H), 8.05 (dd, J = 1.9, 8.0 Hz, 1H), 7.97 (d, J = 7.9 Hz, 1H), 7.47 (dd, J = 4.8, 7.9 Hz, 1H), 7.06 (dd, J = 4.5, 8.0 Hz, 1H), 6.65 (t, J = 5.4 Hz, 1H), 5.06 (d, J = 5.3 Hz, 2H), 4.05-3.58 (m, 4H), 3.20 (m, 1H), 2.39-2.26 (m, 2H).<br>LCMS (ES) $C_{19}H_{17}N_7F_3$ $[M + H]^+$ 400.2. |
| 239 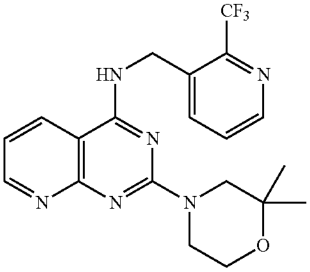 [SMILES: CC1(C)CN(c2nc(NCc3cccnc3C(F)(F)F)c3cccnc3n2)CCO1] | 2-(2,2-dimethylmorpholino)-N-((2-(trifluoroethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.79 (dd, J = 4.5, 1.8 Hz, 1H), 8.63 (br d, J = 4.3 Hz, 1H), 7.84-7.97 (m, 2H), 7.45 (dd, J = 7.5, 5.0 Hz, 1H), 7.03 (dd, J = 7.9, 4.5 Hz, 1H), 6.20 (br s, 1H), 5.03 (d, J = 4.8 Hz, 2H), 3.51-4.00 (m, 6H), 0.85-1.27 (m, 6H).<br>LCMS (ES) $C_{20}H_{22}N_6F_3O$ $[M + H]^+$ 419.2. |
| 240 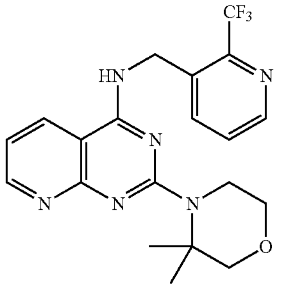 [SMILES: CC1(C)COCCN1c1nc(NCc2cccnc2C(F)(F)F)c2cccnc2n1] | 2-(3,3-dimethylmorpholino)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.88 (s, 1H), 8.74 (d, J = 4.0 Hz, 1H), 8.61 (d, J = 4.0 Hz, 1H), 8.52 (d, J = 4.0 Hz, 1H), 7.90 (d, J = 8.0 Hz, 1H), 7.64 (dd, J = 8.0, 4.0 Hz, 1H), 7.19 (dd, J = 8.0, 4.0 Hz, 1H), 4.90 (s, 2H), 3.68 (s, 4H), 3.30 (s, 2H), 1.23 (s, 6H).<br>LCMS (ES) $C_{20}H_{22}N_6F_3O$ $[M + H]^+$ 419.1. |
| 241 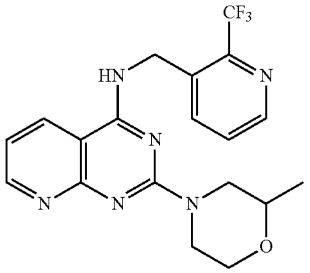 [SMILES: CC1CN(c2nc(NCc3cccnc3C(F)(F)F)c3cccnc3n2)CCO1] | 2-(2-methylmorpholino)-N-((2-(trifluoromethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.77 (dd, J = 4.0, 1.2 Hz, 1H), 8.62 (d, J = 4.0 Hz, 1H), 7.90-7.96 (m, 2H), 7.44 (dd, J = 8.0, 4.0 Hz, 1H), 7.03 (dd, J = 8.0, 4.0 Hz, 1H), 6.33 (br s, 1H), 5.02 (d, J = 4.0 Hz, 2H), 4.58 (br s, 2H), 3.89 (dd, J = 12.0, 4.0 Hz, 1H), 3.49-3.54 (m, 2H), 3.00 (t, J = 12.0 Hz, 1H), 2.63 (t, J = 12.0 Hz, 1H), 1.16 (d, J = 8.0 Hz, 3H).<br>LCMS (ES) $C_{19}H_{20}N_6F_3O$ $[M + H]^+$ 405.1. |
| 242 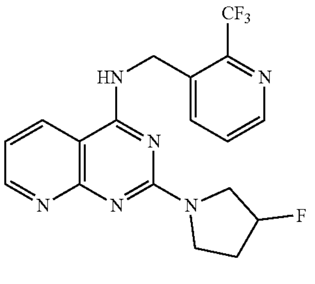 [SMILES: FC1CCN(c2nc(NCc3cccnc3C(F)(F)F)c3cccnc3n2)C1] | 2-(3-fluoropyrrolidin-1-yl)-N-((2-(trifluoromethyl)pyridin-3-yl)methyl)pyrido[2,3-a]pyrimidin-4-amine<br>Synthesised via Route 6<br>$^1$H NMR (400 MHz, $CDCl_3$) δ (ppm) 8.73 (dd, J = 1.8, 4.4 Hz, 1H), 8.59 (d, J = 4.3 Hz, 1H), 8.15 (d, J = 7.8 Hz, 1H), 7.99 (s, 1H), 7.43 (dd, J = 4.7, 7.8 Hz, 1H), 6.99 (dd, J = 4.5, 7.9 Hz, 2H), 5.42-5.17 (m, 1H), 5.04 (d, J = 5.0 Hz, 2H), 4.14-3.54 (m, 4H), 2.35-2.30 (m, 1H), 2.27-2.25 (m, 1H).<br>LCMS (ES) $C_{18}H_{17}N_6F_4$ $[M + H]^+$ 393.1. |

TABLE 1-continued

243

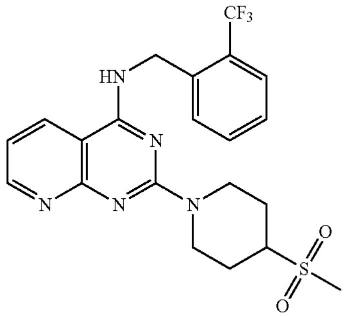

2-(4-(methylsulfonyl)piperidin-1-yl)-N-(2-(trifluoromethyl)benzyl)pyrido[2,3-d]pyrimidin-4-amine Synthesised via Route 6
$^1$H NMR (400 MHz, $CDCl_3$) δ (ppm) 8.77 (dd, J = 1.8, 4.5 Hz, 1H), 8.00 (dd, J = 1.8, 8.0 Hz, 1H), 7.71 (d, J = 7.7 Hz, 1H), 7.57 (d, J = 7.3 Hz, 1H), 7.50 (t, J = 7.6 Hz, 1H), 7.38-7.45 (m, 1H), 7.03 (dd, J = 4.5, 8.0 Hz, 1H), 6.47 (t, J = 5.6 Hz, 1H), 5.15 (s, 2H), 5.01 (d, J = 5.5 Hz, 2H), 3.06-3.10 (m, 1H), 2.84-2.92 (m, 2H), 2.82 (s, 3H), 2.13 (d, J = 12.3 Hz, 2H), 1.71 (s, 2H).
LCMS (ES) $C_{21}H_{23}N_5F_3O_2S$ $[M + H]^+$ 466.1.

244

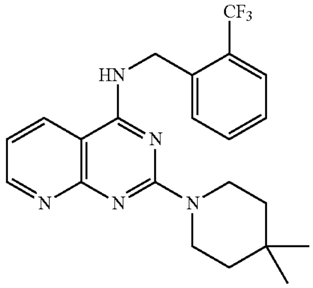 [SMILES: CC1(C)CCN(c2nc(NCc3ccccc3C(F)(F)F)c3cccnc3n2)CC1]

2-(4,4-dimethylpiperidin-1-yl)-N-(2-(trifluoromethyl)benzyl)pyndo[2,3-d]pyrimidin-4-amine Synthesised via Route 6
$^1$H NMR (400 MHz, $CDCl_3$) δ (ppm) 8.71 (dd, J = 4.4, 2.8 Hz, 1H), 7.83 (dd, J = 8.0, 1.6 Hz, 1H), 7.68 (d, J = 8.0 Hz, 1H), 7.59 (d, J = 7.6 Hz, 1H), 7.48 (t, J = 7.2 Hz, 1H), 7.38 (t, J = 7.2 Hz, 1H), 6.92 (dd, J = 7.6, 4.4 Hz, 1H), 6.07 (t, J = 5.2 Hz, 1H), 4.99 (d, J = 5.6 Hz, 2.H), 3.88 (s, 4H), 1.35 (s, 4H), 0.97 (s, 6H).
LCMS (ES) $C_{22}H_{25}N_5F_3$ $[M + H]^+$ 416.2.

245

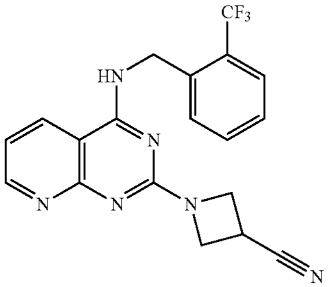 [SMILES: N#CC1CN(c2nc(NCc3ccccc3C(F)(F)F)c3cccnc3n2)C1]

1-(4-((2-(trifluoromethyl)benzyl)amino)pyrido[2,3-d]pyrimidin-2-yl)azetidine-3-carbonitrile Synthesised via Route 6
$^1$H NMR (400 MHz, $CDCl_3$) δ (ppm) 8.82 (dd, J = 4.5, 1.8 Hz, 1H), 7.89 (dd, J = 8.0,1.7 Hz, 1H), 7.72 (d, J = 7.8 Hz, 1H), 7.57-7.63 (m, 1H), 7.50-7.56 (m, 1H), 7.39-7.48 (m, 1H), 7.09 (dd, J = 8.1, 4.4 Hz, 1H), 6.11 (s, 1H), 5.01 (d, J = 5.9 Hz, 2H), 4.35-4.59 (m, 4H), 3.48-3.60 (m, 1H).
LCMS (ES) $C_{19}H_{16}N_6F_3$ $[M + H]^+$ 385.1.

246

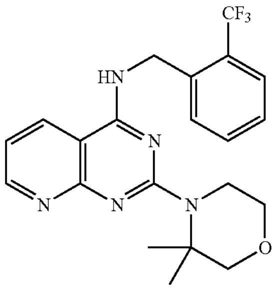

2-(3,3-dimethylmorpholino)-N-(2-(trifluoromethyl)benzyl)pyrido[2,3-d]pyrimidin-4-amine Synthesised via Route 6
$^1$H NMR (400 MHz, DMSO-d6) δ (ppm) 8.84 (t, J = 5.5 Hz, 1H), 8.74 (dd, J = 4.4, 1.7 Hz, 1H), 8.54 (dd, J = 8.1,1.7 Hz, 1H), 7.75 (d, J = 7.7 Hz, 1H), 7.56-7.64 (m, 1H), 7.42-7.51 (m, 2H), 7.19 (dd, J = 8.0, 4.5 Hz, 1H), 4.91 (d, J = 5.0 Hz, 2H), 3.71 (s, 4H), 3.31 (s, 2H), 1.26 (s, 6H).
LCMS (ES) $C_{21}H_{23}N_5F_3O$ $[M + H]^+$ 418.1.

TABLE 1-continued

247

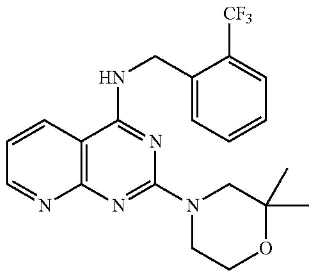 [SMILES: CC1(C)CN(c2nc(NCc3ccccc3C(F)(F)F)c3cccnc3n2)CCO1]

2-(2,2-dimethylmorpholino)-N-(2-(trifluoromethyl)benzyl)pyrido[2,3-d]pyrimidin-4-amine
Synthesised via Route 6
$^1$H NMR (400 MHz, $CDCl_3$) δ (ppm) 8.76 (dd, J = 4.4, 1.7 Hz, 1H), 7.89 (d, J = 7.2 Hz, 1H), 7.71 (d, J = 7.7 Hz, 1H), 7.45-7.59 (m, 2H), 7.36-7.44 (m, 1H), 7.00 (dd, J = 8.0, 4.5 Hz, 1H), 6.16 (br s, 1H), 5.00 (d, J = 5.4 Hz, 2H), 3.56-4.02 (m, 6H), 1.11 (br s, 6H).
LCMS (ES) $C_{21}H_{23}N_5F_3O$ $[M + H]^+$ 418.1.

248

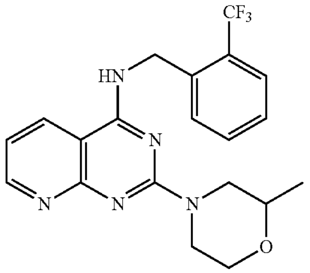 [SMILES: CC1CN(c2nc(NCc3ccccc3C(F)(F)F)c3cccnc3n2)CCO1]

2-(2-methylmorpholino)-N-(2-(trifluoromethyl)benzyl)pyrido[2,3-d]pyrimidin-4-amine
Synthesised via Route 6
$^1$H NMR (400 MHz, $CDCl_3$) δ (ppm) 8.75 (d, J = 3.2 Hz, 1H), 7.89 (d, J = 7.2 Hz, 1H), 7.69 (d, J = 7.6 Hz, 1H), 7.55 (d, J = 7.6 Hz, 1H), 7.49 (t, J = 8.0Hz, 1H), 7.40 (t, J = 7.6 Hz, 1H), 6.90-6.94 (dd, J = 8.0, 4.4 Hz, 1H), 6.17 (s, 1H), 4.99 (d, J = 4.8 Hz, 2H), 4.68 (br s, 2H), 3.91 (dd, J = 11.2, 2.4 Hz, 1H), 3.56 (m, 2H), 3.03 (m, 1H), 2.67 (t, J = 12.0 Hz, 1H), 1.18 (d, J = 6.0 Hz, 3H).
LCMS (ES) $C_{20}H_{21}N_5F_3O$ $[M + H]^+$ 404.1.

249

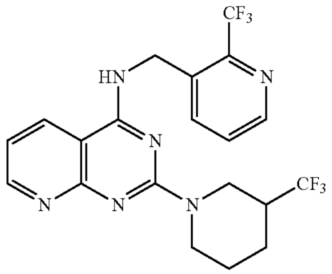 [SMILES: FC(F)(F)c1ncccc1CNc1nc(N2CCCC(C(F)(F)F)C2)nc2ncccc12]

2-(3-(trifluoromethyl)piperidin-1-yl)-N-((2-(trifluoromethyl)pyridin-3-yl)methyl)pyrido[2,3-d]pyrimidin-4-amine
Synthesised via Route 6
$^1$H NMR (400 MHz, DMSO-d6) δ (ppm) 9.00 (t, J = 8.0 Hz, 1H), 8.70 (dd, J = 4.0, 2.0 Hz, 1H), 8.59 (d, J = 4.0 Hz, 1H), 8.50 (dd, J = 8.0, 2.0 Hz, 1H), 7.92 (d, J = 8.0 Hz, 1H), 7.63 (d, J = 8.0, 4.0 Hz, 1H), 7.16 (dd, J = 8.0, 4.0 Hz, 1H), 4.88 (d, J = 4.0 Hz, 2H), 4.49-4.71 (m, 2H), 2.81-2.87 (m, 2H), 2.22 (br s, 1H), 1.88 (d, J = 8.0 Hz, 1H), 1.45-1.60 (m, 2H), 1.27 (br s, 1H).
LCMS (ES) $C_{20}H_{19}N_6F_6$ $[M + H]^+$ 457.1.

250

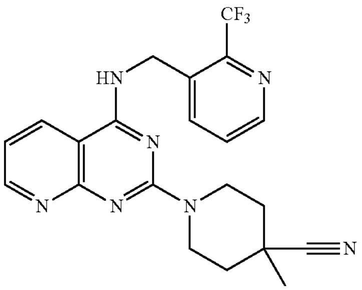 [SMILES: CC1(C#N)CCN(c2nc(NCc3cccnc3C(F)(F)F)c3cccnc3n2)CC1]

4-methyl-1-(4-(((2-(trifluoromethyl)pyridin-3-yl)methyl)amino)pyrido[2,3-d]pyrimidin-2-yl)piperidine-4-carbonitrile
Synthesised via Route 6
$^1$H NMR (400 MHz, $CDCl_3$) δ (ppm) 8.77 (dd, J = 4.0, 2.0 Hz, 1H), 8.61 (d, J = 4.0 Hz, 1H),7.94 (dd, J = 8.0, 4.0 Hz, 1H), 7.91 (d, J = 8.0 Hz, 1H), 7.45 (dd, J = 8.0, 4.0 Hz, 1H), 7.02 (dd, J = 8.0, 4.0 Hz, 1H), 6.34 (t, J = 4.0 Hz, 1H), 5.01-5.02 (m, 4H), 3.16 (t, J = 12.0 Hz, 2H), 1.91 (d, J = 16.0 Hz, 2H), 1.37 (m, 5H).
LCMS (ES) $C_{21}H_{21}N_7F_3$ $[M + H]^+$ 427.9.

251

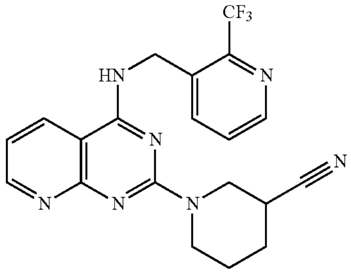 [SMILES: N#CC1CCCN(c2nc(NCc3cccnc3C(F)(F)F)c3cccnc3n2)C1]

Synthesised via Route 6
$^1$H NMR (400 MHz, DMSO-d6) δ (ppm) 8.71-8.76 (m, 2H), 8.61 (d, J = 4.0 Hz, 1H), 8.49 (dd, J = 8.0, 2.0 Hz, 1H), 7.98 (d, J = 8.0 Hz, 1H), 7.62 (dd, J = 8.0, 4.0 Hz, 1H), 7.13 (dd, J = 8.0, 4.0 Hz, 1H), 4.92 (s, 2H), 3.92 (d, J = 4.0 Hz, 2H), 3.63-3.73 (m, 2H), 2.84-2.89 (m, 1H), 1.90-1.96 (m, 1H), 1.78-1.85 (m, 1H), 1.53-1.59 (m, 1H), 1.44-1.47 (m, 1H).
LCMS (ES) $C_{20}H_{19}N_7F_3$ $[M + H]^+$ 413.9.

TABLE 1-continued

| | |
|---|---|
| 252<br>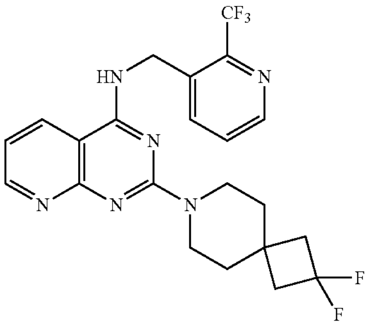 [SMILES: FC1(F)CC2(CCN(c3nc(NCc4cccnc4C(F)(F)F)c4cccnc4n3)CC2)C1] | 2-(2,2-difluoro-7-azaspiro[3.5]nonan-7-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.95 (s, 1H), 8.68 (d, J = 2.7 Hz, 1H), 8.61 (d, J = 4.2 Hz, 1H), 8.47 (d, J = 6.4 Hz, 1H), 7.95 (d, J = 8.0 Hz, 1H), 7.64 (dd, J = 7.8, 4.6 Hz, 1H), 7.12 (dd, J = 7.9, 4.4 Hz, 1H), 4.86 (d, J = 3.8 Hz, 2H), 3.75-3.51 (m, 4H), 2.41-2.26 (m, 4H), 1.57-1.25 (m, 4H).<br>LCMS (ES) $C_{22}H_{22}N_6F_5$ [M + H]$^+$ 465.1. |
| 252_S<br>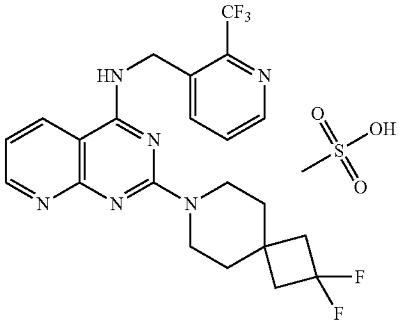 | 2-(2,2-difluoro-7-azaspiro[3.5]nonan-7-yl)-N-((2-(trifluoromethyl)pyridin-3-yl)methyl)pyrido[2,3-d]pyrimidin-4-amine methanesulfonate<br>Synthesised via Route 6<br>$^1$H NMR (400 MHz, DMSO-d6) δ (ppm) 9.88 (s, 1H), 8.86 (d, J = 8.0 Hz, 1H), 8.75 (d, J = 4.9 Hz, 1H), 8.66 (d, J = 4.3 Hz, 1H), 8.04 (d, J = 8.1 Hz, 1H), 7.69 (dd, J = 8.0, 4.6 Hz, 1H), 7.54-7.41 (m, 1H), 4.94 (d, J = 5.2 Hz, 2H), 3.86-3.53 (m, 4H), 2.41 (t, J = 13.0 Hz, 4H), 2.31 (s, 3H), 1.75-1.34 (m, 4H).<br>LCMS (ES) $C_{22}H_{22}N_6F_5$ [M + H]$^+$ 465.3. |
| 253<br>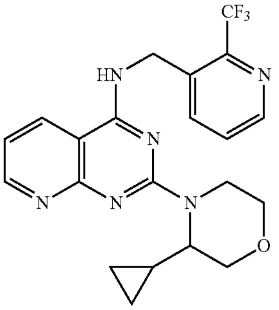 [SMILES: FC(F)(F)c1ncccc1CNc1nc(N2CCOCC2C2CC2)nc2ncccc12] | 2-(3-cyclopropylmorpholino)-N-((2-(trifluoromethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.71 (d, J = 4.0 Hz, 1H), 8.61 (d, J = 4.0 Hz, 1H), 8.04 (d, J = 8.0 Hz, 1H), 7.86 (d, J = 8.0 Hz, 1H), 7.44 (dd, J = 8.0, 4.0 Hz, 1H), 6.97 (dd, J = 8.0, 4.0 Hz, 1H), 6.71 (s, 1H), 4.88-5.07 (m, 2H), 4.63 (s, 1H), 3.87-3.97 (m, 3H), 3.37-3.57 (m, 3H), 1.48-1.51 (m, 1H), 0.43-0.7 (m, 1H), 0.06-0.25 (m, 3H).<br>LCMS (ES) $C_{21}H_{22}N_6F_3O$ [M + H]$^+$ 431.1. |
| 254<br>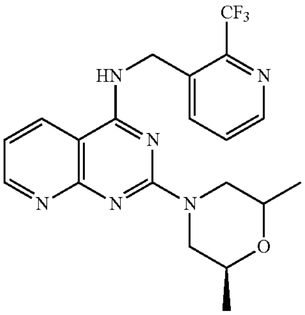 [SMILES: CC1CN(c2nc(NCc3cccnc3C(F)(F)F)c3cccnc3n2)C[C@H](C)O1] | 2-((6S)-2,6-dimethylmorpholino)-N-((2-(trifluoromethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.78 (d, J = 2.6 Hz, 1H), 8.62 (d, J = 3.9 Hz, 1H), 7.92 (t, J = 9.0 Hz, 2H), 7.45 (dd, J = 7.7, 4.6 Hz, 1H), 7.03 (dd, J = 8.0, 4.5 Hz, 1H), 6.27 (s, 1H), 4.48-5.14 (m, 3H), 3.41-4.40 (m, 3H), 2.37-2.81 (m, 2H), 1.18-1.19 (m, J = 5.8 Hz, 6H).<br>LCMS (ES) $C_{20}H_{22}N_6F_3O$ [M + H]$^+$ 419.1. |

TABLE 1-continued

255

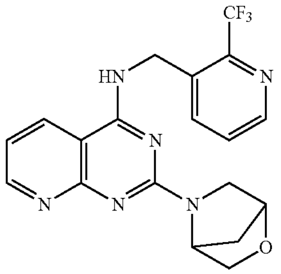 [SMILES: FC(F)(F)c1ncccc1CNc1nc(N2CC3CC2CO3)nc2ncccc12]

2-(2-oxa-5-azabicyclo[2.2.1]heptan-5-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.72 (s, 1H), 8.58 (d, J = 4.0 Hz, 1H), 7.89-8.06 (m, 2H), 7.40-7.45 (m, 1H), 6.98 (dd, J = 8.0, 4.0 Hz, 1H), 6.56-6.76 (m, 1H), 5.22 (br s, 0.5H), 4.93-5.09 (m, 2H), 4.79 (s, 0.5H), 4.63 (s, 1H), 3.81-3.94 (m, 1H), 3.41-3.69 (m, 3H) 1.86-1.69 (m, 2H).
LCMS (ES) $C_{19}H_{18}N_6F_3O$ $[M + H]^+$ 402.9.

256

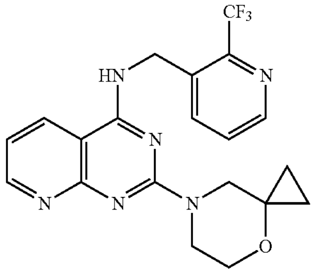 [SMILES: FC(F)(F)c1ncccc1CNc1nc(N2CCOC3(CC3)C2)nc2ncccc12]

2-(4-oxa-7-azaspiro[2.5]octan-7-yl)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 9.01 (s, 1H), 8.69 (dd, J = 4.0, 2.0 Hz, 1H), 8.60 (d, J = 4.0 Hz, 1H), 8.50 (dd, J = 8.0, 2.0 Hz, 1H), 7.94 (d, J = 8.0 Hz, 1H), 7.64 (dd, J = 8.0, 4.0 Hz, 1H), 7.14 (dd, J = 8.0, 4.0 Hz, 1H), 4.81 (s, 2H), 3.56-3.64 (m, 6H), 0.01-0.55 (m, 4H).
LCMS (ES) $C_{20}H_{20}N_6F_3O$ $[M + H]^+$ 416.9.

257

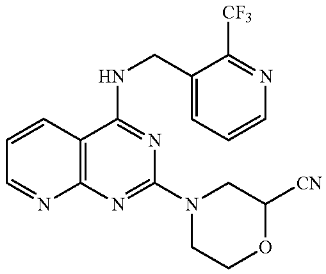 [SMILES: N#CC1CN(c2nc(NCc3cccnc3C(F)(F)F)c3cccnc3n2)CCO1]

4-(4-(((2-(trifluoromethyl)pyridin-3-yl)methyl)amino)pyrido[2,3-d]pyrimidin-2-yl)morpholine-2-carbonitrile Synthesised via Route 6
$^1$H NMR (400 MHz, $CDCl_3$) δ (ppm) 8.81 (d, J = 2.8 Hz, 1H), 8.62 (d, J = 4.4 Hz, 1H), 8.02 (d, J = 7.9 Hz, 1H), 7.93 (d, J = 7.9 Hz, 1H), 7.48? (dd, J = 4.7, 7.8 Hz, 1H), 7.10 (dd, J = 4.5, 7.9 Hz, 1H), 6.62-6.52 (m, 1H), 5.11-4.96 (m, 2H), 4.62-4.56 (m, 3H), 3.94-3.92 (m, 1H), 3.81-3.78 (m, 2H), 3.47-3.42 (m, 1H).
LCMS (ES) $C_{19}H_{17}N_7F_3O$ $[M + H]^+$ 416.1.

258

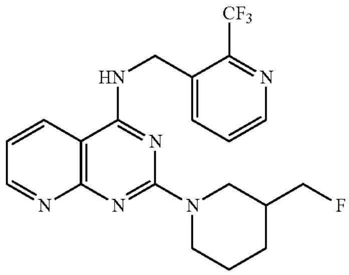 [SMILES: FCC1CCCN(c2nc(NCc3cccnc3C(F)(F)F)c3cccnc3n2)C1]

2-(3-(fluoromethyl)piperidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.76 (dd, J = 4.5, 1.8 Hz, 1H), 8.62 (d, J = 4.2 Hz, 1H), 7.98 (d, J = 7.8 Hz, 1H), 7.89 (dd, J = 7.9, 1.7 Hz, 1H), 7.45 (dd, J = 7.9, 4.7 Hz, 1H), 6.99 (dd, J = 7.9, 4.5 Hz, 1H), 6.20 (t, J = 5.6 Hz, 1H), 4.96-5.11 (m, 2H), 4.65-4.90 (m, 2H), 4.20-4.42 (m, 2H), 2.86-3.19 (m, 2H), 1.84 (d, J = 10.6 Hz, 2H), 1.66-1.76 (m, 1H), 1.31-1.53 (m, 2H).
LCMS (ES) $C_{20}H_{21}N_6F_4$ $[M + H]^+$ 421.1.

TABLE 1-continued

259

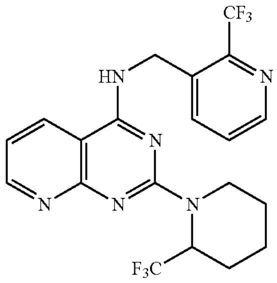 [SMILES: FC(F)(F)c1ncccc1CNc1nc(N2CCCCC2C(F)(F)F)nc2ncccc12]

2-(2-(trifluoromethyl)piperidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.82 (dd, J = 4.3, 1.7 Hz, 1H), 8.62 (d, J = 4.3 Hz, 1H), 7.94 (d, J = 8.1 Hz, 2H), 7.45 (s, 1H), 7.08 (dd, J = 7.9, 4.4 Hz, 1H), 6.25 (s, 1H), 4.79-5.45 (m, 3H), 3.04 (t, J = 13.1 Hz, 1H), 2.00-2.11 (m, 1H), 1.64-1.86 (m, 4H), 1.30-1.54 (m, 2H).
LCMS (ES) $C_{20}H_{19}N_6F_6$ $[M + H]^+$ 457.1.

260

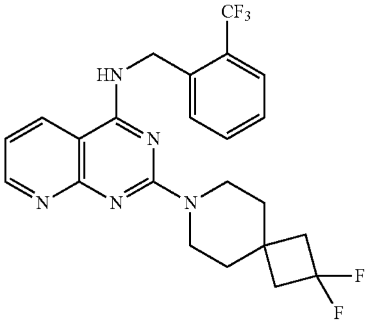 [SMILES: FC1(F)CC2(CCN(c3nc(NCc4ccccc4C(F)(F)F)c4cccnc4n3)CC2)C1]

2-(2,2-difluoro-7-azaspiro[3.5]nonan-7-yl)-N-(2-(trifluoromethyl)benzyl)pyrido[2,3-d]pyrimidin-4-amine Synthesised via Route 6
$^1$H NMR (400 MHz, DMSO-d6) δ (ppm) 8.89 (t, J = 5.6 Hz, 1H), 8.66 (dd, J = 4.4, 1.9 Hz, 1H), 8.48 (dd, J = 8.0,1.9 Hz, 1H), 7.74 (d, J = 7.7 Hz, 1H), 7.55-7.64 (m, 1H), 7.49-7.54 (m, 1H), 7.41-7.48? (m, 1H), 7.10 (dd, J = 8.0, 4.5 Hz, 1H), 4.85 (d, J = 5.1 Hz, 2H), 3.41-3.77 (m, 4H), 2.35 (t, J = 13.1 Hz, 4H), 1.42 (s, 4H).
LCMS (ES) $C_{23}H_{23}N_5F_5$ $[M + H]^+$ 464.2.

261

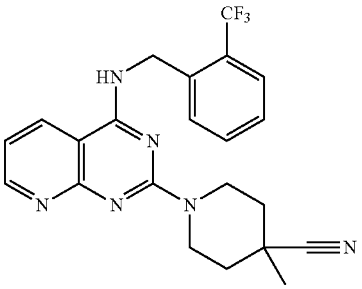 [SMILES: CC1(C#N)CCN(c2nc(NCc3ccccc3C(F)(F)F)c3cccnc3n2)CC1]

(2-(trifluoromethyl)pyridin-3-yl)metha 4-methyl-1-(4-((2-(trifluoromethyl)benzyl)amino)pyrido[2,3-d]pyrimidin-2-yl)piperidine-4-carbonitrile Synthesised via Route 6
$^1$H NMR (400 MHz, DMSO-d6) δ (ppm) 8.94 (s, 1H), 8.69 (dd, J = 4.4 Hz, 1H), 8.52 (d, J = 8.0 Hz, 1H), 7.75 (d, J = 7.6 Hz, 1H), 7.56-7.63 (m, 1H), 7.50-7.55 (m, 1H), 7.42-7.49 (m, 1H), 7.14 (dd, J = 7.8, 4.6 Hz, 1H), 4.86 (d, J = 4.8 Hz, 2H), 4.58 (s, 2H), 2.94 (t, J = 12.0 Hz, 2H), 1.77 (d, J = 12.0 Hz, 2H), 1.29 (s, 5H).
LCMS (ES) $C_{22}H_{22}N_6F_3$ $[M + H]^+$ 427.1.

262

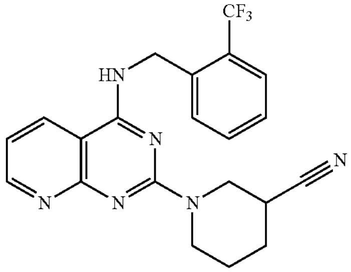 [SMILES: N#CC1CCCN(c2nc(NCc3ccccc3C(F)(F)F)c3cccnc3n2)C1]

1-(4-((2-(trifluoromethyl)benzyl)amino)pyrido[2,3-d]pyrimidin-2-yl)piperidine-3-carbonitrile Synthesised via Route 6
$^1$H NMR (400 MHz, $CDCl_3$) δ (ppm) 8.76 (d, J = 4.4 Hz, 1H), 7.88 (d, J = 7.6 Hz, 1H), 7.70 (d, J = 8.0Hz, 1H), 7.57 (d, J = 7.6 Hz, 1H), 7.51 (t, J = 8.0Hz, 1H), 7.41 (t, J = 7.2 Hz, 1H), 7.02 (dd, J = 8.0, 4.4 Hz, 1H), 6.17 (s, 1H), 5.00 (d, J = 5.6 Hz, 2H), 4.28 (s, 1H), 4.22-4.26 (m, 1H), 3.74-3.80 (m, 1H), 3.59 (s, 1H), 2.64 (s, 1H), 2.05 (m, 1H), 1.86-1.95 (m, 1H), 1.77-1.80 (m, 1H), 1.54 (m, 1H).
LCMS (ES) $C_{21}H_{20}N_6F_3$ $[M + H]^+$ 413.0.

TABLE 1-continued

| | |
|---|---|
| 263 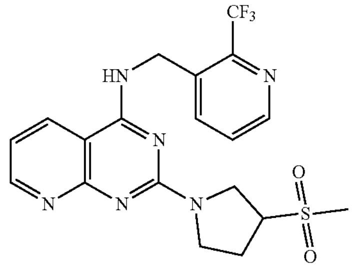 [SMILES: CS(=O)(=O)C1CCN(c2nc(NCc3cccnc3C(F)(F)F)c3cccnc3n2)C1] | 2-(3-(methylsulfonyl)pyrrolidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.79 (dd, J = 4.5, 1.8 Hz, 1H), 8.62 (d, J = 4.4 Hz, 1H), 7.91-8.01 (m, 2H), 7.47 (dd, J = 7.8, 4.7 Hz, 1H), 7.05 (dd, J = 8.0, 4.5 Hz, 1H), 6.33 (s, 1H), 5.03 (d, J = 5.7 Hz, 2H), 3.96-4.29 (m, 2H), 3.73 (m, 2H), 2.91 (s, 3H), 2.32-2.68 (m, 2H).<br>LCMS (ES) $C_{19}H_{20}N_6F_3O_2S$ $[M + H]^+$ 453.1. |
| 264 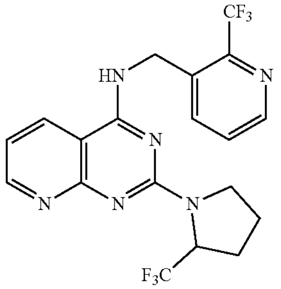 [SMILES: FC(F)(F)c1ncccc1CNc1nc(N2CCCC2C(F)(F)F)nc2ncccc12] | N-((2-(trifluoromethyl)pyridin-3-yl)methyl)-2-(2-(trifluoromethyl)pyrrolidin-1-yl)pyrido[2,3-d]pyrimidin-4-amine<br>Synthesised via Route 6<br>$^1$H NMR (400 MHz, $CDCl_3$) δ (ppm) 8.83 (dd, J = 1.8, 4.4 Hz, 1H), 8.63 (d, J = 4.3 Hz, 1H), 8.04 (dd, J = 1.7, 8.1 Hz, 1H), 7.93 (d, J = 7.6 Hz, 1H), 7.46 (dd, J = 4.7, 7.9 Hz, 1H), 7.09 (dd, J = 4.5, 7.9 Hz, 1H), 6.48 (t, J = 5.7 Hz, 1H), 5.20-4.77 (m, 3H), 4.06-3.64 (m, 2.H), 2.24-2.13 (m, 2H), 2.08-1.97 (m, 2H)<br>LCMS (ES) $C_{19}H_{17}N_6F_6$ $[M + H]^+$ 443.1. |
| 265 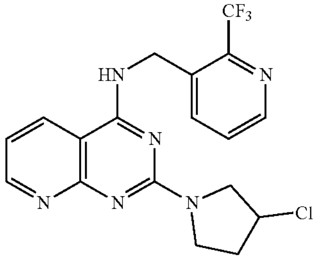 [SMILES: FC(F)(F)c1ncccc1CNc1nc(N2CCC(Cl)C2)nc2ncccc12] | 2-(3-chloropyrrolidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.96 (t, J = 5.1 Hz, 1H), 8.69 (dd, J = 1.8, 4.5 Hz, 1H), 8.61 (d, J = 4.1 Hz, 1H), 8.50 (dd, J = 1.9, 8.0 Hz, 1H), 7.99 (s, 1H), 7.65 (dd, J = 4.8, 7.4 Hz, 1H), 7.13 (dd, J = 4.5, 8.0 Hz, 1H), 4.90-4.77 (m, 3H), 3.82-3.43 (m, 4H), 2.34-2.33 (m, 1H), 2.11 (s, 1H).<br>LCMS (ES) $C_{18}H_{17}N_6F_3Cl$ $[M + H]^+$ 409.0. |
| 266 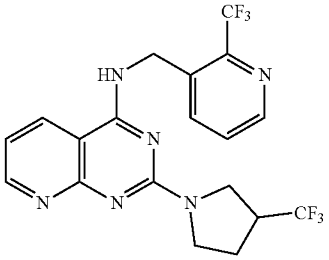 [SMILES: FC(F)(F)c1ncccc1CNc1nc(N2CCC(C(F)(F)F)C2)nc2ncccc12] | N-(2-(trifluoromethyl)benzyl)-2-(3-(trifluoromethyl)pyrrolidin-1-yl)pyrido[2,3-d]pyrimidin-4-amine<br>Synthesised via Route 6<br>$^1$H NMR (400 MHz, $CDCl_3$) δ (ppm) 8.73-8.82 (m, 1H), 7.86 (dd, J = 8.0, 1.5 Hz, 1H), 7.71 (d, J = 7.7 Hz, 1H), 7.62 (d, J = 7.6 Hz, 1H), 7.51 (t, J = 7.5 Hz, 1H), 7.38-7.45 (m, 1H), 7.00 (dd, J = 7.9, 4.4 Hz, 1H), 6.05 (s, 1H), 5.03 (br d, J = 5.7 Hz, 2H), 3.58-4.14 (m, 4H), 3.01 (dd, J = 16.6, 7.9 Hz, 1H), 2.10-2.29 (m, 2H).<br>LCMS (ES) $C_{22}H_{18}N_5F_6$ $[M + H]^+$ 442.0. |
| 267 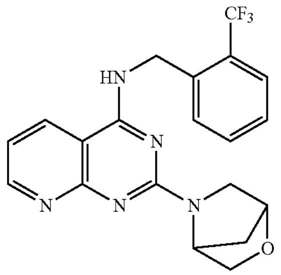 [SMILES: FC(F)(F)c1ccccc1CNc1nc(N2CC3CC2CO3)nc2ncccc12] | 2-(2-oxa-5-azabicyclo[2.2.1]heptan-5-yl)-N-(2-(trifluoromethyl)benzyl)pyrido[2,3-d]pyrimidin-4-amine<br>Synthesised via Route 6<br>$^1$H NMR (400 MHz, $CDCl_3$) δ (ppm) 8.74 (dd, J = 4.0, 1.6 Hz, 1H), 7.70-7.88 (m, 1H), 7.68 (d, J = 7.6 Hz, 1H), 7.48-7.62 (m, 2H), 7.37 (t, J = 5.2 Hz, 1H), 6.97-6.98 (m, 1H), 6.08-6.18 (m, 1H), 5.30 (s, 0.5H), 4.92-5.08 (m, 2.5H), 4.66 (s, 1H), 3.85-3.99 (m, 1H), 3.52-3.77 (m, 3H), 1.90-1.93 (d, J = 11.2 Hz, 2H).<br>LCMS (ES) $C_{20}H_{19}N_5F_3O$ $[M + H]^+$ 401.9. |

TABLE 1-continued

268

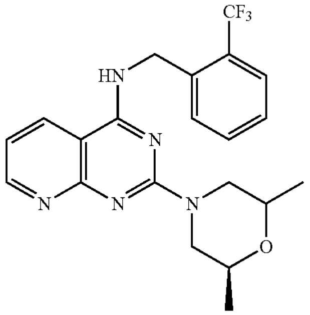 [SMILES: CC1CN(c2nc(NCc3ccccc3C(F)(F)F)c3cccnc3n2)C[C@H](C)O1]

2-((6S)-2,6-dimethylmorpholino)-N-(2-(trifluoromethyl)benzyl)pyrido[2,3-d]pyrimidin-4-amine Synthesised via Route 6

$^1$H NMR (400 MHz, $CDCl_3$) δ (ppm) 8.76 (dd, J = 4.5, 1.8 Hz, 1H), 7.88 (dd, J = 8.1, 1.7 Hz, 1H), 7.71 (d, J = 7.8 Hz, 1H), 7.46-7.60 (m, 2H), 7.37-7.45 (m, 1H), 7.00 (dd, J = 7.9, 4.5 Hz, 1H), 6.11 (t, J = 5.6 Hz, 1H), 4.22-5.18 (m, 4H), 3.96-4.08 (m, 1H), 3.27-3.86 (m, 2H), 2.58 (t, J = 11.9 Hz, 2H), 1.08-1.24 (m, 6H).

LCMS (ES) $C_{21}H_{23}N_5F_3O$ $[M + H]^+$ 418.1.

269

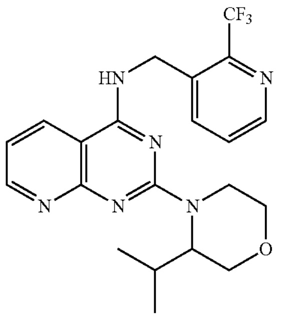 [SMILES: CC(C)C1COCCN1c1nc(NCc2cccnc2C(F)(F)F)c2cccnc2n1]

2-(3-isopropylmorpholino)-N-((2-(trifluoromethyl)pyridin-3-yl)methyl)pyrido[2,3-d]pyrimidin-4-amine Synthesised via Route 6

$^1$H NMR (400 MHz, DMSO-d6) δ (ppm) 8.68 (dd, J = 4.0, 2.0 Hz, 1H), 8.59 (d, J = 4.0 Hz, 1H), 8.46 (dd, J = 8.0, 2.0 Hz, 1H), 7.93 (d, J = 8.0 Hz, 1H), 7.62 (dd, J = 8.0, 4.0 Hz, 1H), 7.08 (dd, J = 8.0, 4.0 Hz, 1H), 4.97 (d, J = 16.0 Hz, 1H), 4.82 (d, J = 16.0 Hz, 1H), 4.52 (d, J = 16.0 Hz, 1H), 4.15 (d, J = 12.0 Hz, 1H), 3.84 (d, J = 12.0 Hz, 1H), 3.76 (dd, J = 12.0, 8.0 Hz, 1H), 3.25-3.31 (m, 2H), 2.98-2.99 (m, 3H), 2.21-2.27 (m, 1H), 0.81-0.83 (d, J = 8.0 Hz, 3H), 0.51-0.53 (d, J = 8.0 Hz, 3H).

LCMS (ES) $C_{21}H_{24}N_6F_3O$ $[M + H]^+$ 433.1.

270

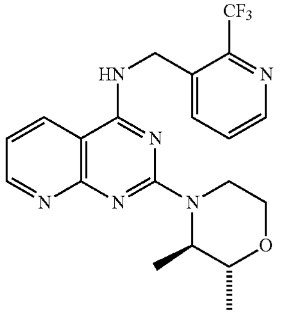 [SMILES: C[C@@H]1[C@@H](C)OCCN1c1nc(NCc2cccnc2C(F)(F)F)c2cccnc2n1]

2-((2R,3R)-2,3-dimethylmorpholino)-N-((2-(trifluoromethyl)pyridin-3-yl)methyl)pyrido[2,3-d]pyrimidin-4-amine Synthesised via Route 6

$^1$H NMR (400 MHz, DMSO-d6) δ (ppm) 9.03 (t, J = 4.0 Hz, 1H), 8.68 (d, J = 4.0 Hz, 1H), 8.59 (d, J = 4.0 Hz, 1H), 8.49-8.51 (m, 1H), 7.93 (d, J = 8.0 Hz, 1H), 7.63 (dd, J = 8.0, 4.0 Hz, 1H), 7.12 (dd, J = 8.0, 4.0 Hz, 1H), 4.84 (d, J = 3.55 Hz, 2H), 4.24-4.29 (m, 2H), 3.56-3.62 (m, 1H), 3.50-3.53 (m, 1H), 3.00-3.09 (m, 2H), 0.98 (d, J = 4.0 Hz, 3H), 0.91 (d, J = 4.0 Hz, 3H).

LCMS (ES) $C_{20}H_{22}N_6F_3O$ $[M + H]^+$ 419.0.

271

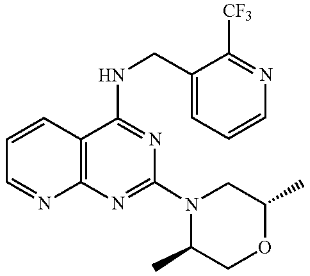 [SMILES: C[C@@H]1CO[C@@H](C)CN1c1nc(NCc2cccnc2C(F)(F)F)c2cccnc2n1]

2-((2S,5R)-2,5-dimethylmorpholino)-N-((2-(trifluoromethyl)pyridin-3-yl)methyl)pyrido[2,3-d]pyrimidin-4-amine Synthesised via Route 6

$^1$H NMR (400 MHz, $CDCl_3$) δ (ppm) 8.77 (dd, J = 4.0, 2.0 Hz, 1H), 8.60 (d, J = 4.0 Hz, 1H), 7.93 (dd, J = 8.0, 2.0 Hz, 1H), 7.89 (d, J = 8.0 Hz, 1H), 7.43 (dd, J = 8.0, 4.0 Hz, 1H), 7.02 (dd, J = 8.0, 4.0 Hz, 1H), 6.27 (t, J = 4.0 Hz, 1H), 5.11 (dd, J = 16.0, 8.0 Hz, 1H), 4.91-4.95 (m, 1H), 4.74 (d, J = 4.0 Hz, 1H), 4.23 (dd, J = 12.0, 2.0 Hz, 1H), 4.07-4.10 (m, 1H), 3.97 (dd, J = 12.0, 4.0 Hz, 1H), 3.48 (dd, J = 12.0, 4.0 Hz, 1H), 3.41 (dd, J = 12.0, 2.0 Hz, 1H), 1.15 (dd, J = 8.0, 4.0 Hz, 6H).

LCMS (ES) $C_{20}H_{22}N_6F_3O$ $[M + H]^+$ 419.0.

TABLE 1-continued

272

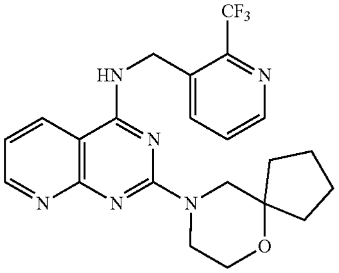 [SMILES: FC(F)(F)c1ncccc1CNc1nc(N2CCOC3(CCCC3)C2)nc2ncccc12]

2-(6-oxa-9-azaspiro[4.5]decan-9-yl)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 9.00 (s, 1H), 8.68 (d, J = 4.0 Hz, 1H), 8.60 (d, J = 4.0 Hz, 1H), 8.49 (d, J = 4.0 Hz, 1H), 7.92 (d, J = 8.0 Hz, 1H), 7.63 (dd, J = 8.0, 4.0 Hz, 1H), 7.13 (dd, J = 8.0, 4.0 Hz, 1H), 4.85 (d, J = 4.0 Hz, 2H), 3.51-3.66 (m, 6H), 1.15-1.50 (m, 8H).
LCMS (ES) $C_{22}H_{24}N_6F_3O$ $[M + H]^+$ 445.1.

273

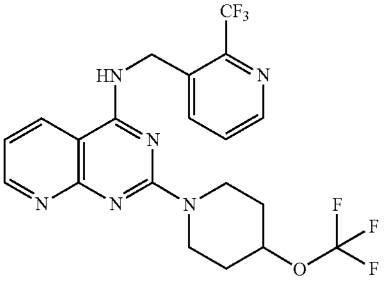 [SMILES: FC(F)(F)OC1CCN(c2nc(NCc3cccnc3C(F)(F)F)c3cccnc3n2)CC1]

2-(4-(trifluoromethoxy)piperidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.77 (dd, J = 4.5, 1.8 Hz, 1H), 8.63 (d, J = 3.9 Hz, 1H), 8.02 (dd, J = 8.0, 1.8 Hz, 1H), 7.93 (d, J = 7.8 Hz, 1H), 7.46 (dd, J = 7.9, 4.7 Hz, 1H), 7.03 (dd, J = 8.0, 4.5 Hz, 1H), 6.57 (t, J = 5.8 Hz, 1H), 5.04 (d, J = 5.6 Hz, 2H), 4.47 (tt, J = 7.7, 3.8 Hz, 1H), 4.35-4.04 (m, 2H), 3.79-3.48 (m, 2H), 1.99-1.77 (m, 2H), 1.80-1.58 (m, 2H).
LCMS (ES) $C_{20}H_{19}N_6F_6O$ $[M + H]^+$ 473.1.

273_S

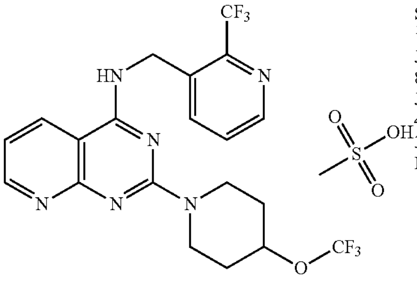

2-(4-(trifluoromethoxy)piperidin-1-yl)-N-((2-(trifluoromethyl)pyridin-3-yl)methyl)pyrido[2,3-d]pyrimidin-4-amine methanesulfonate Synthesised via Route 6
$^1$H NMR (400 MHz, DMSO-d6) δ (ppm) 9.95 (s, 1H), 8.94 (d, J = 7.2 Hz, 1H), 8.78 (d, J = 4.3 Hz, 1H), 8.67 (d, J = 4.3 Hz, 1H), 8.07 (d, J = 7.9 Hz, 1H), 7.70 (dd, J = 8.0, 4.6 Hz, 1H), 7.54 (dd, J = 7.9, 5.5 Hz, 1H), 4.95 (d, J = 4.5 Hz, 2H), 4.72 (dd, J = 8.3, 4.0 Hz, 1H), 4.28-3.88 (m, 2H), 3.74-3.44 (m, 2H), 2.31 (s, 3H), 2.12-1.32 (m,4H).
LCMS (ES) $C_{20}H_{19}N_6F_6O$ $[M + H]^+$ 473.1.

274

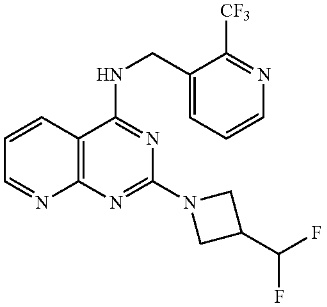 [SMILES: FC(F)C1CN(c2nc(NCc3cccnc3C(F)(F)F)c3cccnc3n2)C1]

2-(3-(difluoromethyl)azetidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.74-8.86 (m, 1H), 8.62 (br d, J = 4.6 Hz, 1H), 7.99 (t, J = 7.3 Hz, 2H), 7.46 (dd, J = 7.8, 4.7 Hz, 1H), 7.05 (dd, J = 8.0, 4.5 Hz, 1H), 6.40-6.55 (m, 1H), 5.79-6.19 (m, 1H), 5.02 (d, J = 5.8 Hz, 2H), 4.04-4.28 (m, 4H), 2.92-3.16 (m, 1H).
LCMS (ES) $C_{18}H_{16}N_6F_5$ $[M + H]^+$ 411.1.

TABLE 1-continued

275

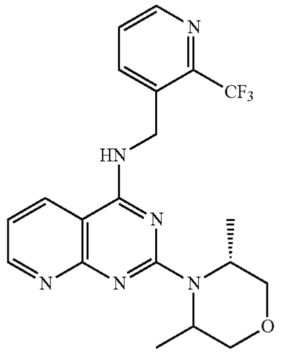 [SMILES: CC1COC[C@@H](C)N1c1nc(NCc2cccnc2C(F)(F)F)c2cccnc2n1]

2-((3R)-3,5-dimethylmorpholino)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.99-9.02 (m, 1H), 8.67-8.71 (m, 1H), 8.59 (d, J = 4.0 Hz, 1 H), 8.49-8.54 (m, 1H), 7.92 (d, J = 8.0 Hz, 1H), 7.63 (dd, J = 8.0, 4.0 Hz, 1H), 7.11-7.18 (m, 1H), 4.97-5.02 (m, 1H), 4.74-4.78 (m, 1H), 4.45-4.47 (m, 0.47H), 4.12-4.15 (m, 1.6H), 3.99 (dd, J = 12.0, 4.0 Hz, 2H), 3.76-3.78 (m, 0.33H), 3.44-3.56 (m, 1.6H), 3.00-3.05 (m, 1.6H), 1.08 (d, J = 4.0 Hz, 4.3H), 0.94 (t, J = 4.0 Hz, 1.6H).
LCMS (ES) $C_{20}H_{22}N_6F_3O$ $[M + H]^+$ 419.1.

276

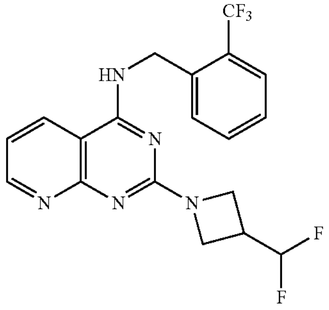 [SMILES: FC(F)C1CN(c2nc(NCc3ccccc3C(F)(F)F)c3cccnc3n2)C1]

2-(3-(difluoromethyl)azetidin-1-yl)-N-(2-(trifluoromethyl)benzyl)pyrido[2,3-d]pyrimidin-4-amine Synthesised via Route 6
$^1$H NMR (400 MHz, $CDCl_3$) δ (ppm) 8.77 (dd, J = 4.4, 1.6 Hz, 1H), 7.89 (dd, J = 8.0, 1.8 Hz, 1H), 7.70 (d, J = 7.8 Hz, 1H), 7.63 (d, J = 7.8 Hz, 1H), 7.52 (t, J = 7.4 Hz, 1H), 7.36-7.46 (m, 1H), 7.02 (dd, J = 8.0, 4.5 Hz, 1H), 5.86-6.22 (m, 2H), 5.01 (d, J = 5.8 Hz, 2H), 4.11-4.35 (m, 4H), 3.00-3.15 (m, 1H).
LCMS (ES) $C_{19}H_{17}N_5F_5$ $[M + H]^+$ 410.1.

277

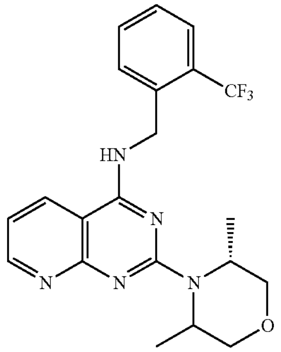 [SMILES: CC1COC[C@@H](C)N1c1nc(NCc2ccccc2C(F)(F)F)c2cccnc2n1]

2-((3R)-3,5-dimethylmorpholino)-N-(2-(trifluoromethyl)benzyl)pyrido[2,3-d]pyrimidin-4-amine Synthesised via Route 6
$^1$H NMR (400 MHz, DMSO-d6) δ (ppm) 8.95 (s, 1H), 8.67-8.71 (m, 1H), 8.53-8.55 (m, 1H), 7.74 (d, J = 8.0 Hz, 1H), 7.58 (t, J = 8.0 Hz, 1H), 7.42-7.49 (m, 2H), 7.11-7.17 (m, 1H), 5.00 (t, J = 16.0 Hz 1H), 4.75 (d, J = 16.0 Hz, 1H), 4.51 (m, 0.32H), 4.17-4.18 (m, 1.7H), 3.98-4.04 (m, 2H), 3.78 (dd, J = 12.0, 4.0 Hz, 0.25H), 3.55 (dd, J = 12.0, 2.0 Hz, 1.57H), 3.02 (d, J = 16.0 Hz, 1H), 1.07 (d, J = 4.0 Hz, 4.8H), 0.95 (dd, J = 16.0, 4.0 Hz, 1.6H).
LCMS (ES) $C_{21}H_{23}N_5F_3O$ $[M + H]^+$ 418.1.

278

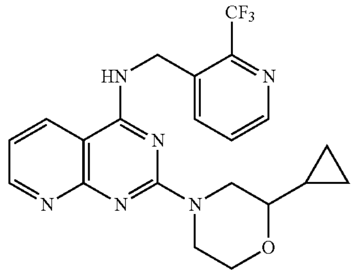 [SMILES: FC(F)(F)c1ncccc1CNc1nc(N2CCOC(C3CC3)C2)nc2ncccc12]

2-(2-cyclopropylmorpholino)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.77 (dd, J = 4.0, 2.0 Hz, 1H), 8.61 (d, J = 4.0 Hz, 1H), 7.96 (d, J = 8.0, 4.0 Hz, 1H), 7.90 (d, J = 8.0 Hz, 1H), 7.45 (dd, J = 8.0, 4.0 Hz, 1H), 7.02 (dd, J = 8.0, 4.0 Hz, 1H), 6.35 (br s, 1H), 5.00-5.09 (m, 2H), 4.58 (br s, 2H), 3.94 (dd, J = 12.0, 2.4 Hz, 1H), 3.47 (t, J = 12.0 Hz, 1H), 2.81-3.01 (m, 2H), 2.65 (br s, 1H), 0.85-0.88 (m, 1H), 0.47-0.60 (m, 2H), 0.35-0.39 (m, 1H), 0.19 (br s, 1H).
LCMS (ES) $C_{21}H_{22}N_6F_3O$ $[M + H]^+$ 430.9.

TABLE 1-continued

279

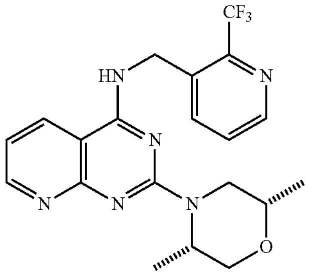 [SMILES: C[C@H]1CN(c2nc(NCc3cccnc3C(F)(F)F)c3cccnc3n2)[C@@H](C)CO1]

2-((2S,5S)-2,5-dimethylmorpholino)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.74 (dd, J = 4.0, 2.0 Hz, 1H), 8.58 (d, J = 4.0 Hz, 1H), 8.02 (d, J = 8.0 Hz, 1H), 7.89 (d, J = 8.0 Hz, 1H), 7.42 (d, J = 4.0 Hz, 1H), 7.01 (dd, J = 8.0, 4.0 Hz, 1H), 6.60-6.66 (m, 1H), 4.89-5.12 (m, 2.6H), 4.65 (d, 0.6H), 4.49 (d, 0.6H), 4.21 (d, 0.3H), 3.63-3.71 (m, 2H), 3.35-3.36 (m, 1H), 2.70-2.81 (m, 1H), 1.10-1.29 (m, 4H), 0.97 (d, J = 8.0 Hz, 2H).
LCMS (ES) $C_{20}H_{22}N_6F_3O$ $[M + H]^+$ 419.0.

280

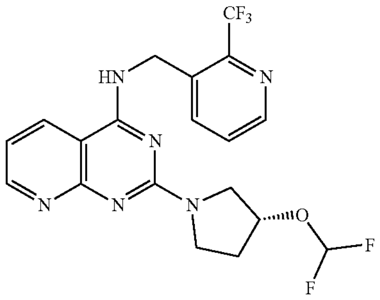 [SMILES: FC(F)O[C@@H]1CCN(c2nc(NCc3cccnc3C(F)(F)F)c3cccnc3n2)C1]

(R)-2-(3-(difluoromethoxy)pyrrolidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.77 (dd, J = 4.5, 1.8 Hz, 1H), 8.62 (d, J = 3.9 Hz, 1H), 8.00 (dd, J = 7.9, 2.0 Hz, 2H), 7.46 (dd, J = 7.8, 4.7 Hz, 1H), 7.02 (dd, J = 8.0, 4.5 Hz, 1H), 6.49 (s, 1H), 6.06-6.44 (m, 1H), 5.06 (s, 2H), 4.91 (s, 1H), 3.56-4.00 (m, 4H), 2.20 (m, 2H).
LCMS (ES) $C_{19}H_{18}N_6F_5O$ $[M + H]^+$ 441.1

281

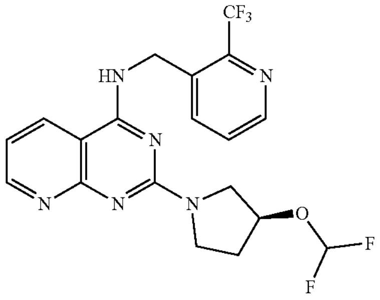 [SMILES: FC(F)O[C@H]1CCN(c2nc(NCc3cccnc3C(F)(F)F)c3cccnc3n2)C1]

(S)-2-(3-(difluoromethoxy)pyrrolidin-1-yl)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.93 (t, J = 4.0 Hz, 1H), 8.68 (dd, J = 4.0, 2.0 Hz, 1H), 8.59 (d, J = 4.0 Hz, 1H), 8.49 (dd, J = 8.0, 2.0 Hz, 1H), 7.98 (d, J = 8.0 Hz, 1H), 7.62-7.65 (m, 1H), 7.12 (dd, J = 8.0, 4.0 Hz, 1H), 6.51-6.94 (m, 1H), 4.82-4.90 (m, 3H), 3.39-3.70 (m, 3H), 3.20-3.29 (m, 1H), 1.99-2.16 (m, 2H).
LCMS (ES) $C_{19}H_{18}N_6F_5O$ $[M + H]^+$ 441.1.

282

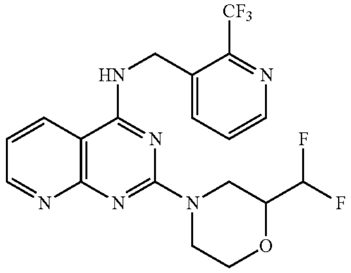 [SMILES: FC(F)C1CN(c2nc(NCc3cccnc3C(F)(F)F)c3cccnc3n2)CCO1]

2-(2-(difluoromethyl)morpholino)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.81 (dd, J = 1.9, 4.5 Hz, 1H), 8.64 (d, J = 3.9 Hz, 1H), 8.04 (dd, J = 1.8, 8.0 Hz, 1H), 7.94 (d, J = 7.9 Hz, 1H), 7.47 (dd, J = 4.8, 7.9 Hz, 1H), 7.08 (dd, J = 4.5, 8.0 Hz, 1H), 6.59 (t, J = 5.3 Hz, 1H), 5.89-5.61 (m, 1H), 5.13-4.53 (m, 4H), 4.00 (dd, J = 2.1, 11.6 Hz, 1H), 3.74-3.51 (m, 2H), 3.12 (t, J = 11.5 Hz, 1H), 3.02 (dd, J = 10.7, 13.4 Hz, 1H).
LCMS (ES) $C_{19}H_{18}N_6F_5O$ $[M + H]^+$ 441.1.

TABLE 1-continued

283

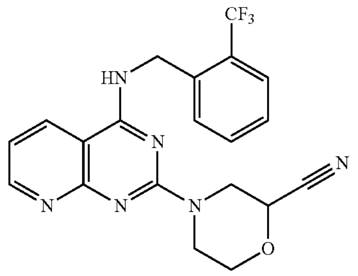 [SMILES: N#CC1CN(c2nc(NCc3ccccc3C(F)(F)F)c3cccnc3n2)CCO1]

4-(4-((2-(trifluoromethyl)benzyl)amino)pyrido[2,3-d]pyrimidin-2-yl)morpholine-2-carbonitrile Synthesised via Route 6
$^{1}$H NMR (400 MHz, $CDCl_3$) δ (ppm) 8.81 (dd, J = 4.5, 1.8 Hz, 1H), 7.98 (dd, J = 8.0, 1.7 Hz, 1H), 7.73 (d, J = 7.8 Hz, 1H), 7.51-7.61 (m, 2H), 7.39-7.47 (m, 1H), 7.09 (dd, J = 7.9, 4.0 Hz, 1H), 6.38 (t, J = 5.4 Hz, 1H), 4.95-5.09 (m, 2H), 4.61 (t, J = 3.7 Hz, 1H), 4.53 (dd, J = 13.8, 3.9 Hz, 1H), 4.37 (br s, 1H),3.93-3.99 (m, 1H), 3.75-3.93 (m, 2H), 3.56-3.63 (m, 1H).
LCMS (ES) $C_{20}H_{18}N_6F_3O$ $[M + H]^+$ 415.1.

284

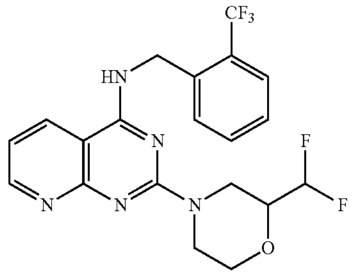 [SMILES: FC(F)C1CN(c2nc(NCc3ccccc3C(F)(F)F)c3cccnc3n2)CCO1]

2-(2-(difluoromethyl)morpholino)-N-(2-(trifluoromethyl)benzyl)pyrido[2,3-d]pyrimidin-4-amine Synthesised via Route 6
$^{1}$H NMR (400 MHz, $CDCl_3$) δ (ppm) 8.80 (dd, J = 1.7, 4.5 Hz, 1H), 7.96 (dd, J = 1.7, 8.1 Hz, 1H), 7.72 (d, J = 7.8 Hz, 1H), 7.61-7.56 (m, 1H), 7.55-7.48 (m, 1H), 7.46-7.38 (m, 1H), 7.06 (dd, J = 4.5, 8.0 Hz, 1H), 6.31 (t, J = 5.5 Hz, 1H), 5.92-5.61 (m, 1H), 5.07-4.96 (m, 2H), 4.96-4.59 (m, 2H), 4.02 (dd, J = 2.1, 11.4 Hz, 1H), 3.75-3.57 (m, 2H), 3.20-3.10 (m, 1H), 3.09-2.99 (m, 1H), 3.04 (dd, J = 10.7, 13.3 Hz, 1H).
LCMS (ES) $C_{20}H_{19}N_5F_5O$ $[M + H]^+$ 440.1.

285

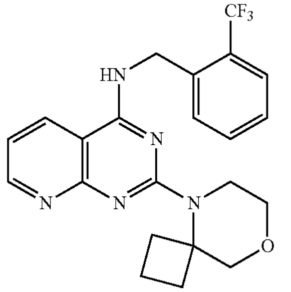 [SMILES: FC(F)(F)c1ccccc1CNc1nc(N2CCOCC23CCC3)nc2ncccc12]

2-(8-oxa-5-azaspiro[3.5]nonan-5-yl)-N-(2-(trifluoromethyl)benzyl)pyrido[2,3-d]pyrimidin-4-amine Synthesised via Route 6
$^{1}$H NMR (400 MHz, DMSO-d6) δ (ppm) 8.83 (t, J = 5.6 Hz, 1H), 8.70 (d, J = 4.0 Hz, 1H), 8.50 (d, J = 8.0 Hz, 1H), 7.73 (d, J = 8.0 Hz, 1H), 7.61 (t, J = 8.0 Hz, 1H), 7.45 (dd, J = 16.0, 8.0 Hz 2H), 7.16 (dd, J = 8.0, 4.0Hz, 1H), 4.84 (d, J = 4.0Hz, 2H), 3.67 (s, 2H), 3.50 (s, 2H), 3.26-3.29 (m 2H), 2.26-2.32 (m, 2H), 2.08 (d, J = 4.0 Hz, 2H), 1.53-1.58 (m, 2H).
LCMS (ES) $C_{22}H_{23}N_5F_3O$ $[M + H]^+$ 430.0.

286

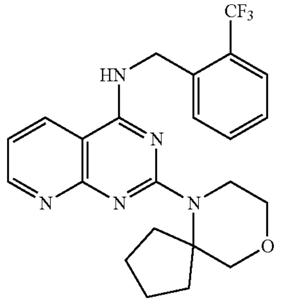 [SMILES: FC(F)(F)c1ccccc1CNc1nc(N2CCOCC23CCCC3)nc2ncccc12]

2-(9-oxa-6-azaspiro[4.5]decan-6-yl)-N-(2-(trifluoromethyl)benzyl)pyrido[2,3-d]pyrimidin-4-amine Synthesised via Route 6
$^{1}$H NMR (400 MHz, DMSO-d6) δ (ppm) 8.82 (s, 1H), 8.73 (d, J = 2.4 Hz, 1H), 8.53 (d, J = 8.0 Hz, 1H), 7.74 (d, J = 8.0 Hz, 1H), 7.60 (t, J = 8.0 Hz, 1H), 7.48 (m, 2H), 7.18 (dd, J = 8.0, 4.0 Hz, 1H), 4.88 (d, J = 4.0 Hz, 2H), 3.66 (s, 4H), 3.32 (s, 2H), 2.27-2.28 (m, 2H), 1.97 (s, 2H), 1.42-1.47 (m, 4H).
LCMS (ES) $C_{23}H_{25}N_5F_3O$ $[M + H]^+$ 444.1.

TABLE 1-continued

287

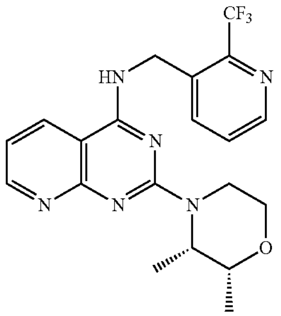 [SMILES: C[C@H]1OCCN(c2nc(NCc3cccnc3C(F)(F)F)c3cccnc3n2)[C@H]1C]

2-((2R,3S)-2,3-dimethylmorpholino)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 9.10 (s, 1H), 8.51-8.70 (m, 3H), 7.91 (s, 1H), 7.62 ( s, 1H), 7.14 (s, 1H), 4.72-4.92 (m, 2H), 3.48-4.30 (m, 4H), 3.13-3.16 (m, 1H), 2.89-3.06 (m, 1H), 0.84-1.14 (m, 4H), 0.50 (br s, 2H)
LCMS (ES) $C_{20}H_{22}N_6F_3O$ [M + H]$^+$ 419.0.

288

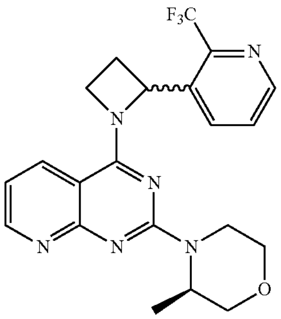 [SMILES: C[C@@H]1COCCN1c1nc(N2CCC2c2cccnc2C(F)(F)F)c2cccnc2n1]

(3R)-3-methyl-4-(4-(2-(2-(trifluoromethyl)pyridin-3-yl)azetidin-1-yl)pyrido[2,3-d]pyrimidin-2-yl)morpholine Synthesised via Route 6
$^1$H NMR (400 MHz, $CDCl_3$) δ (ppm) 8.78-8.67 (m, 1H), 8.56 (t, J = 3.3 Hz, 1H), 7.90-8.10 (m, 2H), 7.43 (m, 1H), 6.92 (m, 1H), 5.98 t, J = 8.1 Hz, 1H), 3.82-5.01 (m, 4H), 3.74-3.76 (m, 1H), 3.16-3.51 (m, 3H), 3.06 (m, 1H), 2.90 (d, J = 7.5 Hz, 1H), 2.29-2.43 (m, 1H), 1.13 (m, 3H).
LCMS (ES) $C_{23}H_{22}N_6F_3O$ [M + H]$^+$ 431.1.

289

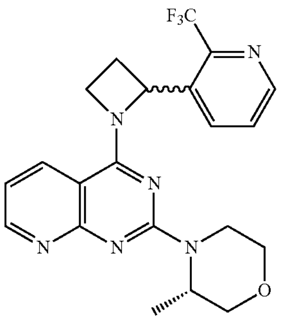 [SMILES: C[C@H]1COCCN1c1nc(N2CCC2c2cccnc2C(F)(F)F)c2cccnc2n1]

(3S)-3-methyl-4-(4-(2-(2-(trifluoromethyl)pyridin-3-yl)azetidin-1-yl)pyrido[2,3-d]pyrimidin-2-yl)morpholine Synthesised via Route 6
$^1$H NMR (400 MHz, DMSO-d6) δ (ppm) 8.64-8.70 (m, 2H), 8.24 (t, J = 8.0 Hz, 2H), 7.69-7.73 (m, 1 H), 7.11 (s, 1H), 5.90 (s, 1H), 4.87 (s, 1H), 4.62-4.69 (m, 1H), 4.08 (s, 2H), 3.73 (d, J = 12.0 Hz, 1H), 3.39-3.51 (m, 2H), 3.21-3.24 (m, 1H), 2.84-2.97 (m, 2H), 2.33 (m, 1H), 1.06 (d, J = 6.4 Hz, 1.7H), 0.56 (br s, 1.3H).
LCMS (ES) $C_{21}H_{22}N_6F_3O$ [M + H]$^+$ 431.1.

290

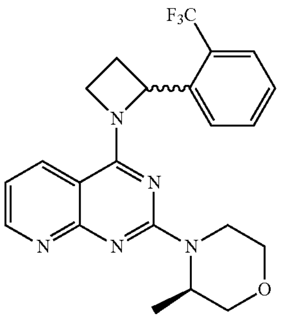 [SMILES: C[C@@H]1COCCN1c1nc(N2CCC2c2ccccc2C(F)(F)F)c2cccnc2n1]

(3R)-3-methyl-4-(4-(2-(2-(trifluoromethyl)phenyl)azetidin-1-yl)pyrido[2,3-d]pyrimidin-2-yl)morpholine Synthesised via Route 6
$^1$H NMR (400 MHz, $CDCl_3$) δ (ppm) 8.73-8.81 (m, 1H), 8.01 (t, J = 9.0 Hz, 1H), 7.68-7.81 (m, 2H), 7.55 (q, J = 7.7 Hz, 1H), 7.37-7.44? (m, 1H), 6.91-7.00 (m, 1H), 6.07 (t, J = 7.8 Hz, 1H), 4.23-4.80 (m, 4H), 3.85 (d, J = 8.3 Hz, 1H), 3.33-3.64 (m, 3H), 3.16 (m, 1H), 2.96 (d, J = 4.4 Hz, 1H), 2.33-2.46 (m, 1H), 1.23 (d, J = 6.8 Hz, 3H).
LCMS (ES) $C_{22}H_{23}N_5F_3O$ [M + H]$^+$ 430.2.

TABLE 1-continued

291

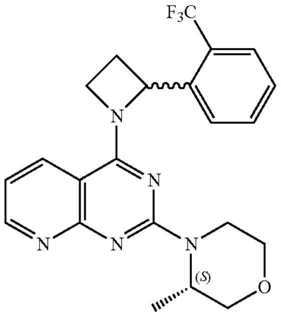

(3S)-3-methyl-4-(4-(2-(2-(trifluoromethyl)phenyl)azetidin-1-yl)pyrido[2,3-d]pyrimidin-2-yl)morpholine Synthesised via Route 6
$^1$H NMR (400 MHz, $CDCl_3$) δ (ppm) 8.75 (s, 1H), 8.00 (t, J = 9.7 Hz, 1H), 7.67-7.79 (m, 2H), 7.54 (q, J = 7.6 Hz, 1H), 7.36-7.44 (m, 1H), 6.90-6.99 (m, 1H), 6.06 (t, J = 7.9 Hz, 1H), 4.12-4.86 (m, 4H), 3.84 (d, J = 8.2 Hz, 1H), 3.27-3.65 (m, 3H), 3.14-3.58 (m, 1H), 2.94 (d, J = 4.9 Hz, 1H), 2.31-2.44 (m, 1H), 1.22 (d, J = 6.8 Hz, 3H).
LCMS (ES) $C_{22}H_{23}N_5F_3O$ $[M + H]^+$ 430.1.

292

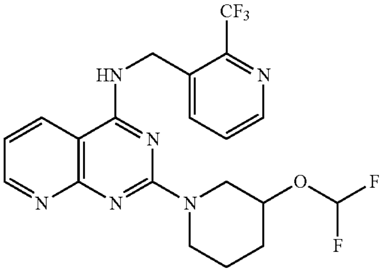 [SMILES: FC(F)OC1CCCN(c2nc(NCc3cccnc3C(F)(F)F)c3cccnc3n2)C1]

2-(3-(difluoromethoxy)piperidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.77 (dd, J = 1.8, 4.5 Hz, 1H), 8.62 (d, J = 3.8 Hz, 1H), 8.01-7.93 (m, 2H), 7.46 (dd, J = 4.6, 7.9 Hz, 1H), 7.02 (dd, J = 4.5, 7.9 Hz, 1H), 6.60-5.97 (m, 2H), 5.05 (d, J = 5.6 Hz, 2H), 4.57-4.11 (m, 3H), 3.59-3.35 (m, 2H), 2.10-1.97 (m, 1H), 1.85-1.73 (m, 2H), 1.54 (br s, 1H).
LCMS (ES) $C_{20}H_{19}N_6F_5O$ $[M + H]^+$ 455.1.

293

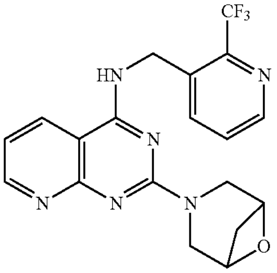 [SMILES: FC(F)(F)c1ncccc1CNc1nc(N2CC3CC(C2)O3)nc2ncccc12]

2-(6-oxa-3-azabicyclo[3.1.1]heptan-3-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.77 (dd, J = 4.0, 2.0 Hz, 1H), 8.59 (d, J = 2.0 Hz, 1H), 8.03 (dd, J = 8.0, 2.0 Hz, 1H), 7.96 (d, J = 8.0 Hz, 1H), 7.43 (dd, J = 8.0, 4.0 Hz, 1H), 7.03 (dd, J = 8.0, 4.0 Hz, 1H), 6.56 (t, J = 6.0 Hz, 1H), 4.97-5.16 (m, 2H), 4.66 (dd, J = 12.0, 4.0 Hz, 2H), 4.11 (d, J = 12.0 Hz, 1H), 3.90 (d, J = 12.0 Hz, 1H), 3.82 (d, J = 12.0 Hz, 1H), 3.67 (d, J = 12.0 Hz, 1H), 3.23 (q, J = 8.0 Hz, 1H), 1.87 (d, J = 8.0 Hz, 1H).
LCMS (ES) $C_{19}H_{18}N_6F_3O$ $[M + H]^+$ 403.0.

294

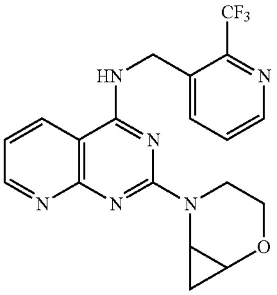 [SMILES: FC(F)(F)c1ncccc1CNc1nc(N2CCOC3CC32)nc2ncccc12]

2-(2-oxa-5-azabicyclo[4.1.0]heptan-5-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.78 (d, J = 3.1 Hz, 1H), 8.60 (d, J = 3.5 Hz, 1H), 7.87-8.14 (m, 2H), 7.39-7.49 (m, 1H), 7.04 (dd, J = 7.3, 4.3 Hz, 1H), 6.61 (s, 1H), 4.95-5.22 (m, 2H), 2.88-3.80 (m, 6H), 0.36-1.09 (m, 2H).
LCMS (ES) $C_{19}H_{18}N_6F_3O$ $[M + H]^+$ 403.1.

TABLE 1-continued

295

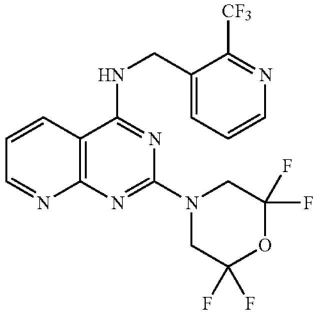 [SMILES: FC1(F)CN(c2nc(NCc3cccnc3C(F)(F)F)c3cccnc3n2)CC(F)(F)O1]

2-(2,2,6,6-tetrafluoromorpholino)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.89 (dd, J = 4.5, 1.8 Hz, 1H), 8.66 (d, J = 4.4 Hz, 1H), 7.99 (dd, J = 8.2, 1.8 Hz, 1H), 7.92 (d, J = 7.8 Hz, 1H), 7.48 (dd, J = 7.8, 4.6 Hz, 1H), 7.19 (dd, J = 8.1, 4.5 Hz, 1H), 6.33 (t, J = 5.7 Hz, 1H), 5.07 (d, J = 5.7 Hz, 2H), 4.39 (br s, 4H).
LCMS (ES) $C_{18}H_{14}N_6F_7O$ [M + H]$^+$ 463.1.

296

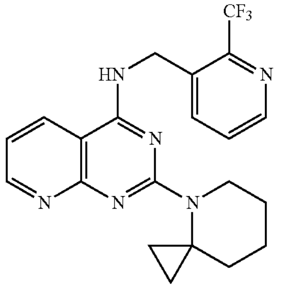 [SMILES: FC(F)(F)c1ncccc1CNc1nc(N2CCCCC23CC3)nc2ncccc12]

2-(4-azaspiro[2.5]octan-4-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.79 (dd, J = 4.4, 1.7 Hz, 1H), 8.61 (d, J = 4.3 Hz, 1H), 7.96 (d, J = 7.8 Hz, 2H), 7.44 (dd, J = 7.9, 4.6 Hz, 1H), 7.00-7.11 (m, 1H), 6.23 (br s, 1H), 5.09 (s, 2H), 3.59-4.20 (m, 2H), 1.70-1.75 (m, 2H), 1.31-1.53 (m, 4H), 0.48-0.97 (m, 4H).
LCMS (ES) $C_{21}H_{22}N_6F_3$ [M + H]$^+$ 415.1.

297

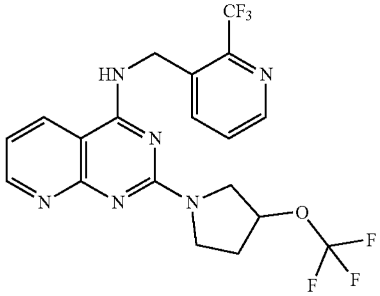 [SMILES: FC(F)(F)OC1CCN(c2nc(NCc3cccnc3C(F)(F)F)c3cccnc3n2)C1]

2-(3-(trifluoromethoxy)pyrrolidin-1-yl)-N-((2-(trifluoromethyl)pyridin-3-yl)methyl)pyrido[2,3-d]pyrimidin-4-amine Synthesised via Route 6
$^1$H NMR (400 MHz, $CDCl_3$) δ (ppm) 8.78 (dd, J = 4.5, 1.8 Hz, 1H), 8.62 (d, J = 4.0 Hz, 1H), 7.91-8.02 (m, 2H), 7.46 (dd, J = 7.5, 4.8 Hz, 1H), 7.03 (dd, J = 8.0, 4.5 Hz, 1H), 6.30 (t, J = 5.5 Hz, 1H), 4.86-5.11 (m, 3H), 3.50-4.16 (m, 4H), 2.11-2.37 (m, 2H).
LCMS (ES) $C_{19}H_{17}N_6F_6O$ [M + H]$^+$ 459.1.

298

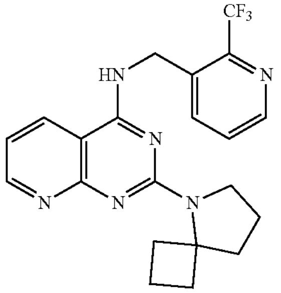 [SMILES: FC(F)(F)c1ncccc1CNc1nc(N2CCCC23CCC3)nc2ncccc12]

2-(5-azaspiro[3.4]octan-5-yl)-N-((2-(trifluororoethyl)pyridin-3-yl)methyl)pyrido[2,3-d]pyrimidin-4-amine Synthesised via Route 6
$^1$H NMR (400 MHz, DMSO-d6) δ (ppm) 8.70 (dd, J = 4.4, 2.0 Hz, 1H), 8.62 (d, J = 3.9 Hz, 1H), 8.51 (t, J = 5.3 Hz, 1H), 8.46 (dd, J = 8.0,1.9 Hz, 1H), 7.95 (d, J = 7.4 Hz, 1H), 7.64 (dd, J = 8.0, 4.6 Hz, 1H), 7.09 (dd, J = 8.0, 4.5 Hz, 1H), 5.02 (d, J = 5.0 Hz, 2H), 3.53 (t, J = 6.6 Hz, 2H), 3.27 (d, J = 8.9 Hz, 2H), 2.10-2.14 (m, 2H), 1.47-1.73 (m, 6H).
LCMS (ES) $C_{21}H_{22}N_6F_3O$ [M + H]$^+$ 415.1.

TABLE 1-continued

| | |
|---|---|
| 299 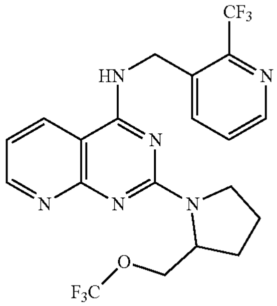 [SMILES: FC(F)(F)OCC1CCCN1c1nc(NCc2cccnc2C(F)(F)F)c2cccnc2n1] | 2-(2-((trifluoromethoxy)methyl)pyrrolidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, $CDCl_3$) δ (ppm) 8.79 (dd, J = 4.5, 1.8 Hz, 1H), 8.63 (d, J = 4.0 Hz, 1H), 7.92 (t, J = 6.9 Hz, 2H), 7.45 (dd, J = 7.9, 4.6 Hz, 1H), 7.04 (dd, J = 8.0, 4.5 Hz, 1H), 6.19 (s, 1H), 4.99-5.15 (m, 2H), 4.12-4.55 (m, 3H), 3.46-3.79 (m, 2H), 2.06 (d, J = 4.0 Hz, 1H), 1.76-1.93 (m, 2H), 1.50-1.57 (m, 1H).<br>LCMS (ES) $C_{20}H_{19}N_6F_6O$ [M + H]$^+$ 473.1. |
| 300 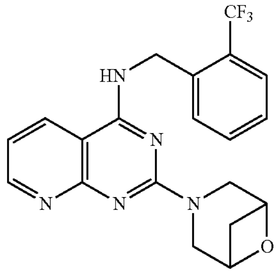 [SMILES: FC(F)(F)c1ccccc1CNc1nc(N2CC3CC(C2)O3)nc2ncccc12] | 2-(6-oxa-3-azabicyelo[3.1.1]heptan-3-yl)-N-(2-(trifluoromethyl)benzyl)pyrido[2,3-d]pyrimidin-4-amine<br>Synthesised via Route 6<br>$^1$H NMR (400 MHz, $CDCl_3$) δ (ppm) 8.79 (d, J = 3.2 Hz, 1H), 7.96 (d, J = 7.8 Hz, 1H), 7.71 (d, J = 7.7 Hz, 1H), 7.63 (d, J = 7.6 Hz, 1H), 7.51 (t, J = 7.5 Hz, 1H), 7.41 (t, J = 7.6 Hz, 1H), 7.02 (dd, J = 7.8, 4.4 Hz, 1H), 6.26 (b, 1H), 5.07 (dt, J = 15.7, 10.4 Hz, 2H), 4.72 (b, 2H), 4.20 (d, J = 13.6 Hz, 1H), 3.97 (t, J = 13.2 Hz, 2H), 3.81 (d, J = 13.2 Hz, 1H), 3.25 (dd, J = 14.4, 6.8 Hz, 1H), 1.94 (d, J = 8.7 Hz, 1H).<br>LCMS (ES) $C_{20}H_{19}N_5F_3O$ [M + H]$^+$ 402.1. |
| 301 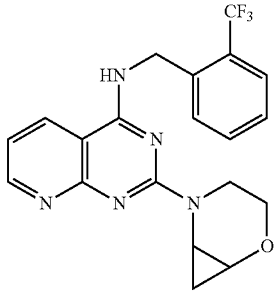 [SMILES: FC(F)(F)c1ccccc1CNc1nc(N2CCOC3CC32)nc2ncccc12] | 2-(2-oxa-5-azabicyclo[4.1.0]heptan-5-yl)-N-(2-(trifluoromethyl)benzyl)pyrido[2,3-d)pyrimidin-4-amine<br>Synthesised via Route 6<br>$^1$H NMR (400 MHz, DMSO-d6) δ (ppm) 8.79 (d, J = 2.9 Hz, 1H), 7.87-7.96 (m, 1H), 7.56-7.74 (m, 2H), 7.50 (t, J = 7.5 Hz, 1H), 7.36-7.44 (m, 1H), 7.03 (dd, J = 7.9, 4.4 Hz, 1H), 6.12 (s, 1H), 4.98-5.25 (m, 2H), 3.52-3.89 (m, 5H), 3.01-3.38 (m, 1H), 0.50-1.17 (m, 2H),<br>LCMS (ES) $C_{20}H_{19}N_5F_3O$ [M + H]$^+$ 402.1. |
| 302 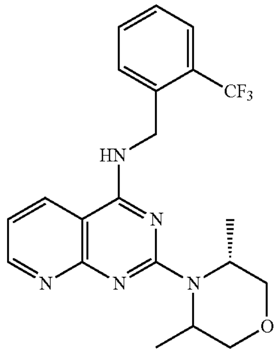 [SMILES: CC1COC[C@@H](C)N1c1nc(NCc2ccccc2C(F)(F)F)c2cccnc2n1] | 2-((3R)-3,5-dimethylmorpholino)-N-(2-(trifluoromethyl)benzyl)pyrido[2,3-d]pyrimidin-4-amine<br>Synthesised via Route 6<br>$^1$H NMR (400 MHz, DMSO-d6) δ (ppm) 8.98-9.03 (m, 1H), 8.67-8.68 (m, 1H), 8.49-8.56 (m, 1.4H), 7.73 (d, J = 8.0 Hz, 1H), 7.58 (t, J = 8.0 Hz, 1H), 7.42-7.49 (m, 2H), 7.11-7.17 (m, 1H), 4.86 (s 2H), 4.41 (s, 1.4H), 4.17-4.18 (m, 0.4H), 3.98-4.04 (m, 0.4H), 3.53-3.66 (m, 1.3H), 3.43-3.62 (m, 2.OH), 3.01 (s, 0.5H), 0.93-1.23 (m, 6.0H).<br>LCMS (ES) $C_{21}H_{23}N_5F_3O$ [M + H]$^+$ 418.1. |

TABLE 1-continued

303

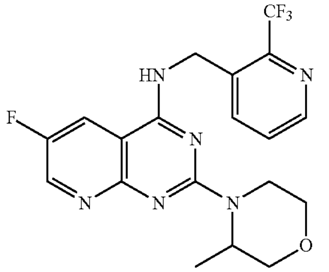 [SMILES: CC1COCCN1c1nc(NCc2cccnc2C(F)(F)F)c2cc(F)cnc2n1]

6-fluoro-2-(3-methylmorpholino)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.97 (s, 1H), 8.75-8.74 (d, J = 2.8 Hz, 1H), 8.61-8.60 (d, J = 4.4 Hz, 2H), 8.45-8.42 (dd, J = 8.8, 3.2 Hz 1H), 7.98-7.96 (d, J = 7.6 Hz, 1H), 7.66-7.63 (dd, J = 8.0, 4.4 Hz 1H), 4.95-4.91 (d, J = 16.4 Hz, 1H), 4.82-4.78 (d, J = 16.4 Hz, 1H), 4.43 (br s, 1H), 4.20-4.17 (d, J = 13.2 Hz, 1H), 3.83-3.80 (d, J = 11.2 Hz, 1H), 3.59-3.56 (d, J = 11.2 Hz, 1H), 3.29-3.26 (m, 1H), 2.99-2.95 (m, 1H), 0.87 (s, 3H).
LCMS (ES) $C_{19}H_{19}N_6F_4O$ [M + H]$^+$ 423.0.

304

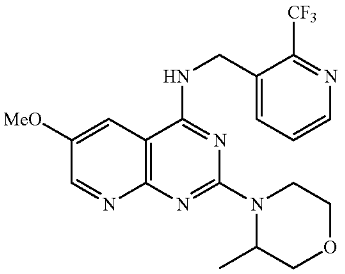 [SMILES: COc1cnc2nc(N3CCOCC3C)nc(NCc3cccnc3C(F)(F)F)c2c1]

6-methoxy-2-(3-methylmorpholino)-N-((2-(trifluoromethyl)pyridin-3-yl)methyl)pyrido[2,3-dipyrimidin-4-amine Synthesised via Route 6
$^1$H NMR (400 MHz, $CDCl_3$) δ (ppm) 8.63 (d, J = 3.1 Hz, 2H), 7.93 (d, J = 7.9 Hz, 1H), 7.46 (d, J = 7.9 Hz, 1H), 7.31 (d, J = 3.1 Hz, 1H), 6.21-6.18 (m, 1H), 5.14-4.96 (m, 2H), 4.70 (s, 1H), 4.43 (d, J = 13.1 Hz, 1H), 4.56-4.41 (m, 1H), 3.95-3.90 (m, 4H), 3.73-3.70 (m, 1H), 3.52-3.45 (m, 1H), 3.27-3.20 (m, 1H), 1.13 (d, J = 6.7 Hz, 3H).
LCMS (ES) $C_{20}H_{22}N_6F_3O$ [M + H]$^+$ 435.2.

305

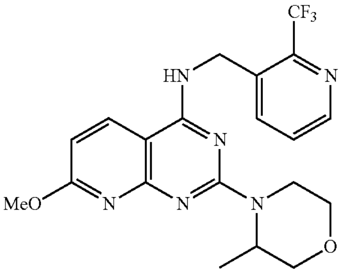 [SMILES: COc1ccc2c(NCc3cccnc3C(F)(F)F)nc(N3CCOCC3C)nc2n1]

7-methoxy-2-(3-methylmorpholino)-N-((2-(trifluoromethyl)pyridin-3-yl)methyl)pyrido[2,3-d]pyrimidin-4-amine Synthesised via Route 6
$^1$H NMR (400 MHz, DMSO-d6) δ (ppm) 8.61 (d, J = 4.3 Hz, 1H), 7.90 (d, J = 8.0 Hz, 1H), 7.76 (d, J = 8.8 Hz, 1H), 7.44 (dd, J = 7.9, 4.6 Hz, 1H), 6.53 (d, J = 8.7 Hz, 1H), 5.89 (t, J = 5.6 Hz, 1H), 5.03-5.12 (m, 1H), 4.87-4.97 (m, 1H), 4.69 (s, 1H), 4.49 (d, J = 13.1 Hz, 1H), 4.08 (s, 3H), 3.92 (dd, J = 11.1, 3.3 Hz, 1H), 3.58-3.74 (m, 2H), 3.47 (m, 1H), 3.25 (m, 1H), 1.10 (d, J = 6.5 Hz, 3H).
LCMS (ES) $C_{20}H_{22}N_6F_3O$ [M + H]$^+$ 435.1.

306

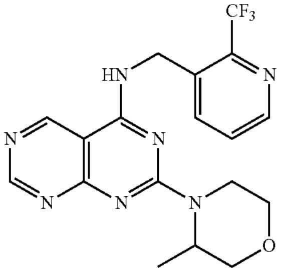 [SMILES: CC1COCCN1c1nc(NCc2cccnc2C(F)(F)F)c2cncnc2n1]

2-(3-methylmorpholino)-N-((2-(trifluoromethyl)pyridin-3-yl)methyl)pyrimido[4,5-d]pyrimidin-4-amine Synthesised via Route 6
$^1$H NMR (400 MHz, $CDCl_3$) δ (ppm) 9.05 (s, 1H), 9.00 (s, 1H), 8.64 (d, J = 4.5 Hz, 1H), 7.90 (d, J = 7.9 Hz, 1H), 7.43-7.54 (m, 1H), 6.55-6.89 (m, 1H), 4.29-5.21 (m, 4H), 3.92 (d, J = 10.3 Hz, 1H), 3.65-3.76 (m, 1H), 3.36-3.63 (m, 2H), 3.18-3.32 (m, 1H), 1.01-1.35 (m, 3H).
LCMS (ES) $C_{18}H_{19}N_7F_3O$ [M + H]$^+$ 406.1.

TABLE 1-continued

307

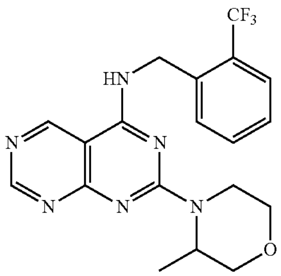 [SMILES: CC1COCCN1c1nc(NCc2ccccc2C(F)(F)F)c2cncnc2n1]

2-(3-methylmorpholino)-N-(2-(trifluoromethyl)benzyl)pyrimido[4,5-d]pyrimidin-4-amine
Synthesised via Route 6
$^1$H NMR (400 MHz, $CDCl_3$) δ (ppm) 9.04 (s, 1H), 8.92 (s, 1H), 7.73 (d, J = 7.7 Hz, 1H), 7.49-7.58 (m, 2H), 7.40-7.48 (m, 1H), 6.33-6.57 (m, 1H), 4.42-5.18 (m, 4H), 3.95 (dd, J = 11.2, 3.2 Hz, 1H), 3.59-3.77 (m, 2H), 3.41-3.55 (m, 1H), 3.30 (t, J = 13.1 Hz, 1H), 1.13-1.38 (m, 3H). LCMS (ES) $C_{19}H_{20}N_6F_3O$ $[M + H]^+$ 405.2.

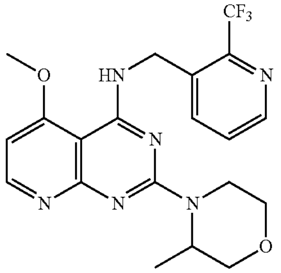 [SMILES: COc1ccnc2nc(N3CCOCC3C)nc(NCc3cccnc3C(F)(F)F)c12]

5-methoxy-2-(3-methylmorpholino)-N-((2-(trifluoromethyl)pyridin-3-yl)methyl)pyrido[2,3-d]pyrimidin-4-amine
Synthesised via Route 6
$^1$H NMR (400 MHz, $CDCl_3$) δ (ppm) 8.52-8.67 (m, 2H), 7.85-8.03 (m, 2.H), 7.44 (dd, J = 7.8, 4.7 Hz, 1H), 6.49 (d, J = 5.5 Hz, 1H), 4.89-5.11 (m, 2H), 4.37-4.86 (m, 2H), 4.06 (s, 3H), 3.91 (br dd, J = 11.4, 3.2 Hz, 1H), 3.58-3.72 (m, 2H), 3.46 (m, 1H), 3.15-3.30 (m, 1H), 1.12 (br s, 3H).
LCMS (ES) $C_{20}H_{22}N_6F_3O_2$ $[M + H]^+$ 435.1.

308

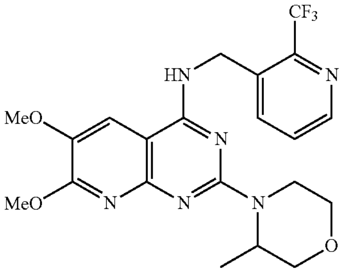 [SMILES: COc1cc2c(NCc3cccnc3C(F)(F)F)nc(N3CCOCC3C)nc2nc1OC]

6,7-dimethoxy-2-(3-methylmorpholino)-N-((2-(trifluoromethyl)pyridin-3-yl)methyl)pyrido[2,3-d]pyrimidin-4-amine
Synthesised via Route 6
$^1$H NMR (400 MHz, DMSO-d6) δ (ppm) 8.59 (d, J = 4.14 Hz, 1H), 8.55 (t, J = 5.33 Hz, 1H), 7.92 (d, J = 7.91 Hz, 1H), 7.89 (s, 1H), 7.64 (dd, J = 7.97, 4.71 Hz, 1H), 4.88-4.98 (m, 1H), 4.71-4.82 (m, 1H), 4.38 (s, 1 H), 4.11 (d, J = 12.42 Hz, 1H), 3.93 (s, 3H), 3.84 (s, 3H), 3.78 (dd, J = 11.11, 2.95 Hz, 1H) 3.52-3.58 (m, 1 H), 3.42 (dd, J = 11.36, 2.95 Hz, 1H), 3.27 (m, 1H), 2.94 (m, 1H), 0.82 (d, J = 6.15 Hz, 3H).
LCMS (ES) $C_{21}H_{24}N_6F_3O_3$ $[M + H]^+$ 465.2.

309

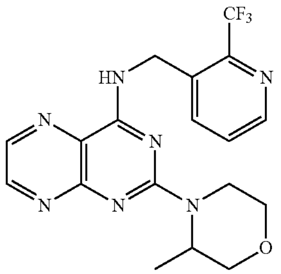

2-(3-methylmorpholino)-N-((2-(trifluoromethyl)pyridin-3-yl)methyl)pteridin-4-amine
Synthesised via Route 6
$^1$H NMR (400 MHz, $CDCl_3$) δ (ppm) 8.73 (d, J = 2.0 Hz, 1H), 8.64 (d, J = 4.0 Hz, 1H), 8.23 (d, J = 2.1 Hz, 1H), 7.94 (d, J = 7.8 Hz, 1H), 7.47 (dd, J = 8.0, 4.7 Hz, 1H), 7.36 (s, 1H), 4.93-5.16 (m, 2H), 4.34-4.93 (m, 2H), 3.96 (dd, J = 11.2, 3.3 Hz, 1H), 3.71-3.79 (m, 1H), 3.61-3.69 (m, 1H), 3.50 (, J = 11.9 Hz, 1H), 3.29 (t, J = 13.1 Hz, 1H), 1.24 (d, J = 16.7 Hz, 3H).
LCMS (ES) $C_{18}H_{19}N_7F_3O$ $[M + H]^+$ 406.1.

310

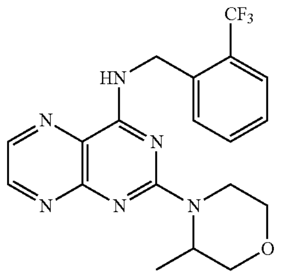

2-(3-methylmorpholino)-N-(2-(trifluoromethyl)benzyl)pteridin-4-amine
Synthesised via Route 6
$^1$H NMR (400 MHz, $CDCl_3$) δ (ppm) 8.70 (d, J = 2.1 Hz, 1H), 8.20 (d, J = 2.0 Hz, 1H), 7.71 (d, J = 7.7 Hz, 1H), 7.56-7.61 (m, 1H), 7.52 (t, J = 7.4 Hz, 1H), 7.38-7.44 (m, 1H), 7.29 (s, 1H), 4.83-5.11 (m, 3H), 4.62 (d, J = 13.6 Hz, 1H), 3.97 (dd, J = 11.3, 3.5 Hz. 1H), 3.73-3.79 (m, 1H), 3.65-3.71 (m, 1H), 3.53 (t, J = 11.8 Hz. 1H), 3.32 (t, J = 13.1 Hz, 1H), 1.26 (s, 3H).
LCMS (ES) $C_{19}H_{20}N_6F_3O$ $[M + H]^+$ 405.1.

TABLE 1-continued

| | | |
|---|---|---|
| 311 | 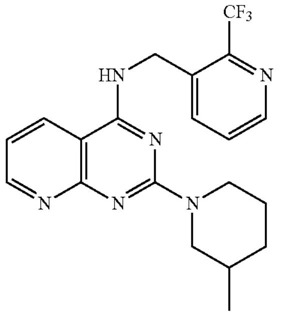 [SMILES: CC1CCCN(c2nc(NCc3cccnc3C(F)(F)F)c3cccnc3n2)C1] | 2-(3-methylpiperidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) δ 8.92 (t, J = 5.3 Hz, 1H), 8.66 (dd, J = 4.4, 1.8 Hz, 1H), 8.60 (d, J = 4.3 Hz, 1H), 8.47 (dd, J = 8.0,1.9 Hz, 1H), 7.93 (d, J = 7.9 Hz, 1H), 7.63 (dd, J = 8.0, 4.6 Hz, 1H), 7.10 (dd, J = 7.9, 4.5 Hz, 1H), 4.86 (s, 2H), 4.46 (br. s, 2H), 2.70 (br. s, 1H), 2.36 (t, J = 11.3 Hz, 1H), 1.67 (d, J = 10.0 Hz, 1H), 1.49 (br. s, 1H), 1.23 (br. s, 2H), 1.12-0.96 (m, 1H), 0.71 (s, 3H).<br>HRMS (ES) $C_{20}H_{22}F_3N_6$ $[M + H]^+$ 403.1844. |
| 312 | 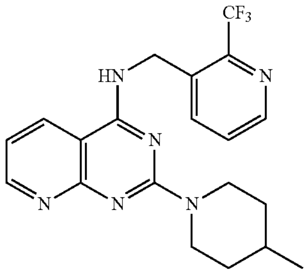 [SMILES: CC1CCN(c2nc(NCc3cccnc3C(F)(F)F)c3cccnc3n2)CC1] | 2-(4-methylpiperidin-1-yl)-N-((2-(trifluoromethyl)pyridin-3-yl)methyl)pyrido[2,3-d]pyrimidin-4-amine<br>Synthesised via Route 6<br>$^1$H NMR (400 MHz, DMSO-d6) δ (ppm) 8.92 (t, J = 5.4 Hz, 1H), 8.66 (dd, J = 4.4,1.6 Hz, 1H), 8.60 (d, J = 4.4 Hz, 1H), 8.47 (dd, J = 8.0, 1.7 Hz, 1H), 7.95 (d, J = 7.9 Hz, 1H), 7.64 (dd, J = 8.0, 4.6 Hz, 1H), 7.10 (dd, J = 7.9, 4.5 Hz, 1H), 4.86 (d, J = 4.5 Hz, 2H), 4.52 (br. s, 2H), 2.69 (t, J = 12.1 Hz, 2H), 1.70-1.37 (m, 3H), 0.83 (m, 5H).<br>HRMS (ES) $C_{20}H_{22}F_3N_6$ $[M + H]^+$ 403.1853. |

Biology

In Vitro Insect Cell Line Assay

A C6/36 *Aedes albopictus* cell line infected with *Wolbachia pipientis* (*Wolbachia* strain wAlbB) derived from Aa23 *A. albopictus* cell line (O'Neill et al., 1997; Insect Mol Biol; Turner et al., (2006) J. Immunol. 7:1240-1249) was used to screen compounds. Cells were cultured in Leibovitz's L15+ L-glutamine supplemented with heat-inactivated Foetal Calf Serum (HI—FCS), non-essential amino acids and tryptose phosphate broth. Culture medium was filter-sterilized through a 0.2 μm filter and stored at 4° C. Compounds were provided as 10 mM stocks in DMSO, diluted to 50 μM working stock to give final concentration of 5 μM on the test plate. Concentrated stocks were frozen at −20° C.

Prior to use in the screening assay, cell cultures were sub-passaged (6 days prior) to provide ~90% confluent cells on Day 0 of screening assay. On Day 0 (assay set-up), the medium was removed from the stock culture flask and replaced with fresh medium. The cells were detached by scraping and cell density was calculated using an automated cell counter. The cells were then diluted at working density and aliquoted at 90 μl to each well of a Cell Carrier 384 well plate (Perkin Elmer). Cell plates were incubated at 26° C.

Control solution (DMSO-medium) was dispensed at 10 μl per well for "untreated" wells. Test solution (Drug-DMSO) was also dispensed at 10 μl (from working plate) per well for "treated" wells. The plates were incubated at 2600, inside plastic wallet in incubator, for 7 days.

On Day 7, 25 μl of staining medium/dye (SYTO 11, Life Technologies) was added to each sample well and allowed to stain for 15 minutes in the dark. All the medium was removed from each sample well without disturbing the cells and replaced with 100 μl of fresh medium. Plates were imaged on the Operetta High Content Imaging system (Perkin Elmer) and analyzed using texture analysis through Harmony software (Perkin Elmer). The cell-based screen and analysis are described in detail in Clare et al. (2014) J Biomol Screen.

Anti-*Wolbachia* activity is catagorised in Table 2 as follows +: 1,000 nM<$EC_{50}$≤100,000 nM; ++: 100 nM<$EC_{50}$≤1,000 nM; +++: 10 nM<$EC_{50}$≤100 nM; ++++: 1 nM<$EC_{50}$≤10 nM; +++++: 0.01 nM<$EC_{50}$≤1 nM; ++++++: $EC_{50}$≤0.01 nM.

TABLE 2
| Entry | Structure | In vitro anti-Wolbachia activity |
|---|---|---|
| 1 | 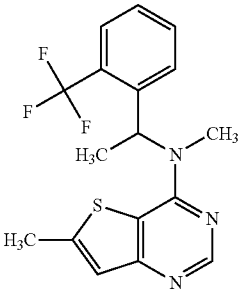 [SMILES: Cc1cc2ncnc(N(C)C(C)c3ccccc3C(F)(F)F)c2s1] | + |
| 2 | 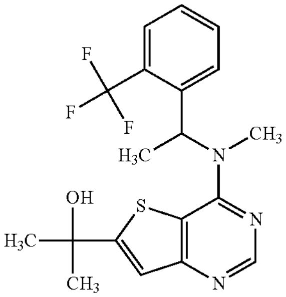 [SMILES: CC(c1ccccc1C(F)(F)F)N(C)c1ncnc2cc(C(C)(C)O)sc12] | + |
| 3 | 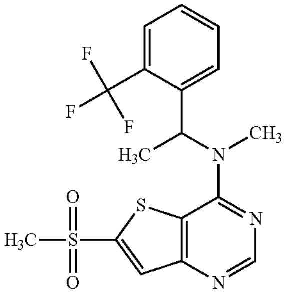 | + |
| 4 | 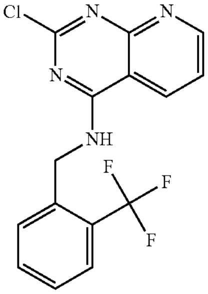 [SMILES: FC(F)(F)c1ccccc1CNc1nc(Cl)nc2ncccc12] | ++ |
| 5 | 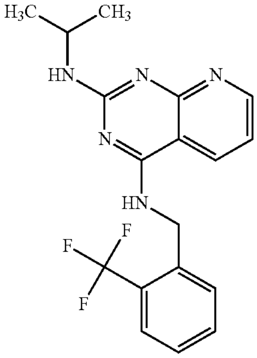 [SMILES: CC(C)Nc1nc(NCc2ccccc2C(F)(F)F)c2cccnc2n1] | ++++ |

TABLE 2-continued
| Entry | Structure | In vitro anti-Wolbachia activity |
| --- | --- | --- |
| 6 | 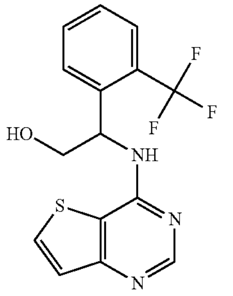 [SMILES: OCC(Nc1ncnc2ccsc12)c1ccccc1C(F)(F)F] | + |
| 7 | 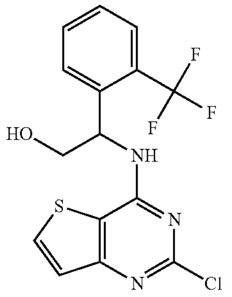 [SMILES: OCC(Nc1nc(Cl)nc2ccsc12)c1ccccc1C(F)(F)F] | ++ |
| 8 | 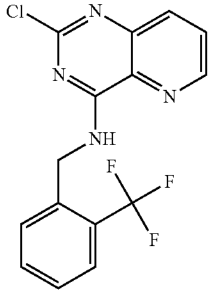 [SMILES: FC(F)(F)c1ccccc1CNc1nc(Cl)nc2cccnc12] | ++ |
| 9 | 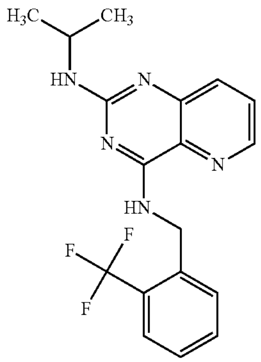 [SMILES: CC(C)Nc1nc(NCc2ccccc2C(F)(F)F)c2ncccc2n1] | ++ |

TABLE 2-continued
| Entry | Structure | In vitro anti-Wolbachia activity |
|---|---|---|
| 10 | 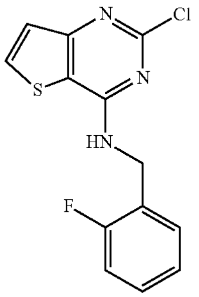 | + |
| 11 | 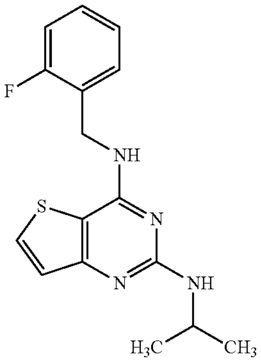 [SMILES: CC(C)Nc1nc(NCc2ccccc2F)c2sccc2n1] | ++ |
| 12 | 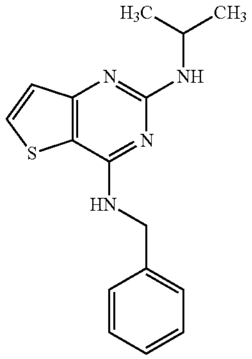 [SMILES: CC(C)Nc1nc(NCc2ccccc2)c2sccc2n1] | + |
| 13 | 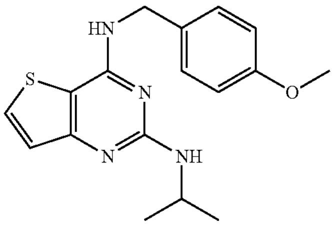 [SMILES: COc1ccc(CNc2nc(NC(C)C)nc3ccsc23)cc1] | + |

TABLE 2-continued
| Entry | Structure | In vitro anti-Wolbachia activity |
|---|---|---|
| 14 | 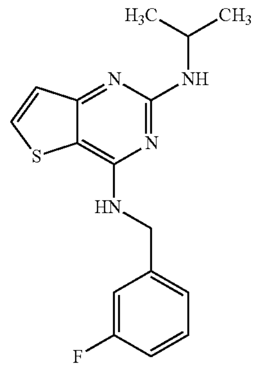 [SMILES: CC(C)Nc1nc(NCc2cccc(F)c2)c2sccc2n1] | ++ |
| 15 | 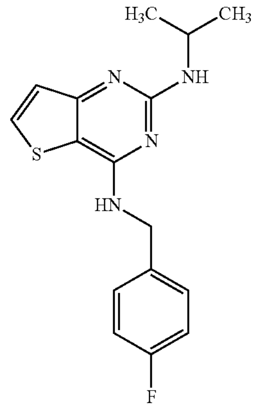 [SMILES: CC(C)Nc1nc(NCc2ccc(F)cc2)c2sccc2n1] | ++ |
| 16 | 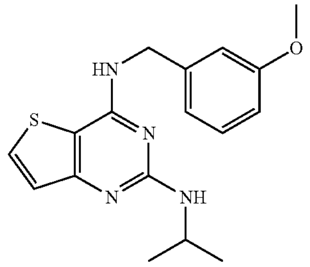 [SMILES: COc1cccc(CNc2nc(NC(C)C)nc3ccsc23)c1] | + |
| 17 | 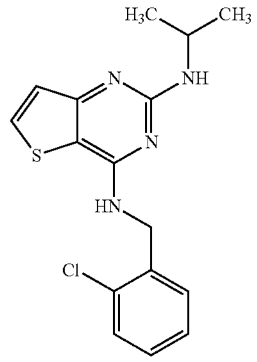 [SMILES: CC(C)Nc1nc(NCc2ccccc2Cl)c2sccc2n1] | +++ |

TABLE 2-continued
| Entry | Structure | In vitro anti-Wolbachia activity |
|---|---|---|
| 18 | 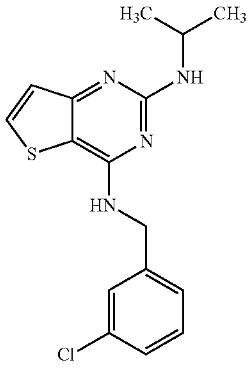 [SMILES: CC(C)Nc1nc(NCc2cccc(Cl)c2)c2sccc2n1] | + |
| 19 | 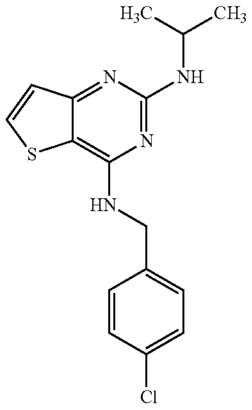 [SMILES: CC(C)Nc1nc(NCc2ccc(Cl)cc2)c2sccc2n1] | + |
| 20 | 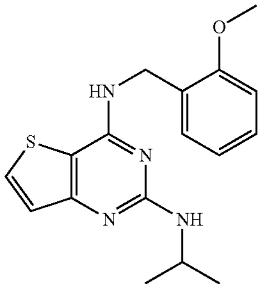 [SMILES: COc1ccccc1CNc1nc(NC(C)C)nc2ccsc12] | + |
| 21 | 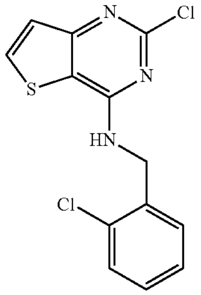 | +++ |

TABLE 2-continued
| Entry | Structure | In vitro anti-Wolbachia activity |
|---|---|---|
| 22 | 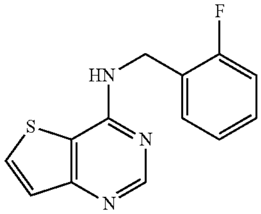 [SMILES: Fc1ccccc1CNc1ncnc2ccsc12] | + |
| 23 | 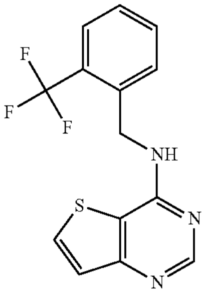 [SMILES: FC(F)(F)c1ccccc1CNc1ncnc2ccsc12] | +++ |
| 24 | 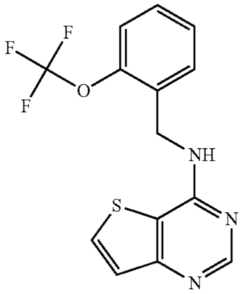 [SMILES: FC(F)(F)Oc1ccccc1CNc1ncnc2ccsc12] | ++ |
| 25 | 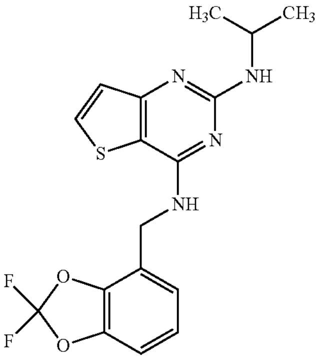 [SMILES: CC(C)Nc1nc(NCc2cccc3c2OC(F)(F)O3)c2sccc2n1] | ++ |
| 26 | 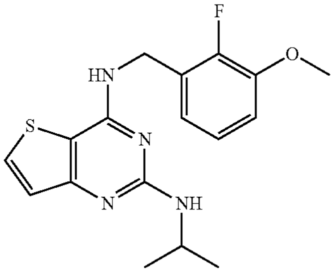 [SMILES: COc1cccc(CNc2nc(NC(C)C)nc3ccsc23)c1F] | ++ |

TABLE 2-continued
| Entry | Structure | In vitro anti-Wolbachia activity |
| --- | --- | --- |
| 27 | 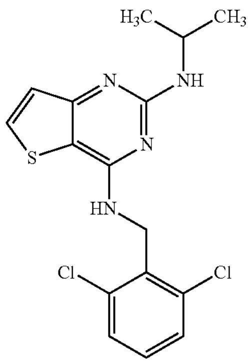 [SMILES: CC(C)Nc1nc(NCc2c(Cl)cccc2Cl)c2sccc2n1] | + |
| 28 | 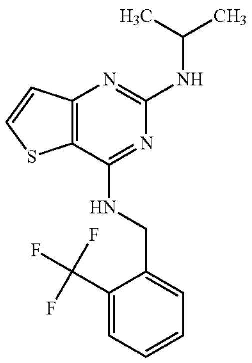 [SMILES: CC(C)Nc1nc(NCc2ccccc2C(F)(F)F)c2sccc2n1] | +++ |
| 29 | 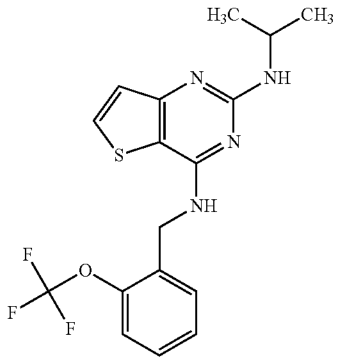 [SMILES: CC(C)Nc1nc(NCc2ccccc2OC(F)(F)F)c2sccc2n1] | ++ |
| 30 | 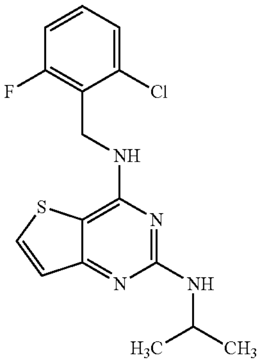 [SMILES: CC(C)Nc1nc(NCc2c(F)cccc2Cl)c2sccc2n1] | ++ |

TABLE 2-continued
| Entry | Structure | In vitro anti-Wolbachia activity |
|---|---|---|
| 31 | 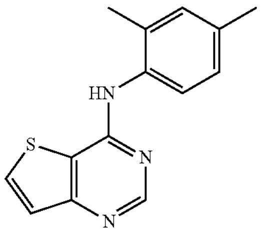 [SMILES: Cc1ccc(Nc2ncnc3ccsc23)c(C)c1] | + |
| 32 | 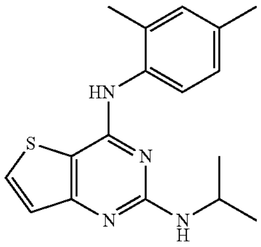 [SMILES: Cc1ccc(Nc2nc(NC(C)C)nc3ccsc23)c(C)c1] | + |
| 33 | 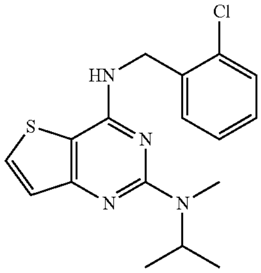 [SMILES: CC(C)N(C)c1nc(NCc2ccccc2Cl)c2sccc2n1] | ++ |
| 34 | 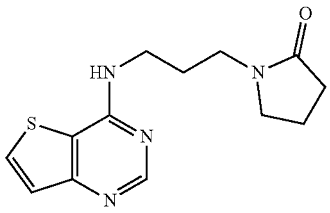 [SMILES: O=C1CCCN1CCCNc1ncnc2ccsc12] | + |
| 35 | 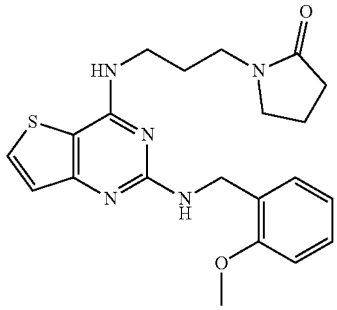 [SMILES: COc1ccccc1CNc1nc(NCCCN2CCCC2=O)c2sccc2n1] | ++ |

TABLE 2-continued
| Entry | Structure | In vitro anti-Wolbachia activity |
| --- | --- | --- |
| 36 | 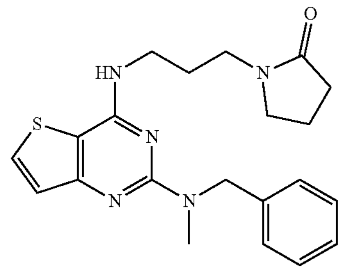 [SMILES: CN(Cc1ccccc1)c1nc(NCCCN2CCCC2=O)c2sccc2n1] | + |
| 37 | 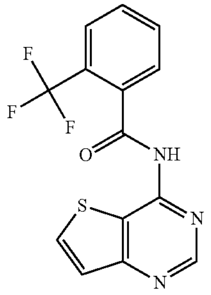 [SMILES: O=C(Nc1ncnc2ccsc12)c1ccccc1C(F)(F)F] | + |
| 38 | 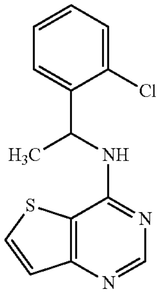 [SMILES: CC(Nc1ncnc2ccsc12)c1ccccc1Cl] | + |
| 39 | 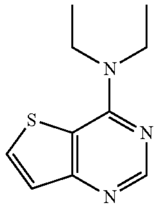 | + |
| 40 | 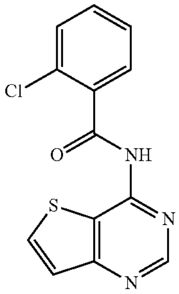 [SMILES: O=C(Nc1ncnc2ccsc12)c1ccccc1Cl] | + |

TABLE 2-continued
| Entry | Structure | In vitro anti-Wolbachia activity |
|---|---|---|
| 41 | 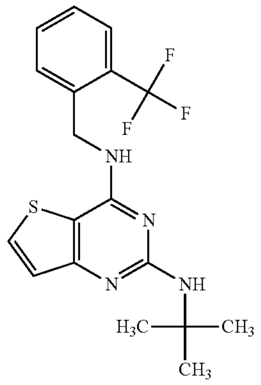 [SMILES: CC(C)(C)Nc1nc(NCc2ccccc2C(F)(F)F)c2sccc2n1] | +++ |
| 42 | 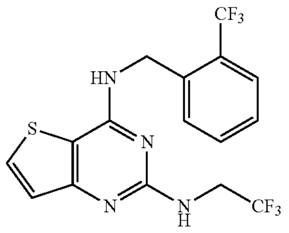 [SMILES: FC(F)(F)CNc1nc(NCc2ccccc2C(F)(F)F)c2sccc2n1] | ++ |
| 43 | 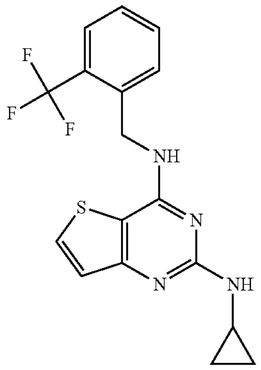 [SMILES: FC(F)(F)c1ccccc1CNc1nc(NC2CC2)nc2ccsc12] | ++ |
| 44 | 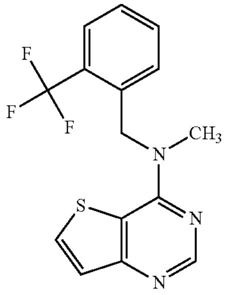 [SMILES: CN(Cc1ccccc1C(F)(F)F)c1ncnc2ccsc12] | +++ |

TABLE 2-continued
| Entry | Structure | In vitro anti-Wolbachia activity |
|---|---|---|
| 45 | 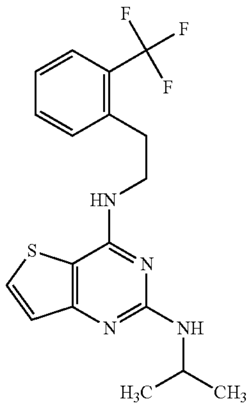 [SMILES: CC(C)Nc1nc(NCCc2ccccc2C(F)(F)F)c2sccc2n1] | ++ |
| 46 | 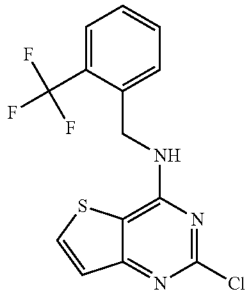 [SMILES: FC(F)(F)c1ccccc1CNc1nc(Cl)nc2ccsc12] | +++ |
| 47 | 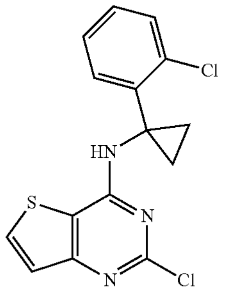 [SMILES: Clc1nc(NC2(c3ccccc3Cl)CC2)c2sccc2n1] | + |
| 48 | 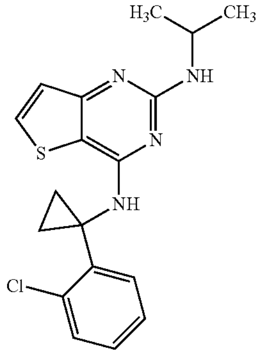 [SMILES: CC(C)Nc1nc(NC2(c3ccccc3Cl)CC2)c2sccc2n1] | ++ |

TABLE 2-continued
| Entry | Structure | In vitro anti-Wolbachia activity |
|---|---|---|
| 49 | 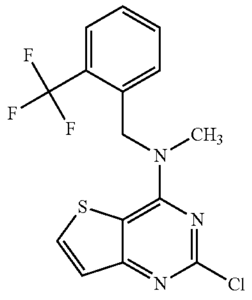 [SMILES: CN(Cc1ccccc1C(F)(F)F)c1nc(Cl)nc2ccsc12] | ++++ |
| 50 | 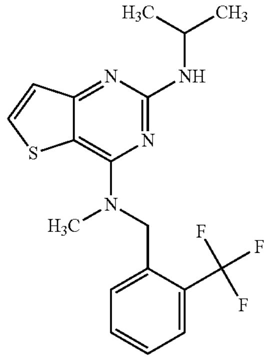 [SMILES: CC(C)Nc1nc(N(C)Cc2ccccc2C(F)(F)F)c2sccc2n1] | +++ |
| 51 | 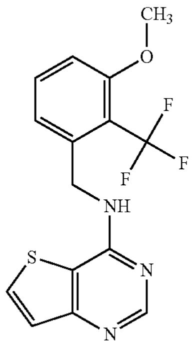 [SMILES: COc1cccc(CNc2ncnc3ccsc23)c1C(F)(F)F] | +++ |
| 52 | 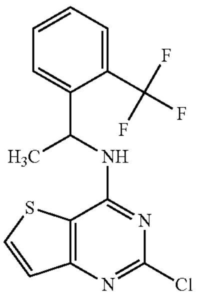 [SMILES: CC(Nc1nc(Cl)nc2ccsc12)c1ccccc1C(F)(F)F] | +++ |

TABLE 2-continued
| Entry | Structure | In vitro anti-Wolbachia activity |
|---|---|---|
| 53 | 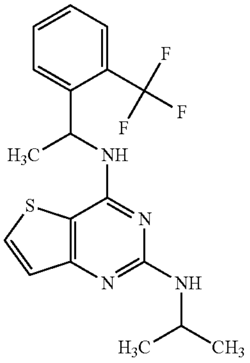 [SMILES: CC(C)Nc1nc(NC(C)c2ccccc2C(F)(F)F)c2sccc2n1] | ++++ |
| 54 | 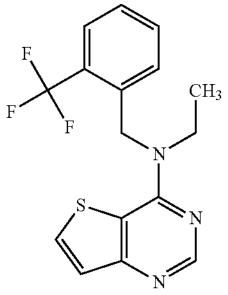 [SMILES: CCN(Cc1ccccc1C(F)(F)F)c1ncnc2ccsc12] | ++++ |
| 55 | 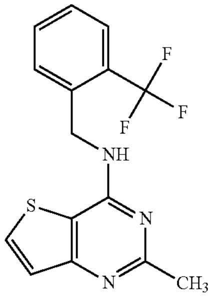 [SMILES: Cc1nc(NCc2ccccc2C(F)(F)F)c2sccc2n1] | +++ |
| 56 | 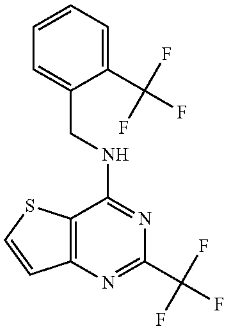 [SMILES: FC(F)(F)c1nc(NCc2ccccc2C(F)(F)F)c2sccc2n1] | +++ |

TABLE 2-continued
| Entry | Structure | In vitro anti-Wolbachia activity |
| --- | --- | --- |
| 57 | 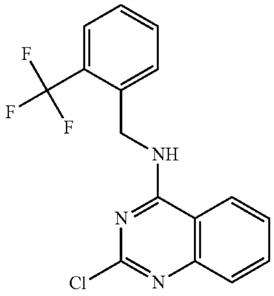 [SMILES: FC(F)(F)c1ccccc1CNc1nc(Cl)nc2ccccc12] | +++ |
| 58 | 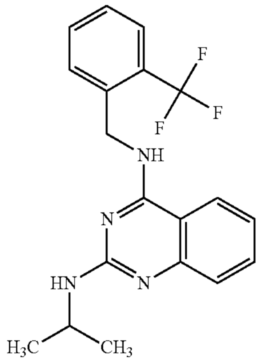 [SMILES: CC(C)Nc1nc(NCc2ccccc2C(F)(F)F)c2ccccc2n1] | ++ |
| 59 | 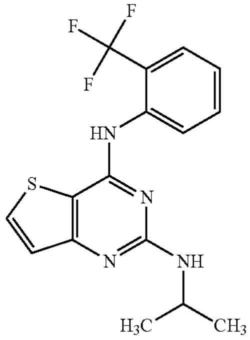 [SMILES: CC(C)Nc1nc(Nc2ccccc2C(F)(F)F)c2sccc2n1] | ++ |
| 60 | 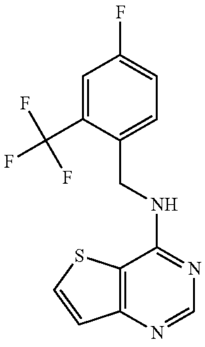 [SMILES: Fc1ccc(CNc2ncnc3ccsc23)c(C(F)(F)F)c1] | +++ |

TABLE 2-continued
| Entry | Structure | In vitro anti-Wolbachia activity |
|---|---|---|
| 61 | 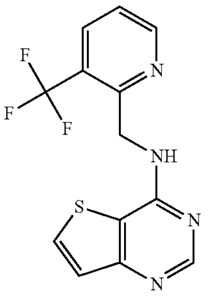 [SMILES: FC(F)(F)c1cccnc1CNc1ncnc2ccsc12] | + |
| 62 | 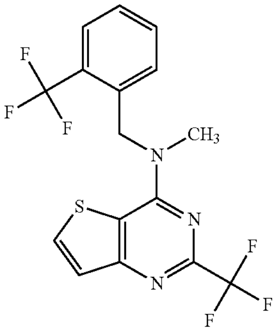 [SMILES: CN(Cc1ccccc1C(F)(F)F)c1nc(C(F)(F)F)nc2ccsc12] | +++ |
| 63 | 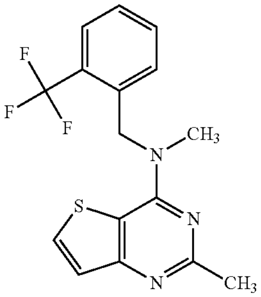 [SMILES: Cc1nc(N(C)Cc2ccccc2C(F)(F)F)c2sccc2n1] | +++ |
| 64 | 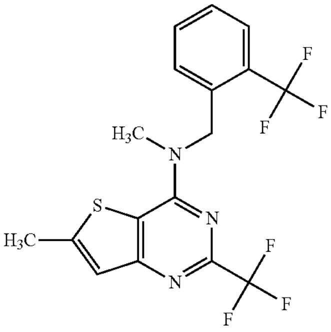 [SMILES: Cc1cc2nc(C(F)(F)F)nc(N(C)Cc3ccccc3C(F)(F)F)c2s1] | ++ |

TABLE 2-continued
| Entry | Structure | In vitro anti-Wolbachia activity |
|---|---|---|
| 65 | 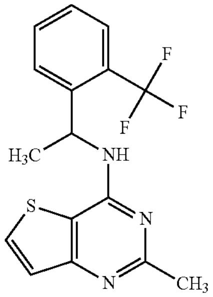 [SMILES: Cc1nc(NC(C)c2ccccc2C(F)(F)F)c2sccc2n1] | +++ |
| 66 | 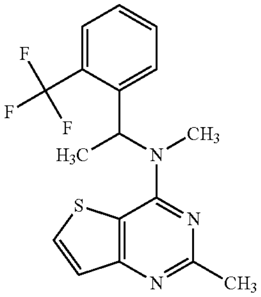 [SMILES: Cc1nc(N(C)C(C)c2ccccc2C(F)(F)F)c2sccc2n1] | ++++ |
| 67 | 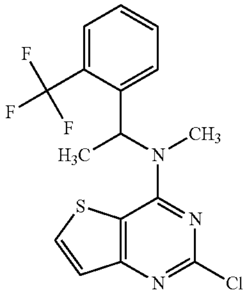 [SMILES: CC(c1ccccc1C(F)(F)F)N(C)c1nc(Cl)nc2ccsc12] | ++ |
| 68 | 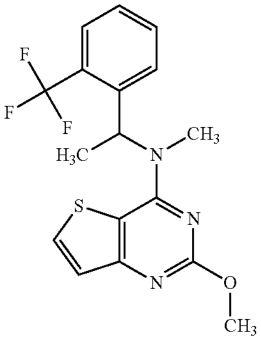 [SMILES: COc1nc(N(C)C(C)c2ccccc2C(F)(F)F)c2sccc2n1] | +++ |
| 69 | 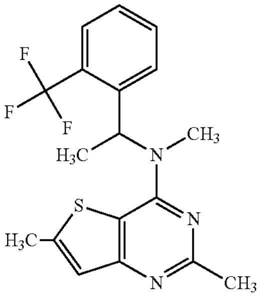 [SMILES: Cc1nc(N(C)C(C)c2ccccc2C(F)(F)F)c2sc(C)cc2n1] | + |

TABLE 2-continued
| Entry | Structure | In vitro anti-Wolbachia activity |
|---|---|---|
| 70 | 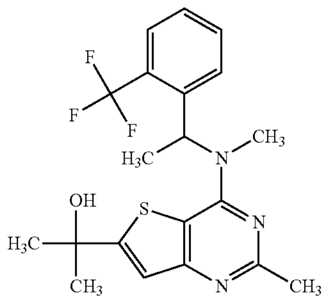 [SMILES: Cc1nc(N(C)C(C)c2ccccc2C(F)(F)F)c2sc(C(C)(C)O)cc2n1] | + |
| 71 | 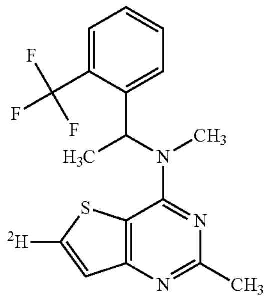 [SMILES: [2H]c1cc2nc(C)nc(N(C)C(C)c3ccccc3C(F)(F)F)c2s1] | +++ |
| 72 | 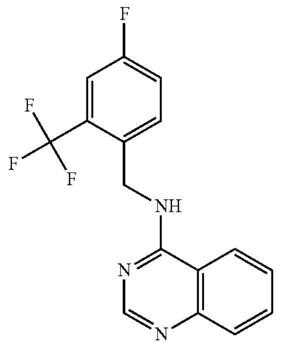 [SMILES: Fc1ccc(CNc2ncnc3ccccc23)c(C(F)(F)F)c1] | +++ |
| 73 | 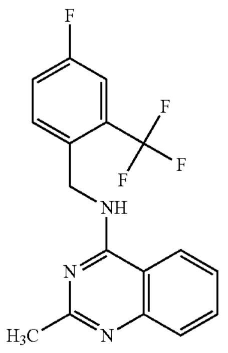 [SMILES: Cc1nc(NCc2ccc(F)cc2C(F)(F)F)c2ccccc2n1] | ++ |

TABLE 2-continued
| Entry | Structure | In vitro anti-Wolbachia activity |
|---|---|---|
| 74 | 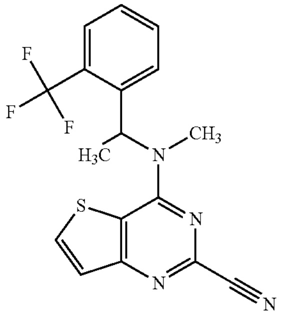 [SMILES: CC(c1ccccc1C(F)(F)F)N(C)c1nc(C#N)nc2ccsc12] | + |
| 75 | 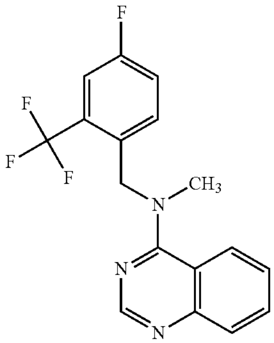 [SMILES: CN(Cc1ccc(F)cc1C(F)(F)F)c1ncnc2ccccc12] | ++ |
| 76 | 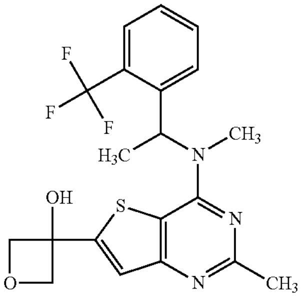 [SMILES: Cc1nc(N(C)C(C)c2ccccc2C(F)(F)F)c2sc(C3(O)COC3)cc2n1] | + |
| 77 | 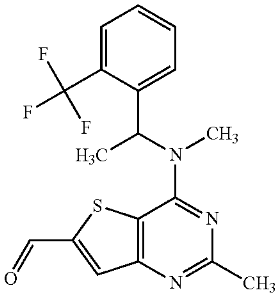 [SMILES: Cc1nc(N(C)C(C)c2ccccc2C(F)(F)F)c2sc(C=O)cc2n1] | ++ |
| 78 | 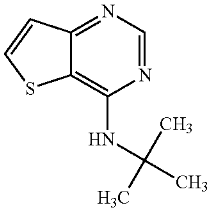 | + |

TABLE 2-continued
| Entry | Structure | In vitro anti-Wolbachia activity |
|---|---|---|
| 79 | 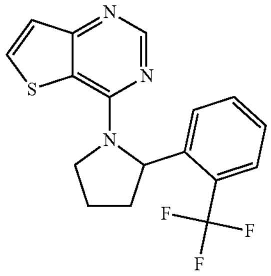 [SMILES: FC(F)(F)c1ccccc1C1CCCN1c1ncnc2ccsc12] | ++ |
| 80 | 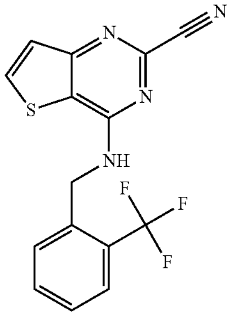 [SMILES: N#Cc1nc(NCc2ccccc2C(F)(F)F)c2sccc2n1] | +++ |
| 81 | 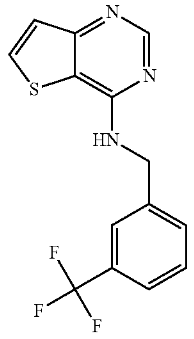 [SMILES: FC(F)(F)c1cccc(CNc2ncnc3ccsc23)c1] | + |
| 82 | 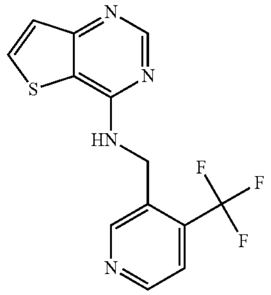 [SMILES: FC(F)(F)c1ccncc1CNc1ncnc2ccsc12] | + |
| 83 | 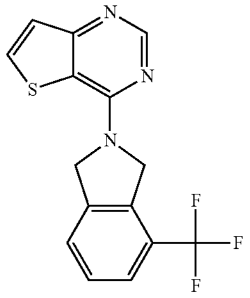 [SMILES: FC(F)(F)c1cccc2c1CN(c1ncnc3ccsc13)C2] | + |

TABLE 2-continued
| Entry | Structure | In vitro anti-Wolbachia activity |
| --- | --- | --- |
| 84 | 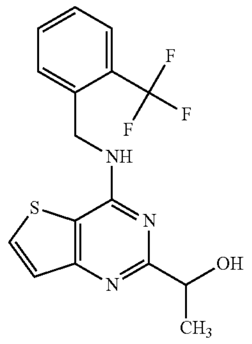 [SMILES: CC(O)c1nc(NCc2ccccc2C(F)(F)F)c2sccc2n1] | + |
| 85 | 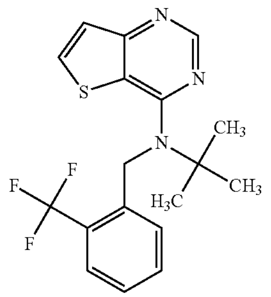 [SMILES: CC(C)(C)N(Cc1ccccc1C(F)(F)F)c1ncnc2ccsc12] | ++ |
| 86 | 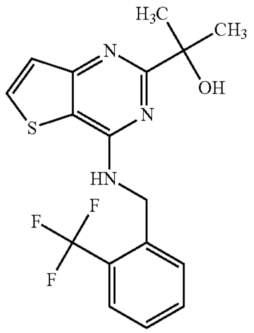 [SMILES: CC(C)(O)c1nc(NCc2ccccc2C(F)(F)F)c2sccc2n1] | + |
| 87 | 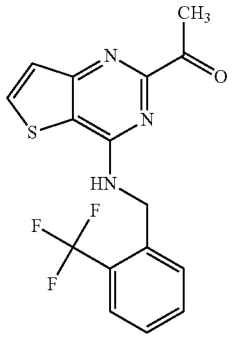 [SMILES: CC(=O)c1nc(NCc2ccccc2C(F)(F)F)c2sccc2n1] | ++ |

TABLE 2-continued
| Entry | Structure | In vitro anti-Wolbachia activity |
| --- | --- | --- |
| 88 | 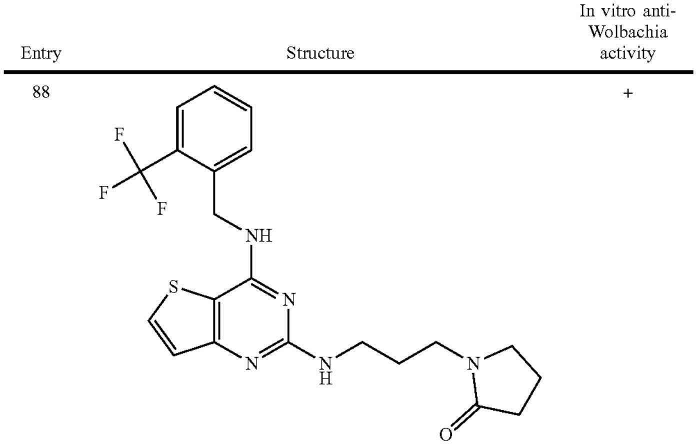 | + |
| 89 | 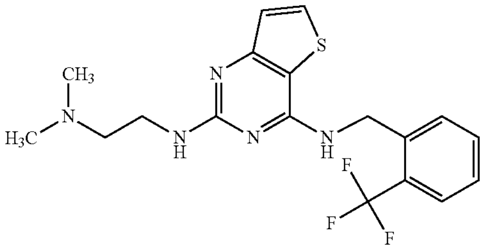 [SMILES: CN(C)CCNc1nc(NCc2ccccc2C(F)(F)F)c2sccc2n1] | + |
| 90 | 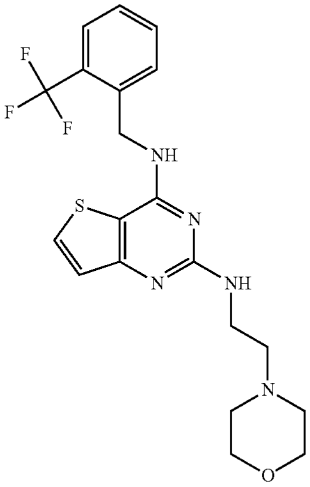 [SMILES: FC(F)(F)c1ccccc1CNc1nc(NCCN2CCOCC2)nc2ccsc12] | + |
| 91 | 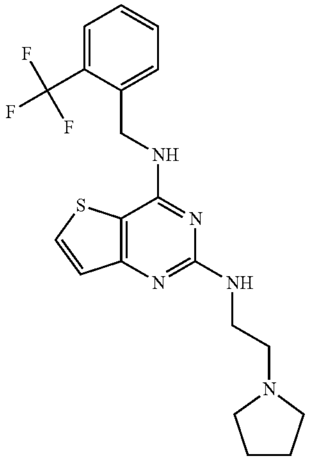 [SMILES: FC(F)(F)c1ccccc1CNc1nc(NCCN2CCCC2)nc2ccsc12] | + |

TABLE 2-continued
| Entry | Structure | In vitro anti-Wolbachia activity |
|---|---|---|
| 92 | 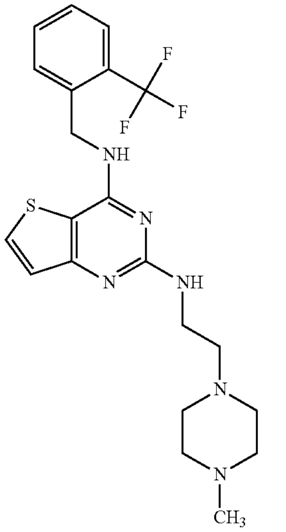 [SMILES: CN1CCN(CCNc2nc(NCc3ccccc3C(F)(F)F)c3sccc3n2)CC1] | + |
| 93 | 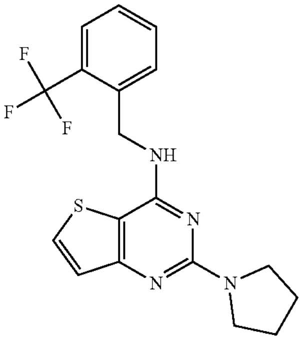 [SMILES: FC(F)(F)c1ccccc1CNc1nc(N2CCCC2)nc2ccsc12] | ++ |
| 94 | 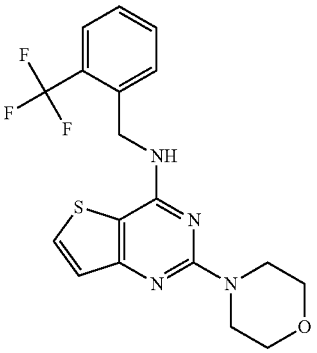 [SMILES: FC(F)(F)c1ccccc1CNc1nc(N2CCOCC2)nc2ccsc12] | + |

TABLE 2-continued
| Entry | Structure | In vitro anti-Wolbachia activity |
|---|---|---|
| 95 | 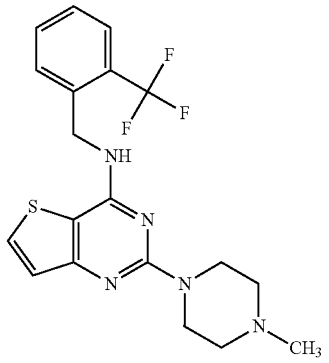 [SMILES: CN1CCN(c2nc(NCc3ccccc3C(F)(F)F)c3sccc3n2)CC1] | + |
| 96 | 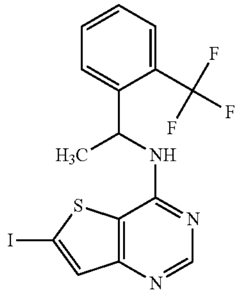 [SMILES: CC(Nc1ncnc2cc(I)sc12)c1ccccc1C(F)(F)F] | + |
| 97 | 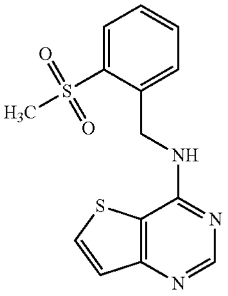 [SMILES: CS(=O)(=O)c1ccccc1CNc1ncnc2ccsc12] | ++ |
| 98 | 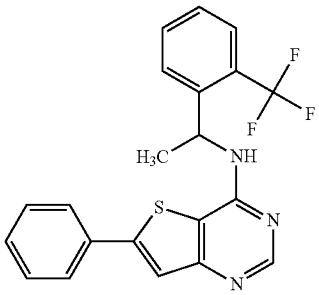 [SMILES: CC(Nc1ncnc2cc(-c3ccccc3)sc12)c1ccccc1C(F)(F)F] | + |
| 99 | 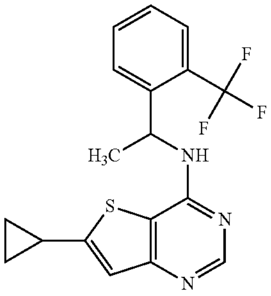 [SMILES: CC(Nc1ncnc2cc(C3CC3)sc12)c1ccccc1C(F)(F)F] | + |

TABLE 2-continued
| Entry | Structure | In vitro anti-Wolbachia activity |
| --- | --- | --- |
| 101 | 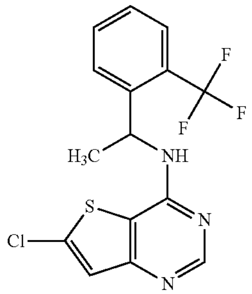 [SMILES: CC(Nc1ncnc2cc(Cl)sc12)c1ccccc1C(F)(F)F] | + |
| 102 | 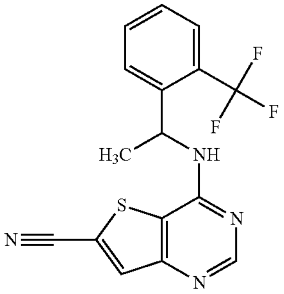 [SMILES: CC(Nc1ncnc2cc(C#N)sc12)c1ccccc1C(F)(F)F] | + |
| 103 | 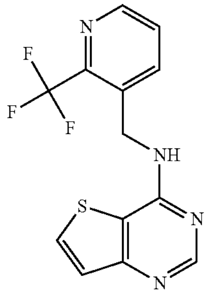 [SMILES: FC(F)(F)c1ncccc1CNc1ncnc2ccsc12] | +++ |
| 104 | 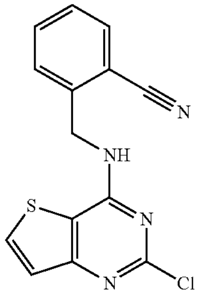 [SMILES: N#Cc1ccccc1CNc1nc(Cl)nc2ccsc12] | ++ |
| 105 | 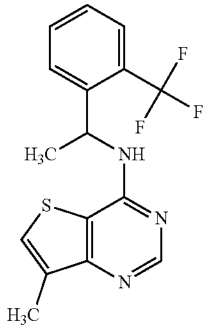 [SMILES: Cc1csc2c(NC(C)c3ccccc3C(F)(F)F)ncnc12] | + |

TABLE 2-continued
| Entry | Structure | In vitro anti-Wolbachia activity |
| --- | --- | --- |
| 106 | 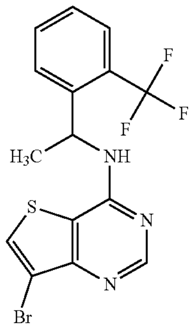 [SMILES: CC(Nc1ncnc2c(Br)csc12)c1ccccc1C(F)(F)F] | + |
| 108 | 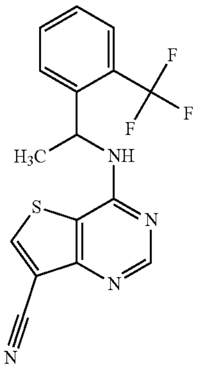 [SMILES: CC(Nc1ncnc2c(C#N)csc12)c1ccccc1C(F)(F)F] | + |
| 109 | 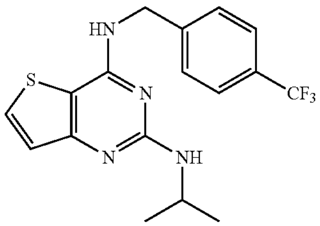 [SMILES: CC(C)Nc1nc(NCc2ccc(C(F)(F)F)cc2)c2sccc2n1] | + |
| 110 | 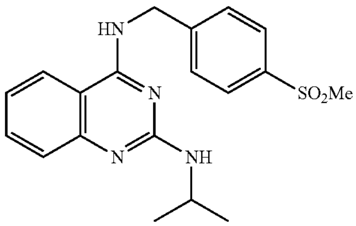 [SMILES: CC(C)Nc1nc(NCc2ccc(S(C)(=O)=O)cc2)c2ccccc2n1] | + |
| 111 | | + |

TABLE 2-continued
| Entry | Structure | In vitro anti-Wolbachia activity |
|---|---|---|
| 112 | 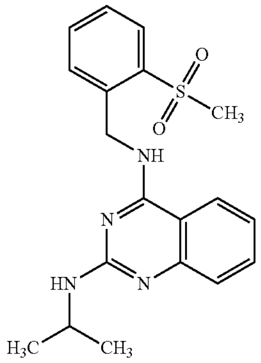 [SMILES: CC(C)Nc1nc(NCc2ccccc2S(C)(=O)=O)c2ccccc2n1] | ++ |
| 113 | 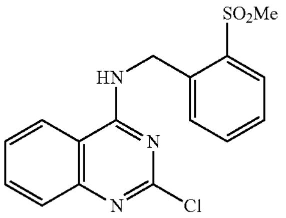 [SMILES: CS(=O)(=O)c1ccccc1CNc1nc(Cl)nc2ccccc12] | + |
| 114 | 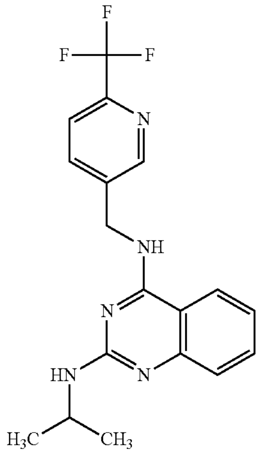 [SMILES: CC(C)Nc1nc(NCc2ccc(C(F)(F)F)nc2)c2ccccc2n1] | ++ |
| 115 | 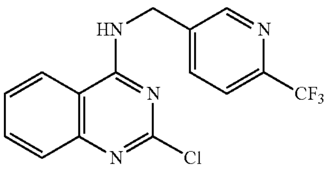 [SMILES: FC(F)(F)c1ccc(CNc2nc(Cl)nc3ccccc23)cn1] | + |

TABLE 2-continued
| Entry | Structure | In vitro anti-Wolbachia activity |
|---|---|---|
| 116 | 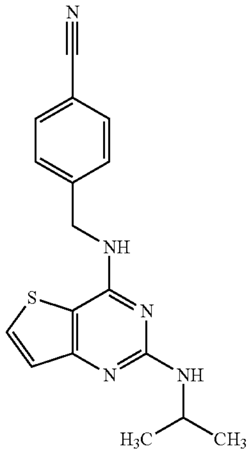 [SMILES: CC(C)Nc1nc(NCc2ccc(C#N)cc2)c2sccc2n1] | ++ |
| 117 | 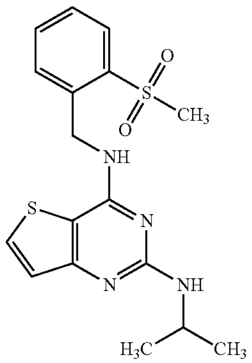 [SMILES: CC(C)Nc1nc(NCc2ccccc2S(C)(=O)=O)c2sccc2n1] | ++ |
| 118 | 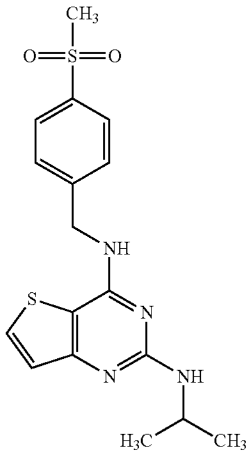 [SMILES: CC(C)Nc1nc(NCc2ccc(S(C)(=O)=O)cc2)c2sccc2n1] | + |

TABLE 2-continued
| Entry | Structure | In vitro anti-Wolbachia activity |
|---|---|---|
| 119 | 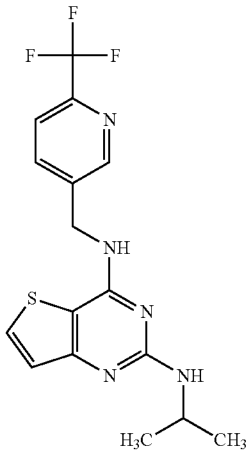 | ++ |
| 120 | 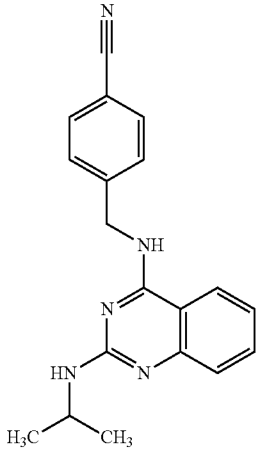 [SMILES: CC(C)Nc1nc(NCc2ccc(C#N)cc2)c2ccccc2n1] | ++ |
| 121 | 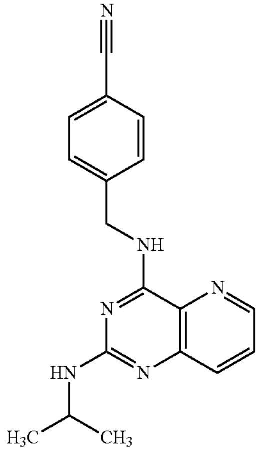 [SMILES: CC(C)Nc1nc(NCc2ccc(C#N)cc2)c2ncccc2n1] | + |

TABLE 2-continued
| Entry | Structure | In vitro anti-Wolbachia activity |
|---|---|---|
| 122 | 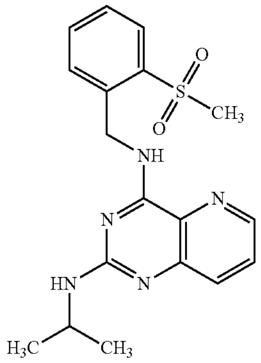 [SMILES: CC(C)Nc1nc(NCc2ccccc2S(C)(=O)=O)c2ncccc2n1] | + |
| 123 | 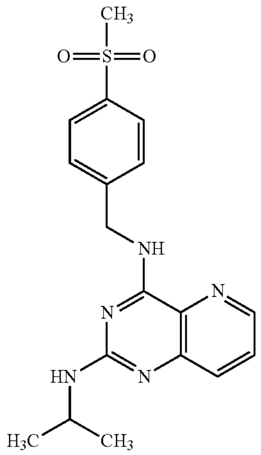 [SMILES: CC(C)Nc1nc(NCc2ccc(S(C)(=O)=O)cc2)c2ncccc2n1] | + |
| 124 | 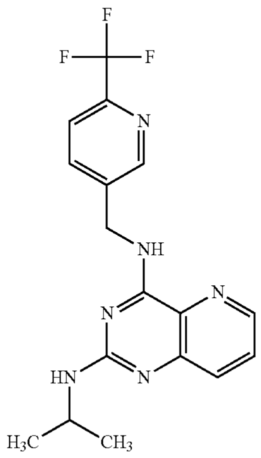 [SMILES: CC(C)Nc1nc(NCc2ccc(C(F)(F)F)nc2)c2ncccc2n1] | + |

TABLE 2-continued
| Entry | Structure | In vitro anti-Wolbachia activity |
|---|---|---|
| 125 | 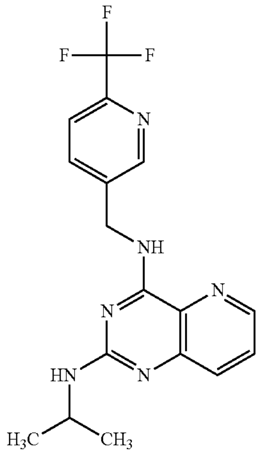 [SMILES: CC(C)Nc1nc(NCc2ccc(C(F)(F)F)nc2)c2ncccc2n1] | + |
| 126 | 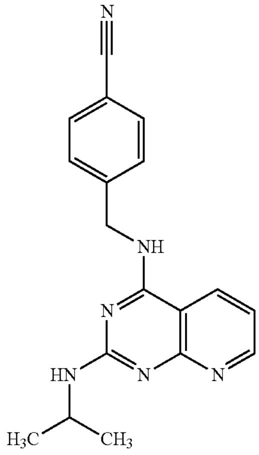 | ++ |
| 127 | 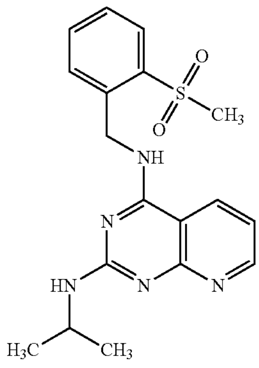 [SMILES: CC(C)Nc1nc(NCc2ccccc2S(C)(=O)=O)c2cccnc2n1] | ++ |

TABLE 2-continued
| Entry | Structure | In vitro anti-Wolbachia activity |
|---|---|---|
| 128 | 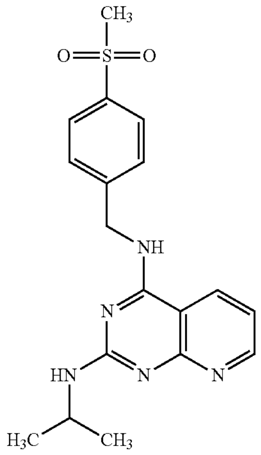 [SMILES: CC(C)Nc1nc(NCc2ccc(S(C)(=O)=O)cc2)c2cccnc2n1] | ++ |
| 129 | 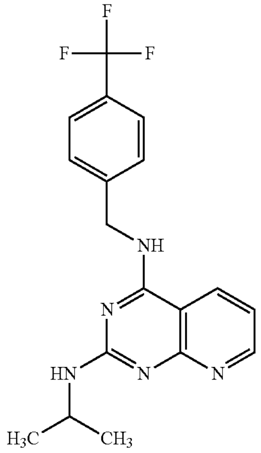 [SMILES: CC(C)Nc1nc(NCc2ccc(C(F)(F)F)cc2)c2cccnc2n1] | ++ |
| 130 | 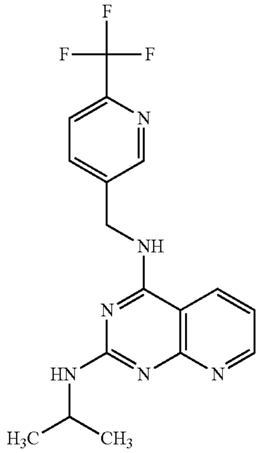 [SMILES: CC(C)Nc1nc(NCc2ccc(C(F)(F)F)nc2)c2cccnc2n1] | + |

TABLE 2-continued
| Entry | Structure | In vitro anti-Wolbachia activity |
|---|---|---|
| 131 | 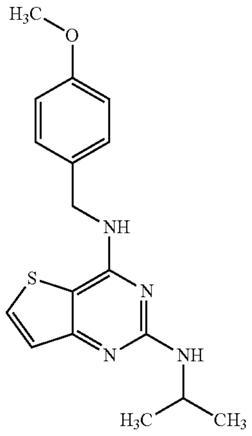 [SMILES: COc1ccc(CNc2nc(NC(C)C)nc3ccsc23)cc1] | + |
| 132 | 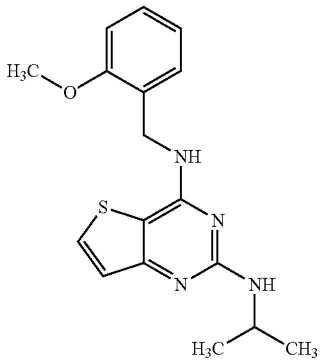 [SMILES: COc1ccccc1CNc1nc(NC(C)C)nc2ccsc12] | + |
| 133 | 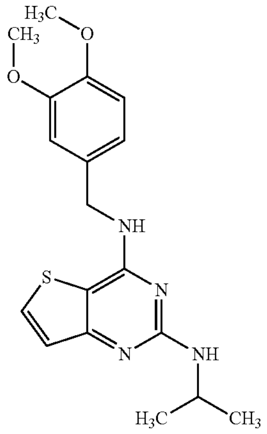 [SMILES: COc1ccc(CNc2nc(NC(C)C)nc3ccsc23)cc1OC] | + |

TABLE 2-continued
| Entry | Structure | In vitro anti-Wolbachia activity |
|---|---|---|
| 134 | 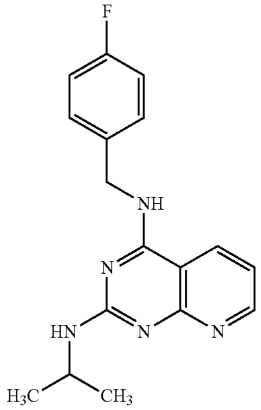 [SMILES: CC(C)Nc1nc(NCc2ccc(F)cc2)c2cccnc2n1] | + |
| 135 | 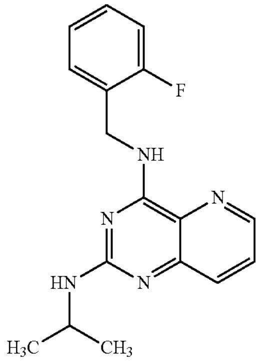 [SMILES: CC(C)Nc1nc(NCc2ccccc2F)c2ncccc2n1] | + |
| 136 | 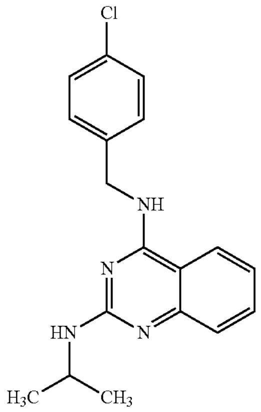 [SMILES: CC(C)Nc1nc(NCc2ccc(Cl)cc2)c2ccccc2n1] | + |
| 137 | 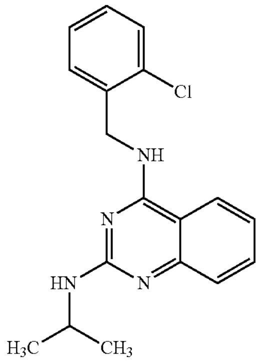 [SMILES: CC(C)Nc1nc(NCc2ccccc2Cl)c2ccccc2n1] | + |

TABLE 2-continued
| Entry | Structure | In vitro anti-Wolbachia activity |
|---|---|---|
| 138 | 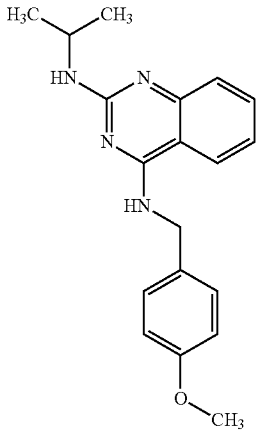 [SMILES: COc1ccc(CNc2nc(NC(C)C)nc3ccccc23)cc1] | + |
| 139 | 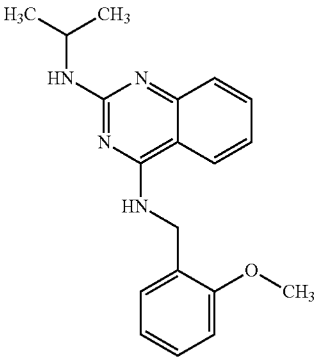 [SMILES: COc1ccccc1CNc1nc(NC(C)C)nc2ccccc12] | ++ |
| 140 | 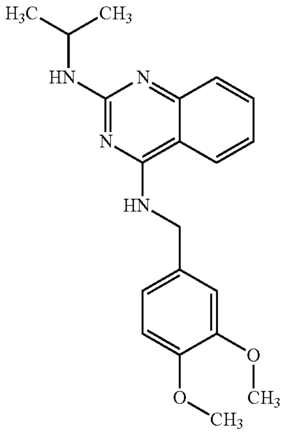 [SMILES: COc1ccc(CNc2nc(NC(C)C)nc3ccccc23)cc1OC] | ++ |
| 141 | 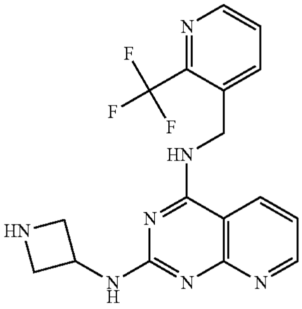 [SMILES: FC(F)(F)c1ncccc1CNc1nc(NC2CNC2)nc2ncccc12] | ++ |

TABLE 2-continued
| Entry | Structure | In vitro anti-Wolbachia activity |
| --- | --- | --- |
| 142 | 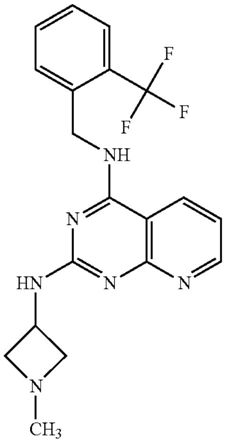 [SMILES: CN1CC(Nc2nc(NCc3ccccc3C(F)(F)F)c3cccnc3n2)C1] | + |
| 143 | 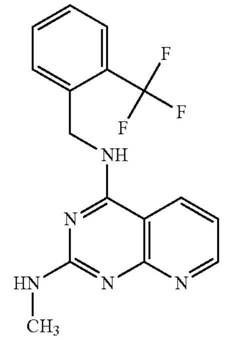 | +++ |
| 144 | 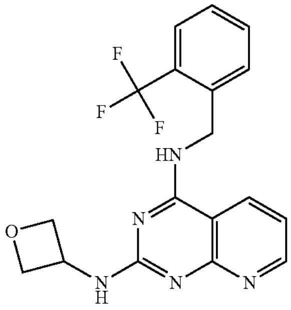 [SMILES: FC(F)(F)c1ccccc1CNc1nc(NC2COC2)nc2ncccc12] | +++ |
| 145 | 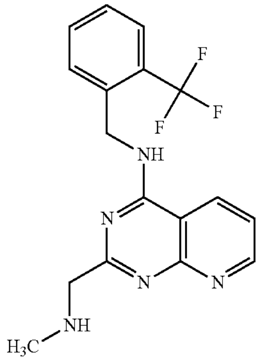 [SMILES: CNCc1nc(NCc2ccccc2C(F)(F)F)c2cccnc2n1] | + |

TABLE 2-continued
| Entry | Structure | In vitro anti-Wolbachia activity |
|---|---|---|
| 146 | 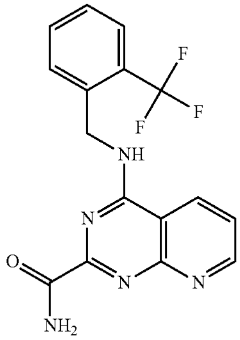 [SMILES: NC(=O)c1nc(NCc2ccccc2C(F)(F)F)c2cccnc2n1] | + |
| 147 | 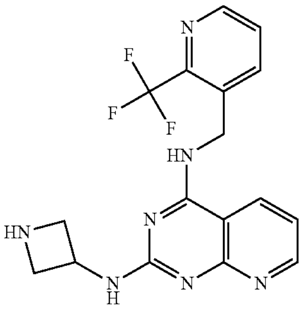 [SMILES: FC(F)(F)c1ncccc1CNc1nc(NC2CNC2)nc2ncccc12] | + |
| 148 | 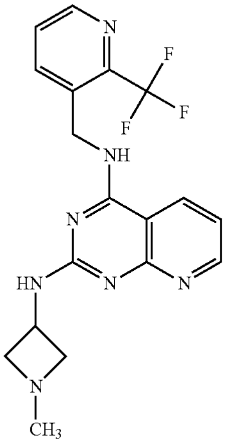 | + |
| 149 | 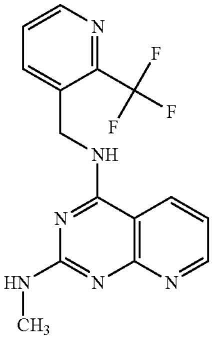 [SMILES: CNc1nc(NCc2cccnc2C(F)(F)F)c2cccnc2n1] | ++ |

TABLE 2-continued
| Entry | Structure | In vitro anti-Wolbachia activity |
|---|---|---|
| 150 | 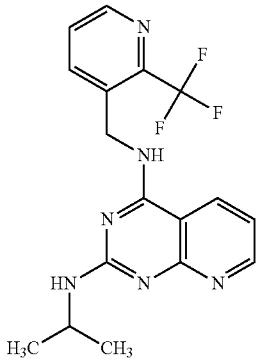 [SMILES: CC(C)Nc1nc(NCc2cccnc2C(F)(F)F)c2cccnc2n1] | +++ |
| 151 | 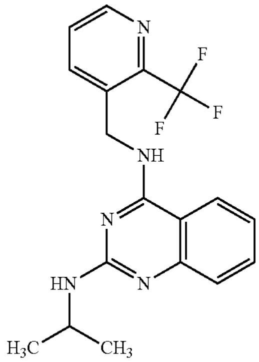 | ++ |
| 152 | 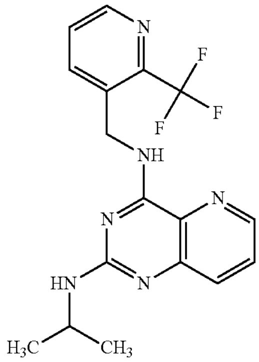 [SMILES: CC(C)Nc1nc(NCc2cccnc2C(F)(F)F)c2ncccc2n1] | ++ |
| 153 | 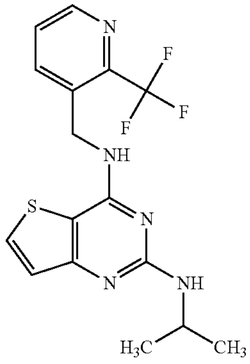 [SMILES: CC(C)Nc1nc(NCc2cccnc2C(F)(F)F)c2sccc2n1] | +++ |

TABLE 2-continued
| Entry | Structure | In vitro anti-Wolbachia activity |
|---|---|---|
| 154 | 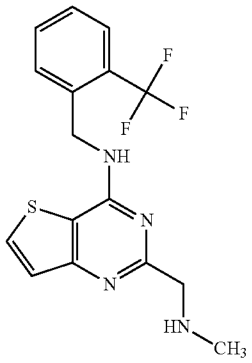 [SMILES: CNCc1nc(NCc2ccccc2C(F)(F)F)c2sccc2n1] | + |
| 155 | 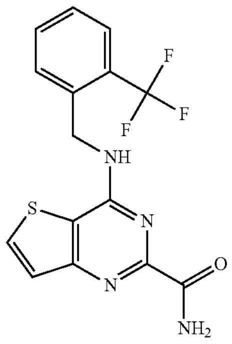 [SMILES: NC(=O)c1nc(NCc2ccccc2C(F)(F)F)c2sccc2n1] | + |
| 156 | 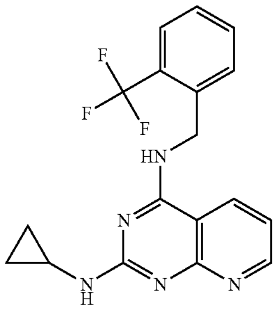 [SMILES: FC(F)(F)c1ccccc1CNc1nc(NC2CC2)nc2ncccc12] | ++++ |
| 157 | 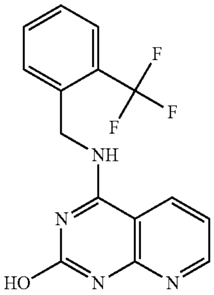 [SMILES: Oc1nc(NCc2ccccc2C(F)(F)F)c2cccnc2n1] | + |

TABLE 2-continued
| Entry | Structure | In vitro anti-Wolbachia activity |
|---|---|---|
| 158 | 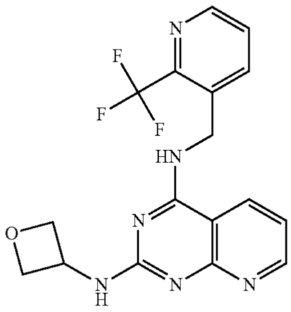 [SMILES: FC(F)(F)c1ncccc1CNc1nc(NC2COC2)nc2ncccc12] | ++ |
| 159 | 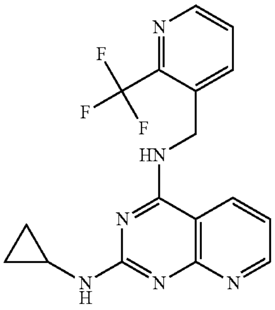 [SMILES: FC(F)(F)c1ncccc1CNc1nc(NC2CC2)nc2ncccc12] | ++++ |
| 160 | 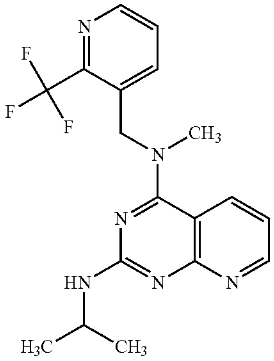 [SMILES: CC(C)Nc1nc(N(C)Cc2cccnc2C(F)(F)F)c2cccnc2n1] | +++ |
| 161 | 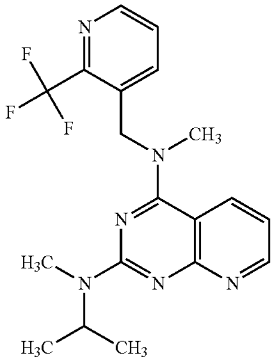 [SMILES: CC(C)N(C)c1nc(N(C)Cc2cccnc2C(F)(F)F)c2cccnc2n1] | ++++ |

TABLE 2-continued
| Entry | Structure | In vitro anti-Wolbachia activity |
| --- | --- | --- |
| 162 | 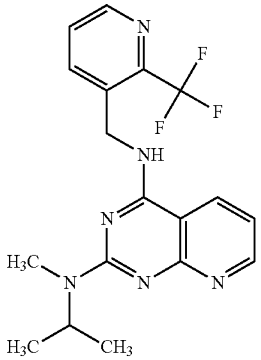 [SMILES: CC(C)N(C)c1nc(NCc2cccnc2C(F)(F)F)c2cccnc2n1] | +++++ |
| 163 | 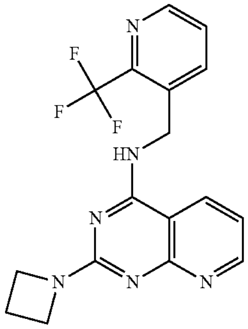 [SMILES: FC(F)(F)c1ncccc1CNc1nc(N2CCC2)nc2ncccc12] | +++ |
| 164 | 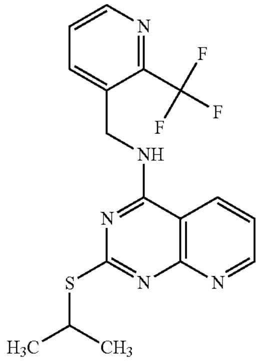 [SMILES: CC(C)Sc1nc(NCc2cccnc2C(F)(F)F)c2cccnc2n1] | ++++ |
| 165 | 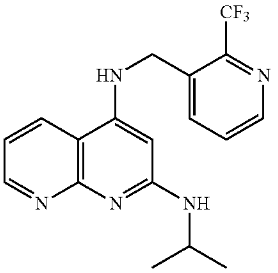 [SMILES: CC(C)Nc1cc(NCc2cccnc2C(F)(F)F)c2cccnc2n1] | +++ |

TABLE 2-continued
| Entry | Structure | In vitro anti-Wolbachia activity |
|---|---|---|
| 166 | 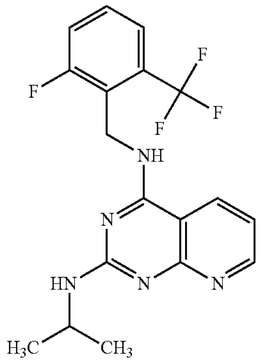 [SMILES: CC(C)Nc1nc(NCc2c(F)cccc2C(F)(F)F)c2cccnc2n1] | ++ |
| 167 | 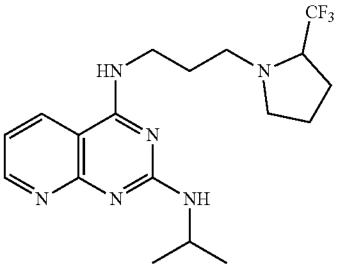 [SMILES: CC(C)Nc1nc(NCCCN2CCCC2C(F)(F)F)c2cccnc2n1] | + |
| 168 | | ++++ |
| 169 | 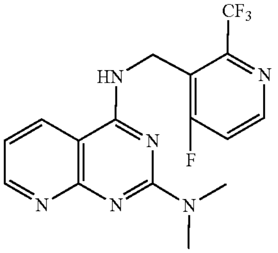 [SMILES: CN(C)c1nc(NCc2c(F)ccnc2C(F)(F)F)c2cccnc2n1] | ++ |
| 170 | 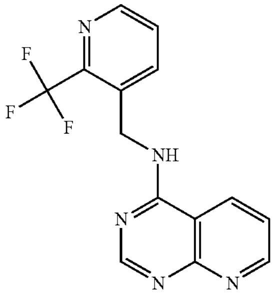 [SMILES: FC(F)(F)c1ncccc1CNc1ncnc2ncccc12] | + |

TABLE 2-continued
| Entry | Structure | In vitro anti-Wolbachia activity |
|---|---|---|
| 171 | 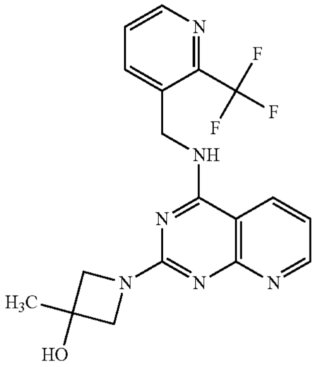 [SMILES: CC1(O)CN(c2nc(NCc3cccnc3C(F)(F)F)c3cccnc3n2)C1] | ++ |
| 172 | 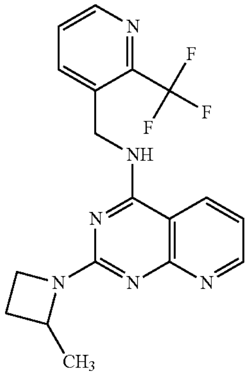 [SMILES: CC1CCN1c1nc(NCc2cccnc2C(F)(F)F)c2cccnc2n1] | +++++ |
| 173 | 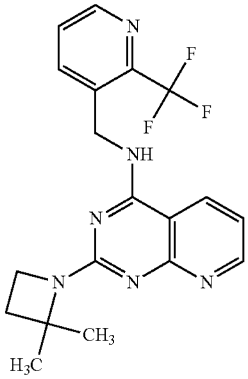 [SMILES: CC1(C)CCN1c1nc(NCc2cccnc2C(F)(F)F)c2cccnc2n1] | ++++ |
| 174 | 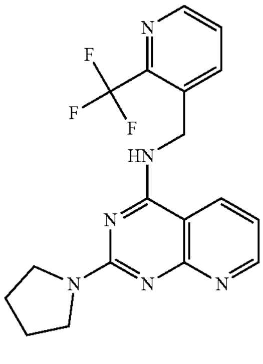 [SMILES: FC(F)(F)c1ncccc1CNc1nc(N2CCCC2)nc2ncccc12] | +++++ |

TABLE 2-continued
| Entry | Structure | In vitro anti-Wolbachia activity |
| --- | --- | --- |
| 175 | 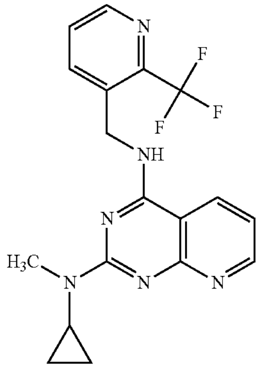 [SMILES: CN(c1nc(NCc2cccnc2C(F)(F)F)c2cccnc2n1)C1CC1] | ++++ |
| 176 | 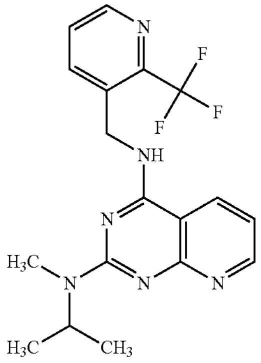 [SMILES: CC(C)N(C)c1nc(NCc2cccnc2C(F)(F)F)c2cccnc2n1] | ++ |
| 177 | 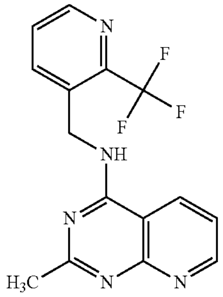 [SMILES: Cc1nc(NCc2cccnc2C(F)(F)F)c2cccnc2n1] | + |
| 178 | 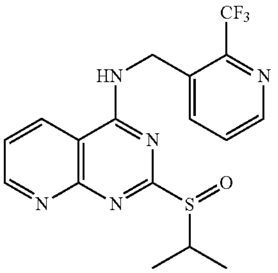 [SMILES: CC(C)S(=O)c1nc(NCc2cccnc2C(F)(F)F)c2cccnc2n1] | + |

TABLE 2-continued
| Entry | Structure | In vitro anti-Wolbachia activity |
|---|---|---|
| 179 | 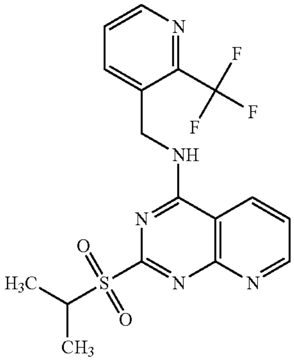 [SMILES: CC(C)S(=O)(=O)c1nc(NCc2cccnc2C(F)(F)F)c2cccnc2n1] | +++ |
| 180 | 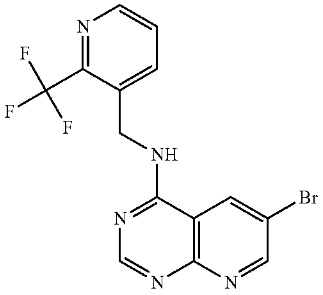 [SMILES: FC(F)(F)c1ncccc1CNc1ncnc2ncc(Br)cc12] | + |
| 181 | 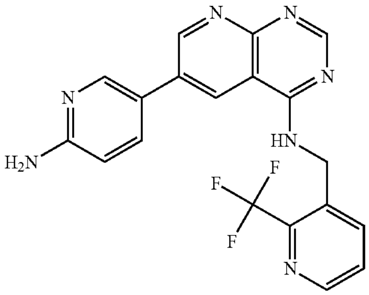 [SMILES: Nc1ccc(-c2cnc3ncnc(NCc4cccnc4C(F)(F)F)c3c2)cn1] | + |
| 182 | 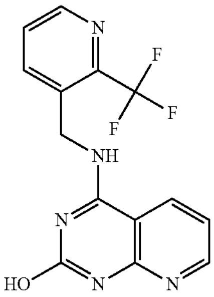 [SMILES: Oc1nc(NCc2cccnc2C(F)(F)F)c2cccnc2n1] | + |

TABLE 2-continued
| Entry | Structure | In vitro anti-Wolbachia activity |
|---|---|---|
| 183 | 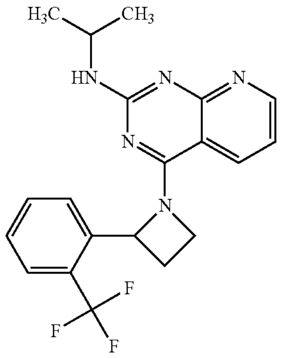 [SMILES: CC(C)Nc1nc(N2CCC2c2ccccc2C(F)(F)F)c2cccnc2n1] | ++++ |
| 184 | 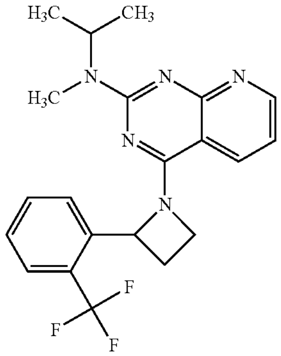 [SMILES: CC(C)N(C)c1nc(N2CCC2c2ccccc2C(F)(F)F)c2cccnc2n1] | +++++ |
| 185 | 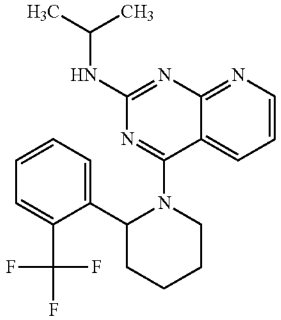 [SMILES: CC(C)Nc1nc(N2CCCCC2c2ccccc2C(F)(F)F)c2cccnc2n1] | + |
| 186 | 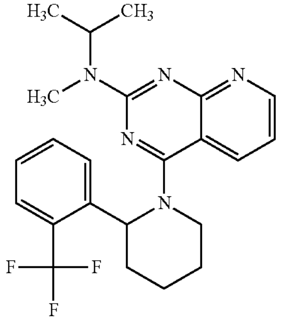 [SMILES: CC(C)N(C)c1nc(N2CCCCC2c2ccccc2C(F)(F)F)c2cccnc2n1] | + |

TABLE 2-continued
| Entry | Structure | In vitro anti-Wolbachia activity |
|---|---|---|
| 187 | 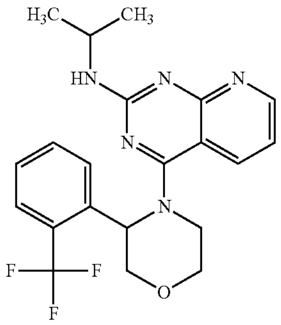 | + |
| 188 | 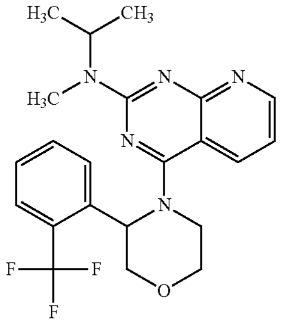 [SMILES: CC(C)N(C)c1nc(N2CCOCC2c2ccccc2C(F)(F)F)c2cccnc2n1] | + |
| 189 | 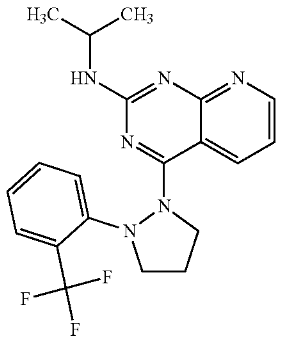 [SMILES: CC(C)Nc1nc(N2CCCN2c2ccccc2C(F)(F)F)c2cccnc2n1] | + |
| 190 | 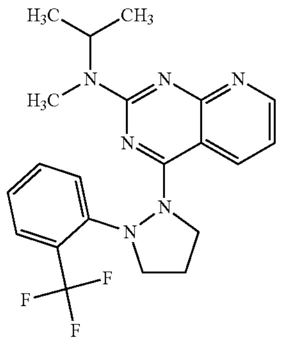 | ++ |

TABLE 2-continued
| Entry | Structure | In vitro anti-Wolbachia activity |
|---|---|---|
| 191 | 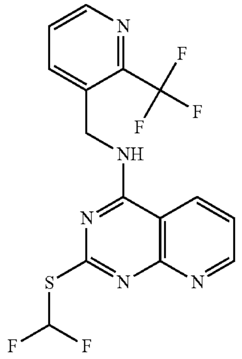 [SMILES: FC(F)Sc1nc(NCc2cccnc2C(F)(F)F)c2cccnc2n1] | ++ |
| 192 | 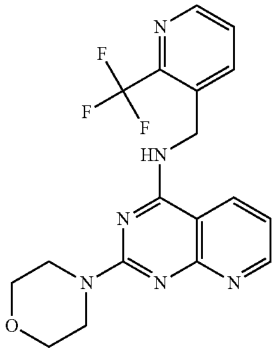 [SMILES: FC(F)(F)c1ncccc1CNc1nc(N2CCOCC2)nc2ncccc12] | +++ |
| 193 | 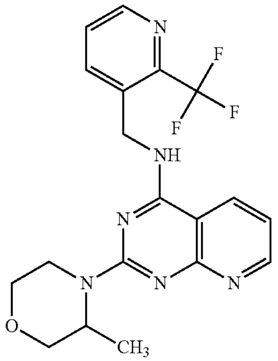 [SMILES: CC1COCCN1c1nc(NCc2cccnc2C(F)(F)F)c2cccnc2n1] | ++++ |
| 194 | 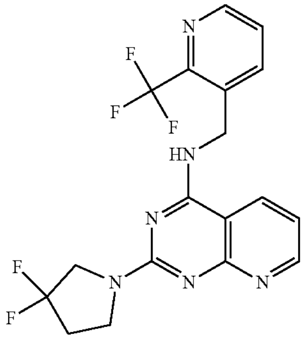 [SMILES: FC1(F)CCN(c2nc(NCc3cccnc3C(F)(F)F)c3cccnc3n2)C1] | ++++ |

TABLE 2-continued
| Entry | Structure | In vitro anti-Wolbachia activity |
|---|---|---|
| 195 | 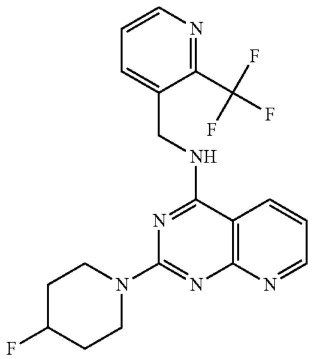 [SMILES: FC1CCN(c2nc(NCc3cccnc3C(F)(F)F)c3cccnc3n2)CC1] | ++++ |
| 196 | 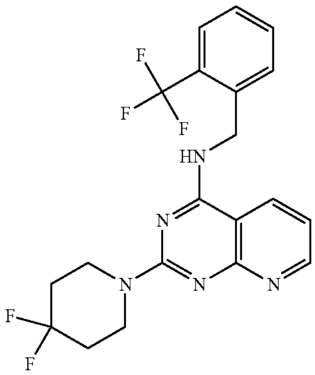 [SMILES: FC1(F)CCN(c2nc(NCc3ccccc3C(F)(F)F)c3cccnc3n2)CC1] | +++++ |
| 197 | 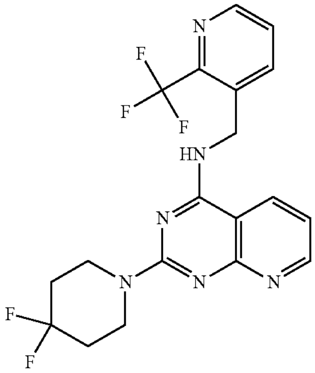 [SMILES: FC1(F)CCN(c2nc(NCc3cccnc3C(F)(F)F)c3cccnc3n2)CC1] | ++++ |
| 198 | 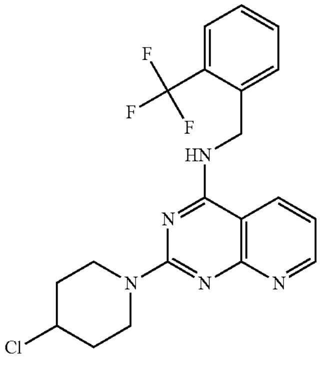 [SMILES: FC(F)(F)c1ccccc1CNc1nc(N2CCC(Cl)CC2)nc2ncccc12] | ++++ |

TABLE 2-continued
| Entry | Structure | In vitro anti-Wolbachia activity |
| --- | --- | --- |
| 199 | 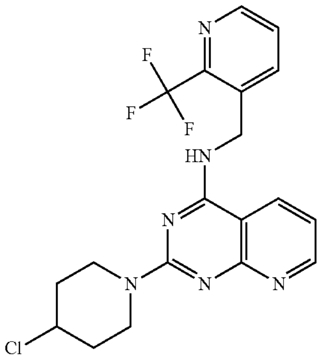 [SMILES: FC(F)(F)c1ncccc1CNc1nc(N2CCC(Cl)CC2)nc2ncccc12] | ++++ |
| 200 | 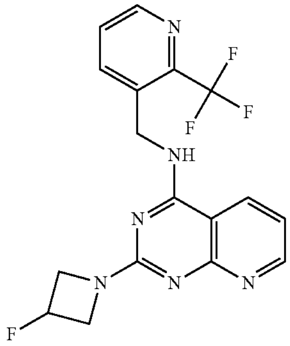 [SMILES: FC1CN(c2nc(NCc3cccnc3C(F)(F)F)c3cccnc3n2)C1] | +++ |
| 201 | 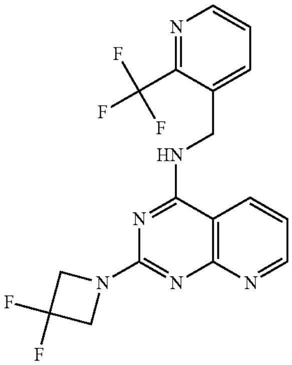 [SMILES: FC1(F)CN(c2nc(NCc3cccnc3C(F)(F)F)c3cccnc3n2)C1] | +++ |
| 202 | 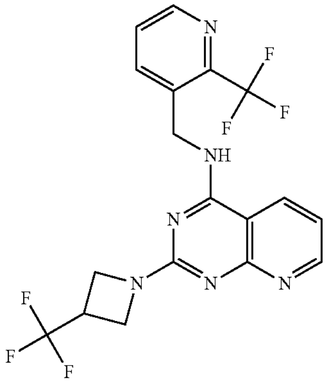 [SMILES: FC(F)(F)c1ncccc1CNc1nc(N2CC(C(F)(F)F)C2)nc2ncccc12] | ++++ |

TABLE 2-continued
| Entry | Structure | In vitro anti-Wolbachia activity |
|---|---|---|
| 203 | 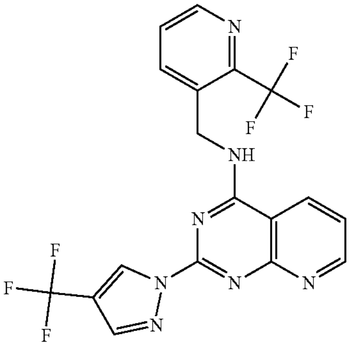 [SMILES: FC(F)(F)c1cnn(-c2nc(NCc3cccnc3C(F)(F)F)c3cccnc3n2)c1] | ++ |
| 204 | 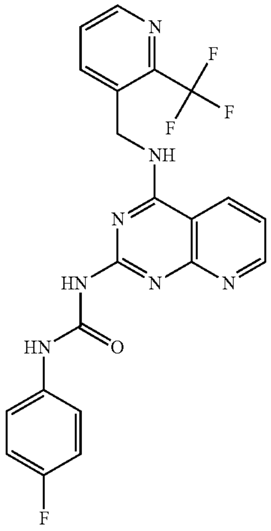 [SMILES: O=C(Nc1ccc(F)cc1)Nc1nc(NCc2cccnc2C(F)(F)F)c2cccnc2n1] | +++ |
| 205 | 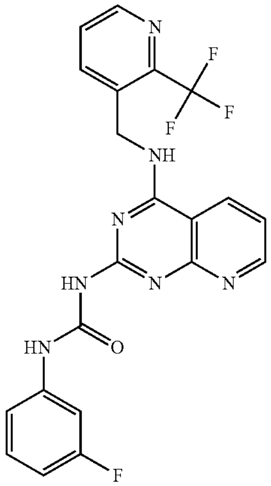 [SMILES: O=C(Nc1cccc(F)c1)Nc1nc(NCc2cccnc2C(F)(F)F)c2cccnc2n1] | +++ |

TABLE 2-continued
| Entry | Structure | In vitro anti-Wolbachia activity |
| --- | --- | --- |
| 206 | 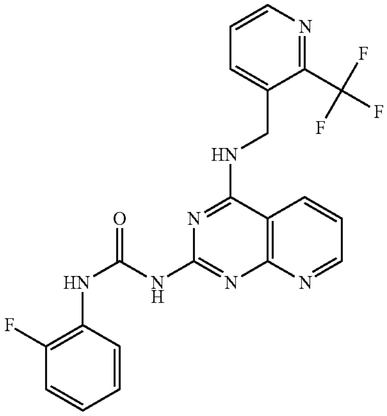 [SMILES: O=C(Nc1nc(NCc2cccnc2C(F)(F)F)c2cccnc2n1)Nc1ccccc1F] | ++ |
| 207 | 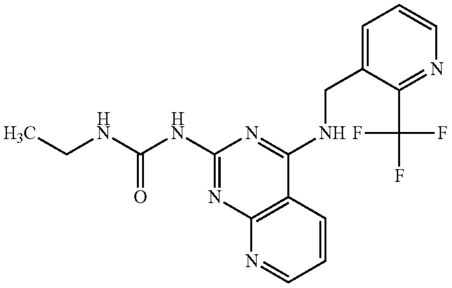 [SMILES: CCNC(=O)Nc1nc(NCc2cccnc2C(F)(F)F)c2cccnc2n1] | ++ |
| 208 | 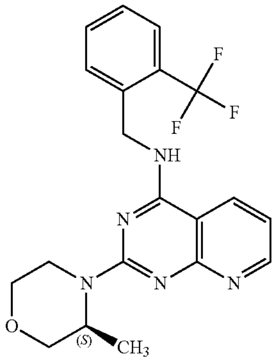 | ++++++ |
| 209 | 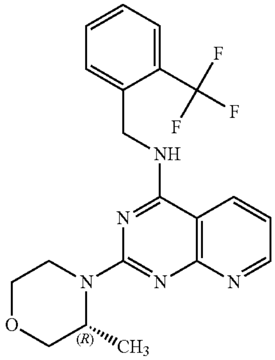 | +++ |

TABLE 2-continued
| Entry | Structure | In vitro anti-Wolbachia activity |
|---|---|---|
| 210 | 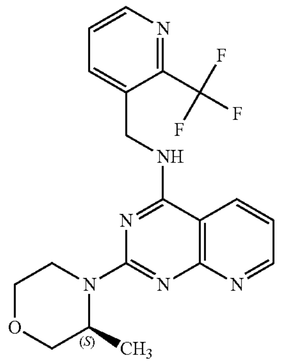 | ++++ |
| 211 | 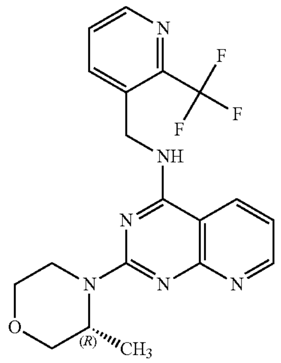 | +++ |
| 212 | 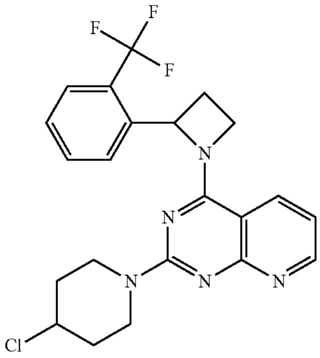 [SMILES: FC(F)(F)c1ccccc1C1CCN1c1nc(N2CCC(Cl)CC2)nc2ncccc12] | ++ |
| 213 | 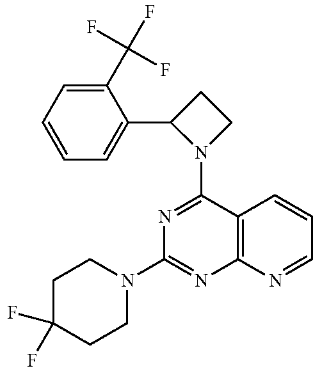 [SMILES: FC1(F)CCN(c2nc(N3CCC3c3ccccc3C(F)(F)F)c3cccnc3n2)CC1] | +++ |

TABLE 2-continued
| Entry | Structure | In vitro anti-Wolbachia activity |
|---|---|---|
| 214 | 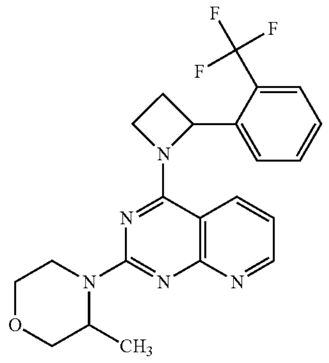 [SMILES: CC1COCCN1c1nc(N2CCC2c2ccccc2C(F)(F)F)c2cccnc2n1] | +++++ |
| 215 | 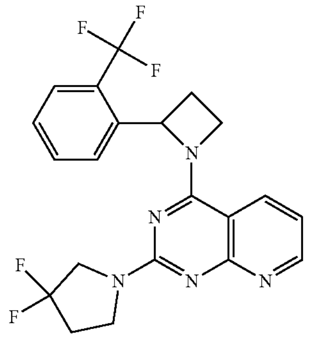 [SMILES: FC1(F)CCN(c2nc(N3CCC3c3ccccc3C(F)(F)F)c3cccnc3n2)C1] | +++ |
| 216 | 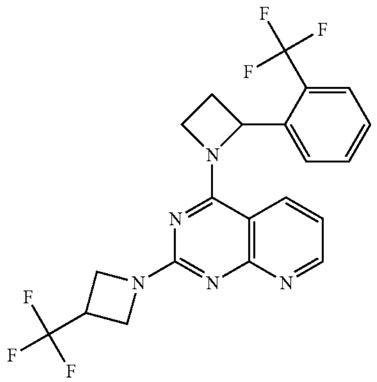 [SMILES: FC(F)(F)c1ccccc1C1CCN1c1nc(N2CC(C(F)(F)F)C2)nc2ncccc12] | ++ |
| 217 | 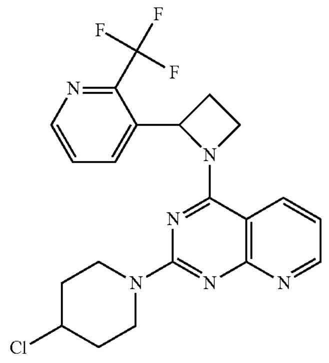 [SMILES: FC(F)(F)c1ncccc1C1CCN1c1nc(N2CCC(Cl)CC2)nc2ncccc12] | ++++++ |

TABLE 2-continued
| Entry | Structure | In vitro anti-Wolbachia activity |
|---|---|---|
| 218 | 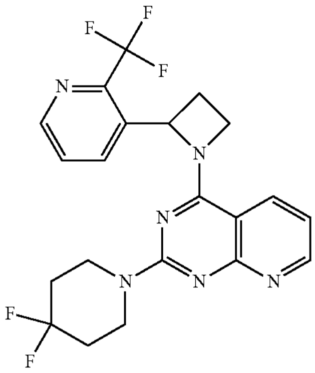 [SMILES: FC1(F)CCN(c2nc(N3CCC3c3cccnc3C(F)(F)F)c3cccnc3n2)CC1] | +++++ |
| 219 | 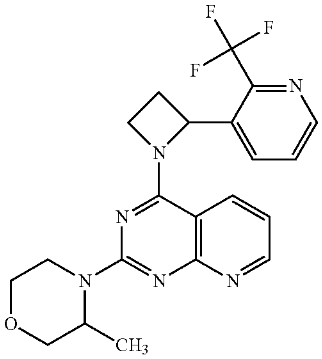 [SMILES: CC1COCCN1c1nc(N2CCC2c2cccnc2C(F)(F)F)c2cccnc2n1] | ++++ |
| 220 | 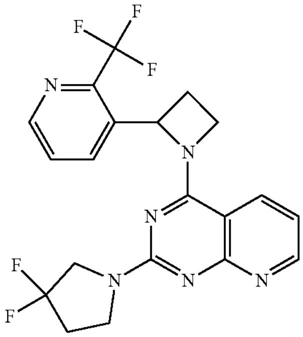 [SMILES: FC1(F)CCN(c2nc(N3CCC3c3cccnc3C(F)(F)F)c3cccnc3n2)C1] | +++++ |
| 221 | 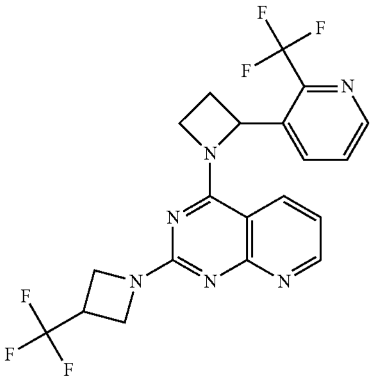 [SMILES: FC(F)(F)c1ncccc1C1CCN1c1nc(N2CC(C(F)(F)F)C2)nc2ncccc12] | ++++ |

TABLE 2-continued
| Entry | Structure | In vitro anti-Wolbachia activity |
|---|---|---|
| 222 | 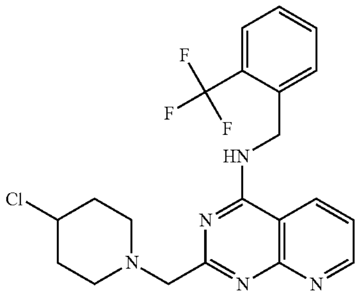 | + |
| 223 | 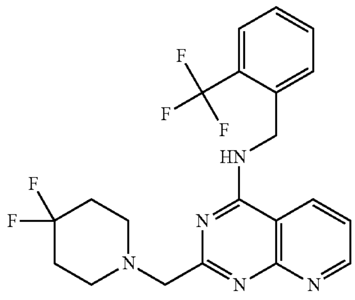 | ++ |
| 224 | 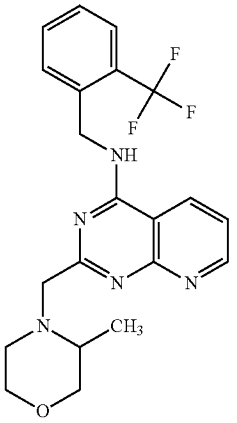 [SMILES: CC1COCCN1Cc1nc(NCc2ccccc2C(F)(F)F)c2cccnc2n1] | + |
| 225 | 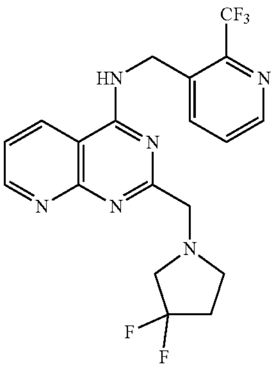 [SMILES: FC1(F)CCN(Cc2nc(NCc3cccnc3C(F)(F)F)c3cccnc3n2)C1] | + |

TABLE 2-continued
| Entry | Structure | In vitro anti-Wolbachia activity |
|---|---|---|
| 226 | 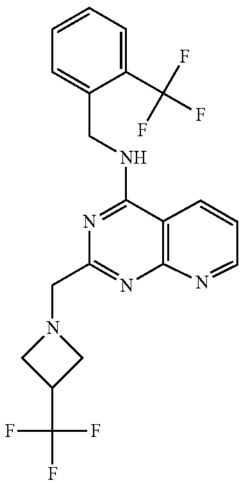 | ++ |
| 227 | 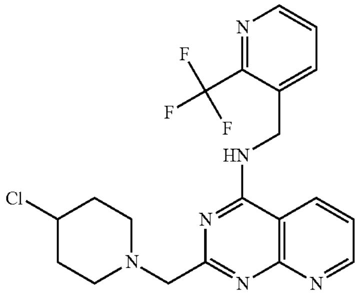 [SMILES: FC(F)(F)c1ncccc1CNc1nc(CN2CCC(Cl)CC2)nc2ncccc12] | ++ |
| 228 | 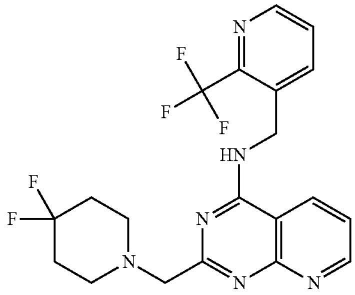 [SMILES: FC1(F)CCN(Cc2nc(NCc3cccnc3C(F)(F)F)c3cccnc3n2)CC1] | ++ |
| 229 | 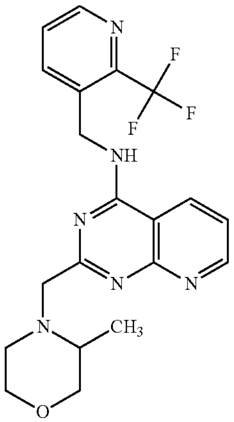 [SMILES: CC1COCCN1Cc1nc(NCc2cccnc2C(F)(F)F)c2cccnc2n1] | + |

TABLE 2-continued
| Entry | Structure | In vitro anti-Wolbachia activity |
|---|---|---|
| 230 | 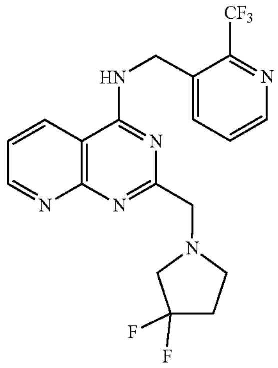 [SMILES: FC1(F)CCN(Cc2nc(NCc3cccnc3C(F)(F)F)c3cccnc3n2)C1] | + |
| 231 | 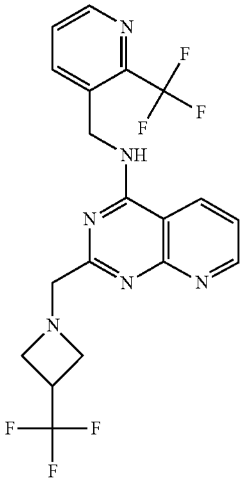 | ++ |
| 232 | 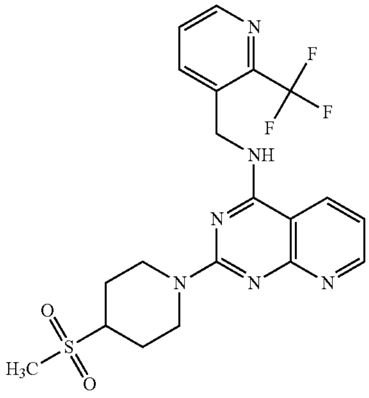 [SMILES: CS(=O)(=O)C1CCN(c2nc(NCc3cccnc3C(F)(F)F)c3cccnc3n2)CC1] | ++ |

TABLE 2-continued
| Entry | Structure | In vitro anti-Wolbachia activity |
| --- | --- | --- |
| 233 | 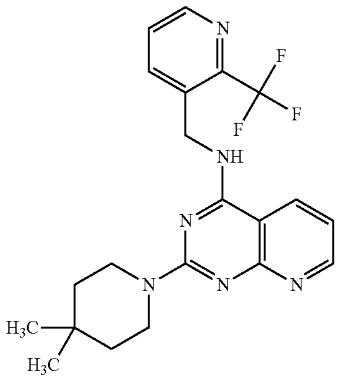 [SMILES: CC1(C)CCN(c2nc(NCc3cccnc3C(F)(F)F)c3cccnc3n2)CC1] | +++ |
| 234 | 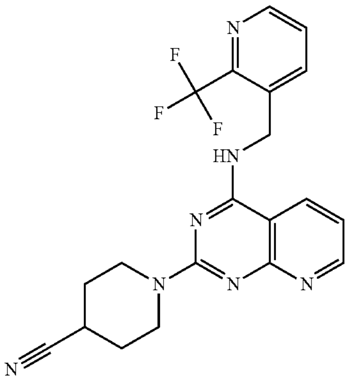 [SMILES: N#CC1CCN(c2nc(NCc3cccnc3C(F)(F)F)c3cccnc3n2)CC1] | ++++ |
| 235 | 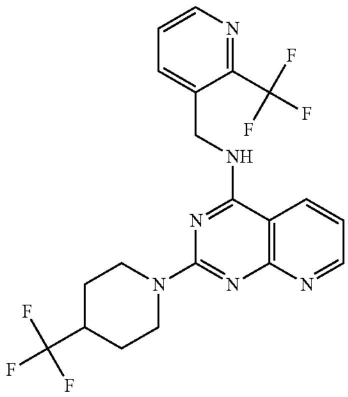 | +++++ |

TABLE 2-continued
| Entry | Structure | In vitro anti-Wolbachia activity |
|---|---|---|
| 236 | 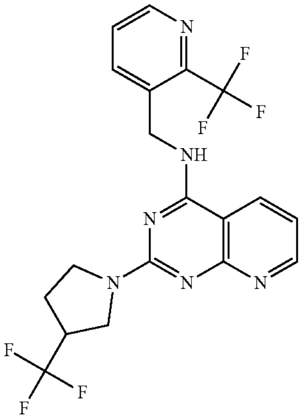 [SMILES: FC(F)(F)c1ncccc1CNc1nc(N2CCC(C(F)(F)F)C2)nc2ncccc12] | ++++++ |
| 237 | 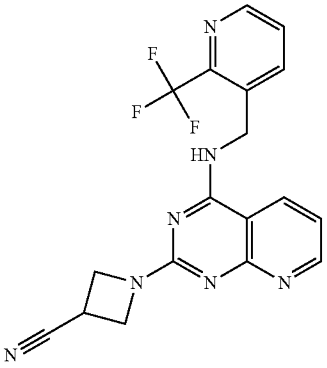 [SMILES: N#CC1CN(c2nc(NCc3cccnc3C(F)(F)F)c3cccnc3n2)C1] | ++ |
| 238 | 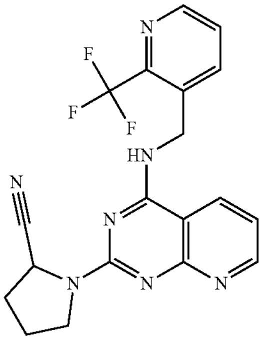 [SMILES: N#CC1CCCN1c1nc(NCc2cccnc2C(F)(F)F)c2cccnc2n1] | +++ |
| 239 | 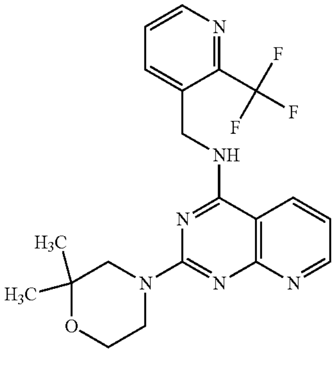 [SMILES: CC1(C)CN(c2nc(NCc3cccnc3C(F)(F)F)c3cccnc3n2)CCO1] | +++++ |

TABLE 2-continued
| Entry | Structure | In vitro anti-Wolbachia activity |
| --- | --- | --- |
| 240 | 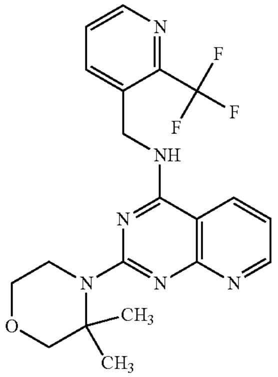 [SMILES: CC1(C)COCCN1c1nc(NCc2cccnc2C(F)(F)F)c2cccnc2n1] | +++++ |
| 241 | 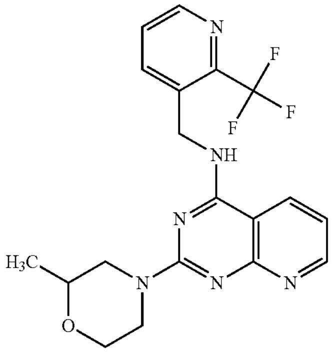 [SMILES: CC1CN(c2nc(NCc3cccnc3C(F)(F)F)c3cccnc3n2)CCO1] | +++++ |
| 242 | 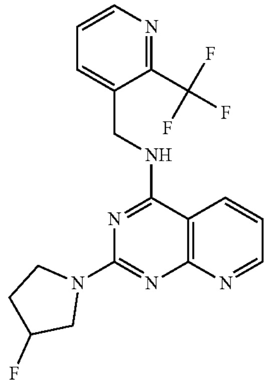 [SMILES: FC1CCN(c2nc(NCc3cccnc3C(F)(F)F)c3cccnc3n2)C1] | ++++ |
| 243 | 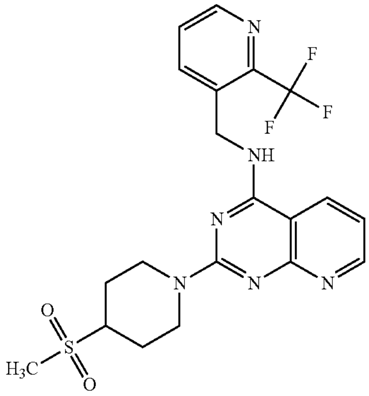 [SMILES: CS(=O)(=O)C1CCN(c2nc(NCc3cccnc3C(F)(F)F)c3cccnc3n2)CC1] | ++ |

TABLE 2-continued
| Entry | Structure | In vitro anti-Wolbachia activity |
|---|---|---|
| 244 | 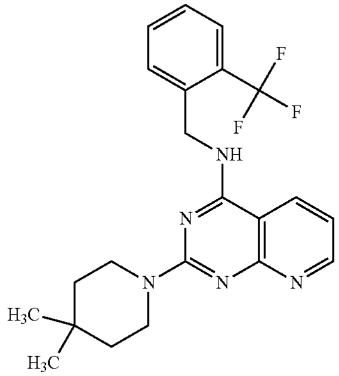 [SMILES: CC1(C)CCN(c2nc(NCc3ccccc3C(F)(F)F)c3cccnc3n2)CC1] | ++++ |
| 245 | 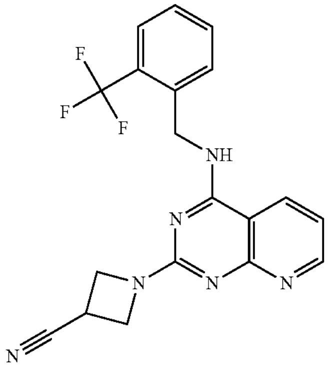 [SMILES: N#CC1CN(c2nc(NCc3ccccc3C(F)(F)F)c3cccnc3n2)C1] | ++++ |
| 246 | 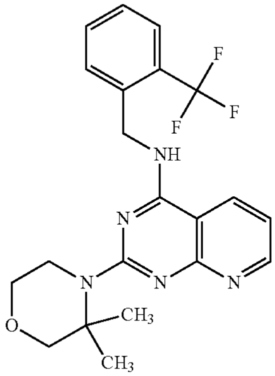 [SMILES: CC1(C)COCCN1c1nc(NCc2ccccc2C(F)(F)F)c2cccnc2n1] | ++ |
| 247 | 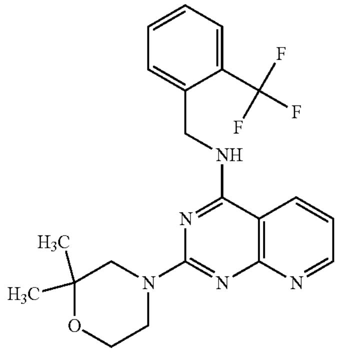 [SMILES: CC1(C)CN(c2nc(NCc3ccccc3C(F)(F)F)c3cccnc3n2)CCO1] | ++++++ |

TABLE 2-continued
| Entry | Structure | In vitro anti-Wolbachia activity |
|---|---|---|
| 248 | 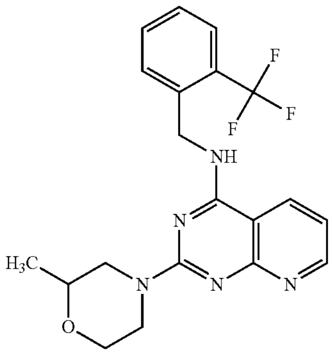 [SMILES: CC1CN(c2nc(NCc3ccccc3C(F)(F)F)c3cccnc3n2)CCO1] | +++++ |
| 249 | 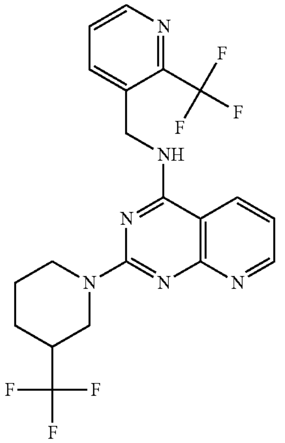 [SMILES: FC(F)(F)c1ncccc1CNc1nc(N2CCCC(C(F)(F)F)C2)nc2ncccc12] | ++++++ |
| 250 | 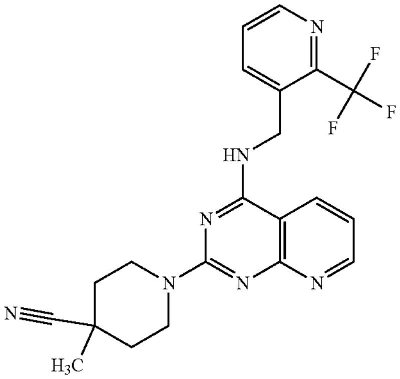 [SMILES: CC1(C#N)CCN(c2nc(NCc3cccnc3C(F)(F)F)c3cccnc3n2)CC1] | +++++ |
| 251 | 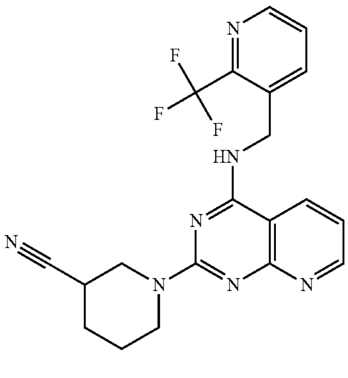 [SMILES: N#CC1CCCN(c2nc(NCc3cccnc3C(F)(F)F)c3cccnc3n2)C1] | ++++ |

TABLE 2-continued
| Entry | Structure | In vitro anti-Wolbachia activity |
| --- | --- | --- |
| 252 | 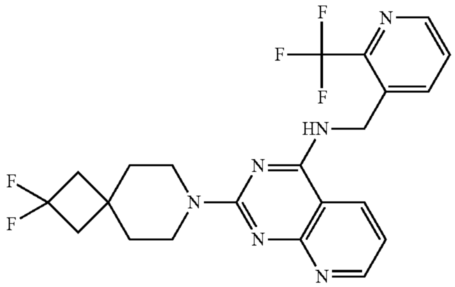 [SMILES: FC1(F)CC2(CCN(c3nc(NCc4cccnc4C(F)(F)F)c4cccnc4n3)CC2)C1] | +++++ |
| 253 | 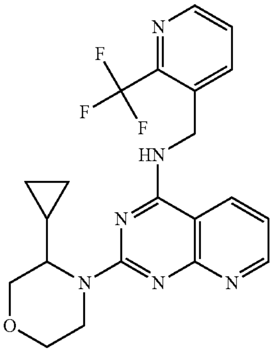 [SMILES: FC(F)(F)c1ncccc1CNc1nc(N2CCOCC2C2CC2)nc2ncccc12] | ++++ |
| 254 | 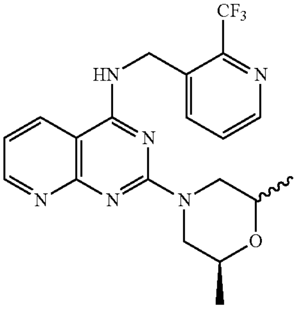 [SMILES: CC1CN(c2nc(NCc3cccnc3C(F)(F)F)c3cccnc3n2)C[C@H](C)O1] | +++++ |
| 255 | 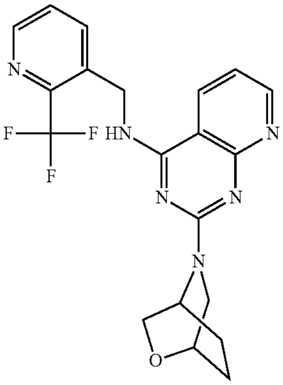 [SMILES: FC(F)(F)c1ncccc1CNc1nc(N2CC3CCC2CO3)nc2ncccc12] | ++++ |

TABLE 2-continued
| Entry | Structure | In vitro anti-Wolbachia activity |
|---|---|---|
| 256 | 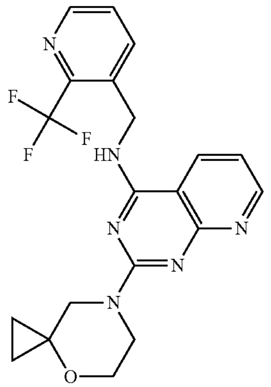 [SMILES: FC(F)(F)c1ncccc1CNc1nc(N2CCOC3(CC3)C2)nc2ncccc12] | ++++++ |
| 257 | 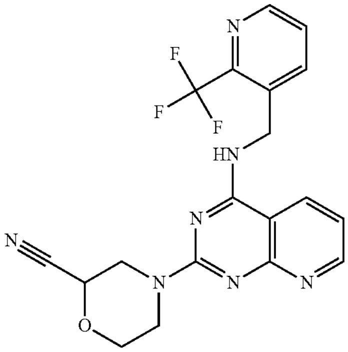 [SMILES: N#CC1CN(c2nc(NCc3cccnc3C(F)(F)F)c3cccnc3n2)CCO1] | +++ |
| 258 | 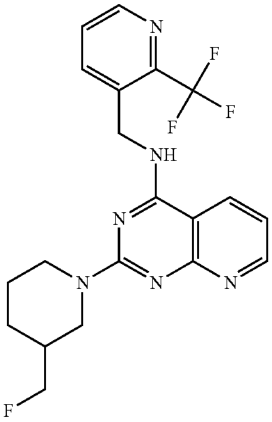 [SMILES: FCC1CCCN(c2nc(NCc3cccnc3C(F)(F)F)c3cccnc3n2)C1] | ++++++ |
| 259 | 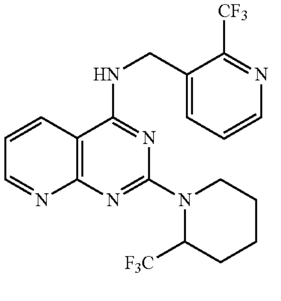 [SMILES: FC(F)(F)c1ncccc1CNc1nc(N2CCCCC2C(F)(F)F)nc2ncccc12] | +++++ |

TABLE 2-continued
| Entry | Structure | In vitro anti-Wolbachia activity |
| --- | --- | --- |
| 260 | 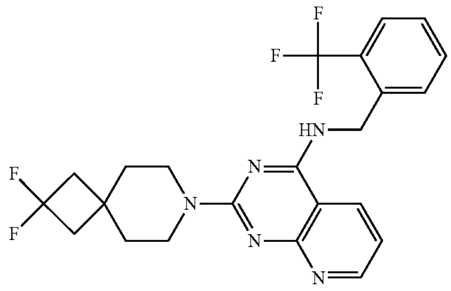 [SMILES: FC1(F)CC2(CCN(c3nc(NCc4ccccc4C(F)(F)F)c4cccnc4n3)CC2)C1] | ++++ |
| 261 | 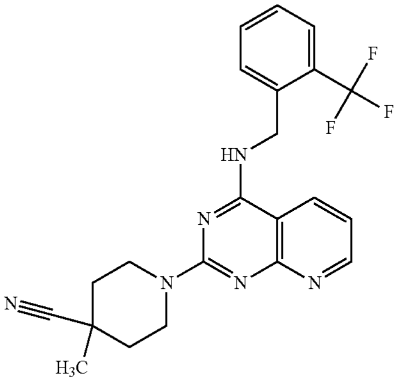 [SMILES: CC1(C#N)CCN(c2nc(NCc3ccccc3C(F)(F)F)c3cccnc3n2)CC1] | ++++++ |
| 262 | 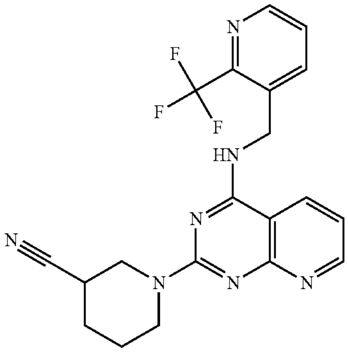 [SMILES: N#CC1CCCN(c2nc(NCc3cccnc3C(F)(F)F)c3cccnc3n2)C1] | +++++ |
| 263 | 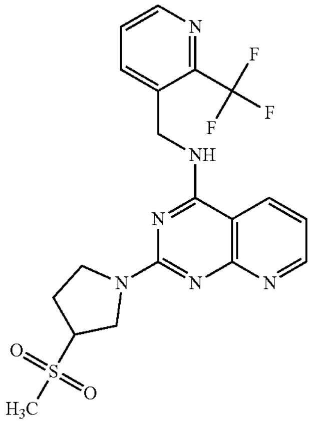 [SMILES: CS(=O)(=O)C1CCN(c2nc(NCc3cccnc3C(F)(F)F)c3cccnc3n2)C1] | ++ |

TABLE 2-continued
| Entry | Structure | In vitro anti-Wolbachia activity |
|---|---|---|
| 264 | 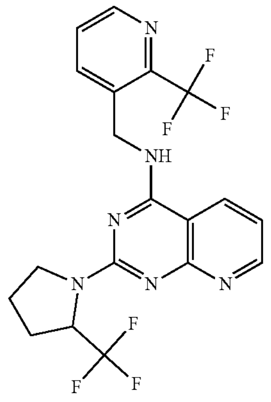 [SMILES: FC(F)(F)c1ncccc1CNc1nc(N2CCCC2C(F)(F)F)nc2ncccc12] | ++++++ |
| 265 | 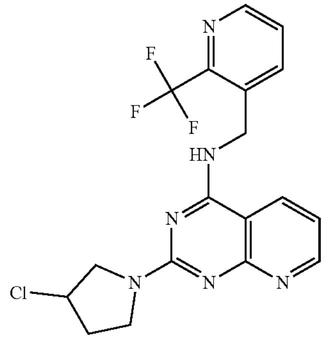 [SMILES: FC(F)(F)c1ncccc1CNc1nc(N2CCC(Cl)C2)nc2ncccc12] | ++++++ |
| 266 | 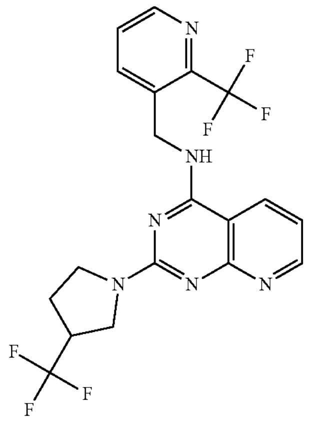 [SMILES: FC(F)(F)c1ncccc1CNc1nc(N2CCC(C(F)(F)F)C2)nc2ncccc12] | ++++ |
| 267 | 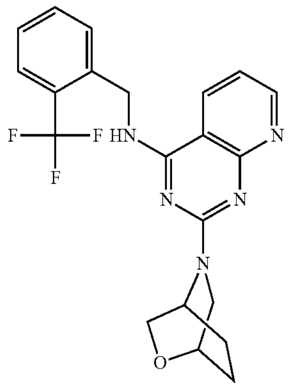 [SMILES: FC(F)(F)c1ccccc1CNc1nc(N2CC3CCC2CO3)nc2ncccc12] | ++++++ |

TABLE 2-continued
| Entry | Structure | In vitro anti-Wolbachia activity |
| --- | --- | --- |
| 268 | 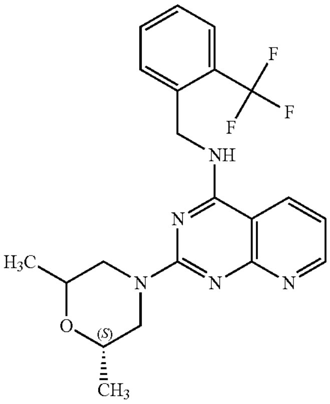 | +++ |
| 269 | 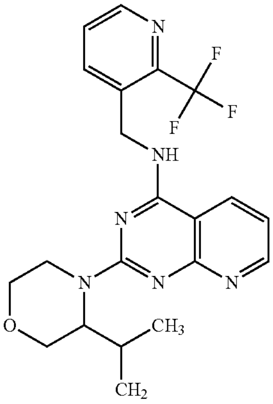 [SMILES: CC(C)C1COCCN1c1nc(NCc2cccnc2C(F)(F)F)c2cccnc2n1] | ++++ |
| 270 | 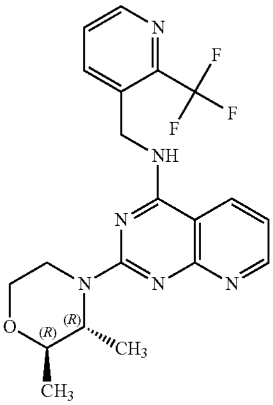 | ++++ |

TABLE 2-continued
| Entry | Structure | In vitro anti-Wolbachia activity |
|---|---|---|
| 271 | 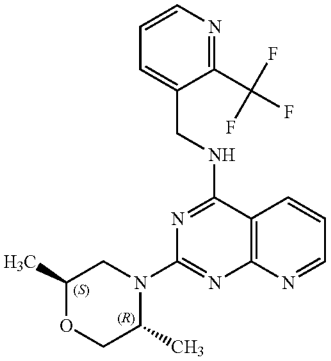 | +++++ |
| 272 | 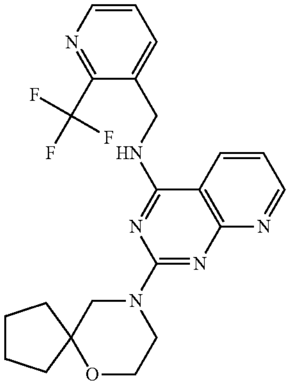 [SMILES: FC(F)(F)c1ncccc1CNc1nc(N2CCOC3(CCCC3)C2)nc2ncccc12] | +++++ |
| 273 | 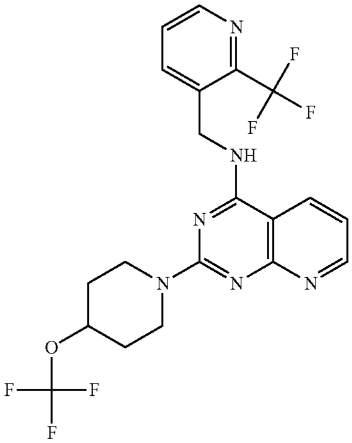 [SMILES: FC(F)(F)OC1CCN(c2nc(NCc3cccnc3C(F)(F)F)c3cccnc3n2)CC1] | ++++++ |

TABLE 2-continued
| Entry | Structure | In vitro anti-Wolbachia activity |
|---|---|---|
| 274 | 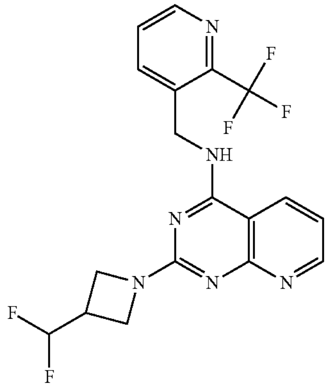 [SMILES: FC(F)C1CN(c2nc(NCc3cccnc3C(F)(F)F)c3cccnc3n2)C1] | ++++ |
| 275 | 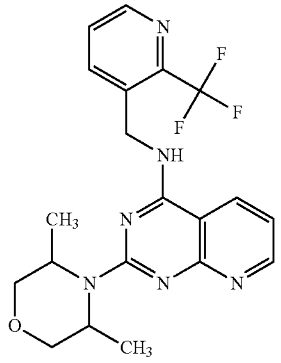 | +++++ |
| 276 | 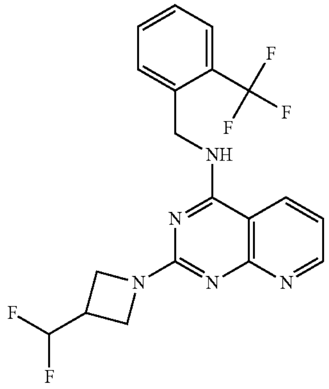 [SMILES: FC(F)C1CN(c2nc(NCc3ccccc3C(F)(F)F)c3cccnc3n2)C1] | ++++++ |
| 277 | 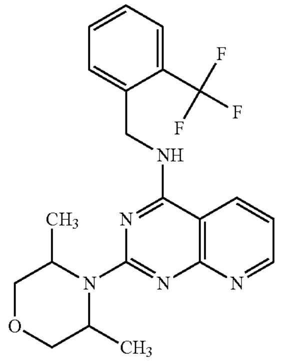 [SMILES: CC1COCC(C)N1c1nc(NCc2ccccc2C(F)(F)F)c2cccnc2n1] | +++ |

TABLE 2-continued
| Entry | Structure | In vitro anti-Wolbachia activity |
|---|---|---|
| 278 | 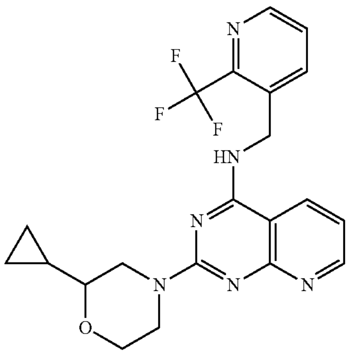 [SMILES: FC(F)(F)c1ncccc1CNc1nc(N2CCOC(C3CC3)C2)nc2ncccc12] | +++++ |
| 279 | 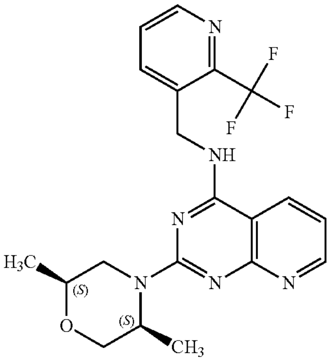 | +++++ |
| 280 | 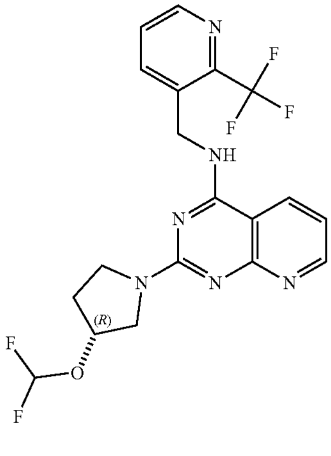 | +++++ |

TABLE 2-continued
| Entry | Structure | In vitro anti-Wolbachia activity |
|---|---|---|
| 281 | 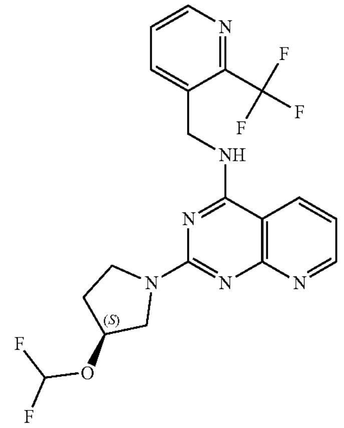 | +++++ |
| 282 | 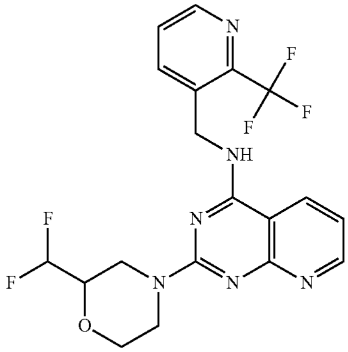 [SMILES: FC(F)C1CN(c2nc(NCc3cccnc3C(F)(F)F)c3cccnc3n2)CCO1] | +++++ |
| 283 | 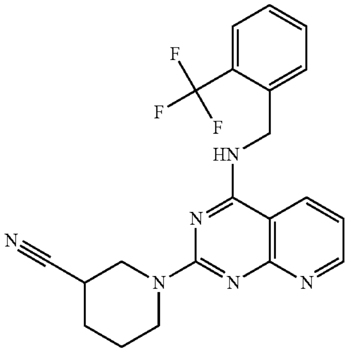 | +++++ |
| 284 | 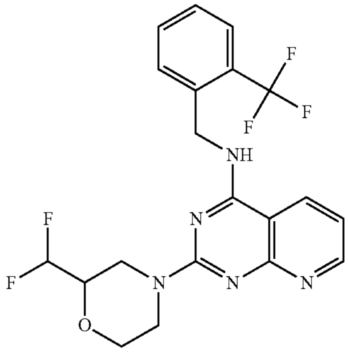 | ++++++ |

TABLE 2-continued
| Entry | Structure | In vitro anti-Wolbachia activity |
|---|---|---|
| 285 | 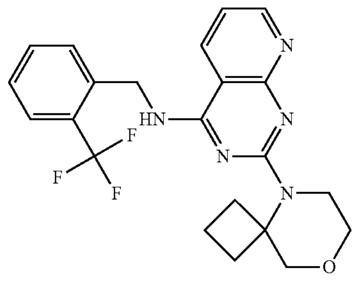 [SMILES: FC(F)(F)c1ccccc1CNc1nc(N2CCOCC23CCC3)nc2ncccc12] | +++ |
| 286 | 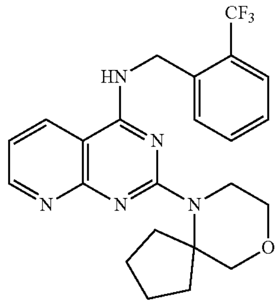 [SMILES: FC(F)(F)c1ccccc1CNc1nc(N2CCOCC23CCCC3)nc2ncccc12] | ++ |
| 287 | 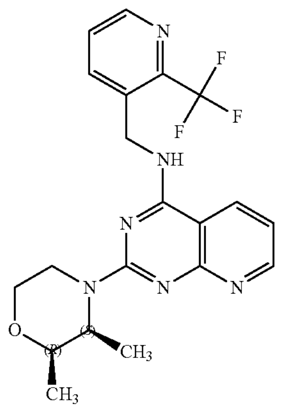 | +++++ |
| 288 | 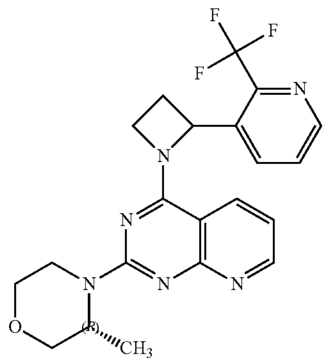 | ++++ |

TABLE 2-continued
| Entry | Structure | In vitro anti-Wolbachia activity |
|---|---|---|
| 289 | 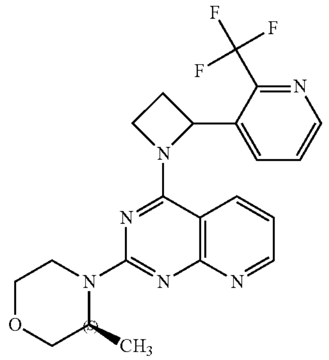 | +++++ |
| 290 | 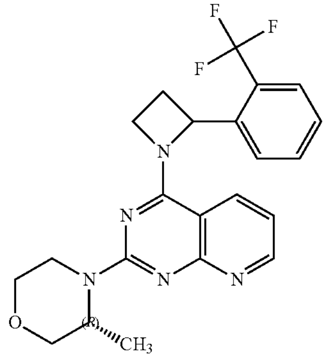 | +++++ |
| 291 | 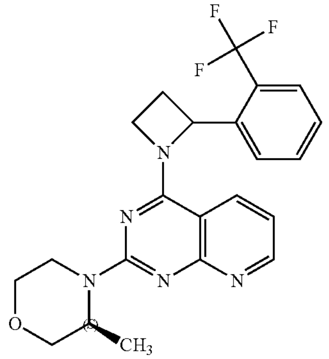 | +++++ |
| 292 | 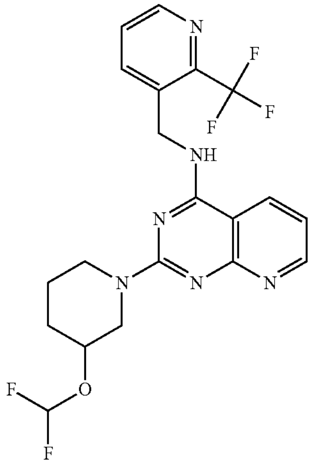 [SMILES: FC(F)OC1CCCN(c2nc(NCc3cccnc3C(F)(F)F)c3cccnc3n2)C1] | ++++++ |

TABLE 2-continued
| Entry | Structure | In vitro anti-Wolbachia activity |
|---|---|---|
| 293 | 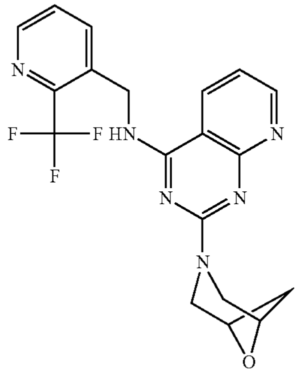 [SMILES: FC(F)(F)c1ncccc1CNc1nc(N2CC3CC(C2)O3)nc2ncccc12] | ++++ |
| 294 | 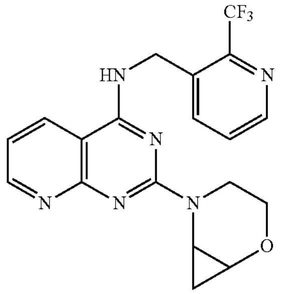 [SMILES: FC(F)(F)c1ncccc1CNc1nc(N2CCOC3CC32)nc2ncccc12] | +++++ |
| 295 | 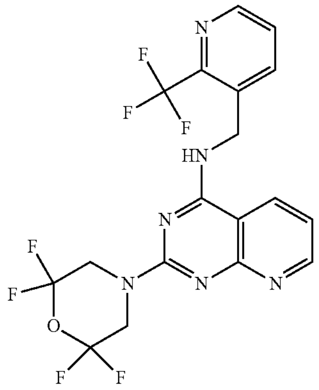 [SMILES: FC1(F)CN(c2nc(NCc3cccnc3C(F)(F)F)c3cccnc3n2)CC(F)(F)O1] | +++ |
| 296 | 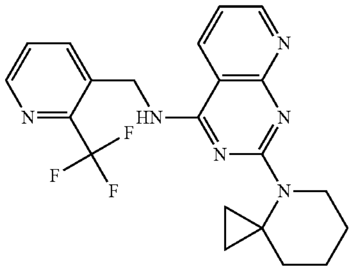 [SMILES: FC(F)(F)c1ncccc1CNc1nc(N2CCCCC23CC3)nc2ncccc12] | ++++++ |

TABLE 2-continued
| Entry | Structure | In vitro anti-Wolbachia activity |
|---|---|---|
| 297 | 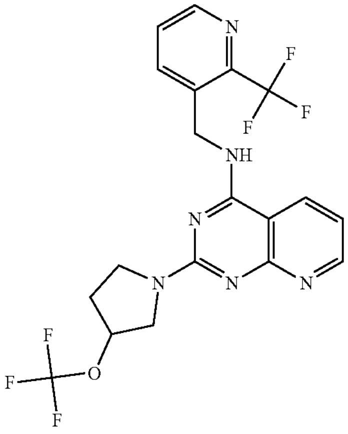 [SMILES: FC(F)(F)OC1CCN(c2nc(NCc3cccnc3C(F)(F)F)c3cccnc3n2)C1] | ++++++ |
| 298 | 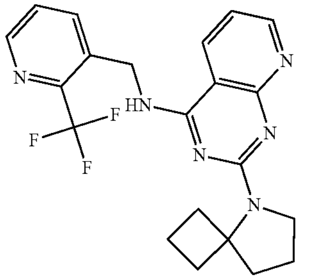 [SMILES: FC(F)(F)c1ncccc1CNc1nc(N2CCCC23CCC3)nc2ncccc12] | ++++++ |
| 299 | 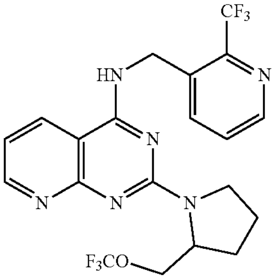 [SMILES: FC(F)(F)OCC1CCCN1c1nc(NCc2cccnc2C(F)(F)F)c2cccnc2n1] | ++++++ |
| 300 | 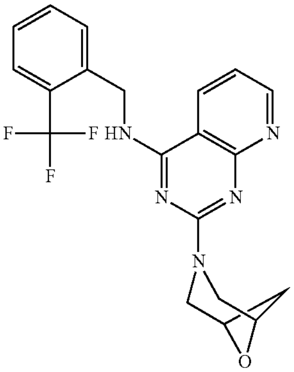 | ++++++ |

TABLE 2-continued
| Entry | Structure | In vitro anti-Wolbachia activity |
| --- | --- | --- |
| 301 | 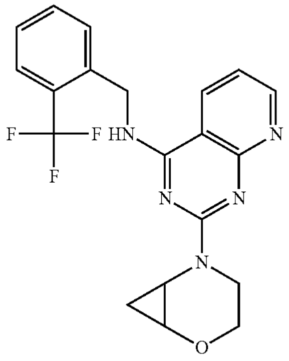 [SMILES: FC(F)(F)c1ccccc1CNc1nc(N2CCOC3CC32)nc2ncccc12] | +++++ |
| 302 | 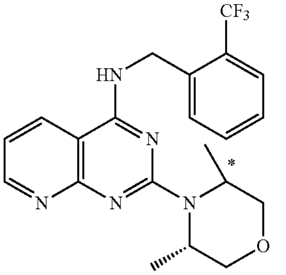 [SMILES: CC1COC[C@H](C)N1c1nc(NCc2ccccc2C(F)(F)F)c2cccnc2n1] | ++++++ |
| 303 | 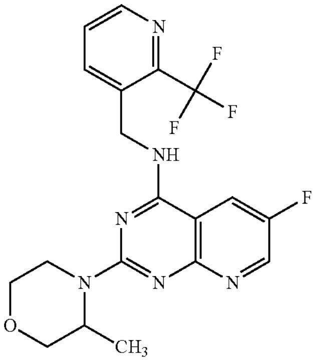 [SMILES: CC1COCCN1c1nc(NCc2cccnc2C(F)(F)F)c2cc(F)cnc2n1] | ++ |
| 304 | 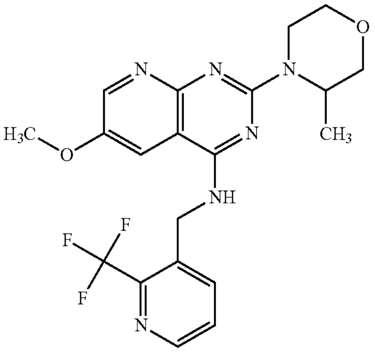 [SMILES: COc1cnc2nc(N3CCOCC3C)nc(NCc3cccnc3C(F)(F)F)c2c1] | + |

TABLE 2-continued
| Entry | Structure | In vitro anti-Wolbachia activity |
|---|---|---|
| 305 | 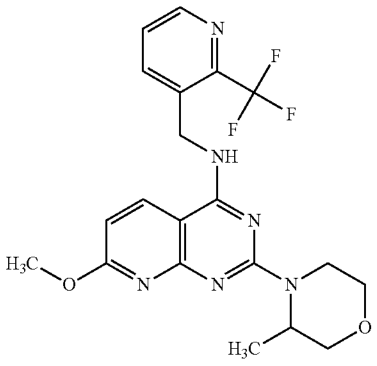 [SMILES: COc1ccc2c(NCc3cccnc3C(F)(F)F)nc(N3CCOCC3C)nc2n1] | + |
| 306 | 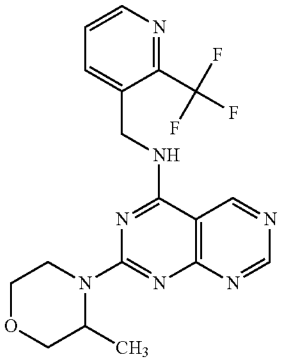 [SMILES: CC1COCCN1c1nc(NCc2cccnc2C(F)(F)F)c2cncnc2n1] | + |
| 307 | 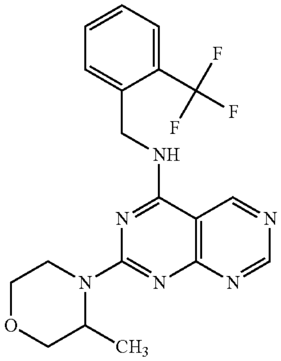 [SMILES: CC1COCCN1c1nc(NCc2ccccc2C(F)(F)F)c2cncnc2n1] | + |
| 308 | 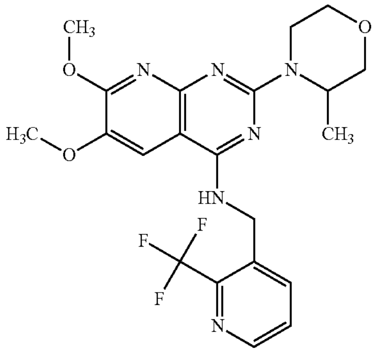 [SMILES: COc1cc2c(NCc3cccnc3C(F)(F)F)nc(N3CCOCC3C)nc2nc1OC] | + |

TABLE 2-continued
| Entry | Structure | In vitro anti-Wolbachia activity |
|---|---|---|
| 309 | 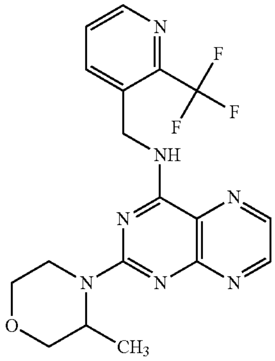 [SMILES: CC1COCCN1c1nc(NCc2cccnc2C(F)(F)F)c2nccnc2n1] | ++ |
| 310 | 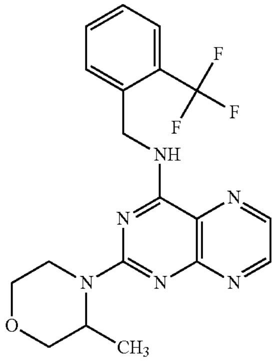 [SMILES: CC1COCCN1c1nc(NCc2ccccc2C(F)(F)F)c2nccnc2n1] | ++ |
| 311 | 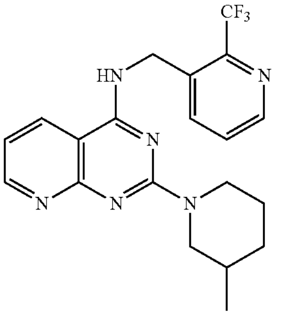 [SMILES: CC1CCCN(c2nc(NCc3cccnc3C(F)(F)F)c3cccnc3n2)C1] | +++++ |
| 312 | 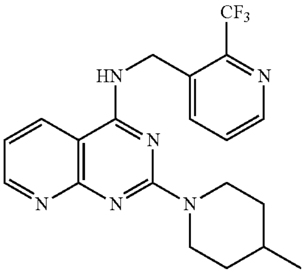 [SMILES: CC1CCN(c2nc(NCc3cccnc3C(F)(F)F)c3cccnc3n2)CC1] | +++++ |

In Vitro Microfilariae (Mf) *Brugia malayi* Screen

An in vitro microfilariae (Mf) assay was used to screen against *Wolbachia* of the target parasite, *Brugia malayi*. The Mf were obtained by peritoneal lavage of gerbils (*Meriones unguiculatus*) harbouring a patent infection of *Brugia malayi* as described previously (Griffiths et al., 2010, Lab Animal).

Mf were purified using a PD-10 desalting column (Fisher) followed by centrifugation (1200 rpm for 5 minutes at room temperature) then re-suspended in filter-sterilised culture medium consisting of RPMI supplemented with heat-inactivated Foetal Calf Serum (HI—FCS), 1% Penicillin-Streptomycin and 1% Amphotericin B.

After determining the concentration of Mf, the stock solution was diluted in culture medium to ensure a final concentration of 8000 Mf/well of a 96 well plate (100 µl per well). Compounds to be tested (10 mM stock in 100% DMSO) were diluted to appropriate working concentrations in culture medium and 100 µl was added to the appropriate wells of the 96 well plate containing the Mf. Five replicates were used for each compound and each plate contained doxycycline (5 µM) and vehicle (DMSO) controls. The plates were incubated at 37° C., 5% $CO_2$, for 6 days.

On day 6, a visual assessment of motility was performed and wells scored from 0 to 4 (where 0=no movement and 4=highly motile) in order to assess whether there were any direct effects against the Mf. To perform the anti-*Wolbachia* readout, DNA was extracted from each individual well using the QIAmp DNA Mini Kit (Qiagen) 'DNA Purification from Tissues' protocol.

The number of *Wolbachia* present in Mf was assessed by quantification of the *Wolbachia* surface protein (wsp) gene copy number and normalised to the nematode glutathione S-transferase (gst) gene by qPCR based on methods described by McGarry et al., 2004, Mol Biochem Parasitol. DNA samples were amplified in duplicate in the following 20 µl reactions containing 1× QuantiTect SYBR Green PCR master mix (Qiagen): for wsp, 0.3 µM each of forward (CCCTGCAAAGGCACAAGTTATTG) and reverse (CGAGCTCCAGCAAAGAGTTTAATTT) primer, 3 mM $MgCl_2$ and 2 µl of DNA. For gst, 0.35 µM of forward (GAGACATCTTGCTCGCAAAC) and reverse primer (ATCACGGACGCCTTCACAG), 3.5 mM $MgCl_2$ and 1 µl of DNA. qPCR was performed using the Bio-Rad CFX384 C1000 thermal cycler (Bio-Rad laboratories LTD) with a denaturation step of 95° C. for 15 min then 40 cycles at 95° C. for 15 s, 57° C. (gst) or 60° C. (wsp) for 30 s, and 72° C. for 30 s. Quantification was determined by Bio-Rad CFX manager software by comparing the DNA samples to that of a standard curve generated from serial dilution of plasmid DNA of the appropriate gene. Data in Table 3 are expressed as a reduction in *Wolbachia* load in comparison to the vehicle control group and normalized by positive control (doxycycline at 5 µM).

TABLE 3

| Compound (Conc.) | % *Wolbachia* reduction cf. DMSO | % Reduction level normalised to DOX (5 µm) |
|---|---|---|
| 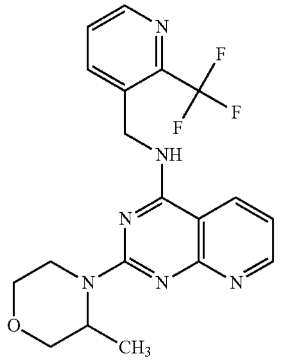 (500nM) | 89.4 | 99.8 |
| 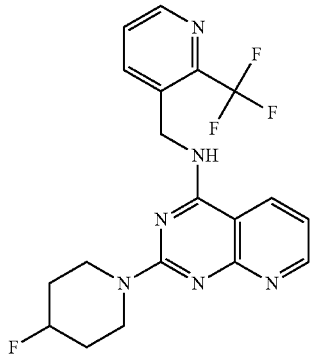 (500nM) | 87.3 | 97.4 |
| 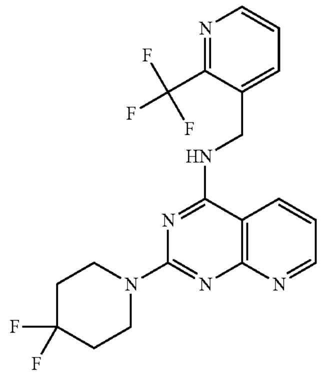 (500nM) | 88.0 | 98.2 |

TABLE 3-continued

| Compound (Conc.) | % *Wolbachia* reduction cf. DMSO | % Reduction level normalised to DOX (5 μm) |
|---|---|---|
| 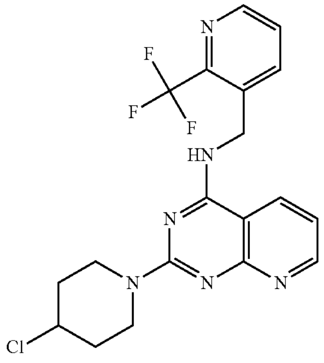 (500nM) | 83.3 | 92.9 |
| DOX (500 nM) | 80.0 | 92.9 |
| DOX (5 μM) | 89.6 | 100.0 |
| DMSO | 0 | 0 |

DOX = doxycycline

Larval *Brugia malayi* Mouse Model

In a larval *Brugia malayi* mouse model treatment groups (BALB/c IL4Rα−/− mice, 6-8 week old) received compounds by oral delivery for 7 to 14 days commencing on the day of intraperitoneal infection with *Brugia malayi* third-stage larvae. At 14 days post-infection, larvae were recovered from the peritoneal cavity, counted, and length measured. Genomic DNA was extracted from individual worms (10/group) and quantification of the *Wolbachia* surface protein (wBm-wsp) gene copy numbers performed by quantitative PCR.

Table 4 shows *Wolbachia* reductions in *Brugia malayi* larval infection mouse model (% compared to median vehicle control) following treatment with Compound X orally. Treatment dosage unit is mg/kg (MK) and duration stated in days (d). Abbreviations: DOX (doxycycline), bid (twice daily), Ms (mesylate). Data in Table 4 are expressed as a reduction in *Wolbachia* load in comparison to the vehicle control group.

TABLE 4

| Drug Dose/duration | % *Wolbachia* reduction* |
|---|---|
| DOX 25 MK bid + 14 d | 99.05 |
| 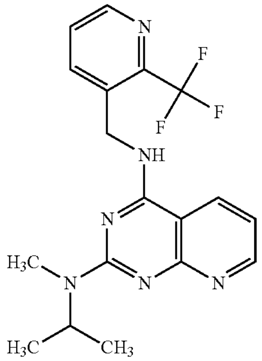 (Ms salt) 126MKbid + 14d | 99.99 |
| 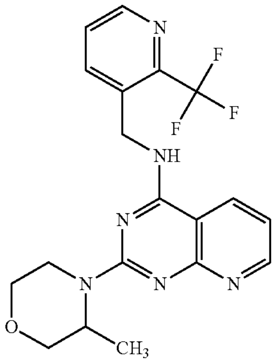 (Ms salt) 124MKbid + 14d | 99.91 |
| 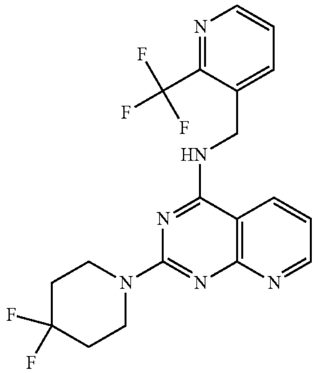 (Ms salt) 123MKbid + 14d | 99.84 |

*cf median Vehicle

Adult *Brugia malayi* Mouse Model

In an adult *Brugia malayi* mouse model treatment groups (BALB/c CCR3−/− mice, 6-8 week old) received compounds by oral delivery for 7-28 days beginning at 6-10 weeks post-infection intraperitoneal with *Brugia malayi* third-stage larvae. Following treatment, at 12 weeks post-infection, adult worms and released microfilariae were recovered from the peritoneal cavity, counted and staged for sex. Genomic DNA was extracted from individual adult worms (10/group) and quantification of the *Wolbachia* surface protein (wBm-wsp) performed by quantitative PCR.

Table 5A shows *Wolbachia* reductions in *Brugia malayi* adult infection mouse model (% compared to median vehicle control) following treatment with Compound X orally. Treatment dosage unit is mg/kg (MK) and duration stated in days (d). Abbreviations: MIN (minocycline), bid (twice daily), Ms (mesylate). Data in Table 5A are expressed as a reduction in *Wolbachia* load in comparison to the vehicle control group.

TABLE 5A

| Drug Dose/duration | % *Wolbachia* reduction* |
|---|---|
| MIN 25 MK bid + 28 d | 83.6 |
| 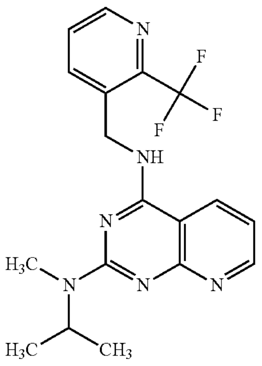 (Ms salt) 126MKbid + 28d | 99.4 |
| 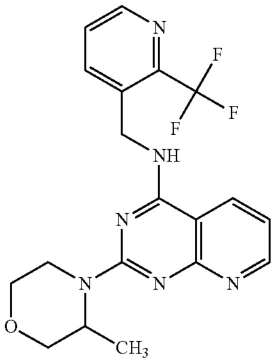 (free base) 100MKbid + 28d | 97.8 |
| 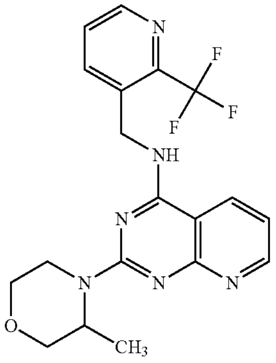 (free base) 100MKbid + 14d | 98.8 |

TABLE 5A-continued

| Drug Dose/duration | % *Wolbachia* reduction* |
|---|---|
| 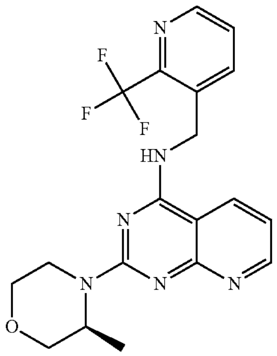 (free base) 100MKbid + 28d | 98.5 |

*cf median Vehicle

Table 5B provides a comparison of two stereoisomers in the adult *Brugia malayi* mouse model above at a range of doses and durations of treatment. Data in Table 5B are expressed as a reduction in *Wolbachia* load in comparison to the vehicle control group.

| Drug Dose/duration | % *Wolbachia* reduction* | % Microfilaria (Mf) production reduction* |
|---|---|---|
| Min 25 MK bid + 28 d treatment + 14 d wash-out | 98.2 | 100 |
| 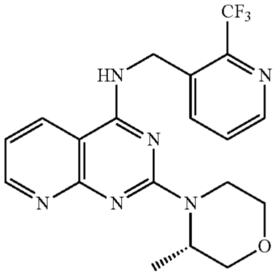 100MK bid + 14d treatment + 28d wash-out | 99.7 | 100 |
| 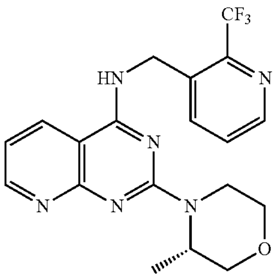 150MK bid + 07d treatment + 35d wash-out | 99.9 | 100 |

-continued

| Drug Dose/duration | % *Wolbachia* reduction* | % Microfilaria (Mf) production reduction* |
|---|---|---|
| 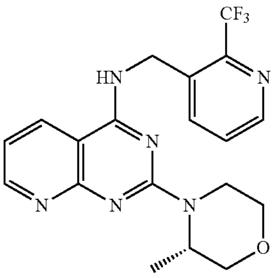 100MK bid + 07d treatment + 35d wash-out | 97.8 | 100 |
| 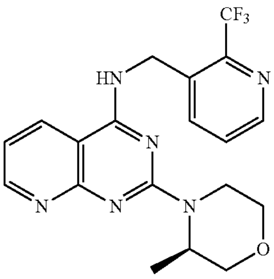 100MK bid + 14d treatment + 28d wash-out | 99.7 | 100 |
| 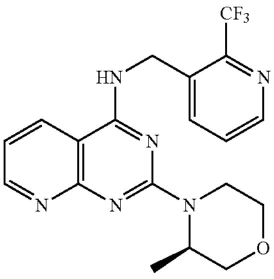 150MK bid + 7d treatment + 35d wash-out | 99.6 | 100 |
| 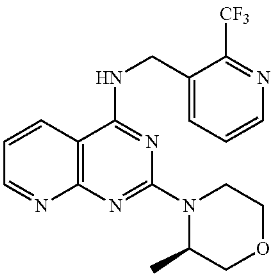 100MK bid + 07d treatment + 35d wash-out | 86.8 | 100 |

-continued

| Drug Dose/duration | % *Wolbachia* reduction* | % Microfilaria (Mf) production reduction* |
|---|---|---|
| 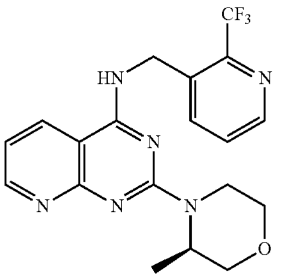 50MK bid + 07d treatment + 35d wash-out | 82.2 | 91.4 |

*cf median Vehicle

Adult *Onchocerca ochengi* Mouse Model

Viable male *Onchocerca ochengi* were aseptically isolated from naturally parasitized cattle. Between 10-11 male *Onchocerca* were surgically implanted into the peritoneal cavity of CB.17(BALB/c) SCID mice under anaesthesia. 3 days post *O. ochengi* surgical implantation, SCID mice received compounds by oral delivery for 14 days. 38 Days after *O. ochengi* surgical implantation, mice were necropsied to recover the live worms. Genomic DNA was extracted from individual adult worms (10/group) and quantification of the *O. ochengi*-specific *Wolbachia* surface protein (wsp) performed by quantitative PCR. Data in Table 6 is expressed as a reduction in *Wolbachia* load in comparison to the vehicle control group.

| Drug Dose/duration | % *Wolbachia* Reduction* |
|---|---|
| DOX 25 MK bid + 28 d | 98.7 |
| 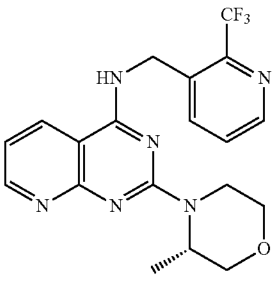 100MK bid + 14d | 96.2 |

*cf median Vehicle

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A compound of Formula I:

(I)

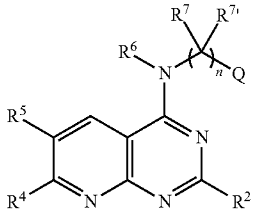

or a salt or solvate thereof, wherein,

Q is a group of Formula IIIa:

(IIIa)

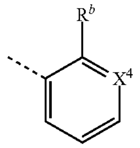

wherein $X^4$ is selected from CH and N;

$R^6$ is selected from hydrogen and $C_{1-6}$ alkyl;

$R^7$ and $R^{7'}$ are independently selected from hydrogen, $C_{3-6}$ cycloalkyl, $C_{1-6}$ alkyl, where said $C_{3-6}$ cycloalkyl and $C_{1-6}$ alkyl are optionally substituted by one or more $R^a$; or $R^7$ and $R^{7'}$, together with the carbon to which they are attached form a 3-7 membered cycloalkyl ring, optionally substituted with one or more $R^a$, or $R^7$ and $R^{7'}$, together with the carbon to which they are attached form a carbonyl group; or $R^6$ and $R^7$, together with the atoms to which they are attached form a 3-7 membered heterocyclic ring, optionally substituted with one or more $R^a$;

n is a number selected from 1, 2 and 3;

$R^2$ is selected from —CN, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —N$R^c$S(═O)$_2$N$R^cR^d$, —O$R^d$, —S$R^d$—OC(═O)$R^d$, —OC(═O)N$R^cR^d$, —OC(═O)O$R^d$, —S(═O)$R^d$, —S(═O)$_2R^d$, —OS(═O)$R^d$, —OS(═O)$_2R^d$, —OS(═O)$_2$O$R^d$, —S(═O)N$R^cR^d$, —OS(═O)$_2$N$R^cR^d$, —S(═O)$_2$N$R^cR^d$, $C_{1-10}$ haloalkyl, $C_{1-10}$alkyl optionally substituted by one or more $R^e$, $C_{2-6}$alkenyl optionally substituted by one or more $R^e$, $C_{2-6}$alkynyl optionally substituted by one or more $R^e$, $C_{6-11}$aryl optionally substituted by one or more $R^c$, $(C_{7-16})$alkylaryl optionally substituted by one or more $R^e$, $C_{3-11}$cycloalkyl optionally substituted by one or more $R^e$, $(C_{4-17})$cycloalkylalkyl optionally substituted by one or more $R^e$, 3-15 membered heterocycloalkyl optionally substituted by one or more $R^e$, 4-21 membered alkylheterocycloalkyl optionally substituted by one or more $R^e$, 5-15 membered heteroaryl optionally substituted by one or more $R^e$, and 6-21 membered alkylheteroaryl optionally substituted by one or more $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl and 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

$R^b$ and each $R^e$ is independently selected from hydroxyl, ═O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-7 membered heterocycloalkyl, —C(═O)$R^d$, —C(═O)O$R^d$, —C(═O)N$R^cR^d$, —C(O)C(═O)$R^d$, —N$R^cR^d$, —N$R^c$C(═O)$R^d$, —N$R^c$C(═O)O$R^d$, —N$R^c$C(═O)N$R^cR^d$, —N$R^c$S(═O)$_2R^d$, —NR'S(═O)$_2$N$R^cR^d$, —O$R^d$, —S$R^d$, —OC(═O)$R^d$, —OC(═O)N$R^cR^d$, —OC(═O)O$R^d$, —S(═O)$_2R^d$, —S(═O)$R^d$, —OS(═O)$R^d$, —OS(═O)$_2R^d$, —OS(═O)$_2$O$R^d$, —S(═O)N$R^cR^d$, —OS(═O)$_2$N$R^cR^d$, and —S(═O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, ═O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl and $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, amino, $C_{1-6}$ haloalkyl, $C_{3-6}$ cycloalkyl, $C_{6-11}$ aryl, 3-7 membered heterocycloalkyl, $C_{1-6}$ alkyl and O—$C_{1-6}$ alkyl; or $R^c$ and $R^d$, when attached to the same atom, together with the atom to which they are attached form a 3-7 membered ring, optionally containing one or more for heteroatoms selected from O, NH and S, and wherein said ring is optionally substituted with one or more $R^a$; and $R^4$ and $R^5$ are independently selected from hydrogen, hydroxyl, halogen, CN, $C_{1-6}$ haloalkyl, $C_{1-6}$ haloalkoxy, $C_{1-6}$ alkyl, phenyl and cyclopropyl, wherein said $C_{1-6}$ alkyl, phenyl and cyclopropyl are optionally substituted by one or more $R^a$.

2. The compound according to claim 1, or a salt or solvate thereof, wherein $R^b$ is selected from fluoro, chloro, and $CF_3$.

3. The compound according to claim 1, wherein $R^6$, $R^7$ and $R^{7'}$ are each hydrogen.

4. The compound according to claim 1, or a salt or solvate thereof, wherein n is 1.

5. The compound according to claim 1, or a salt or solvate thereof, wherein $R^2$ is selected from

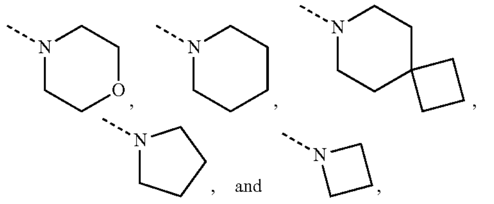

, and , each of which may optionally be substituted with one or more $R^e$.

6. The compound according to claim 1, or a salt or solvate thereof, wherein each $R^e$ is independently selected from fluoro, chloro, CN, $CF_3$, $OCF_3$, and methyl.

7. The compound according to claim 1, or a salt or solvate thereof, which is a sub-Formula Ia:

(Ia)

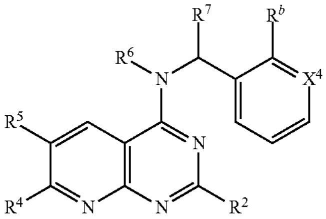

wherein, $R^6$ is selected from hydrogen and $C_{1-6}$ alkyl;

$R^7$ is selected from hydrogen, =O, $C_{3-6}$ cycloalkyl, $C_{1-6}$ alkyl, where said $C_{3-6}$ cycloalkyl, $C_{1-6}$ alkyl are optionally substituted by one or more $R^a$; or $R^6$ and $R^7$, together with the atoms to which they are attached form a 3-7 membered heterocyclic ring, optionally substituted with one or more $R^a$;

$X^4$ is selected from CH and N;

$R^2$ is selected from —CN, —C(=O)$R^d$, —C(=O)O$R^d$, —C(=O)N$R^cR^d$, —C(O)C(=O)$R^d$, —N$R^cR^d$, —N$R^c$C(=O)$R^d$, —N$R^c$C(=O)O$R^d$, —N$R^c$C(=O)N$R^cR^d$, —N$R^c$S(=O)$_2R^d$, —N$R^c$S(=O)$_2$N$R^cR^d$, —O$R^d$, —S$R^d$—OC(=O)$R^d$, —OC(=O)N$R^cR^d$, —OC(=O)O$R^d$, —S(=O)$R^d$, —S(=O)$_2R^d$, —OS(=O)$R^d$, —OS(=O)$_2R^d$, —OS(=O)$_2$O$R^d$, —S(=O)N$R^cR^d$, —OS(=O)$_2$N$R^cR^d$, —S(=O)$_2$N$R^cR^d$, $C_{1-10}$ haloalkyl, $C_{1-10}$alkyl optionally substituted by 1-13 $R^e$, $C_{2-6}$alkenyl optionally substituted by 1-11 $R^e$, $C_{2-6}$alkynyl optionally substituted by 1-9 $R^e$, $C_{6-11}$aryl optionally substituted by 1-11 $R^e$, $(C_{7-16})$alkylaryl optionally substituted by 1-9 $R^e$, $C_{3-11}$cycloalkyl optionally substituted by 1-21 $R^e$, $(C_{4-17})$cycloalkylalkyl optionally substituted by 1-32 $R^e$, 3-15 membered heterocycloalkyl optionally substituted by 1-28 $R^e$, 4-21 membered alkylheterocycloalkyl optionally substituted by 1-40 $R^e$, 5-15 membered heteroaryl optionally substituted by 1-15 $R^e$, and 6-21 membered alkylheteroaryl optionally substituted by 1-27 $R^e$;

each $R^a$ is independently selected from hydroxyl, halogen, CN, $C_{1-6}$ haloalkyl, $C_{1-6}$ haloalkoxy, $C_{1-6}$ alkyl, $C_{3-6}$ cycloalkyl, 3-7 membered heterocycloalkyl, wherein said $C_{3-6}$ cycloalkyl, 3-7 membered heterocycloalkyl are optionally substituted with one or more groups selected from hydroxyl, halogen, CN, $C_{1-6}$ haloalkyl, $C_{3-6}$ cycloalkyl, $C_{1-6}$ alkyl and O—$C_{1-6}$ alkyl;

$R^b$ and each $R^e$ is independently selected from hydroxyl, =O, halogen, CN, $C_{1-6}$ haloalkyl, $C_{1-6}$ haloalkoxy, $C_{3-6}$ cycloalkyl, $C_{1-6}$ alkyl, O—$C_{1-6}$ alkyl, $C_{3-6}$ cycloalkyl, 3-7 membered heterocycloalkyl, —C(=O)$R^d$, —C(=O)O$R^d$, —C(=O)N$R^cR^d$, —C(O)C(=O)$R^d$, —N$R^cR^d$, —N$R^c$C(=O)$R^d$, —N$R^c$C(=O)O$R^d$, —N$R^c$C(=O)N$R^cR^d$, —N$R^c$S(=O)$_2R^d$, —NR'S(=O)$_2$N$R^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2$O$R^d$, —S(=O)N$R^cR^d$, —OS(=O)$_2$N$R^cR^d$, and —S(=O)$_2$N$R^cR^d$, where said $C_{3-6}$ cycloalkyl, $C_{1-6}$ alkyl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $C_{1-6}$ alkyl and O—$C_{1-6}$ alkyl;

each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl and O—$C_{1-6}$ alkyl, $C_{6-11}$ aryl, wherein said $C_{1-6}$ alkyl, $C_{6-11}$ aryl, 3-7 membered heterocycloalkyl and $C_{3-6}$ cycloalkyl are optionally substituted with one or more groups selected from hydroxyl, halogen, CN, $C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-7 membered ring, optionally substituted with one or more $R^a$; and $R^4$ and $R^5$ are independently selected from hydrogen, hydroxyl, halogen, CN, $C_{1-6}$ haloalkyl, $C_{1-6}$ haloalkoxy, and $C_{1-6}$ alkyl.

8. The compound according to claim 7, or a salt or solvate thereof, wherein $R^4$ and $R^5$ are hydrogen.

9. The compound according to claim 7, or a salt or solvate thereof, wherein $R^b$ is selected from fluoro, chloro, and $CF_3$.

10. The compound according to claim 7, wherein $R^6$ and $R^7$ are both hydrogen.

11. The compound according to claim 7, or a salt or solvate thereof, wherein $R^2$ is selected from

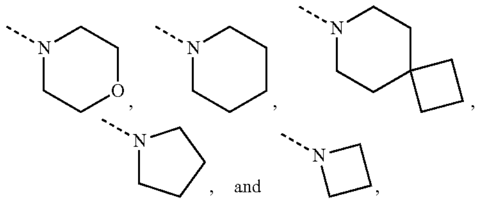

, and , each of which may optionally be substituted with one or more $R^e$.

12. The compound according to claim 7, or a salt or solvate thereof, wherein each $R^e$ is independently selected from fluoro, chloro, CN, $CF_3$, $OCF_3$, and methyl.

13. A pharmaceutical composition comprising a compound according to claim 1, or a pharmaceutically acceptable salt or solvate thereof, in admixture with a pharmaceutically acceptable diluent or carrier.

14. A combination comprising a compound according to claim 1, or a pharmaceutically acceptable salt or solvate thereof, with one or more additional therapeutic agents.

15. The compound according to claim 1, or a salt or solvate thereof, wherein $R^b$ is selected from hydroxyl, halogen, CN, $C_{1-6}$ haloalkyl, $C_{1-6}$ haloalkoxy, $C_{1-6}$ alkyl and O—$C_{1-6}$ alkyl.

16. The compound according to claim 7, or a salt or solvate thereof, wherein $R^b$ is selected from hydroxyl, halogen, CN, $C_{1-6}$ haloalkyl, $C_{1-6}$ haloalkoxy, $C_{1-6}$ alkyl and O—$C_{1-6}$ alkyl.

* * * * *